US006720408B2

(12) United States Patent
Fisher et al.

(10) Patent No.: US 6,720,408 B2
(45) Date of Patent: *Apr. 13, 2004

(54) MDA-7 NUCLEIC ACID MOLECULES AND PHARMACEUTICAL COMPOSITIONS THEREOF

(75) Inventors: Paul B. Fisher, Scarsdale, NY (US); Hongping Jiang, New York, NY (US)

(73) Assignee: The Trustees of Columbia University in the City of New York, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 8 days.

(21) Appl. No.: 09/221,268

(22) Filed: Dec. 23, 1998

(65) Prior Publication Data

US 2002/0183509 A1 Dec. 5, 2002

Related U.S. Application Data

(63) Continuation of application No. 08/316,537, filed on Sep. 30, 1994, now Pat. No. 6,051,376, which is a continuation-in-part of application No. 08/143,576, filed on Oct. 27, 1993, now Pat. No. 5,643,761.

(51) Int. Cl.[7] .......................... C07H 21/00; C12Q 1/68; C12P 21/06; C12N 5/00
(52) U.S. Cl. .......................... 536/23.1; 435/6; 435/69.1; 435/325; 536/24.1; 536/24.3; 536/24.31; 536/24.32; 536/24.33
(58) Field of Search .......................... 435/6, 69.1, 325; 536/22.1, 23.1, 24.1, 24.3–24.33; 514/44

(56) References Cited

U.S. PATENT DOCUMENTS

| 5,302,706 A | 4/1994 | Smith .......................... 536/23.1 |
| 5,480,968 A | 1/1996 | Kraus et al. |
| 5,643,761 A | 7/1997 | Fisher et al. ............... 435/91.1 |
| 5,710,137 A | 1/1998 | Fisher |
| 6,051,376 A | 4/2000 | Fisher et al. |
| 6,190,909 B1 | 2/2001 | Levinson et al. |
| 6,355,622 B1 | 3/2002 | Fisher |
| 6,413,717 B1 | 7/2002 | Sun et al. |

FOREIGN PATENT DOCUMENTS

| EP | 0212285 | 3/1987 |
| EP | 0372524 | 6/1990 |
| WO | 8807585 | 10/1988 |
| WO | 8912695 | 12/1989 |
| WO | 9105861 | 5/1991 |
| WO | 9511986 | 5/1995 |
| WO | 9806441 | 2/1998 |
| WO | 9828425 | 7/1998 |
| WO | 0105437 | 1/2001 |

OTHER PUBLICATIONS

Sigma Chemical Company 1990 Catalog (Sigma Chemical Company, St. Louis, Missouri, USA), p. 778, 1990.*

(List continued on next page.)

*Primary Examiner*—Ardin H. Marschel
(74) *Attorney, Agent, or Firm*—Baker Botts L.L.P.

(57) ABSTRACT

This invention provides a method of generating a subtracted cDNA library of a cell comprising: a) generating a cDNA library of the cell; b) isolating double-stranded DNAs from the cDNA library; c) releasing the double-stranded cDNA inserts from the double-stranded DNAs; d) denaturing the isolated double-stranded cDNA inserts; e) hybridizing the denatured double-stranded cDNA inserts with a labelled single-stranded nucleic acid molecules which are to be subtracted from the cDNA library; and f) separating the hybridized labeled single-stranded nucleic acid molecule from the double-stranded cDNA inserts, thereby generating a subtracted cDNA library of a cell. This invention also provides different uses of the subtracted library.

18 Claims, 45 Drawing Sheets

OTHER PUBLICATIONS

Dugid, J.R., et al., (1988) "Isolation of cDNAs of scrapie–modulated RNAs by subtractive hybridization of a cDNA library", *Proc. Natl. Acad. Sci. USA*, 85:5738–5742 (Exhibit 4).

Hara, E., et al., (1993) "DNA–DNA subtractive cDNA cloning using oligo $(dT)_{30}$ –latex and PCR: Identification of cellular genes which are overexpressed in senescent human diploid fibroblasts", *Anal. Biochem.*, 214:58–64 (Exhibit 5).

Hara, E., et al., (1991) "Subtractive cDNA cloning using oligo $(dT)_{30}$ –latex and PCR: isolation of cDNA clones specific to undifferentiated human embryonal carcinoma cells", *Nuc. Acd. Res.*, 19(25):7097–7104 (Exhibit 6).

Hertfort, M.R. and Garbre, A.T., (1991) "Simple and efficient subractive hybridization screening", *BioTechniques*, 11(5):598–603 (Exhibit 7).

Jiang, H., et al., (1994) "A Molecular Definition of Terminal Cell Differentiation in Human Melanoma Cells", *Mol. and Cell. Diff.*, 2(3):221–239 (Exhibit 8).

Lee, S.W., et al., (1991) "Positive selection of candidate tumor–suppressor genes by subtractive hybridization", *Proc. Natl. Acad. Sci. USA*, 88:2825–2829 (Exhibit 9).

Maniatis, T., et al., (1982) "Strategies for cDNA Cloning", *Mol. Clon.*, 224–228 (Exhibit 10); Rubenstein, J.L.R., et al., (1990) "Subtractive hybridization system using single–stranded phagemids with directional inserts", *Nuc. Acd. Res.*, 18:4833–4842 (Exhibit 11).

Singh, J., et al., (1992) "Intermediate biomarker of colon cancer: modulation of expression of ras oncogene by chemopreventive agents during azoxymethane induced colon carcinogenesis", *Oxford Uni. Pres.*, 699–704 (Exhibit 12).

Sive, H.L., et al., (1988) "A simple subtractive hybridization technique employing photoactivatable biotin and phenol extraction", *Nucl. Acd. Res.*, 16(22):10937 (Exhibit 13).

Sumiya, H., et al., (1990) "Histochemical Examination of Expression of ras p21 Protein and R 1881–binding Protein in Human Prostatic Cancers", *Eur. J. Cancer*, 26(7):786–789 (Exhibit 14).

Travis, G., et al., (1988) "Phenol emulsion–enchanced DNA–driven subtractive cDNA cloning: Isolation of Low–abundance monkey cortex–specific mRNAs", *Proc. Natl. Acad. Sci. USA*, 85:1696–1700 (Exhibit 15); and.

Wieland, I., et al., (1990) "A method for difference cloning: Gene amplification following subtractive hybridization", *Proc. Natl. Acad. Sci., USA*, 87:2720–2724 (Exhibit 16).

Duguid JR, et al. (1990) "Library Subtraction of In Vitro cDNA Libraries to Identify Differentially Expressed Genes in Scrapie Infection" *Nuc Acid Res*, 18(9):2789–2792.

Gu, J.R., et al., (1991) "Transthyretin (prealbumin) Gene in Human Primary Hepatic Cancer" *Scientia Sinica*, 34(11):1312–1318.

Jiang H, and Fisher, PB (1993) "Use of a Sensitive and Efficient Subtraction Hybridization Protocol for the Identification of Genes Differentially Regulated During the Induction of Differentiation in Human Melanoma Cells" *Mol and Cell Diff*, 1(3):285–299.

Lopez–Fernandez LA, et al. (1993) "Construction of Subtractive cDNA Libraries from Limited Amounts of mRNA and Multiple Cycles of Subtraction" *BioTechniques*, 15(4):654, 656, 658, 659.

Su ZZ, Madireddi MT, Lin JJ, Young CS, Kitada S, Reed JC, Goldstein NI, Fisher PB. The cancer growth suppressor gene mda–7 selectively induces apoptosis in human breast cancer cells and inhibits tumor growth in nude mice. Proc Natl Acad Sci USA 1998;95(24):14400–14405.

Jiang H, Su ZZ, Lin JJ, Goldstein NI, Young CS, Fisher PB. The Melanoma differentiation associated gene mda–7 suppresses cancer cell growth. Proc Natl Acad Sci USA 1996;93(17):9160–9165.

Jiang H, Lin JJ, Su ZZ, Goldstein NI, Fisher PB. Subtraction hybridization identifies a novel melanoma differentiation associated gene, mda–7, modulated during human melanoma differentiation, growth and progression. Oncogene 1995;11(12):2477–2486.

Jiang H, Fisher PB. A sensitive and efficient subtraction hybridization protocol for the identification of genes differentially regulated during the induction of differentiation in human melanoma cells. Mol Cell Different 1993;1(3):285–299.

U.S. patent application Ser. No. 09/991,452, Fisher et al., filed Nov. 21, 2001.

* cited by examiner

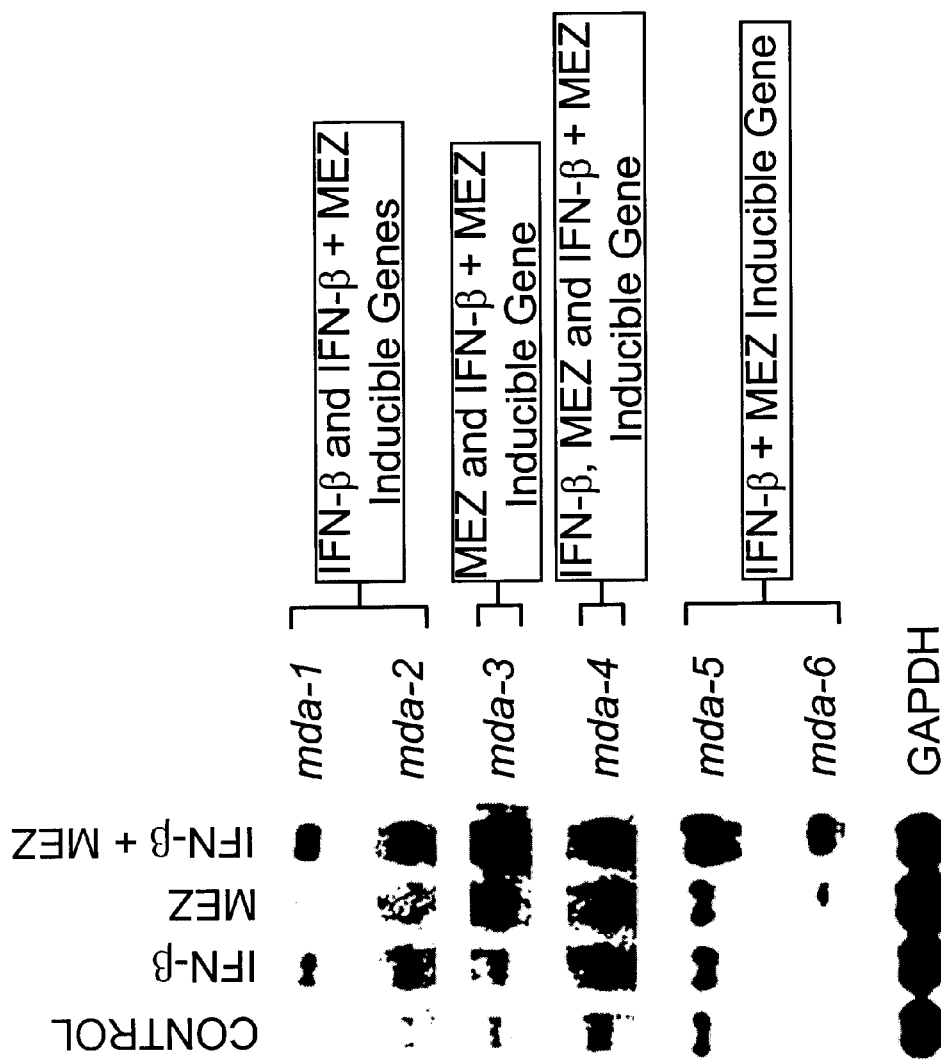

```
  1 TCCTCCTCTGCACCATGGCTCTCTGCAACCAGTTCTCTGCATCACTTGCT   50
    ||||||||||||||||||||||||||||||||||||||||||||||||||
112 TCCTCCTCTGCACCATGGCTCTCTGCAACCAGTTCTCTGCATCACTTGCT  161

51 GCTGACACGCCGACCGCCTGCTGCTTCAGCTACACCTCCCGGCAGATTCC  100
    ||||||||||||||||||||||||||||||||||||||||||||||||||
162 GCTGACACGCCGACCGCCTGCTGCTTCAGCTACACCTCCCGGCAGATTCC  211

101 ACAGAATTTCATAGCTGACTACTTTGAGACGAGCAGCCAGTGCTCCAAGC  150
    ||||||||||||||||||||||||||||||||||||||||||||||||||
212 ACAGAATTTCATAGCTGACTACTTTGAGACGAGCAGCCAGTGCTCCAAGC  261

151 CCGGTGTCATCTTCCTAACCAAGCGAACCGGGCAGGTCTGTGCTGACCCC  200
    |||||||||||||||||||||||||| | ||||||||||||||||||||
262 CCGGTGTCATCTTCCTAACCAAGCGAAGCCGGCAGGTCTGTGCTGACCCC  311

201 AGTGAGGAGTGGGTCCAGAAATATGTCAGCGACCTGGAGCTGAGT       245
    |||||||||||||||||||||||||||||||||||||||||||||
312 AGTGAGGAGTGGGTCCAGAAATATGTCAGCGACCTGGAGCTGAGT       356
```

FIG. 11

| FIG.23A |
|---|
| FIG.23B |

```
AGCTGAGGTGTGAGCAGCTGCCGAAGTCAGTTCCTTGTGGAGCCGGAGCTGGGCGCGGAT      60
TCGCCGAGGCACCGAGGCACTCAGAGGAGGCGCCATGTCAGAACCGGCTGGGGATGTCCG     120
                                 M  S  E  P  A  G  D  V  R
TCAGAACCCATGCGGCAGCAAGGCCTGCCGCCGCCTCTTCGGCCCAGTGGACAGCGAGCA     180
 Q  N  P  C  G  S  K  A  C  R  R  L  F  G  P  V  D  S  E  Q
GCTGAGCCGCGACTGTGATGCGCTAATGGCGGGCTGCATCCAGGAGGCCCGTGAGCGATG     240
 L  S  R  D  C  D  A  L  M  A  G  C  I  Q  E  A  R  E  R  W
GAACTTCGACTTTGTCACCGAGACACCACTGGAGGGTGACTTCGCCTGGGAGCGTGTGCG     300
 N  F  D  F  V  T  E  T  P  L  E  G  D  F  A  W  E  R  V  R
GGGCCTTGGCCTGCCCAAGCTCTACCTTCCCACGGGGCCCCGGCGAGGCCGGGATGAGTT     360
 G  L  G  L  P  K  L  Y  L  P  T  G  P  R  R  G  R  D  E  L
GGGAGGAGGCAGGCGGCCTGGCACCTCACCTGCTCTGCTGCAGGGGACAGCAGAGGAAGA     420
 G  G  G  R  R  P  G  T  S  P  A  L  L  Q  G  T  A  E  E  D
CCATGTGGACCTGTCACTGTCTTGTACCCTTGTGCCTCGCTCAGGGGAGCAGGCTGAAGG     480
 H  V  D  L  S  L  S  C  T  L  V  P  R  S  G  E  Q  A  E  G
GTCCCCAGGTGGACCTGGAGACTCTCAGGGTCGAAAACGGCGGCAGACCAGCATGACAGA     540
 S  P  G  G  P  G  D  S  Q  G  R  K  R  R  Q  T  S  M  T  D
TTTCTACCACTCCAAACGCCGGCTGATCTTCTCCAAGAGGAAGCCCTAATCCGCCCACAG     600
 F  Y  H  S  K  R  R  L  I  F  S  K  R  K  P  *
GAAGCCTGCAGTCCTGGAAGCGCGAGGGCCTCAAAGGCCCGCTCTACATCTTCTGCCTTA     660
GTCTCAGTTTGTGTGTCTTAATTATTATTTGTGTTTTAATTTAAACACCTCCTCATGTAC     720
ATACCCTGGCCGCCCCCTGCCCCCCAGCCTCTGGCATTAGAATTATTTAAACAAAAACTA     780
```

FIG.23A

```
GGCGGTTGAATGAGAGGTTCCTAAGAGTGCTGGGCATTTTTATTTTATGAAATACTATTT    840
AAAGCCTCCTCATCCCGTGTTCTCCTTTTCCTCTCTCCCGGAGGTTGGGTGGGCCGGCTT    900
CATGCCAGCTACTTCCTCCTCCCCACTTGTCCGCTGGGTGGTACCCTCTGGAGGGGTGTG    960
GCTCCTTCCCATCGCTGTCACAGGCGGTTATGAAATTCACCCCCTTTCCTGGACACTCAG   1020
ACCTGAATTCTTTTTTCATTTGAGAAGTAAACAGATGGCACTTTGAAGGGGCCTCACCGAG  1080
TGGGGGCATCATCAAAAACTTTGGAGTCCCCTCACCTCCTCTAAGGTTGGGCAGGGTGAC   1140
CCTGAAGTGAGCACAGCCTAGGGCTGAGCTGGGGACCTGGTACCCTCCTGGCTCTTGATA   1200
CCCCCCTCTGTCTTGTGAAGGCAGGGGGAAGGTGGGGTCCTGGAGCAGACCACCCCGCCT   1260
GCCCTCATGGCCCCTCTGACCTGCACTGGGGAGCCCGTCTCAGTGTTGAGCCTTTTCCCT   1320
CTTTGGCTCCCCTGTACCTTTTGAGGAGCCCCAGCTACCCTTCTTCTCCAGCTGGGCTCT   1380
GCAATTCCCCTCTGCTGCTGTCCCTCCCCCTTGTCCTTTCCCTTCAGTACCCTCTCAGCT   1440
CCAGGTGGCTCTGAGGTGCCTGTCCCACCCCCACCCCCAGCTCAATGGACTGGAAGGGGA   1500
AGGGACACACAAGAAGAAGGGCACCCTAGTTCTACCTCAGGCAGCTCAAGCAGCGACCGC   1560
CCCCTCCTCTAGCTGTGGGGGTGAGGGTCCCATGTGGTGGCACAGGCCCCCTTGAGTGGG   1620
GTTATCTCTGTGTTAGGGGTATATGATGGGGGAGTAGATCTTTCTAGGAGGGAGACACTG   1680
GCCCCTCAAATCGTCCAGCGACCTTCCTCATCCACCCCATCCCTCCCCAGTTCATTGCAC   1740
TTTGATTAGCAGCGGAACAAGGAGTCAGACATTTTAAGATGGTGGCAGTAGAGGCTATGG   1800
ACAGGGCATGCCACGTGGGCTCATATGGGGCTGGGAGTAGTTGTCTTTCCTGGCACTAAC   1860
GTTGAGCCCCTGGAGGCACTGAAGTGCTTAGTGTACTTGGAGTATTGGGGTCTGACCCCA   1920
AACACCTTCCAGCTCCTGTAACATACTGGCCTGGACTGTTTTCTCTCGGCTCCCCATGTG   1980
TCCTGGTTCCCGTTTCTCCACCTAGACTGTAAACCTCTCGAGGGCAGGGACCACACCCTG   2040
TACTGTTCTGTGTCTTTCACAGCTCCTCCCACAATGCTGAATAAACAGCAGGTGCTCAAT   2100
AAATGATTCTTAGTGACTTTAAAAAAAAAAAAAAAAAAAAAAAAAAAA   2147
```

FIG.23B

```
ATGTCAGAACCGGCTGGGGATGTCCGTCAGAACCCATGCGGCAGCAAGGCCTGCCGCCGC
 M   S   E   P   A   G   D   V   R   Q   N   P   C   G   S   K   A   C   R   R
CTCTTCGGCCCAGTGGACAGCGAGCAGCTGAGCCGCGACTGTGATGCGCTAATGGCGGGC
 L   F   G   P   V   D   S   E   Q   L   S   R   D   C   D   A   L   M   A   G
TGCATCCAGGAGGCCCGTGAGCGATGGAACTTCGACTTTGTCACCGAGACACCACTGGAG
 C   I   Q   E   A   R   E   R   W   N   F   D   F   V   T   E   T   P   L   E
GGTGACTTCGCCTGGGAGCGTGTGCGGGGCCTTGGCCTGCCCAAGCTCTACCTTCCCACG
 G   D   F   A   W   E   R   V   R   G   L   G   L   P   K   L   Y   L   P   T
GGGCCCCGGCGAGGCCGGGATGAGTTGGGAGGAGGCAGGCGGCCTGGCACCTCACCTGCT
 G   P   R   R   G   R   D   E   L   G   G   G   R   R   P   G   T   S   P   A
CTGCTGCAGGGGACAGCAGAGGAAGACCATGTGGACCTGTCACTGTCTTGTACCCTTGTG
 L   L   Q   G   T   A   E   E   D   H   V   D   L   S   L   S   C   T   L   V
CCTCGCTCAGGGGAGCAGGCTGAAGGGTCCCCAGGTGGACCTGGAGACTCTCAGGGTCGA
 P   R   S   G   E   Q   A   E   G   S   P   G   G   P   G   D   S   Q   G   R
AAACGGCGGCAGACCAGCATGACAGATTTCTACCACTCCAAACGCCGGCTGATCTTCTCC
 K   R   R   Q   T   S   M   T   D   F   Y   H   S   K   R   R   L   I   F   S
AAGAGGAAGCCCTAA
 K   R   K   P   *
```

FIG.30

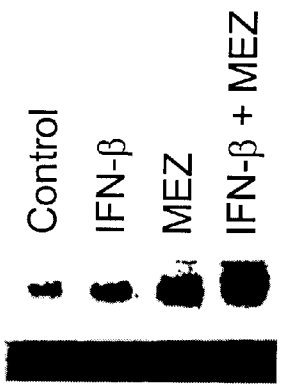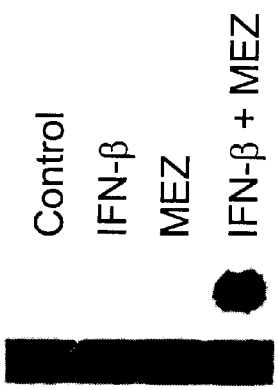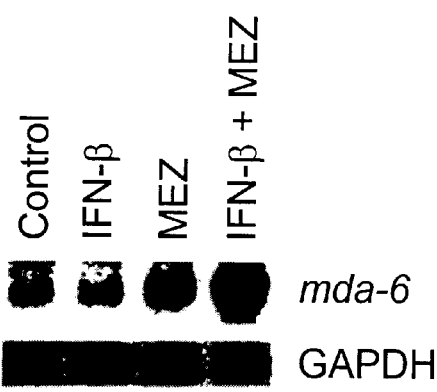
FIG.31A   FIG.31B   FIG.31C
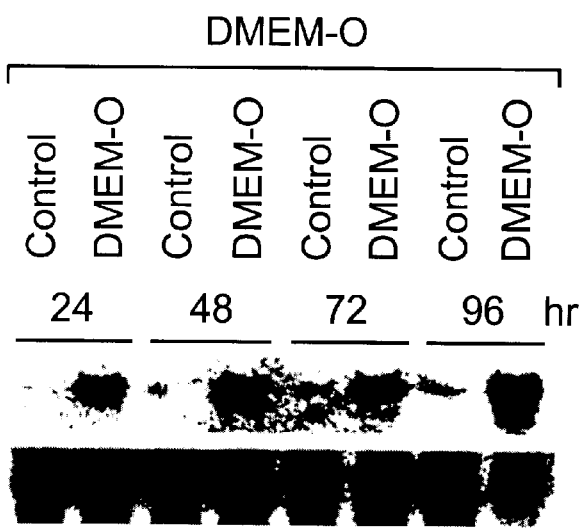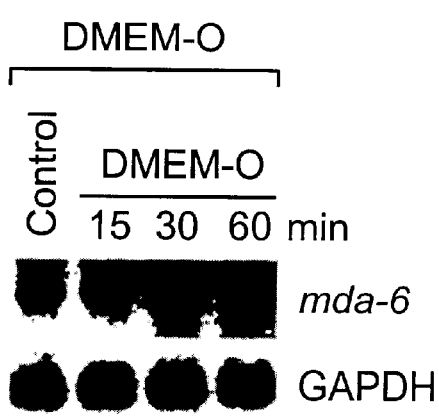
FIG.31D   FIG.31E

FIG.38A
FIG.38B

MDA-7.Seq
CTTGCCTGCAAACCTTTACTTCTGAAATGACTTCCACGGCTGGGACGGGAACCTTCCACC   60
CACAGCTATGCCTCTGATTGGTGAATGGTGAAGGTGCCTGTCTAACTTTTCTGTAAAAAG  120
AACCAGCTGCCTCCAGGCAGCCAGCCCTCAAGCATCACTTACAGGACCAGAGGGACAAGA  180
CATGACTGTGATGAGGAGCTGCTTTCGCCAATTTAACACCAAGAAGAATTGAGGCTGCTT  240
GGGAGGAAGGCCAGGAGGAACACGAGACTGAGAGATGAATTTTCAACAGAGGCTGCAAAG  300
                     M N F Q Q R L Q S

CCTGTGGACTTTAGCCAGACCCTTCTGCCCTCCTTTGCTGGCGACAGCCTCTCAAATGCA  360
L W T L A R P F C P P L L A T A S Q M Q

GATGGTTGTGCTCCCTTGCCTGGGTTTTACCCTGCTTCTCTGGAGCCAGGTATCAGGGGC  420
M V V L P C L G F T L L L W S Q V S G A

CCAGGGCCAAGAATTCCACTTTGGGCCCTGCCAAGTGAAGGGGGTTGTTCCCCAGAAACT  480
Q G Q E F H F G P C Q V K G V V P Q K L

GTGGGAAGCCTTCTGGGCTGTGAAAGACACTATGCAAGCTCAGGATAACATCACGAGTGC  540
W E A F W A V K D T M Q A Q D N I T S A

CCGGCTGCTGCAGCAGGAGGTTCTGCAGAACGTCTCGGATGCTGAGAGCTGTTACCTTGT  600
R L L Q Q E V L Q N V S D A E S C Y L V

CCACACCCTGCTGGAGTTCTACTTGAAAACTGTTTTCAAAAACTACCACAATAGAACAGT  660
H T L L E F Y L K T V F K N Y H N R T V

FIG.38A

```
TGAAGTCAGGACTCTGAAGTCATTCTCTACTCTGGCCAACAACTTTGTTCTCATCGTGTC    720
 E  V  R  T  L  K  S  F  S  T  L  A  N  N  F  V  L  I  V  S

ACAACTGCAACCCAGTCAAGAAAATGAGATGTTTTCCATCAGAGACAGTGCACACAGGCG    780
 Q  L  Q  P  S  Q  E  N  E  M  F  S  I  R  D  S  A  H  R  R

GTTTCTGCTATTCCGGAGAGCATTCAAACAGTTGGACGTAGAAGCAGCTCTGACCAAAGC    840
 F  L  L  F  R  R  A  F  K  Q  L  D  V  E  A  A  L  T  K  A

CCTTGGGGAAGTGGACATTCTTCTGACCTGGATGCAGAAATTCTACAAGCTCTGAATGTC    900
 L  G  E  V  D  I  L  L  T  W  M  Q  K  F  Y  K  L  *

TAGACCAGGACCTCCCTCCCCCTGGCACTGGTTTGTTCCCTGTGTCATTTCAAACAGTCT    960
CCCTTCCTATGCTGTTCACTGGACACTTCACGCCCTTGGCCATGGGTCCCATTCTTGGCC   1020
CAGGATTATTGTCAAAGAAGTCATTCTTTAAGCAGCGCCAGTGACAGTCAGGGAAGGTGC   1080
CTCTGGATGCTGTGAAGAGTCTACAGAGAAGATTCTTGTATTTATTACAACTCTATTTAA   1140
TTAATGTCAGTATTTCAACTGAAGTTCTATTTATTTGTGAGACTGTAAGTTACATGAAGG   1200
CAGCAGAATATTGTGCCCCATGCTTCTTTACCCCTCACAATCCTTGCCACAGTGTGGGGC   1260
AGTGGATGGGTGCTTAGTAAGTACTTAATAAACTGTGGTGCTTTTTTTGGCCTGTCTTTG   1320
GATTGTTAAAAAACAGAGAGGGATGCTTGGATGTAAAACTGAACTTCAGAGCATGAAAAT   1380
CACACTGTCTGCTGATATCTGCAGGGACAGAGCATTGGGGTGGGGGTAAGGTGCATCTGT   1440
TTGAAAAGTAAACGATAAAATGTGGATTAAAGTGCCCAGCACAAAGCAGATCCTCAATAA   1500
ACATTTCATTTCCCACCCACACTCGCCAGCTCACCCCATCATCCCTTTCCCTTGGTGCCC   1560
TCCTTTTTTTTTTATCCTAGTCATTCTTCCCTAATCTTCCACTTGAGTGTCAAGCTGACC   1620
TTGCTGATGGTGACATTGCACCTGGATGTACTATCCAATCTGTGATGACATTCCCTGCTA   1680
ATAAAAGACAACATAACTCAAAAAAAAAAAAAAAAAAAA   1718
```

FIG.38B

SEQUENCE LISTING

```
<160> NUMBER OF SEQ ID NOS: 30

<210> SEQ ID NO 1
<211> LENGTH: 245
<212> TYPE: DNA
<213> ORGANISM: homo sapiens

<400> SEQUENCE: 1
tcctcctctg caccatggct ctctgcaacc agttctctgc atcacttgct gctgacacgc     60
cgaccgcctg ctgcttcagc tacacctccc ggcagattcc acagaatttc atagctgact    120
actttgagac gagcagccag tgctccaagc ccggtgtcat cttcctaacc aagcgaaccg    180
ggcaggtctg tgctgacccc agtgaggagt gggtccagaa atatgtcagc gacctggagc    240
tgagt                                                                245

<210> SEQ ID NO 2
<211> LENGTH: 2147
<212> TYPE: DNA
<213> ORGANISM: homo sapiens
<220> FEATURE:
<221> NAME/KEY: CDS
```

<222> LOCATION: (95)...(589)

<400> SEQUENCE: 2

```
agctgaggtg tgagcagctg ccgaagtcag ttccttgtgg agccggagct gggcgcggat      60
tcgccgaggc accgaggcac tcagaggagg cgcc atg tca gaa ccg gct ggg gat     115
                                      Met Ser Glu Pro Ala Gly Asp
                                       1               5 gtc cgt cag aac cca tgc ggc agc aag gcc tgc cgc cgc ctc ttc ggc      163
Val Arg Gln Asn Pro Cys Gly Ser Lys Ala Cys Arg Arg Leu Phe Gly
        10                  15                  20 cca gtg gac agc gag cag ctg agc cgc gac tgt gat gcg cta atg gcg      211
Pro Val Asp Ser Glu Gln Leu Ser Arg Asp Cys Asp Ala Leu Met Ala
     25                  30                  35 ggc tgc atc cag gag gcc cgt gag cga tgg aac ttc gac ttt gtc acc      259
Gly Cys Ile Gln Glu Ala Arg Glu Arg Trp Asn Phe Asp Phe Val Thr
 40                  45                  50                  55 gag aca cca ctg gag ggt gac ttc gcc tgg gag cgt gtg cgg ggc ctt      307
Glu Thr Pro Leu Glu Gly Asp Phe Ala Trp Glu Arg Val Arg Gly Leu
                 60                  65                  70 ggc ctg ccc aag ctc tac ctt ccc acg ggg ccc cgg cga ggc cgg gat      355
Gly Leu Pro Lys Leu Tyr Leu Pro Thr Gly Pro Arg Arg Gly Arg Asp
             75                  80                  85 gag ttg gga gga ggc agg cgg cct ggc acc tca cct gct ctg ctg cag      403
Glu Leu Gly Gly Gly Arg Arg Pro Gly Thr Ser Pro Ala Leu Leu Gln
         90                  95                 100 ggg aca gca gag gaa gac cat gtg gac ctg tca ctg tct tgt acc ctt      451
Gly Thr Ala Glu Glu Asp His Val Asp Leu Ser Leu Ser Cys Thr Leu
    105                 110                 115 gtg cct cgc tca ggg gag cag gct gaa ggg tcc cca ggt gga cct gga      499
Val Pro Arg Ser Gly Glu Gln Ala Glu Gly Ser Pro Gly Gly Pro Gly
120                 125                 130                 135 gac tct cag ggt cga aaa cgg cgg cag acc agc atg aca gat ttc tac      547
Asp Ser Gln Gly Arg Lys Arg Arg Gln Thr Ser Met Thr Asp Phe Tyr
                140                 145                 150 cac tcc aaa cgc cgg ctg atc ttc tcc aag agg aag ccc taa              589
His Ser Lys Arg Arg Leu Ile Phe Ser Lys Arg Lys Pro
                155                 160 tccgcccaca ggaagcctgc agtcctggaa gcgcgagggc ctcaaaggcc cgctctacat     649
cttctgcctt agtctcagtt tgtgtgtctt aattattatt tgtgttttaa tttaaacacc     709
tcctcatgta catacctgg ccgccccctg ccccccagcc tctggcatta gaattattta     769
aacaaaaact gggcggttga atgagaggtt cctaagagtg ctgggcattt ttatttatg     829 aaatactatt taaagcctcc tcatcccgtg ttctccttt cctctctccc ggaggttggg     889
tgggccggct tcatgccagc tacttcctcc tccccacttg tccgctgggt ggtaccctct    949 ggagggtgt ggctccttcc catcgctgtc acaggcggtt atgaaattca ccccctttcc    1009
tggacactca gacctgaatt cttttttcatt tgagaagtaa acagatggca ctttgaaggg   1069
gcctcaccga gtgggggcat catcaaaaac tttggagtcc cctcacctcc tctaaggttg   1129
ggcagggtga ccctgaagtg agcacagcct agggctgagc tggggacctg gtaccctcct   1189
ggctcttgat acccccctct gtcttgtgaa ggcaggggga aggtggggtc ctggagcaga   1249 ccacccgcc tgcctcatg gcccctctga cctgcactgg ggagcccgtc tcagtgttga    1309
gccttttccc tctttggctc ccctgtacct tttgaggagc cccagctacc cttcttctcc   1369
agctgggctc tgcaattccc ctctgctgct gtccctcccc cttgtccttt cccttcgta    1429 ccctctcagc tccaggtggc tctgaggtgc ctgtcccacc cccacccca gctcaatgga    1489
```

```
ctggaagggg aagggacaca caagaagaag ggcaccctag ttctacctca ggcagctcaa    1549
gcagcgaccg cccctcctc tagctgtggg ggtgagggtc ccatgtggtg gcacaggccc     1609
ccttgagtgg ggttatctct gtgttagggg tatatgatgg gggagtagat ctttctagga   1669
gggagacact ggcccctcaa atcgtccagc gaccttcctc atccacccca tccctcccca   1729
gttcattgca ctttgattag cagcggaaca aggagtcaga cattttaaga tggtggcagt   1789
agaggctatg gacagggcat gccacgtggg ctcatatggg gctgggagta gttgtctttc   1849
ctggcactaa cgttgagccc ctggaggcac tgaagtgctt agtgtacttg gagtattggg   1909
gtctgacccc aaacaccttc cagctcctgt aacatactgg cctggactgt tttctctcgg   1969
ctccccatgt gtcctggttc ccgtttctcc acctagactg taaacctctc gagggcaggg   2029
accacaccct gtactgttct gtgtctttca cagctcctcc cacaatgctg aataaacagc   2089
aggtgctcaa taatgattc ttagtgactt taaaaaaaaa aaaaaaaaaa aaaaaaa       2147
```

<210> SEQ ID NO 3
<211> LENGTH: 164
<212> TYPE: PRT
<213> ORGANISM: homo sapiens

<400> SEQUENCE: 3

```
Met Ser Glu Pro Ala Gly Asp Val Arg Gln Asn Pro Cys Gly Ser Lys
 1               5                  10                  15

Ala Cys Arg Arg Leu Phe Gly Pro Val Asp Ser Glu Gln Leu Ser Arg
            20                  25                  30

Asp Cys Asp Ala Leu Met Ala Gly Cys Ile Gln Glu Ala Arg Glu Arg
        35                  40                  45

Trp Asn Phe Asp Phe Val Thr Glu Thr Pro Leu Glu Gly Asp Phe Ala
    50                  55                  60

Trp Glu Arg Val Arg Gly Leu Gly Leu Pro Lys Leu Tyr Leu Pro Thr
65                  70                  75                  80

Gly Pro Arg Arg Gly Arg Asp Glu Leu Gly Gly Gly Arg Arg Pro Gly
                85                  90                  95

Thr Ser Pro Ala Leu Leu Gln Gly Thr Ala Glu Glu His Val Asp
            100                 105                 110

Leu Ser Leu Ser Cys Thr Leu Val Pro Arg Ser Gly Glu Gln Ala Glu
        115                 120                 125

Gly Ser Pro Gly Gly Pro Gly Asp Ser Gln Gly Arg Lys Arg Arg Gln
    130                 135                 140

Thr Ser Met Thr Asp Phe Tyr His Ser Lys Arg Arg Leu Ile Phe Ser
145                 150                 155                 160

Lys Arg Lys Pro
```

<210> SEQ ID NO 4
<211> LENGTH: 495
<212> TYPE: DNA
<213> ORGANISM: homo sapiens
<220> FEATURE:
<221> NAME/KEY: CDS
<222> LOCATION: (1)...(495)

<400> SEQUENCE: 4

```
atg tca gaa ccg gct ggg gat gtc cgt cag aac cca tgc ggc agc aag    48
Met Ser Glu Pro Ala Gly Asp Val Arg Gln Asn Pro Cys Gly Ser Lys
 1               5                  10                  15 gcc tgc cgc cgc ctc ttc ggc cca gtg gac agc gag cag ctg agc cgc   96
```

-continued

```
Ala Cys Arg Arg Leu Phe Gly Pro Val Asp Ser Glu Gln Leu Ser Arg
            20                  25                  30 gac tgt gat gcg cta atg gcg ggc tgc atc cag gag gcc cgt gag cga       144
Asp Cys Asp Ala Leu Met Ala Gly Cys Ile Gln Glu Ala Arg Glu Arg
            35                  40                  45 tgg aac ttc gac ttt gtc acc gag aca cca ctg gag ggt gac ttc gcc       192
Trp Asn Phe Asp Phe Val Thr Glu Thr Pro Leu Glu Gly Asp Phe Ala
 50                  55                  60 tgg gag cgt gtg cgg ggc ctt ggc ctg ccc aag ctc tac ctt ccc acg       240
Trp Glu Arg Val Arg Gly Leu Gly Leu Pro Lys Leu Tyr Leu Pro Thr
 65                  70                  75                  80 ggg ccc cgg cga ggc cgg gat gag ttg gga gga ggc agg cgg cct ggc       288
Gly Pro Arg Arg Gly Arg Asp Glu Leu Gly Gly Gly Arg Arg Pro Gly
                 85                  90                  95 acc tca cct gct ctg ctg cag ggg aca gca gag gaa gac cat gtg gac       336
Thr Ser Pro Ala Leu Leu Gln Gly Thr Ala Glu Glu Asp His Val Asp
            100                 105                 110 ctg tca ctg tct tgt acc ctt gtg cct cgc tca ggg gag cag gct gaa       384
Leu Ser Leu Ser Cys Thr Leu Val Pro Arg Ser Gly Glu Gln Ala Glu
            115                 120                 125 ggg tcc cca ggt gga cct gga gac tct cag ggt cga aaa cgg cgg cag       432
Gly Ser Pro Gly Gly Pro Gly Asp Ser Gln Gly Arg Lys Arg Arg Gln
130                 135                 140 acc agc atg aca gat ttc tac cac tcc aaa cgc cgg ctg atc ttc tcc       480
Thr Ser Met Thr Asp Phe Tyr His Ser Lys Arg Arg Leu Ile Phe Ser
145                 150                 155                 160 aag agg aag ccc taa                                                    495
Lys Arg Lys Pro
```

<210> SEQ ID NO 5
<211> LENGTH: 164
<212> TYPE: PRT
<213> ORGANISM: homo sapiens

<400> SEQUENCE: 5

```
Met Ser Glu Pro Ala Gly Asp Val Arg Gln Asn Pro Cys Gly Ser Lys
 1               5                  10                  15

Ala Cys Arg Arg Leu Phe Gly Pro Val Asp Ser Glu Gln Leu Ser Arg
            20                  25                  30

Asp Cys Asp Ala Leu Met Ala Gly Cys Ile Gln Glu Ala Arg Glu Arg
            35                  40                  45

Trp Asn Phe Asp Phe Val Thr Glu Thr Pro Leu Glu Gly Asp Phe Ala
 50                  55                  60

Trp Glu Arg Val Arg Gly Leu Gly Leu Pro Lys Leu Tyr Leu Pro Thr
 65                  70                  75                  80

Gly Pro Arg Arg Gly Arg Asp Glu Leu Gly Gly Gly Arg Arg Pro Gly
                 85                  90                  95

Thr Ser Pro Ala Leu Leu Gln Gly Thr Ala Glu Glu Asp His Val Asp
            100                 105                 110

Leu Ser Leu Ser Cys Thr Leu Val Pro Arg Ser Gly Glu Gln Ala Glu
            115                 120                 125

Gly Ser Pro Gly Gly Pro Gly Asp Ser Gln Gly Arg Lys Arg Arg Gln
130                 135                 140

Thr Ser Met Thr Asp Phe Tyr His Ser Lys Arg Arg Leu Ile Phe Ser
145                 150                 155                 160

Lys Arg Lys Pro
```

-continued

```
<210> SEQ ID NO 6
<211> LENGTH: 1718
<212> TYPE: DNA
<213> ORGANISM: homo sapiens
<220> FEATURE:
<221> NAME/KEY: CDS
<222> LOCATION: (275)...(895)

<400> SEQUENCE: 6
cttgcctgca aacctttact tctgaaatga cttccacggc tgggacggga accttccacc      60
cacagctatg cctctgattg gtgaatggtg aaggtgcctg tctaactttt ctgtaaaaag     120
aaccagctgc ctccaggcag ccagccctca agcatcactt acaggaccag agggacaaga    180
catgactgtg atgaggagct gctttcgcca atttaacacc aagaagaatt gaggctgctt    240
gggaggaagg ccaggaggaa cacgagactg agag atg aat ttt caa cag agg ctg    295
                                     Met Asn Phe Gln Gln Arg Leu
                                      1               5 caa agc ctg tgg act tta gcc aga ccc ttc tgc cct cct ttg ctg gcg      343
Gln Ser Leu Trp Thr Leu Ala Arg Pro Phe Cys Pro Pro Leu Leu Ala
        10                  15                  20 aca gcc tct caa atg cag atg gtt gtg ctc cct tgc ctg ggt ttt acc      391
Thr Ala Ser Gln Met Gln Met Val Val Leu Pro Cys Leu Gly Phe Thr
 25                  30                  35 ctg ctt ctc tgg agc cag gta tca ggg gcc cag ggc caa gaa ttc cac      439
Leu Leu Leu Trp Ser Gln Val Ser Gly Ala Gln Gly Gln Glu Phe His
 40                  45                  50                  55 ttt ggg ccc tgc caa gtg aag ggg gtt gtt ccc cag aaa ctg tgg gaa      487
Phe Gly Pro Cys Gln Val Lys Gly Val Val Pro Gln Lys Leu Trp Glu
                 60                  65                  70 gcc ttc tgg gct gtg aaa gac act atg caa gct cag gat aac atc acg      535
Ala Phe Trp Ala Val Lys Asp Thr Met Gln Ala Gln Asp Asn Ile Thr
             75                  80                  85 agt gcc cgg ctg ctg cag cag gag gtt ctg cag aac gtc tcg gat gct      583
Ser Ala Arg Leu Leu Gln Gln Glu Val Leu Gln Asn Val Ser Asp Ala
         90                  95                 100 gag agc tgt tac ctt gtc cac acc ctg ctg gag ttc tac ttg aaa act      631
Glu Ser Cys Tyr Leu Val His Thr Leu Leu Glu Phe Tyr Leu Lys Thr
    105                 110                 115 gtt ttc aaa aac tac cac aat aga aca gtt gaa gtc agg act ctg aag      679
Val Phe Lys Asn Tyr His Asn Arg Thr Val Glu Val Arg Thr Leu Lys
120                 125                 130                 135 tca ttc tct act ctg gcc aac aac ttt gtt ctc atc gtg tca caa ctg      727
Ser Phe Ser Thr Leu Ala Asn Asn Phe Val Leu Ile Val Ser Gln Leu
                140                 145                 150 caa ccc agt caa gaa aat gag atg ttt tcc atc aga gac agt gca cac      775
Gln Pro Ser Gln Glu Asn Glu Met Phe Ser Ile Arg Asp Ser Ala His
            155                 160                 165 agg cgg ttt ctg cta ttc cgg aga gca ttc aaa cag ttg gac gta gaa      823
Arg Arg Phe Leu Leu Phe Arg Arg Ala Phe Lys Gln Leu Asp Val Glu
        170                 175                 180 gca gct ctg acc aaa gcc ctt ggg gaa gtg gac att ctt ctg acc tgg      871
Ala Ala Leu Thr Lys Ala Leu Gly Glu Val Asp Ile Leu Leu Thr Trp
    185                 190                 195 atg cag aaa ttc tac aag ctc tga atgtctagac caggacctcc ctcccctgg      925
Met Gln Lys Phe Tyr Lys Leu
200                 205 cactggtttg ttccctgtgt catttcaaac agtctccctt cctatgctgt tcactggaca    985
cttcacgccc ttggccatgg gtcccattct tgggccagga ttattgtcaa agaagtcatt   1045
ctttaagcag cgccagtgac agtcagggaa ggtgcctctg gatgctgtga agagtctaca   1105
```

```
gagaagattc ttgtatttat tacaactcta tttaattaat gtcagtattt caactgaagt    1165
tctatttatt tgtgagactg taagttacat gaaggcagca gaatattgtg ccccatgctt    1225
ctttacccct cacaatcctt gccacagtgt ggggcagtgg atgggtgctt agtaagtact    1285
taataaactg tggtgctttt tttggcctgt ctttggattg ttaaaaaaca gagagggatg    1345
cttggatgta aaactgaact tcagagcatg aaaatcacac tgtctgctga tatctgcagg    1405
gacagagcat tggggtgggg gtaaggtgca tctgtttgaa aagtaaacga taaaatgtgg    1465
attaaagtgc ccagcacaaa gcagatcctc aataaacatt tcatttccca cccacactcg    1525
ccagctcacc ccatcatccc tttcccttgg tgccctcctt ttttttttat cctagtcatt    1585
cttccctaat cttccacttg agtgtcaagc tgaccttgct gatggtgaca ttgcacctgg    1645
atgtactatc caatctgtga tgacattccc tgctaataaa agacaacata actcaaaaaa    1705
aaaaaaaaaa aaa                                                       1718
```

<210> SEQ ID NO 7
<211> LENGTH: 206
<212> TYPE: PRT
<213> ORGANISM: homo sapiens

<400> SEQUENCE: 7

```
Met Asn Phe Gln Gln Arg Leu Gln Ser Leu Trp Thr Leu Ala Arg Pro
1               5                   10                  15

Phe Cys Pro Pro Leu Leu Ala Thr Ala Ser Gln Met Gln Met Val Val
            20                  25                  30

Leu Pro Cys Leu Gly Phe Thr Leu Leu Leu Trp Ser Gln Val Ser Gly
        35                  40                  45

Ala Gln Gly Gln Glu Phe His Phe Gly Pro Cys Gln Val Lys Gly Val
    50                  55                  60

Val Pro Gln Lys Leu Trp Glu Ala Phe Trp Ala Val Lys Asp Thr Met
65                  70                  75                  80

Gln Ala Gln Asp Asn Ile Thr Ser Ala Arg Leu Leu Gln Gln Glu Val
                85                  90                  95

Leu Gln Asn Val Ser Asp Ala Glu Ser Cys Tyr Leu Val His Thr Leu
            100                 105                 110

Leu Glu Phe Tyr Leu Lys Thr Val Phe Lys Asn Tyr His Asn Arg Thr
        115                 120                 125

Val Glu Val Arg Thr Leu Lys Ser Phe Ser Thr Leu Ala Asn Asn Phe
    130                 135                 140

Val Leu Ile Val Ser Gln Leu Gln Pro Ser Gln Glu Asn Glu Met Phe
145                 150                 155                 160

Ser Ile Arg Asp Ser Ala His Arg Arg Phe Leu Leu Phe Arg Arg Ala
                165                 170                 175

Phe Lys Gln Leu Asp Val Glu Ala Ala Leu Thr Lys Ala Leu Gly Glu
            180                 185                 190

Val Asp Ile Leu Leu Thr Trp Met Gln Lys Phe Tyr Lys Leu
        195                 200                 205
```

<210> SEQ ID NO 8
<211> LENGTH: 158
<212> TYPE: DNA
<213> ORGANISM: homo sapiens

<400> SEQUENCE: 8

```
tggacttgtg ttctgactag aactcaacat gttactaggc acatgtgtca tgtctcaggt    60
```

```
cagtgctgtg acagaattga tacgagagaa atgtcgctta tgctatcact gatctacaca    120
tgtctgatag atagtcagat acagatgatg aggaatct                            158

<210> SEQ ID NO 9
<211> LENGTH: 270
<212> TYPE: DNA
<213> ORGANISM: homo sapiens

<400> SEQUENCE: 9
gaattcagtg aactcttttc tcattctctt tgttttgtgg cacttcacaa tgtagaggaa     60
aaaaccaaat gaccgcactg tgatgtgaat ggcaccgaag tcagtgagt atcctgtagg    120 tcacctgcag cctggcttgc cacttgtctt aactctgaat atttcatttc aaaggtgcta   180
aaatctgaaa tctgctagtg tgaacttgct ctactctctg aatgattcaa tcctattcat   240
actatcttgt agatatatca actaaaaaaa                                    270

<210> SEQ ID NO 10
<211> LENGTH: 144
<212> TYPE: DNA
<213> ORGANISM: homo sapiens

<400> SEQUENCE: 10
ttcttctttg taaaagtttt taatacactg ctgaaagata aattcattcc aaagagaata    60
attatatagc aagatattat cggcacagtg gtttcttaga ggtaaatagc gcctcacgtg   120
tgttagatgc tgaatctgac caaa                                          144

<210> SEQ ID NO 11
<211> LENGTH: 193
<212> TYPE: DNA
<213> ORGANISM: homo sapiens

<400> SEQUENCE: 11
ctgcaaaaga agtgtgccga ctataaataa atggtgaaat catctgcaaa tgtggccagg     60
cttggggaac aatgatggtg cacaaaggct tagatttgcc ttgtctcaaa ataaggaatt   120
ttgtagtggt ttcaaaatat cacaagaacg tacaagtggt agatactatc acattcactg   180
actatcagag tcg                                                      193

<210> SEQ ID NO 12
<211> LENGTH: 301
<212> TYPE: DNA
<213> ORGANISM: homo sapiens

<400> SEQUENCE: 12
acaaaccagt gattcccctt cctcagatac tgggactaac agcttcacct ggtgttggag     60
gggccacgaa gcaagccaaa gctgaagaac acattttaaa actatgtgcc tatcttgatg   120
catttactat taaaactgtt aaagaaaacc ttgatcaact gaaaaccaa atacaggagc    180 atgcaagaag tttgccattg cagatgcaac cagagaagat ccatttaaag agaaacttct   240
agaaataatg acaaggattc aaacttattg tcaaatgagt ccaatgtcag attttggact   300
c                                                                   301

<210> SEQ ID NO 13
<211> LENGTH: 218
<212> TYPE: DNA
<213> ORGANISM: homo sapiens
```

-continued

```
<400> SEQUENCE: 13
atgccacgtg ggctcatatg gggctgggag tagttgtctt tcctggcact aacgttgagc      60
ccctggaggc actgaagtgc ttagtgtact tggagtattg gggtctgacc caaacacctt     120
ccagctcctg taacatactg gcctggactg ttttctctcg cgcctcccca tgtgctcctg     180
gttcccgttt cctccaccta gactgtaaac ctctcgca                             218

<210> SEQ ID NO 14
<211> LENGTH: 279
<212> TYPE: DNA
<213> ORGANISM: homo sapiens

<400> SEQUENCE: 14
cctgcagtcc tggaagcgcg agggcctcaa acgcgctcta catcttctgc cttagtctca      60
gtttgcgtgt cttaattatt atttgtgttt taatttaaac acctcctcat gtacataccc     120
tggccgcccc ctgcccccca gcctctcgga ttagaattat ttaaacaaaa actaggcggt     180
tgaatgagag gttcctatga gtactgggca tttttatttt atgaaatact atttaaagcc     240
tcctcatccc atgttctcct tttcctctct cccggagtt                            279

<210> SEQ ID NO 15
<211> LENGTH: 193
<212> TYPE: DNA
<213> ORGANISM: homo sapiens

<400> SEQUENCE: 15
cagaatattg tgccccatgc ttctttaccc ctcacaatcc ttgccacagt gtgggcagtg      60
gatgggtgct tagtaagtac ttaataaact gtggtgcttt ttttggcctg tctttggatt     120
gttaaaaaac agagagggat gcttggatgt aaactgaact tcagagcatg aaatcacact     180
gtctctgata tct                                                        193

<210> SEQ ID NO 16
<211> LENGTH: 182
<212> TYPE: DNA
<213> ORGANISM: homo sapiens

<400> SEQUENCE: 16
ttaaagtttg cccttgtgct aaagtgccag tgtatgtatg ttatacttga tttggttgta      60
aactatattt caaagtaaac cctagtgtaa taagtttttat aactaaaaag gtttaagctg    120
ctaaaactat ttttaagaga tgtgaaatcg agtatgggac tatctttttt tcctcctcta     180
aa                                                                    182

<210> SEQ ID NO 17
<211> LENGTH: 216
<212> TYPE: DNA
<213> ORGANISM: homo sapiens

<400> SEQUENCE: 17
aaaactttca agagatttac tgactttcct agaatagttt ctctactgga aacctgatgc      60
ttttataagc cattgtgatt aggatgactg ttacaggctt agctttgtgt gaaaaccagt     120
cacctttctc ctaggtaatg agtagtgctg ttcatattac tttagttcta tagcatactc    180
gatctttaac atgctatcat agtacattag atgatg                               216

<210> SEQ ID NO 18
<211> LENGTH: 257
```

```
<212> TYPE: DNA
<213> ORGANISM: homo sapiens

<400> SEQUENCE: 18
cgcacgtcac ccaccttccg gcggccgaag acactgcgac tccggagaca gcccaaatat      60
cctcggaaga gcgctcccag gagaaacaag cttgaccact atgctatcat caagtttccg     120
ctgaccactg agtctgccat gaagaagata aagacaacaa cacacttgt gttcattgtg      180 gatgttaaag ccaacaagca ccagattaac agctgtgaga gctgtatgac attgatgtgc    240
agtacacctg atcgtct                                                    257

<210> SEQ ID NO 19
<211> LENGTH: 241
<212> TYPE: DNA
<213> ORGANISM: homo sapiens

<400> SEQUENCE: 19
taaaaaaatt cattctctgt ggtatccaag aatcagtgaa gatgccagtg aaacttcaag     60
caaatctact tcaacacttc atgtattgtg tgggtctgtt gtagggttgc cagatgcaat    120
acaagattcc tggttaaatt tgaatttcag taaacaatga atagttttc attgtacatg     180 aaatatcaga acatacttat atgtaagtat attattgatg acaaacacaa tatttaatat    240
a                                                                    241

<210> SEQ ID NO 20
<211> LENGTH: 177
<212> TYPE: DNA
<213> ORGANISM: homo sapiens

<400> SEQUENCE: 20
gggggtgaaa ctttccagtt tactgaactc cagaccatgc atgtagtcca ctccagaaat     60
catgctcgct tccttggcac acagtgttct cctgccaaat gaccctagac cctctgtcct    120
gcagagtcag ggtggctttt accctgactg tgtcgatgca gagtctgctc gacagat       177

<210> SEQ ID NO 21
<211> LENGTH: 143
<212> TYPE: DNA
<213> ORGANISM: homo sapiens

<400> SEQUENCE: 21
tacgatcaga ctgttacatt tagcaatcaa cagcatgggg cgaaaaaaaa aaatctactt     60
aaaacccttt gttggaatgc tttacacttt ccacagaaca gaaactaaaa taactgttta    120
cattagtcac aatacagtct cga                                            143

<210> SEQ ID NO 22
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 22
ctccaagtac actaagcact                                                  20

<210> SEQ ID NO 23
<211> LENGTH: 20
<212> TYPE: DNA
<213> ORGANISM: Artificial Sequence
<220> FEATURE:
```

```
<223> OTHER INFORMATION: synthetic oligonucleotide

<400> SEQUENCE: 23
tagttctacc tcaggcagct                                          20

<210> SEQ ID NO 24
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 24
catggcctcc aaggagtaag a                                        21

<210> SEQ ID NO 25
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 25
cgtcttcacc accatggaga a                                        21

<210> SEQ ID NO 26
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 26
ctccaagtac actaagcact                                          20

<210> SEQ ID NO 27
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 27
tagttctacc tcaggcagct                                          20

<210> SEQ ID NO 28
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 28
tcttactcct tggaggccat g                                        21

<210> SEQ ID NO 29
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 29
cgtcttcacc accaccatgg agaa                                     24
```

-continued

```
<210> SEQ ID NO 30
<211> LENGTH: 245
<212> TYPE: DNA
<213> ORGANISM: homo sapiens

<400> SEQUENCE: 30
tcctcctctg caccatggct ctctgcaacc agttctctgc atcacttgct gctgacacgc      60
cgaccgcctg ctgcttcagc tacacctccc ggcagattcc acagaatttc atagctgact     120
actttgagac gagcagccag tgctccaagc ccggtgtcat cttcctaacc aagcgaagcc     180
ggcaggtctg tgctgacccc agtgaggagt gggtccagaa atatgtcagc gacctggagc     240
tgagt                                                                  245
```

MDA-7 NUCLEIC ACID MOLECULES AND PHARMACEUTICAL COMPOSITIONS THEREOF

This application is a continuation of Ser. No. 08/316,537, filed Sep. 30, 1994 U.S. Pat. No. 6,051,376 which is a continuation-in-part of U.S. application Ser. No. 08/143,576 filed Oct. 27, 1993, now U. S. Pat. No. 5,643,761, the contents of which are hereby incorporated by reference.

The invention described herein was supported in part by National Cancer Institute grants CA35675 and CA43208. The United States Government has certain rights in this invention.

BACKGROUND OF THE INVENTION

Throughout this application, various publications are referenced by within parentheses. Full citations for these publications may be found at the end of each series of experiments. The disclosures of these publications in their entireties are hereby incorporated by reference into this application in order to more fully describe the state of the art as known to those skilled therein as of the date of the invention described and claimed therein.

Malignant melanoma is increasing at a rapid rate in North American populations and it is estimated that 1 in 100 children currently born may eventually develop superficial spreading-type melanoma (1). Although readily curable at early stages, surgical and chemotherapeutic intervention are virtually ineffective in preventing metastatic disease and death in patients with advanced states of malignant melanoma (1). These observations emphasize the need for improved therapeutic approaches to more efficaciously treat metastatic melanoma. A potentially useful therapeutic modality for this and other malignancies could involve the use of agents capable of inducing an irreversible loss in proliferative capacity in tumor cells without the requirement for direct cytotoxicity, that is, the differentiation therapy of cancer (2–5). In previous studies, applicants have demonstrated that it is possible to reprogram human melanoma cells to undergo terminal cell differentiation with a concomitant loss of proliferative capacity by treatment with the combination of recombinant human fibroblast interferon (IFN-$\beta$) plus the antileukemic compound mezerein (MEZ) (6, 7). The combination of IFN-$\beta$+MEZ induces terminal differentiation in melanoma cells, innately resistant to the antiproliferative effect of either agent alone, and in human melanoma cells selected for resistance to growth suppression induced by IFN-$\beta$ (6, 7). In contrast, treatment with IFN-$\beta$ or MEZ alone results in the development of specific components of the differentiation program in human melanoma cells, but these agents do not induce most melanoma cells to undergo terminal cell differentiation (6–8).

Terminal differentiation induced by IFN-$\beta$ plus MEZ in human melanoma cells is associated with an increase in melanin synthesis, changes in cellular morphology (characterized by the production of dendrite-like processes), modifications in cell surface antigenic profile, and an irreversible loss of proliferative capacity (3, 6–10). When used separately, IFN-$\beta$ and MEZ induce both growth suppression and increased melanin synthesis and MEZ induces the production of dendrite-like processes in specific human melanoma cells (6, 8). Trans-retinoic acid (RA) is effective in inducing tyrosinase activity and enhancing melanin synthesis in specific human melanoma cultures without altering cell growth, whereas mycophenolic acid (MPA) can induce growth suppression, increased tyrosinase activity and melanin synthesis, and dendrite formation (11). In contrast, the combination of IFN-$\beta$+recombinant immune interferon (IFN-$\gamma$ results in a synergistic suppression in the growth of human melanoma cells without inducing enhanced melanin synthesis or morphologic changes (10, 12). These observations suggest that the various changes induced during the process of differentiation in human melanoma cells, that is, increased tyrosinase activity and melanin synthesis, antigenic changes, dendrite formation, and growth suppression, can occur with and without the induction of terminal cell differentiation.

An unresolved issue is the nature of the gene expression changes that occur in human melanoma cells reversibly committed to differentiation vs. human melanoma cells irreversibly committed to terminal differentiation. This information will be important in defining on a molecular level the critical gene regulatory pathways involved in growth and differentiation in human melanoma cells. To begin to address these questions, applicants have used various experimental protocols that result in either growth suppression without the induction of differentiation-associated properties, a reversible induction of differentiation-associated traits, or terminal cell differentiation in the H0-1 human melanoma cell line. As potential target genes relevant to these processes, applicants have analyzed early growth response, extracellular matrix, extracellular matrix receptor, and interferon-responsive genes. No unique gene expression change was observed solely in H0-1 cells induced to terminally differentiate vs. cultures reversibly growth arrested. However, treatment of H0-1 cells with IFN-$\beta$+MEZ was associated with specific patterns of gene expression changes that were also apparent in H0-1 cells cultured in conditioned medium obtained from terminal-differentiation-inducer-treated H0-1 cells. Exposure to either the terminal differentiation-inducing compounds or -conditioned medium resulted in the enhanced expression of HLA Class I antigen, melanoma growth stimulatory activity (gro-MGSA), interferon-stimulated gene-15 (ISG-15), and fibronectin. These observations support the potential involvement of a type I interferon and a gro/MGSA autocrine loop in the chemical induction of differentiation in H0-1 cells

SUMMARY OF THE INVENTION

This invention provides a method of generating a subtracted cDNA library of a cell comprising: a) generating a cDNA library of the cell; b) isolating double-stranded DNAs from the cDNA library; c) releasing the double-stranded cDNA inserts from the double-stranded DNAs; d) denaturing the isolated double-stranded cDNA inserts; e) hybridizing the denatured double-stranded cDNA inserts with a labelled single-stranded nucleic acid molecules which are to be subtracted from the cDNA library; and f) separating the hybridized labeled single-stranded nucleic acid molecule from the double-stranded cDNA inserts, thereby generating a subtracted cDNA library of a cell. The invention also provides different uses of the generated library.

This invention also provides an isolated nucleic acid molecule encoding a protein produced by a melanoma differentiation associated gene. This invention further provides different uses of the isolated malanoma differentiation genes.

BRIEF DESCRIPTION OF THE FIGURES

FIG. 10 Northern blot analyses of untreated control and IFN-β, MEZ and IFN-β+MEZ treated H0-1 cells probed with cDNA clones isolated from an H0-1 IFN-β+MEZ (Ind$^+$) subtracted cDNA library. RNA was isolated from cells untreated or treated for 24 hours with IFN-β (2000 units/ml), MEZ (10 ng/ml) or IFN-β+MEZ (2000 units/ml and 10 ng/ml). Ten micrograms of total cellular RNA were separated on a 1% agarose gel, transferred to nylon membranes and then hybridized individually with radioactive probes prepared using appropriate inserts from the cDNA clones. The series of cDNAs isolated from inducer treated H0-1 cells have been tentatively called mda, melanoma differentiation associated, genes, Glyceraldehyde phosphate dehydrogenase (GAPDH) was used as a control for uniform loading and expression of the RNA samples.

FIG. 11 Homology of mda-3 to the cDNA of human macrophage inflammatory protein (GOS19-1). The DNA sequence of mda-3 was obtained using the Sanger dideoxynucleotide sequencing method. For sequence homology with known genes, the DNA sequence of mda-3 was compared using the GCG/FASTA program and the GenBank/EMBL database. The top sequence corresponds to the mda-3 cDNA (SEQ. ID No:1) and the bottom sequence corresponds to GOS19-1 (SEQ. ID No:30).

FIGS. 23A–B cDNA (SEQ. ID NO:2) and predicted amino acid sequence (SEQ. ID NO:3) of mda-6. The predicted translation begins at nucleotide 95 and ends at nucleotide 589. Accession number U09579(GeneBank).

FIG. 30 Open-reading frame of mda-6. Predicted translation of the mda-6 cDNA begins at nucleotide 95 and ends a nucleotide 589 (SEQ. ID NO:4). Accession number U09579 (Genbank). mda-6 encodes a 164 amino acid protein (SEQ ID. NO:5) with an M of 21,000 that is identical to the cyclin dependent kinase inhibitor, p21 (SEQ ID Nos. 24 and 25).

FIGS. 31A–E Induction of mda-6 (p21) expression in H0-1 human melanoma cells as a function of differentiation and growth suppression. H0-1 cells were untreated (control) or treated for 24 h (panel A), 96 h (panel B) or treated for 24 h followed by growth for 72 h in the absence of inducer (panel C) with IFN-β (2000 units/ml), MEZ (10 ng/ml) or IFN-β+MEZ (2000 units/ml+10 ng/ml). In panel D, H0-1 cells were grown for the indicated time in medium containing 5% fetal bovine serum (Control) or without fetal bovine serum (DMEM-0). In panel E, high-density H0-1 cells were incubated in DMEM-0 for the times indicated. RNA isolation, Northern blotting and hybridization with mda-6 and GAPDH was performed as described (Jiang & Fisher, 1993; Jiang et al., 1993).

FIGS. 38A–B Nucleotide sequence (SEQ ID. NO:6) and deduced encoded amino acid sequence (SEQ ID. NO:7) of the mda-7 cDNA. The hydrophobic putative transmembrane domain and three potential N-glycosylation residues are underlined; the 3' untranslated sequence contains three putative instability motifs ATTA (underlined) and two consensus signals AATAAA for poly(A) addition (underlined) (SEQ. ID Nos. 26 and 27).

DETAILED DESCRIPTION OF THE INVENTION

Figure 1A:
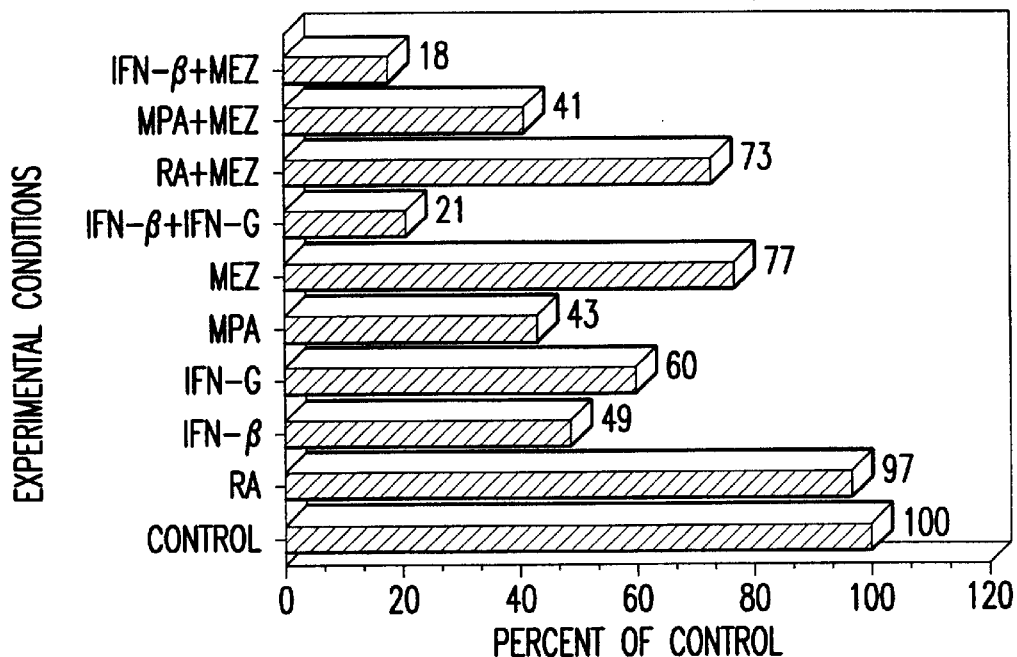
FIGS. 1A–B Effect of continuous exposure to various growth and differentiation modulating agents on the 96-h growth of the human melanoma cell line, H0-1. Cells were seeded at $5\times10^4$/35-mm tissue culture plate and 24 h later the medium was changed with the indicated compounds. Cell numbers were determined by Coulter Counter after 96-h growth. Further details can be found in Materials and Methods. The abbreviations and the concentrations of test compounds uses: IFN-β+MEZ (recombinant human fibroblast interferon+mezerein)) (2,000 U/ml+10 ng/ml); MPA+MEZ (mycophenolic acid+MEZ) (3.0 μM+10 ng/ml); RA+MEZ (trans-retinoic acid+MEZ) (2.5 μM+10 ng/ml); IFN-β+IFN-G (IFN-β+recombinant human gamma interferon) (1,000 U/ml+1,000 U/ml); MEZ (10 ng/ml); MPA (3.0 μM); IFN-G (2,000 U/ml); IFN-β (2,000 U/ml); RA (2.5 μM); and Control (media only).

Throughout this application, the following standard abbreviations are used to indicate specific nucleotides:

| C = cytosine | A = adenosine |
|---|---|
| T = thymidine | G = guanosine |

This invention provides a method of generating a subtracted cDNA library of a cell comprising: a) generating a cDNA library of the cell; b) isolating double-stranded DNAs from the cDNA library; c) releasing the double-stranded cDNA inserts from the double-stranded DNAs; d) denaturing the isolated double-stranded cDNA inserts; e) hybridizing the denatured double-stranded cDNA inserts with a labelled single-stranded nucleic acid molecules which are to be subtracted from the cDNA library; and f) separating the hybridized labeled single-stranded nucleic acid molecule from the double-stranded cDNA inserts, thereby generating a subtracted cDNA library of a cell.

In an embodiment, the cDNA library of the cell is a λZAP cDNA library.

This invention provides the above-described method, wherein the releasing of the double-stranded cDNA is performed by digestion with appropriate restriction enzymes.

This invention also provides the above-method of generating a subtracted cDNA library of a cell, wherein the denaturing of step d) is by boiling.

In an embodiment, the single-stranded nucleic acid molecules are DNAs. In a further embodiment, the single-stranded nucleic acid molecules are labelled with biotin. In a still further embodiment, the single-stranded nucleic acid molecules are labelled with biotin, wherein the separating of step f) is performed by extraction with streptavidin-phenol: Chloroform.

Other methods for labelling single-stranded nucleic acid molecules are well-known in the art.

This invention further provides the above-described methods of generating a subtracted cDNA library of a cell, wherein the single-stranded nucleic acid molecules are from another cDNA library. In another embodiment, this cDNA library is a λZAP cDNA library.

In another embodiment, the single-stranded nucleic acid molecules are from another cDNA library, wherein the cDNA library is a λZAP cDNA library, wherein the cell is an H0-1 melanoma cell treated with IFN-β and MEZ.

In another embodiment, wherein the cDNA library is a λZAP cDNA library, the cell is an H0-1 melanoma cell treated with IFN-β and MEZ and the single-stranded nucleic acid molecules are from another cDNA library of a H0-1 melanoma cell.

In still another embodiment of the above-described methods of generating a subtracted cDNA library of a cell, wherein the cDNA library is a λZAP cDNA library, wherein the cell is terminally differentiated and the single-stranded nucleic acid molecules are from another cDNA library of an undifferentiated cell.

In still another embodiment of the above-described methods of generating a subtracted cDNA library of a cell, wherein the cDNA library is a λZAP cDNA library, wherein the cell is undifferentiated and the single-stranded nucleic acid molecules are from another cDNA library of a terminally differentiated cell.

In one embodiment of the above-described method of generating a subtracted cDNA library of a cell, the cell is selected from a group consisting essentially of neuroblastoma cell, glioblastoma multiforme cell, myeloid leukemic cell, breast carcinoma cell, colon carcinoma cell, endometrial carcinoma cell, lung carcinoma cell, ovarian carcinoma cell and prostate carcinoma cell.

In another embodiment of the above-described method of generating a subtracted cDNA library of a cell, the cell is induced to undergo reversible growth arrest or DNA damage and the single-stranded nucleic acid molecules are from another cDNA library of an uninduced cell.

In still another embodiment of the above-described method of generating a subtracted cDNA library of a cell, the cell is at one developmental stage and the single-stranded nucleic acid molecules are from another cDNA library from the cell at different developmental stage.

In still another embodiment of the above-described method of generating a subtracted cDNA library of a cell, the cell is cancerous and the single-stranded nucleic acid molecules are from another cDNA library from a normal cell.

In another embodiment, the cell is from the breast, brain, meninges, spinal cord, colon, endometrium, lung, prostate and ovary.

This invention also provides a method of generating a subtracted cDNA library of a cell comprising: a) generating a cDNA library of the cell; b) isolating double-stranded DNAs from the cDNA library; c) releasing the double-stranded cDNA inserts from the double-stranded DNAs; d) denaturing the isolated double-stranded cDNA inserts; e) hybridizing the denatured double-stranded cDNA inserts with a labelled single-stranded nucleic acid molecules which are to be subtracted from the cDNA library; and f) separating the hybridized labeled single-stranded nucleic acid molecule from the double-stranded cDNA inserts, thereby generating a subtracted cDNA library of a cell, wherein the single-stranded nucleic acid molecules are from another cDNA library, wherein the cDNA library is a λZAP cDNA library, further comprising introducing the subtracted library into host cells.

This invention provides a subtracted library generated by the method generating a subtracted cDNA library of a cell comprising: a) generating a cDNA library of the cell; b) isolating double-stranded DNAs from the cDNA library; c) releasing the double-stranded cDNA inserts from the double-stranded DNAs; d) denaturing the isolated double-stranded cDNA inserts; e) hybridizing the denatured double-stranded cDNA inserts with a labelled single-stranded nucleic acid molecules which are to be subtracted from the cDNA library; and f) separating the hybridized labeled single-stranded nucleic acid molecule from the double-stranded cDNA inserts, thereby generating a subtracted cDNA library of a cell.

This invention provides a subtracted library generated by the method of generating a subtracted cDNA library of a cell comprising: a) generating a cDNA library of the cell; b) isolating double-stranded DNAs from the cDNA library; c) releasing the double-stranded cDNA inserts from the double-stranded DNAs; d) denaturing the isolated double-stranded cDNA inserts; e) hybridizing the denatured double-stranded cDNA inserts with a labelled single-stranded nucleic acid molecules which are to be subtracted from the cDNA library; and f) separating the hybridized labeled single-stranded nucleic acid molecule from the double-stranded cDNA inserts, thereby generating a subtracted cDNA library of a cell, wherein the single-stranded nucleic acid molecules are from another cDNA library, wherein the cDNA library is a λZAP cDNA library, wherein the cell is an H0-1 melanoma cell treated with IFN-β and MEZ, wherein the single-stranded nucleic acid molecules are from another cDNA library of a H0-1 melanoma cell.

This invention provides a method of identifying a melanoma differentiation associated gene comprising: a) generating probes from clones of the above-described subtracted library; and b) hybridizing the probe with total RNAs or mRNAs from H0-1 cells treated with IFN-β and MEZ and total RNAs or mRNAs from untreated H0-1 cells, hybridization of the probe with the mRNAs from the treated H0-1 cell but no or reduced hybridization with the total RNAs or mRNAs from untreated cells indicating that the clone from which the probe is generated carries a melanoma differentiation associated gene.

This invention further provides a melanoma differentiation associated gene identified by the above method.

This invention provides a nucleic acid molecule of at least 15 nucleotides capable of specifically hybridizing with a sequence of mda-4 gene.

This invention further provides a method of detecting the expression of mda-4 gene in a cell comprising: a) isolating the nucleic acids in the cell; b) hybridizing the isolated nucleic acids with the nucleic acid molecule capable of specifically hybridizing with a sequence of mda-4 gene under conditions permitting hybrid formation; and c) detecting hybrids formed, the detection of the hybrids indicating expression of mda-4 gene in the cell.

This invention also provides a method to indicate the tissue lineage of a cell comprising detecting the expression of mda-4 gene using the above-described method, the expression of mda-4 gene indicating that the tissue lineage of the cell is neuroectodermal.

This invention also provides a method for distinguishing a fibroblast or epithelial cell from a melanoma or central nervous system cell comprising detecting the expression of mda-4 gene using the above-described method, the expression of mda-4 indicating that the cell is a melanoma cell or a central nervous system lineage cell.

This invention provides a method to monitor the response to DNA damage induced by gamma irradiation and UV irradiation of a cell comprising hybridizing the nucleic acid molecule capable of specifically hybridizing with a sequence of mda-4 gene, hybridization of the nucleic acids from the cell indicating that there is a response to the DNA damage of the cell.

This invention provides a method of monitoring a response to treatment with chemotherapeutic agents which work in a similar manner as cis-platinum in a cell comprising hybridizing the nucleic acids from the cell with the nucleic acid molecule capable of specifically hybridizing with a sequence of mda-4 gene, hybridization of the nucleic acids from the cell responds to the treatment with the chemotherapeutic agents.

This invention further provides a method for detecting types I or II interferons in a sample comprising: a) incubating the sample with the 5' regulatory element of the mda-4 gene under conditions permitting binding of types I and II interferons transcriptional regulatory proteins to the regulatory elements; and b) detecting the binding of types I or II interferons transcriptional regulatory proteins to the regulatory elements, the binding indicating the presence of type I or II interferons in the sample.

As used herein, the term "sample" is broadly defined. It includes, but not limited to bodily fluids such as urine, saliva, blood and other clinical samples.

Transcriptional regulatory proteins which are responsive to type I or II interferons are well-known in the art.

In an embodiment, the target cell is a eukaryotic cell. In a separate embodiment, the 5' regulatory element is linked to the native mda-4 gene and the detection of binding is by examination of the elevated expression of the mda-4 gene. In an embodiment, the 5' regulatory element is linked to a marker gene. In a further embodiment, the marker gene is β-galactosidase or CAT.

This invention provides an isolated nucleic acid molecule encoding a protein produced by a melanoma differentiation associated gene designated mda-1. In an embodiment, the nucleic acid is a cDNA. In another embodiment, the nucleic acid is genomic DNA.

In a separate embodiment, the mda-1 gene is coding for a human protein.

This invention provides an isolated nucleic acid molecule encoding a protein produced by a melanoma differentiation associated gene designated mda-2. In an embodiment, the nucleic acid is a cDNA. In another embodiment, the nucleic acid is genomic DNA.

In a separate embodiment, the mda-2 gene is coding for a human protein.

This invention provides an isolated nucleic acid molecule encoding a protein produced by a melanoma differentiation associated gene designated mda-4. In an embodiment, the nucleic acid is a cDNA. In another embodiment, the nucleic acid is genomic DNA.

In a separate embodiment, the mda-4 gene is coding for a human protein.

This invention provides an isolated nucleic acid molecule encoding a protein produced by a melanoma differentiation associated gene designated mda-5. In an embodiment, the nucleic acid is a cDNA. In another embodiment, the nucleic acid is genomic DNA.

In a separate embodiment, the mda-5 gene is coding for a human protein.

This invention provides a nucleic acid molecule of at least 15 nucleotides capable of specifically hybridizing with a sequence of the nucleic acid molecule, mda-5.

This invention provides a method of detecting the expression of mda-5 gene in a cell comprising: a) isolating the nucleic acids in the cell; b) hybridizing the isolated nucleic acids with the nucleic acid molecules of at least 15 nucleotides capable of specifically hybridizing with a sequence of the nucleic acid molecule mda-5 under conditions permitting hybrids formation; and c) detecting hybrids formed, the detection of the hybrids formed indicating the expression of mda-5 gene in the cell.

This invention provides a method for distinguishing a normal neuroectodermal cell from a malignant neuroectodermal cell comprising detecting the expression of mda-5 gene using the method of detecting the expression of mda-5 gene in a cell comprising: a) isolating the nucleic acids in the cell; b) hybridizing the isolated nucleic acids with the nucleic acid molecules of at least 15 nucleotides capable of specifically hybridizing with a sequence of the nucleic acid molecule mda-5 under conditions permitting hybrids formation; and c) detecting hybrids formed, the detection of the hybrids formed indicating the expression of mda-5 gene in the cell, the expression of mda-5 gene indicating that the cell is normal neuroectodermal cell.

This invention provides a method for detecting types I or II interferons in a sample comprising: a) incubating the sample with the 5' regulatory element of the mda-5 gene under conditions permitting binding of types I and II interferons transcriptional regulatory proteins to the regulatory elements; and b) detecting the binding of the types I or II interferons transcriptional regulatory proteins to the regulatory elements, the binding indicating the presence of type I or type II interferons in the sample.

In an embodiment, the cell is a eukaryotic cell. In another embodiment, the 5' regulatory element is linked to the native mda-5 gene and the detection of binding is by the examination of the elevated expression of mda-5 gene.

In a separate embodiment, the 5' regulatory element is linked to a marker gene. In a further embodiment, the marker gene is β-galactosidase, luciferase or CAT.

This invention provides a method for identifying a compound capable of inducing terminal differentiation in human melanoma cells comprising: a) incubating the human melanoma cells with an appropriate concentration of the compound; and b) detecting the expression of mda-5 using the above-described method, the expression of mda-5 gene indicating that the compound is capable of inducing terminal differentiation in human melanoma cells.

This invention provides an isolated nucleic acid molecule encoding a protein produced by a melanoma differentiation associated gene designated mda-6. In an embodiment, the nucleic acid is a cDNA. In another embodiment, the nucleic acid is genomic DNA.

In a separate embodiment, the mda-6 gene is coding for a human protein.

This invention provides a nucleic acid molecule of at least 15 nucleotides capable of specifically hybridizing with a sequence of the nucleic acid molecule, an isolated nucleic acid molecule encoding a protein produced by a melanoma differentiation associated gene designated mda-6.

This invention provides a method of detecting the expression of mda-6 gene in a cell comprising: a) isolating the nucleic acids in the cell; b) hybridizing the isolated nucleic acids with the nucleic acid molecules of a nucleic acid molecule of at least 15 nucleotides capable of specifically hybridizing with a sequence of the nucleic acid molecule, an isolated nucleic acid molecule encoding a protein produced by a melanoma differentiation associated gene designated mda-6 under conditions permitting hybrids formation; and c) detecting hybrids formed, the detection of the hybrids formed indicating the expression of mda-6 gene in the cell.

This invention provides a method for distinguishing a normal neuroectodermal cell from a malignant neuroectodermal cell comprising detecting the expression of mda-6 gene using the method of detecting the expression of mda-6 gene in a cell comprising: a) isolating the nucleic acids in the cell; b) hybridizing the isolated nucleic acids with the nucleic acid molecules capable of recognizing the mda-6 gene under conditions permitting hybrids formation; and c) detecting hybrids formed, the detection of the hybrids formed indicating the expression of mda-6 gene in the cell, the expression of mda-6 gene indicating that the cell is normal neuroectodermal cell.

The invention also provides a method for distinguishing an adenocarcinoma cell from a carcinoma cell comprising detecting the expression of mda-6 gene using the above-described method, the expression of mda-6 gene indicating that the cell is a carcinoma cell.

The invention further provides a method for monitoring the response of a cell to an anticancer agent such as actinomycin-D or adriamycin comprising detecting the expression of mda-6 gene using the above-described method, the expression of mda-6 gene indicating that the cell responds to the anticancer agent.

This invention provides a method for monitoring response to topoisomerase inhibitor by a cell comprising detecting the expression of mda-6 using the above-described method of detecting the expression of mda-6 gene in a cell, the expression of mda-6 indicating that the cell responds to the topoisomerase inhibitor.

This invention provides a method for identifying a compound capable of inducing terminal differentiation in human melanoma cells comprising: a) incubating the human melanoma cells with an appropriate concentration of the compound; and b) detecting the expression of mda-6 in a cell using the above-described method, the expression of mda-6 gene indicating that the compound is capable of inducing terminal differentiation in human melanoma cells.

This invention provides a method for identifying a compound capable of inducing terminal differentiation in human leukemia cells comprising a) incubating the human leukemia cells with an appropriate concentration of the compound; and b) detecting the expression of mda-6 using the above-described method, the expression of mda-6 gene indicating that the compound is capable of inducing terminal differentiation in human leukemia cells.

This invention also provides a method for identifying a compound capable of inducing terminal differentiation in human lymphoma cells comprising: a) incubating the human lymphoma cells with an appropriate concentration of the compound; and b) detecting the expression of mda-6 using the above-described method, the expression of mda-6 gene indicating that the compound is capable of inducing terminal differentiation in human lymphoma cells.

This invention provides a method for identifying a compound capable of inducing terminal differentiation in human neuroblastoma cells comprising: a) incubating the human neuroblastoma cells with an appropriate concentration of the compound; and b) detecting the expression of mda-6 using the above-described method, the expression of mda-6 gene indicating that the compound is capable of inducing terminal differentiation in human neuroblastoma cells.

This invention also provides a method for identifying a compound capable of inducing terminal differentiation in human glioblastoma multiforme cells comprising: a) incubating the human glioblastoma cells with an appropriate concentration of the compound; and b) detecting the expression of mda-6 using the above-described method, the expression of mda-6 gene indicating that the compound is capable of inducing terminal differentiation in human glioblastoma multiforme cells.

This invention also provides a method for distinguishing an early stage from a more progressed human melanoma cell comprising detecting the expression of mda-6 gene using the above-described method, the expression of mda-6 gene indicating that the cell is a less progressed human melanoma cell.

This invention provides a method for reversing the malignant phenotype of cells comprising: (a) linking the mda-6 gene to a regulatory element such that the expression of the mda-6 gene is under the control of the regulatory element; and (b) introducing the linked mda-6 gene into the malignant cells for the expression of the mda-6 gene, thereby reversing the malignant phenotype of cells.

This invention also provides a method for reversing the malignant phenotype of cells comprising: (a) linking the mda-6 gene to a regulatory element such that the expression of the mda-6 gene is under the control of the regulatory element; (b) introducing the linked mda-6 gene into the malignant cells; and (c) placing the cells from step (b) in appropriate conditions to express the mda-6 gene such that the expression of the mda-6 gene will reverse the transforming phenotype of the malignant cells.

This invention also provides a method of reversing the phenotype of malignant cells in a subject comprising: (a) linking the mda-6 gene to a regulatory element such that the expression of the mda-6 gene is under the control of the regulatory element; (b) introducing the linked mda-6 gene into the malignant cells for the expression of the mda-6 gene, thereby reversing the phenotype of the malignant cells.

This invention also provides a method of reversing the phenotype of malignant cells in a subject comprising: (a) linking the mda-6 gene to a regulatory element such that the expression of the mda-6 gene is under the control of the regulatory element; (b) introducing the linked mda-6 gene into the malignant cells of the subject; and (c) inducing the expression of the mda-6 gene which will reverse the transforming properties of the cells, thereby reversing the phenotype of the malignant cells in the subject.

This invention also provides a method of inducing growth suppression in tumorigenic and metastatic cells comprising: (a) linking the mda-6 gene to a regulatory element such that the expression of the mda-6 gene is under the control of the regulatory element; (b) introducing the linked mda-6 gene into the tumorigenic and metastatic cells; and (c) inducing the expression of the mda-6 gene, thereby inducing growth suppression in tumorigenic and metastatic cells.

This invention also provides a method of inducing terminal differentiation in tumorigenic and metastatic cells comprising: (a) linking the mda-6 gene to a regulatory element such that the expression of the mda-6 gene is under the control of the regulatory element; (b) introducing the linked mda-6 gene into the tumorigenic and metastatic cells; and (c) inducing the expression of the mda-6 gene, thereby inducing terminal differentiation in tumorigenic and metastatic cells.

In an embodiment, the cell is a melanoma, leukemia, lymphoma, neuroblastoma, glioblastoma or carcinoma cell.

In a separate embodiment, the regulatory element is a promoter. In a further embodiment, the promoter is a tissue-specific promoter. In another embodiment, the promoter is an inducible promoter.

The linked mda-6 gene may be introduced into the cells by naked DNA technology, retroviral vectors, antibody-coated liposomes, mechanical or electrical means. These technologies are known in the art.

This invention provides a method of determining the stage of a melanoma comprising: (a) obtaining appropriate amount of cells from the melanoma; (b) measuring the expression level of the mda-6 gene in the cells; and (b) comparing the expression level with predetermined standards of normal and melanoma cells in different stages, thereby determining the stage of a melanoma.

In an embodiment, the expression is measured by the antibodies against the mda-6 protein. In another embodiment, the expression is measured by in situ hybridization.

This invention also provides a method for indicating the effectiveness of a treatment against cancer comprising measuring the expression level of mda-6 gene in the cells of the cancer, the increase of the expression level indicating the effectiveness of the treatment. In an embodiment, the cancer is melanoma. In another embodiment, the cancer is leukemia. In a separate embodiment, the cancer is lymphoma. In another embodiment, the cancer is neuroblastoma. In a further embodiment, the cancer is a glioblastoma multiforme tumor. In a still further embodiment, the cancer is a carcinoma.

This invention provides an isolated nucleic acid molecule encoding a protein produced by a melanoma differentiation associated gene designated mda-7. In an embodiment, the nucleic acid is a cDNA. In another embodiment, the nucleic acid is genomic DNA.

In a separate embodiment, the mda-7 gene is coding for a human protein.

This invention provides an isolated nucleic acid molecule of a cDNA, wherein the protein is a human protein.

This invention provides a nucleic acid molecule of at least 15 nucleotides capable of specifically hybridizing with a sequence of the nucleic acid molecule of mda-7.

This invention provides a method of detecting the expression of mda-7 gene in a cell comprising: a) isolating the nucleic acids in the cell; b) hybridizing the isolated nucleic acids with the nucleic acid molecules of at least 15 nucleotides capable of specifically hybridizing with a sequence of the nucleic acid molecule of an isolated nucleic acid molecule encoding a protein produced by a melanoma differentiation associated gene designated mda-7 under conditions permitting hybrids formation; and c) detecting hybrids formed, the detection of the hybrids formed indicating the expression of mda-7 gene in the cell.

This invention provides a method for determining whether a cell is a melanoma cell or a carcinoma cell comprising detecting the expression of mda-7 gene using the above-described method of detecting the expression of mda-7 gene in a cell, the expression of mda-7 gene indicating that the cell is a melanoma cell.

The invention further provides a method for distinguishing a melanocyte or early stage melanoma cell from an advanced metastatic melanoma cell comprising detecting the expression of mda-7 gene using the above-described method, the expression of mda-7 gene indicating that the cell is a melanocyte or early stage melanoma cell.

This invention provides a method for distinguishing a normal neuroectodermal cell from a malignant neuroectodermal cell comprising detecting the expression of mda-7 gene using the above-described method of detecting the expression of mda-7 gene in a cell, the expression of mda-7 gene indicating that the tissue lineage of the cell is normal neuroectodermal cell.

The invention also provides a method for distinguishing a fibroblast from an epithelial cell comprising detecting the expression of mda-7 gene using the above-described method, the expression of mda-7 gene indicating that the cell is a fibroblast.

This invention provides a method for identifying a compound capable of inducing growth suppression in human melanoma cells comprising: a) incubating appropriate concentration of the human melanoma cells with an appropriate concentration of the compound; and b) detecting the expression of mda-7 using the above-described method, the expression of mda-7 gene indicating that the compound is capable of inducing growth suppression in human melanoma cells.

The invention further provides a method for monitoring the response of a cell to an anticancer agent such as adriamycin or vincristine comprising detecting the expression of mda-7 gene using the above-described method, the expression of mda-7 gene indicating that the cell responds to the anticancer agent.

The invention also provides a method for monitoring the response of a cell to DNA damage induced by UV irradiation comprising detecting the expression of mda-7 gene using the above-described method, the expression of mda-7 gene indicating that the cell responds to the DNA damage.

This invention provides a method for reversing the malignant phenotype of cells comprising: (a) linking the mda-7 gene to a regulatory element such that the expression of the mda-7 gene is under the control of the regulatory element; and (b) introducing the linked mda-7 gene into the malignant cells for the expression of the mda-7 gene, thereby reversing the malignant phenotype of cells.

This invention also provides a method for reversing the malignant phenotype of cells comprising: (a) linking the mda-7 gene to a regulatory element such that the expression of the mda-7 gene is under the control of the regulatory element;(b) introducing the linked mda-7 gene into the malignant cells; and (c) placing the cells from step (b) in appropriate conditions to express the mda-7 gene such that the expression of the mda-7 gene will reverse the transforming phenotype of the malignant cells.

This invention also provides a method for reversing the phenotype of malignant cells in a subject comprising: (a) linking the mda-7 gene to a regulatory element such that the expression of the mda-7 gene is under the control of the regulatory element; and (b) introducing the linked mda-7 gene into the malignant cells for the expression of the mda-7 gene, thereby reversing the phenotype of the malignant cells.

This invention also provides a method to reversing the phenotype of malignant cells in a subject comprising: (a) linking the mda-7 gene to a regulatory element such that the expression of the mda-7 gene is under the control of the regulatory element; (b) introducing the linked mda-7 gene into the malignant cells of the subject; and (c) inducing the expression of the mda-7 gene which will reverse the transforming properties of the cells, thereby reversing the phenotype of the malignant cells in the subject.

This invention also provides a method of inducing growth suppression in tumorigenic and metastatic cells comprising: (a) linking the mda-7 gene to a regulatory element such that the expression of the mda-7 gene is under the control of the regulatory element; (b) introducing the linked mda-7 gene into the tumorigenic and metastatic cells; and (c) inducing the expression of the mda-7 gene, thereby inducing growth suppression in tumorigenic and metastatic cells.

This invention also provides a method of inducing terminal differentiation in tumorigenic and metastatic cells comprising: (a) linking the mda-7 gene to a regulatory element such that the expression of the mda-7 gene is under the control of the regulatory element; (b) introducing the linked mda-7 gene into the tumorigenic and metastatic cells; and (c) inducing the expression of the mda-7 gene, thereby inducing terminal differentiation in tumorigenic and metastatic cells. In an embodiment, the cell is a melanoma cell. In another embodiment, the cell is a leukemia cell. In a further embodiment, the cell is a lymphoma cell. In a still further embodiment, the cell is a neuroblastoma cell. In another still further embodiment, the cell is a glioblastoma multiforme cell.

In a separate embodiment, the regulatory element is a promoter. In a further embodiment, the promoter is a tissue-specific promoter. In another embodiment, the promoter is an inducible promoter.

The linked mda-7 gene may be introduced into the cells by naked DNA technology, retroviral vectors, antibody-coated liposomes, mechanical or electrical means. These technologies are known in the art.

This invention also provides a method of determining the stage of a melanoma comprising: (a) obtaining appropriate amount of cells from the melanoma; (b) measuring the expression level of the mda-7 gene in the cells; and (b) comparing the expression level with predetermined standards of normal and melanoma cells in different stages, thereby determining the stage of a melanoma.

In an embodiment, the expression is measured by the antibodies against the mda-7 protein. In another embodiment, the expression is measured by in situ hybridization.

This invention also provides a method for indicating the effectiveness of a treatment against cancer comprising measuring the expression level of mda-7 gene in the cells of the cancer, the increase of the expression level indicating the effectiveness of the treatment. The cancer may be a melanoma, leukemia, lymphoma, neuroblastoma or a glioblastoma multiforme tumor.

This invention provides a method of determining whether a cell is senescent comprising detecting the expression of mda-7, the expression of the mda-7 gene indicating that the cell is senescent.

This invention provides a method of identifying a compound inhibiting senescence comprising: a) incubating a plurality of cells with an appropriate amount of a compound; b) detecting the expression of mda-7, the inhibition of the expression of mda-7 indicating that the compound is inhibiting senescence.

This invention provides an isolated nucleic acid molecule encoding a protein produced by a melanoma differentiation associated gene designated mda-8. In an embodiment, the nucleic acid is a cDNA. In another embodiment, the nucleic acid is genomic DNA.

In a separate embodiment, the mda-8 gene is coding for a human protein.

This invention provides a nucleic acid molecule of at least 15 nucleotides capable of specifically hybridizing with a sequence of the nucleic acid molecule of an isolated nucleic acid molecule encoding a protein produced by a melanoma differentiation associated gene designated mda-8.

This invention provides a method of detecting the expression of mda-8 gene in a cell comprising: a) isolating the nucleic acids in the cell; b) hybridizing the isolated nucleic acids with the nucleic acid molecules capable of mda-8, under conditions permitting hybrids formation; and c) detecting hybrids formed, the detection of the hybrids formed indicating the expression of mda-8 gene in the cell.

This invention provides a method for distinguishing a glial cell from a malignant astrocytoma cell comprising detecting the expression of mda-8 gene using the above-described method, the expression of mda-8 gene indicating that the cell is a normal glial cell.

The invention also provides a method for monitoring the response of a cell to an anticancer agent such as actinomycin D, adriamycin or cis-platinum comprising detecting the expression of mda-8 gene using the above-described method, the expression of mda-8 gene indicating that the cell responds to the anticancer agent.

The invention further provides a method for monitoring the response of a cell to DNA damage induced by UV irradiation comprising detecting the expression of mda-8 gene using the above-described method, the expression of mda-8 gene indicating that the cell responds to the DNA damage.

This invention provides a method for detecting type II interferons in a sample comprising: a) incubating the sample with a target cell containing the 5' regulatory element of mda-8 permitting binding of type II interferon transcriptional regulatory proteins to the 5' regulatory element; and b) detecting the binding, the binding indicating the presence of type II interferons in the sample.

In an embodiment, the cell is an eukaryotic cell.

In another embodiment, the 5' regulatory element is linked to the native mda-8 gene and the detection of binding is by the examination of the elevated level of mda-8 gene expression.

In one embodiment, the 5' regulatory element is linked to a marker gene. In a still further embodiment, the marker gene is β-galactosidase, luciferase or CAT.

This invention provides a method for identifying a compound capable of inducing terminal differentiation in human melanoma cells comprising: a) inducing appropriate concentration of the human melanoma cells with an appropriate concentration of the compound; and b) detecting the expression of mda-8 using the above-described method, the expression of mda-8 gene indicating that the compound is capable of inducing terminal differentiation in human melanoma cells.

This invention provides an isolated nucleic acid molecule encoding a protein produced by a melanoma differentiation associated gene designated mda-9. In an embodiment, the nucleic acid is a cDNA. In another embodiment, the nucleic acid is genomic DNA.

In a separate embodiment, the mda-9 gene is coding for a human protein.

This invention provides an isolated nucleic acid molecule of an isolated nucleic acid molecule encoding a protein produced by a melanoma differentiation associated gene designated mda-9, wherein the protein is a human protein.

This invention provides a nucleic acid molecule of at least 15 nucleotides capable of specifically hybridizing with a sequence of the nucleic acid molecule of an isolated nucleic acid molecule encoding a protein produced by a melanoma differentiation associated gene designated mda-9.

This invention provides a method of detecting the expression of mda-9 gene in a cell comprising: a) isolating the nucleic acids in the cell; b) hybridizing the isolated nucleic acids with the nucleic acid molecules of at least 15 nucleotides capable of specifically hybridizing with a sequence of the nucleic acid molecule of an isolated nucleic acid molecule encoding a protein produced by a melanoma differentiation associated gene designated mda-9 under conditions permitting hybrids formation; and c) detecting hybrids formed, detection of hybrids formed indicating the expression of mda-9 gene in the cell.

This invention provides a method for indicating the stage of progression of a human melanoma cell comprising detecting the expression of mda-9 gene using the method of detecting the expression of mda-9 gene in a cell comprising: a) isolating the nucleic acids in the cell; b) hybridizing the isolated nucleic acids with the nucleic acid molecules of at least 15 nucleotides capable of specifically hybridizing with a sequence of the nucleic acid molecule of an isolated nucleic acid molecule encoding a protein produced by a melanoma differentiation associated gene designated mda-9 under conditions permitting hybrids formation; and c) detecting hybrids formed, detection of hybrids formed indicating the expression of mda-9 gene in the cell, the expression of mda-9 gene indicating the stage of progression of the human melanoma cell.

This invention provides a method for identifying a compound capable of inducing terminal differentiation in human melanoma cells comprising: a) incubating appropriate concentration of the human melanoma cells with an appropriate concentration of the compound; b) detecting the expression of mda-9 using the method of detecting the expression of mda-9 gene in a cell comprising: a) isolating the nucleic acids in the cell; b) hybridizing the isolated nucleic acids with the nucleic acid molecules of at least 15 nucleotides capable of specifically hybridizing with a sequence of the nucleic acid molecule of an isolated nucleic acid molecule encoding a protein produced by a melanoma differentiation associated gene designated mda-9 under conditions permitting hybrids formation; and c) detecting hybrids formed, detection of hybrids formed indicating the expression of mda-9 gene in the cell, the expression of mda-9 gene indicating that the compound is capable of inducing terminal differentiation in human melanoma cells.

This invention provides a method for identifying a compound capable of inducing specific patterns of DNA damage caused by UV irradiation and gamma irradiation in human melanoma cells comprising: a) inducing appropriate concentration of the human melanoma cells with an appropriate concentration of the compound; and b) detecting the expression of mda-9 using the method of detecting the expression of mda-9 gene in a cell comprising: a) isolating the nucleic acids in the cell; b) hybridizing the isolated nucleic acids with the nucleic acid molecules of at least 15 nucleotides capable of specifically hybridizing with a sequence of the nucleic acid molecule of an isolated nucleic acid molecule encoding a protein produced by a melanoma differentiation associated gene designated mda-9 under conditions permitting hybrids formation; and c) detecting hybrids formed, detection of hybrids formed indicating the expression of mda-9 gene in the cell, the expression of mda-9 gene indicating that the compound is capable of inducing specific patterns of DNA damage caused by UV irradiation and gamma irradiation in human melanoma cells.

The invention also provides a method for identifying the presence of tumor necrosis factor or a similarly acting agent comprising detecting the expression of mda-9 gene using the above-described method, the expression of mda-9 gene indicating that the tumor necrosis factor or similar agent is present.

The invention further provides a method for monitoring the response of a cell to an anticancer agent such as phenyl butyrate or VP-16 comprising detecting the expression of mda-9 gene using the above-described method, the expression of mda-9 gene indicating that the cell responds to the anticancer agent.

In a separate embodiment, the mda-9 gene is coding for a human protein.

This invention provides a nucleic acid molecule of at least 15 nucleotides capable of specifically hybridizing with a sequence of the nucleic acid molecule of mda-9.

This invention provides a method of detecting the expression of mda-9 gene in a cell comprising: a) isolating the nucleic acids in the cell; b) hybridizing the isolated nucleic acid with the nucleic acid capable of specifically hybridizing with mda-9 under conditions permitting hybrid formation and c) detecting hybrids formed, detection of hybrids formed indicating the expression of mda-9 gene in the cell.

This invention provides a method for distinguishing an early stage and more progressed human melanoma cell comprising detecting the expression of mda-9 gene indicating that the cell is more progressed human melanoma cell.

This invention provides a method for identifying a compound capable of inducing terminal differentiation in human melanoma cells comprising: a) incubating human melanoma cell with the compound effective of inducing terminal differentiation in human melanoma cells; and b) detecting the expression of mda-9 using the above-described method, the expression of mda-9 gene indicating that the compound is capable of inducing terminal differentiation in human melanoma cells.

This invention provides a method for identifying a compound capable of inducing specific patterns of DNA damage caused by UV irradiation and gamma irradiation in human melanoma cells comprising: a) incubating human melanoma cells with the compound effective of inducing specific patterns of DNA damage caused by UV irradiation and gamma irradiation in human melanoma cells; and b) detecting the expression of mda-90 using the above-described method, the expression of mda-9 gene indicating that the compound is capable of inducing specific patterns of DNA damage caused by UV irradiation and gamma irradiation in human melanoma cells.

This invention provides an isolated nucleic acid molecule encoding a protein produced by a melanoma differentiation associated gene designated mda-11. In an embodiment, the nucleic acid is a cDNA. In another embodiment, the nucleic acid is genomic DNA.

In a separate embodiment, the mda-11 gene is coding for a human protein.

This invention provides an isolated nucleic acid molecule encoding a protein produced by a melanoma differentiation associated gene designated mda-14. In an embodiment, the nucleic acid is a cDNA. In another embodiment, the nucleic acid is genomic DNA.

In a separate embodiment, the mda-14 gene is coding for a human protein.

This invention provides an isolated nucleic acid molecule encoding a protein produced by a melanoma differentiation associated gene designated mda-17. In an embodiment, the nucleic acid is a cDNA. In another embodiment, the nucleic acid is genomic DNA.

In a separate embodiment, the mda-17 gene is coding for a human protein.

This invention provides an isolated nucleic acid molecule encoding a protein produced by a melanoma differentiation associated gene designated mda-18. In an embodiment, the nucleic acid is a cDNA. In another embodiment, the nucleic acid is genomic DNA.

In a separate embodiment, the mda-18 gene is coding for a human protein.

In an embodiment, the above-described isolated nucleic acid molecule is cDNA. In another embodiment, the nucleic acid molecule is from humans.

This invention also encompasses DNAs and cDNAs which encode amino acid sequences which differ from those of protein encoded by the melanoma differentiation associated genes, but which should not produce phenotypic changes. Alternatively, this invention also encompasses DNAs and cDNAs which hybridize to the DNA and cDNA of the subject invention. Hybridization methods are well known to those of skill in the art.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The DNA molecules described and claimed herein are useful for the information which they provide concerning the amino acid sequence of the polypeptide and as products for the large scale synthesis of the polypeptide by a variety of recombinant techniques. The molecule is useful for generating new cloning and expression vectors, transforming and transfecting prokaryotic and eukaryotic host cells, and new and useful methods for cultured growth of such host cells capable of expression of the polypeptide and related products.

Moreover, the isolated nucleic acid molecules encoding a protein coded by the melanoma differentiation associated gene are useful for the development of probes to study melanoma differentiation. In addition, the isolated nucleic acid molecules encoding a protein coded by the melanoma differentiation associated gene are useful for screening for agents with anticancer activity, agents which can induce DNA damage and agents which induce cell growth arrest in human melanoma.

The isolated nucleic acid molecules encoding a protein coded by the melanoma differentiation associated gene are also useful for distinguishing normal from malignant central nervous system cells, adenocarcinomas from carcinomas, and fibroblasts from epithelial cells.

This invention further provides a nucleic acid molecule of at least 15 nucleotides capable of specifically hybridizing with a sequence of the above-described nucleic acid molecule, i.e., the melanoma differentiation associated genes.

This nucleic acid molecule produced can either be DNA or RNA. As used herein, the phrase "specifically hybridizing" means the ability of a nucleic acid molecule to recognize a nucleic acid sequence complementary to its own and to form double-helical segments through hydrogen bonding between complementary base pairs.

When a situation arises that requires the nucleic acid molecule to be uniquely recognizing a gene, it is well-known in the art to select regions in the sequence which will distinguish one gene from the other. Simple experiments may be designed to find such unique regions.

This nucleic acid molecule of at least 15 nucleotides capable of specifically hybridizing with a sequence of the above-described nucleic acid molecule can be used as a probe. Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes a protein produced by a melanoma differentiation associated gene into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the above-described isolated nucleic acid molecule downstream of a bacteriophage promoter such as T3, T7 or SP6. Large amounts of RNA probe may be produced by incubating the labeled nucleotides with the linearized fragment containing the above-described molecule where it contains an upstream promoter in the presence of the appropriate RNA polymerase.

This invention also provides a method of detecting expression of a melanoma differentiation associated gene in a cell which comprises obtaining total cellular RNA or mRNA from the cell, contacting the total cellular RNA or mRNA so obtained with a labelled nucleic acid molecule of at least 15 nucleotides capable of specifically hybridizing with a sequence of the above-described nucleic acid molecule under hybridizing conditions, determining the presence of total cellular RNA or mRNA hybridized to the molecule, and thereby detecting the expression of the melanoma differentiation associated gene in the cell. The nucleic acid molecules synthesized above may be used to detect expression of melanoma differentiation associated genes by detecting the presence of the correspondent RNA or mRNA. Total cellular RNA or mRNA from the cell may be isolated by many procedures well known to a person of ordinary skill in the art. The hybridizing conditions of the labelled nucleic acid molecules may be determined by routine experimentation well known in the art. The presence of total cellular RNA or mRNA hybridized to the probe may be determined by gel electrophoresis or other methods known in the art. By measuring the amount of the hybrid made, the expression of the melanoma differentiation associated genes by the cell can be determined. The labelling may be radioactive. For an example, one or more radioactive nucleotides can be incorporated in the nucleic acid when it is made.

In one embodiment of this invention, nucleic acids are extracted from lysed cells and the mRNA is isolated from the extract using an oligo-dT column which binds the poly-A tails of the mRNA molecules. The mRNA is then exposed to radioactively labelled probe on a nitrocellulose membrane, and the probe hybridizes to and thereby labels complementary mRNA sequences. Binding may be detected by luminescence autoradiography or scintillation counting. However, other methods for performing these steps are well known to those skilled in the art, and the discussion above is merely an example.

This invention also provides a method of detecting expression of a melanoma differentiation associated gene in tissue sections which comprises contacting the tissue sections with a labelled nucleic acid molecule of at least 15 nucleotides capable of specifically hybridizing with a sequence of the above-described nucleic acid molecule under hybridizing conditions, determining the presence of mRNA hybridized to the molecule, and thereby detecting the expression of the melanoma differentiation associated gene in tissue sections.

This invention also provides the above-describe nucleic acid molecules operatively linked to a promoter of RNA transcription.

This invention provides vectors which comprise the above-described isolated nucleic acid molecules. In an embodiment, the vector is a plasmid.

Various vectors including plasmid vectors, cosmid vectors, bacteriophage vectors and other viruses are well known to ordinary skilled practitioners. This invention further provides a vector which comprises the isolated nucleic acid molecule encoding a protein produced by a melanoma differentiation gene.

As an example to obtain these vectors, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are also available and known to an ordinary skilled practitioner.

In an embodiment, the nucleic acid molecule is cloned in the XhoI/EcoRI site of pBlueScript. Plasmids, mda-1, mda-4, mda-5, mda-6, mda-7, mda-8, mda-9, mda-11, mda-14, mda-17, and mda-18 were deposited on Oct. 26, 1993 with the American Type Culture Collection (ATCC), 10801 University Blvd., Manassas, Va. 20110-2209, U.S.A. under the provisions of the Budapest Treaty for the International Recognition of the Deposit of Microorganism for the Purposes of Patent Procedure. Plasmids, mda-1, mda-4, mda-5, mda-6, mda-7, mda-8, mda-9, mda-11, mda-14, mda-17, and mda-18 were accorded ATCC Accession Numbers 75582, 75583, 75584, 75585, 75586, 75587, 75588, 75589, 75590, 75591 and 75592 respectively.

In another embodiment, a 3' fragment of the mda-6 gene is cloned in the EcoRI and XbaI site of the pBluescript plasmid and designed as mda-6.3'. The mda-6.3' was deposited on Sep. 30, 1994 with the American Type Culture Collection (ATCC),10801 University Blvd. Manassas, Va. 20110-2209, U.S.A. under the provisions of the Budapest Treaty for the International Recognition of the Deposit of Microorganism for the Purposes of Patent Procedure. Plasmid, mda-6.3' was accorded ATCC Accession Numbers 75903.

In another embodiment, a 5' fragment of the mda-6 gene is cloned in the salI site of the pSP64 plasmid and designed as mda-6.5'. The mda-6.5' was deposited on Sep. 30, 1994 with the American Type Culture Collection (ATCC), 10801 University Blvd. Manassas, Va. 20110-2209, U.S.A. under the provisions of the Budapest Treaty for the International Recognition of the Deposit of Microorganism for the Purposes of Patent Procedure. Plasmid, mda-6.5' was accorded ATCC Accession Number 75904.

Plasmids mda-6.3' and mda-6.5' constitute the full-length of the mda-6 gene. An ordinary skilled artisan can easily obtain the inserts from the plasmids and ligate the inserts to obtain the full-length gene.

In another embodiment, a 3' fragment of the mda-7 gene is cloned in the EcoRI and XbaI site of the pBluescript plasmid and designed as mda-7.3'. The mda-7.3' was deposited on Sep. 30, 1994 with the American Type Culture Collection (ATCC), 10801 University Blvd. Manassas, Va. 20110-2209, U.S.A. under the provisions of the Budapest Treaty for the International Recognition of the Deposit of Microorganism for the Purposes of Patent Procedure. Plasmid, mda-7.3' was accorded ATCC Accession Number 75905.

In another embodiment, a 5' fragment of the mda-7 gene is cloned in the salI site of the pSP64 plasmid and designed as mda-7.5'. The mda-7.5' was deposited an Sep. 30, 1994 with the American Type Culture Collection (ATCC), 10801 University Blvd. Manassas, Va. 20110-2209, U.S.A. under the provisions of the Budapest Treaty for the International Recognition of the Deposit of Microorganism for the Purposes of Patent Procedure. Plasmid, mda-7.5' was accorded ATCC Accession Numbers 75906.

Plasmids mda-7.3' and mda-7.5' constitute the full-length of the mda-7 gene. An ordinary skilled artisan can easily obtain the inserts from the plasmids and ligate the inserts to obtain the full-length gene.

This invention provides a host vector system for the production of a polypeptide having the biological activity of a protein encoded by melanoma differentiation associated gene which comprises the above-described vector and a suitable host. These vectors may be transformed into a suitable host cell to form a host cell vector system for the production of a protein produced by the melanoma differentiation associated genes.

Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general. Expression vectors are useful to produce cells that express the protein produced by the melanoma differentiation associated genes.

This invention further provides an isolated DNA or cDNA molecule described hereinabove wherein the host cell is selected from the group consisting of bacterial cells (such as *E. coli*), yeast cells, fungal cells, insect cells and animal cells. Suitable animal cells include, but are not limited to Vero cells, HeLa cells, Cos cells, CV1 cells and various primary mammalian cells.

As stated above and in the text which follows, this invention provides gene(s) which express when a cell becomes terminally differentiated and irreversibly growth arrested, treated with a DNA damaging agent and/or exposed to an anticancer agent. Therefore, this invention is useful for inducing a target cell to a terminally differentiated stage. Such a target cell may be a cancerous cell such as a melanoma cell or a glioblastoma multiforme cell. The gene which expresses when a cell becomes terminally differentiated may be introduced into the target cell via retroviral technology or other technologies known in the art. The gene may be controlled by its own promoter or other heterologous promoters. Expression of this gene will then result in terminal differentiation and an irreversible loss of proliferative capacity in the cancerous cell.

This invention has also provided nucleic acid molecules which will suppress the terminal differentiation of a cell. Such molecules are useful for preventing terminal differentiation by switching off a target gene in a cell which has been treated with differentiation inducing agents, anticancer agents or DNA damaging agents. The target gene may be switched off via antisense technology. After the gene has been switched off, normal cells, such as bone marrow stem cells, can be prevented from becoming terminally differentiated and irreversibly growth arrested when treated with differentiation inducing agents, anticancer agents or DNA damaging agents.

Antisense technology is well known in the art. Essentially, a segment of the melanoma differentiation associated gene will be selected to be the antisense sequence. The expression of the antisense sequence will switch off the expression of the gene. The antisense sequence may be introduced into the cell via technologies which are well known in the art, such as electroporation transduction, retroviral insertion or liposome-mediated gene transfer.

This invention also provides a method of producing a polypeptide having the biological activity of a protein encoded by melanoma differentiation associated gene which comprises growing the host cells of the above-described host vector system under suitable conditions permitting production of the polypeptide and recovering the polypeptide so produced.

This invention provides a mammalian cell comprising a DNA molecule encoding a protein produced by a melanoma differentiation associated gene, such as a mammalian cell comprising a plasmid adapted for expression in a mammalian cell, which comprises a DNA molecule encoding a protein produced by the melanoma differentiation associated gene and the regulatory elements necessary for expression of the DNA in the mammalian cell so located relative to the DNA encoding a protein produced by a melanoma differentiation gene as to permit expression thereof.

Numerous mammalian cells may be used as hosts, including, but not limited to, the mouse fibroblast cell NIH3T3, CREF cells, CHO cells, HeLa cells, Ltk$^-$ cells, Cos cells, etc. Expression plasmids such as that described supra may be used to transfect mammalian cells by methods well known in the art such as calcium phosphate precipitation, electroporation or the plasmid may be otherwise introduced into mammalian cells, e.g., by microinjection, to obtain mammalian cells which comprise DNA, e.g., cDNA or a plasmid, encoding a protein produced by a melanoma differentiation associated gene.

Also provided by this invention is a purified protein encoded by the above-described isolated nucleic acid molecule. As used herein, the term "purified protein" shall mean isolated naturally-occurring protein encoded by a melanoma differentiation associated gene (purified from nature or manufactured such that the primary, secondary and tertiary conformation, and posttranslational modifications are identical to naturally-occurring material) as well as non-naturally occurring polypeptides having a primary structural conformation (i.e. continuous sequence of amino acid residues). Such polypeptides include derivatives and analogs.

This invention also provides a method to produce antibody using the above purified protein. In an embodiment, the antibody is monoclonal. In another embodiment, the antibody is polyclonal.

This invention further provides antibodies capable of binding to the purified protein produced by the melanoma differentiation associated genes.

With the protein sequence information which can either be derived from the above described nucleic molecule or by direct protein sequencing of the above described purified protein, antigenic areas may be identified and antibodies directed against these areas may be generated and targeted to the cancer for imaging the cancer or therapies.

This invention provides a method to select specific regions on the protein produced by a melanoma differentiation associated gene to generate antibodies. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer of the cell membrane, while hydrophilic regions are located on the cell surface, in an aqueous environment. Usually, the hydrophilic regions will be more immunogenic than the hydrophobic regions. Therefore the hydrophilic amino acid sequences may be selected and used to generate antibodies specific to protein produced by the melanoma differentiation genes. The selected peptides may be prepared using commercially available machines. As an alternative, DNA, such as a cDNA or a fragment thereof, may be cloned and expressed and the resulting polypeptide recovered and used as an immunogen.

Polyclonal antibodies against these peptides may be produced by immunizing animals using the selected peptides. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced by in vitro techniques known to a person of ordinary skill in the art. These antibodies are useful to detect the expression of protein produced by the melanoma differentiation associated genes in living animals, in humans, or in biological tissues or fluids isolated from animals or humans.

This invention will be better understood from the Experimental Details which follow. However, one skilled in the art will readily appreciate that the specific methods and results discussed are merely illustrative of the invention as described more fully in the claims which follow thereafter.

Experimental Details

First Series of Experiments

Materials and Methods

Cell Line Growth Conditions, and Preparation of Conditioned Medium

The H0-1 cell line is a melanotic melanoma derived from a 49-year-old female and was used between passage 100 and 125 (6, 8, 13). H0-1 cells were kindly provided by Dr. Beppino C. Giovanella, Stehlin Foundation for Cancer Research, Houston, Tex. Cultures were grown at 37° C. in a 95% air 5% $CO_2$-humidified incubator in Dulbecco's modified Eagle's medium (DMEM) supplemented with 10% fetal bovine serum (DMEM-10) (Hyclone, Logan, Utah). H0-1 cells were maintained in the logarithmic stage of growth by subculturing (1:5 or 1:10) prior to confluency approximately every 4 to 5 days. The effect of IFN-β (2000 units/ml), IFN-γ (2000 units/ml), IFN-β+IFN-γ (1000 units/ml of each interferon), MPA (3.0 μM), RA (2.5 μM), MEZ (10 ng/ml), IFN-β+MEZ (2000 units/ml+10 ng/ml), MPA+MEZ (3.0 μM+10 ng/ml, and RA+MEZ (2.5 μM+10 ng/ml) on growth was determined after 4 days of treatment, as described previously (6, 8, 9). Terminal cell differentiation, with a concomitant loss of proliferative capacity, was assayed by treating cells with the various agents for either 4 or 7 days, washing cultures two times with serum-free DMEM, followed by incubation in DMEM-10 in the absence of inducer (s) for an additional 14 days. Total cell numbers were determined after days 4, 7, 14, and 21, using a $Z_M$ Coulter Counter, and viable cell numbers were determined by trypan blue dye exclusion (6). Terminal cell differentiation was indicated if no proliferation occurred, but cells remained viable, after growth for 14 days, with medium changes every 3 or 4 days, in the absence of the inducer(s). Increases in cell number (two or more population doublings) after removal of the inducing agent(s) was considered reversible growth suppression. Conditioned medium was prepared from H0-1 cells treated with a high dose of MEZ (50 ng/ml), IFN-β+MEZ (2000 U/ml+10 ng/ml), MPA+MEZ (3.0 μM+10 ng/ml), or RA+MEZ (2.5μ+10 ng/ml) for 24 hours followed by three washes in DMEM without FBS and growth for 72 hours in inducer-free medium (DMEM-10). Conditioned medium was collected from treated cultures, contaminating cells were removed by centrifugation at 1000 rpm/10 min., and conditioned medium was stored at 4° C. until assayed for gene modulatory activity. Control conditioned medium was obtained as experimental conditioned medium from cells receiving only a medium change 24 hours after plating in the absence of test compound(s) and growth for 72 hours in DMEM-10.

RNA Isolation and Northern Hybridization Analysis

Steady-state levels of specific mRNAs were determined by Northern blotting analysis of total RNA probed with appropriate $^{32}$P-labeled gene probes as described previously (14–16). RNAs were analyzed from cells treated with inducer for 24 hours, treated for 24 hours with inducer followed by growth for 72 hours in the absence of inducer, or treated continuously for 96 hours with the inducer. The concentration of inducing compounds used were the same as those used for growth studies. The effect of conditioned medium on gene expression changes was determined by treating H0-1 cells for 24 hours with a 1:2 dilution of conditioned medium (equal volumes of conditioned medium and DMEM supplemented with 10% fetal bovine serum (DMEM-10) or for 96 hours with a 1:4 dilution of conditioned medium (1 vol. of conditioned medium to 3 vol. of DMEM-10). The probes used in the present study were specific for β-actin (17), γ-actin (17), c-jun (18), c-myc (19), fibronectin (20), gro/MGSA (21), HLA Class I antigen (22), HLA Class II antigen (HLA-DR$_β$) (22), $α_5$ integrin (23), $β_1$ integrin (24), ISG-15 (25), ISG-54 (25), jun-B (26), and tenascin (27). Northern blots were also probed with a $^{32}$P-labeled GAPDH gene (15) to verify similar mRNA expression under the various experimental conditions. Following hybridization, the filters were washed and exposed for autoradiography.

Reagents

Recombinant human IFN-β, with a serine substituted for a cysteine at position 17 of the molecule (28), was kindly provided by Triton Bioscience (Alameda, Calif.). IFN-β was obtained as a lyophilized powder with a concentration of $4.5 \times 10^7$ U/ml. Recombinant human immune interferon (IFN-γ) was produced and purified to homogeneity as described previously (29). IFN-γ was kindly provided by Dr. Sidney Pestka, UMDNJ-Robert Wood Johnson Medical School, Piscataway, N.J. The interferon titers were determined using a cytopathic effect inhibition assay with vesicular stomatitis virus on a bovine kidney cell line (MDBK) or human fibroblast AG-1732 cells (30). Concentrated stocks of IFN-β and IFN-γ were diluted to $1 \times 10^6$ U/ml in DMEM-10, frozen at −80° C., thawed immediately prior to use, and diluted to the appropriate concentration in DMEM-10. MEZ, RA, and MPA were obtained from Sigma Scientific Co. (St. Louis, Mo.). Stock solutions were prepared in dimethyl sulfoxide (DMSO), aliquoted into small portions, and stored at −20° C. The final concentration of DMSO used in solvent controls was 0.01%. This concentration of DMSO did not alter growth, melanin synthesis, tyrosinase activity, or antigen expression in H0-1 cells.

Experimentals Results

Figure 1B:
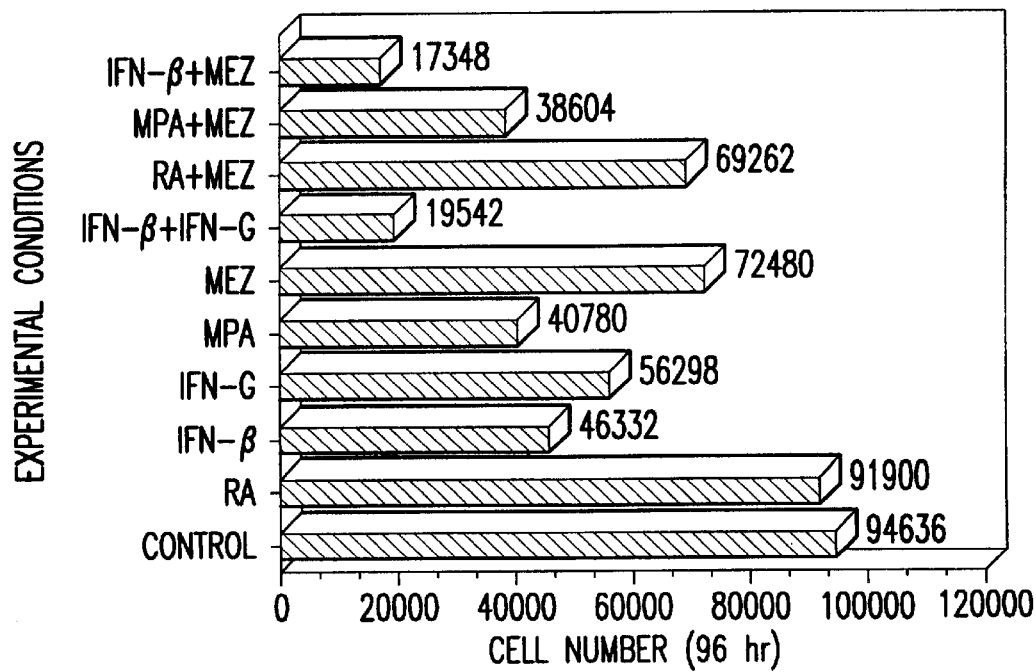

Induction of Reversible and Irreversible Growth Suppression (Terminal Cell Differentiation) in H0-1 Cells The effect of RA, MPA, MEZ, IFN-β and IFN-γ, used alone or in various combinations, on growth (reversible and irreversible growth suppression), melanin synthesis, tyrosinase activity, and cellular morphology of H0-1 cells is summarized in Table 1. The most effective agents in inhibiting H0-1 growth were the combinations of IFN-β+MEZ and IFN-β+IFN-γ (FIG. 1). The relative order of antiproliferative activity of the remaining compounds was MPA=MPA+MEZ>IFN-γ>MEZ=RA+MEZ. In the case of RA, no inhibition of growth occurred. Treatment of H0-1 cells with IFN-β+MEZ for 96 hours resulted in an irreversible loss of proliferative capacity, that is, terminal cell differentiation. This was indicated by the failure of treated cells to resume growth, even though they remained viable, after removal of the test agents. In contrast, all of the other compounds resulted in a reversible inhibition of growth (data not shown). These findings indicate a dissociation between growth suppression and terminal cell differentiation in H0-1 cells.

Treatment of H0-1 cells with MPA, MEZ, RA+MEZ, MPA+MEZ, or IFN-β+MEZ resulted in distinctive morphologic changes that were characterized by dendrite-like processes (data not shown) (6, 8, 10). RA, MPA, MEZ, IFN-β, and IFN-β+MEZ have been shown previously to enhance melanin synthesis, a marker of melanoma differentiation, in H0-1 cells (6, 8, 12). In contrast, IFN-γ, alone or in combination with IFN-β, did not induce morphologic changes or increase melanin levels above

TABLE 1

| Experimental Conditions[a] | Morphology changes[b] | Melanin Synthesis[c] | Tyrosinase activity[d] |
|---|---|---|---|
| RA (2.5 μM) | − | 1+ | 2+ |
| MPA (3.0 μM) | + | 2+ | 3+ |
| MEZ (10 ng/ml) | + | 1+ | NT |
| IFN-β (2000 U/ml) | − | 1+ | NT |
| IFN-γ (2000 U/ml) | − | − | NT |
| RA + MEZ (2.5 μM + 10 ng/ml) | + | NT | NT |
| MPA + MEZ (3.0 μM + 10 ng/ml) | + | NT | NT |
| IFN-β + IFN-γ (1000 U/ml + 1000 U/ml) | − | 1+ | NT |
| IFN-β + MEZ (2000 U/ml + 10 ng/ml) | + | 4+ | NT |

| Experimental conditions[a] | Growth Suppression (reversible)[e] | Terminal cell differentiation[f] |
|---|---|---|
| RA (2.5 μM) | − | − |
| MPA (3.0 μM) | 3+ | − |
| MEZ (10 ng/ml) | 1+ | − |
| IFN-β (2000 U/ml) | 3+ | − |

TABLE 1-continued

| | | |
|---|---|---|
| IFN-γ (2000 U/ml) | 2+ | − |
| RA + MEZ (2.5 μM + 10 ng/ml) | 1+ | − |
| MPA + MEZ (3.0 μM + 10 ng/ml) | 3+ | − |
| IFN-β + IFN-γ (1000 U/ml + 1000 U/ml) | 4+ | − |
| IFN-β + MEZ (2000 U/ml + 10 ng/ml) | 4+[g] | + |

[a]H0-1 cells were grown for 96 hr or for 6 or 7 days (with medium changes after 3 or 4 days) in the presence of the agents indicated. For morphology, cells grown for 96 hr in the test agent were observed microscopically. For melanin synthesis, results are for 6-d assays for RA and MPA (11) or 7-d assays for MEZ, IFN-β, IFN-γ, IFN-β + IFN-γ and IFN-β + MEZ (6, 12). For tyrosinase assays, results are for 6-d assays for RA, MPA and MEZ (10). Growth suppression (reversible and terminal cell differentiation) assays, refer to cultures treated with the indicated compound(s) for 96 hr prior to cell number determination, or treated for 96 hr and then grown for 2 weeks (with medium changes every 4 days) in the absence of compound prior to cell number determination.
[b]Morphology changes refer to the development of dendrite-like processes 96 hr after growth in the indicated compound. + = presence of dendrite-like processes; − = no dendrite-like processes.
[c]Melanin assays were determined as described in refs. 6, 8, 11, 12. Results are expressed as relative increases based on separate data presented in refs. 6, 8, 11, 12. N.T. = not tested.
[d]Tyrosinase assays were performed as described in ref. 11. Relative increases (of a similar magnitude) were found for RA, MPA and MEZ after 6 days exposure to these agents (11). N.T. = not tested.
[e]Reversible growth suppression indicates resumption of cell growth after treatment with the indicated compound(s) for 96 hr, removal of the test agent and growth for 14 days in compound(s) free medium. Further details can be found in materials and methods. The degree of initial 96 hr growth suppression is indicated as: − = no significant change in growth (<10% reduction in growth in comparison with untreated control cultures); 1+ = ~30% reduction in growth in comparison with untreated control cultures; 2+ = ~40% reduction in growth in comparison with untreated control cultures; 3+ = ~50 to 60% reduction in growth in comparison with untreated control cultures; 4+ = ~80% reduction in growth in comparison with untreated control cultures.
[f]The combination of IFN-β + MEZ results in irreversible growth suppression.
[g]The combination of IFN-β + MEZ results in irreversible growth suppression that induced by IFN-β alone (10, 12). With the exception of IFN-β+MEZ, morphologic and melanin changes were reversible following removal of the test agent(s) (data not shown). These data indicate that specific cellular and biochemical changes induced in H0-1 cells, such as reversible growth suppression, melanin synthesis, and morphologic changes, can occur with or without the induction of terminal cell differentiation. However, an irreversible loss of proliferative capacity with the retention of cell viability is a property unique to the terminal cell differentiation phenotype.

Figure 2:
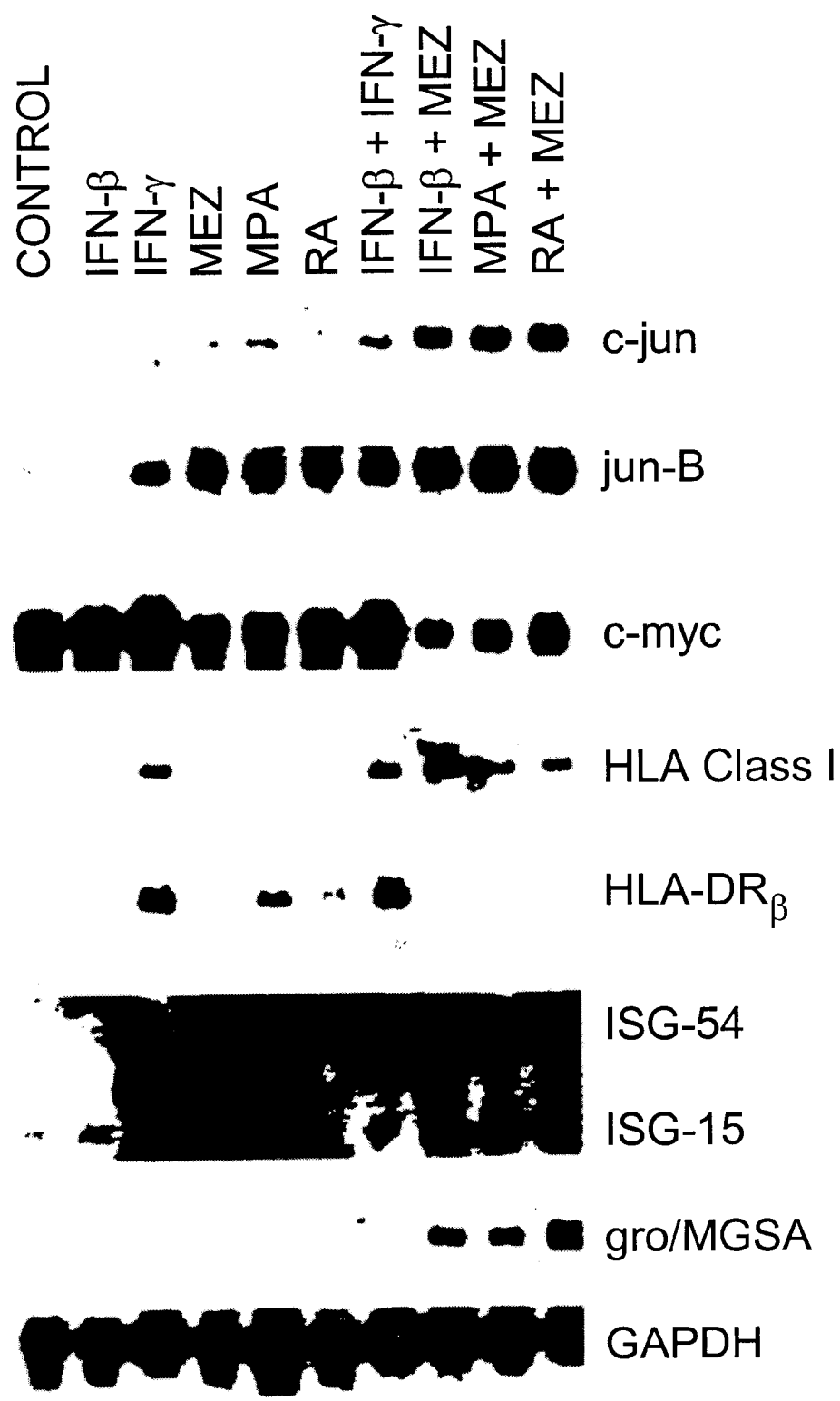
FIG. 2 Effect of growth and differentiation modulating agents on steady-state c-jun, jun-B, c-myc, HLA Class I antigen, HLA Class II ($DR_\beta$), ISG-54, ISG-15, gro/MGSA, and GAPDH mRNA levels in H0-1 cells. Total RNA was isolated 96 h after treatment with the various agents. The concentrations of compounds used were the same as those used for growth studies (see legend to FIG. 1). Ten micrograms of total cytoplasmic RNA was electrophoresed, transferred to nylon filters, and hybridized with the indicated $^{32}$P-labeled gene probes. Further details can be found in Materials and Methods of the first series of experiments.

Changes in the Expression of Early Growth Response and Interferon-Responsive Genes During Reversible and Irreversible Growth Suppression (Terminal Cell Differentiation) in H0-1 Cells Initial studies were conducted to determine the effect of the various differentiation and growth modulating agents on the 96-hour expression of the early response genes c-fos, c-jun, jun-B, jun-D, and c-myc (FIG. 2). None of the experimental treatments resulted in altered c-fos expression and no hybridization was obtained with RNA isolated from control or treated cells probed with jun-D (data not shown). Increases were observed, however, in both c-jun and jun-B expression in H0-1 cells treated for 96 hours with all of the test agents, with the exception of IFN-β and RA (see FIG. 2).

The magnitude of the increase was similar in H0-1 cells treated with IFN-γ, MEZ, or MPA and was greatest for H0-1 cells treated with IFN-β+MEZ, MPA+MEZ, or RA+MEZ (see FIG. 2). Unlike c-jun and jun-B expression c-myc expression was downregulated in H0-1 cells grown for 96 hours in MEZ, MPA, IFN-β+MEZ, MPA+MEZ, and RA+MEZ (FIG. 2). The magnitude of suppression was greater in H0-1 cells treated with IFN-β+MEZ, MPA+MEZ, and RA+MEZ. In contrast, treatment of H0-1 cells with IFN-γ, alone or in combination with IFN-β, resulted in increased c-myc expression.

Figure 3:
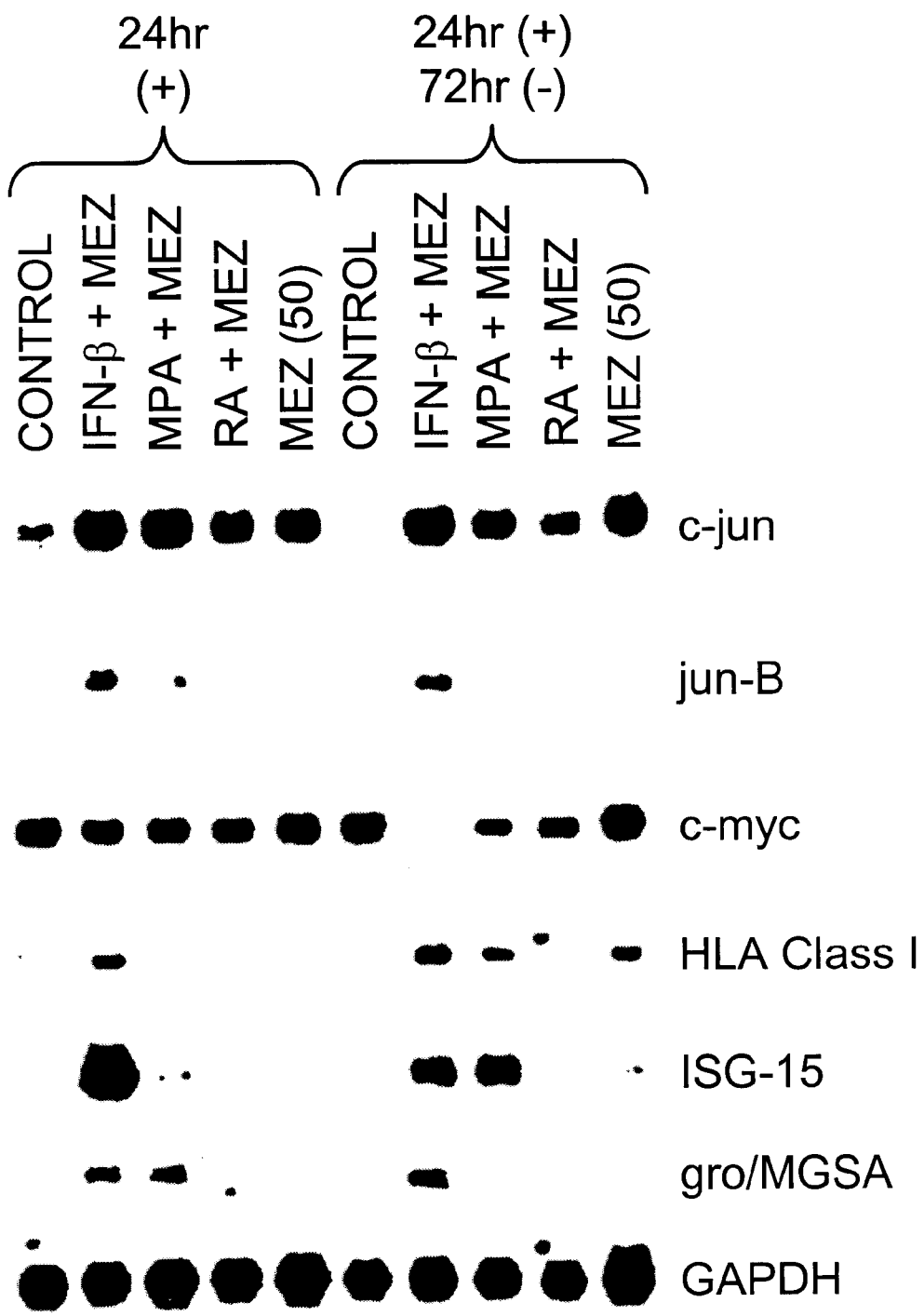
FIG. 3 Effect on gene expression in H0-1 cells of continuous and transient exposure to agents inducing a reversible commitment to differentiation or terminal cell differentiation. In the left panel [24 h (+)], H0-1 cells were treated with IFN-β+MEZ (2,000 U/ml+10 ng/ml), MPA+MEZ (3.0 μM+10 ng/ml), RA+MEZ (2.5 μM+10 ng/ml), or MEZ (50) (50 ng/ml) for 24 h. In the right panel [24 h (+) 72 h (−)], H0-1 cells were treated with the same test agents used in the left panel for 24 h, the cells were washed three times in serum-free medium and cells were cultured for an additional 72 h in DMEM-10 in the absence of test compound. Total RNA was isolated, electrophoresed, transferred to nylon filters, and hybridized with the indicated $^{32}$P-labeled gene probes. Further details can be found in Materials and Methods of the first series of experiments.

To determine the temporal relationship between treatment with IFN-β+MEZ, MPA+MEZ, and RA+MEZ and changes in c-jun, jun-B, and c-myc levels, H0-1 cells were treated with the inducers for 24 h and total cytoplasmic RNA was isolated and analyzed by Northern blotting (FIG. 3). Because many of the effects observed when MEZ is combined with IFN-β, MPA, or RA are observed to a lesser extent in cells treated with 10 mg/ml of MEZ alone, RNA was also isolated from H0-1 cell treated for 24 h with a high dose of MEZ (50 ng/ml) (FIG. 3). Under these experimental conditions, c-jun and jun-B expression were induced under all experimental conditions and c-myc expression was only marginally reduced in cultures treated with IFN-β+MEZ, MPA+MEZ, and RA+MEZ. Twenty-four-hour exposure to IFN-β+MEZ resulted in the largest induction in c-jun and jun-B expression.

To determine if the gene expression changes induced during the induction of reversible and irreversible growth suppression/differentiation persist in H0-1 cells treated with specific inducers, cultures were grown for 24 h in the presence of inducer and then incubated for an additional 72 h in inducer-free medium prior to isolating total cellular RNA (FIG. 3). Under these experimental conditions, c-jun and jun-B expression were induced to the greatest extract in IFN-β+MEZ-treated cultures. Smaller increases in c-jun and jun-B expression were apparent in high-dose MEZ-, MPA+MEZ-, and RA+MEZ-treated H0-1 cells. In the case of c-myc, expression was dramatically reduced in IFN-β+MEZ-treated cultures and reduced to a lesser extent in MPA+MEZ- and RA+MEZ-treated cultures. These results suggest that the hierarchy for inducing c-jun, jun-B, and c-myc gene expression changes in H0-1 cells is IFN-β+MEZ>MPA+MEZ>RA+MEZ. As will be discussed, this same pattern of potency in inducing gene expression changes in H0-1 cells is also observed with a number of additional genes. Treatment of H0-1 cells for 96 h with the combination of IFN-β+MEZ, MPA+MEZ, or RA+MEZ resulted in the enhanced expression of the cytokine-responsive genes HLA Class I antigen and gro/MGSA (FIG. 2). In contrast, treatment with IFN-β, MEZ, MPA, or RA alone did not significantly alter HLA Class I antigen gene expression or induce gro/MGSA gene expression. Treatment of H0-1 cells for 96 h with IFN-γ, alone or in combination with IFN-β, also enhanced HLA Class I antigen expression in H0-1 cells, whereas it did not induce gro/MGSA expression (FIG. 2). In contrast, although a 96-h exposure of H0-1 cells to IFN-γ, alone and in combination with IFN-β, enhanced expression of the HLA Class II antigen gene (HLA-DR$_β$), expression of this gene was not significantly enhanced by treatment with IFN-β+MEZ, MPA+MEZ, or RA+MEZ (FIG. 2). These observations indicate possible autocrine loops involving both a type I interferon (leukocyte interferon IFN-α) and IFN-β as opposed to a type II interferon (IFN-γ) and gro/MGSA in the induction of gene expression changes occurring during both reversible (MPA+MEZ and RA+MEZ) and terminal cell differentiation (IFN-β+MEZ).

To determine if an interferon or an interferon-like molecule might be associated with the induction of reversible or irreversible differentiation or both in H0-1 cells, the effect of the various differentiation-inducing and growth-suppressing agents on expression of the interferon-responsive genes, ISG-15 and ISG-54 (25, 31, 32) were determined. As can be seen in FIG. 2, treatment of H0-1 cells for 96 h with the combination of IFN-β+MEZ, MPA+MEZ, or RA+MEZ resulted in the induction in ISG-15 and ISG-54 gene expression.

Further support for a type I interferon and a gro/MGSA autocrine loop in the reversible commitment to differentiation (MPA+MEZ) and terminal cell differentiation (IFN-β+MEZ) processes in H0-1 cells was indicated by analysis of gene expression changes occurring in cultures treated with inducers for 24 h or in cultures treated with inducers for 24 h followed by growth in the absence of inducers for 72 h (FIG. 3). Growth of H0-1 cells for 24 h in the presence of IFN-β+MEZ resulted in the induction or enhanced expression of the gro/MGSA, HLA Class I antigen, and ISG-15 gene. Similarly, a 24-h treatment with MPA+MEZ induced expression of gro/MGSA to a similar extent as IFN-β+MEZ, whereas the effects on HLA Class I antigen and ISG-15 expression were more modest. In contrast, a 24-h treatment with RA+MEZ or a high dose of MEZ did not induce gro/MGSA or ISG-15 expression, but these treatments did induce a modest increase in HLA Class I antigen expression (FIG. 3). Treatment of H0-1 cells for 24 h with inducer (IFN-β+MEZ, MPA+MEZ, RA+MEZ or a high dose of MEZ) followed by growth for 72 hours in the absence of inducer resulted in the following changes in H0-1 gene expression: (1) gro/MGSA was induced only by IFN-β+MEZ treatment; (2) enhanced HLA Class I antigen expression was induced by all of the treatments with the following potencies, IFN-β+MEZ>MPA+MEZ≧high dose MEZ>RA+MEZ; and (3) ISG-15 was induced to a similar extent by IFN-β+MEZ and MPA+MEZ, whereas RA+MEZ and high-dose MEZ did not induce ISG-15 expression.

Figure 4:
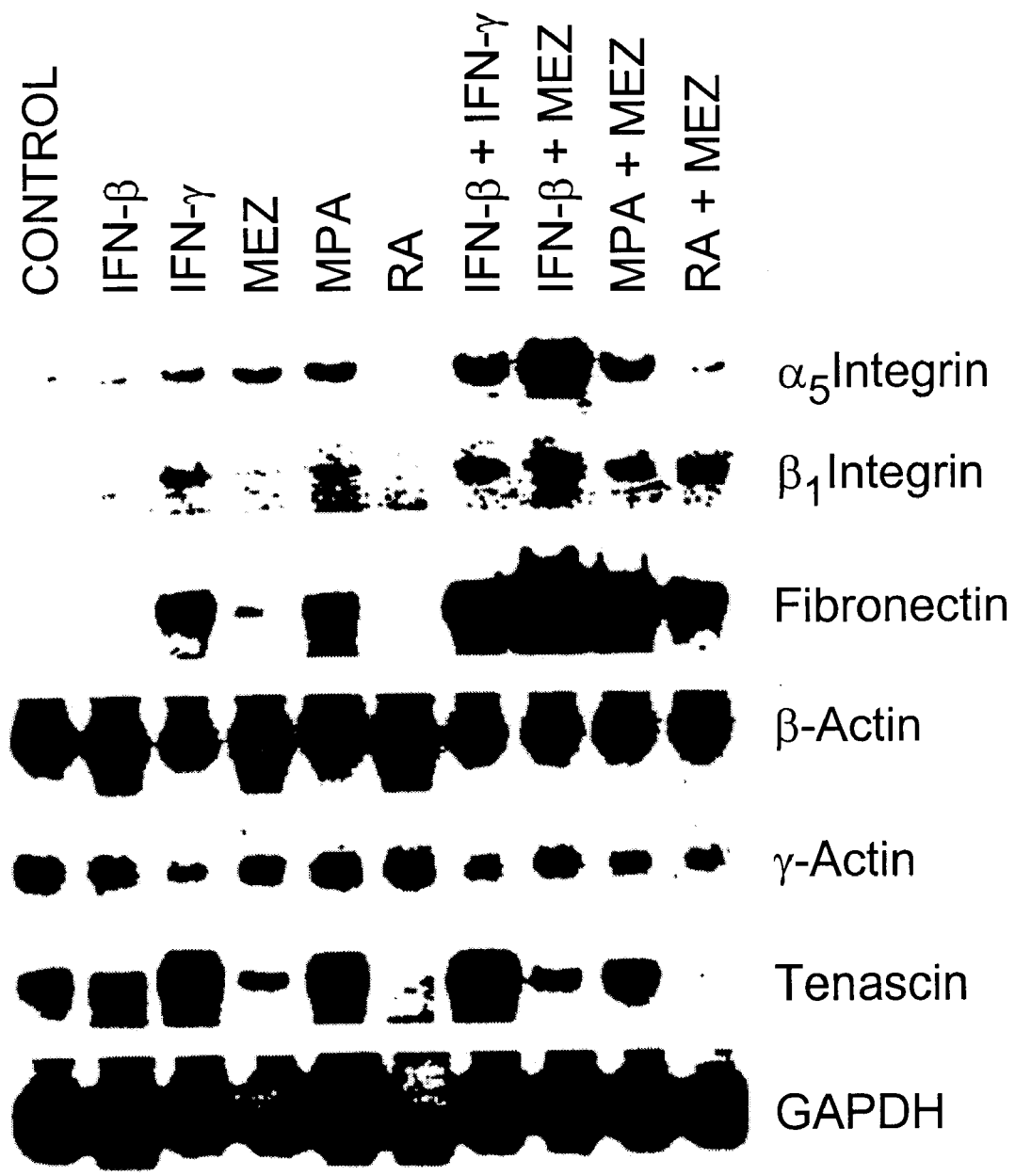
FIG. 4 Effect of growth and differentiation modulating agents on steady-state $α_5$ integrin, $β_1$ integrin, fibronectin, β-actin, γ-actin, tenascin, and GAPDH mRNA levels in H0-1 cells. Total RNA was isolated 96 h after treatment with the various agents. The concentrations of compounds used were the same as those used for growth studies (see legend to FIG. 1). Ten micrograms of total RNA was electrophoresed, transferred to nylon filters, and hybridized with the indicated $^{32}$P-labeled gene probes. Further details can be found in Materials and Methods of the first series of experiments.
Figure 5:
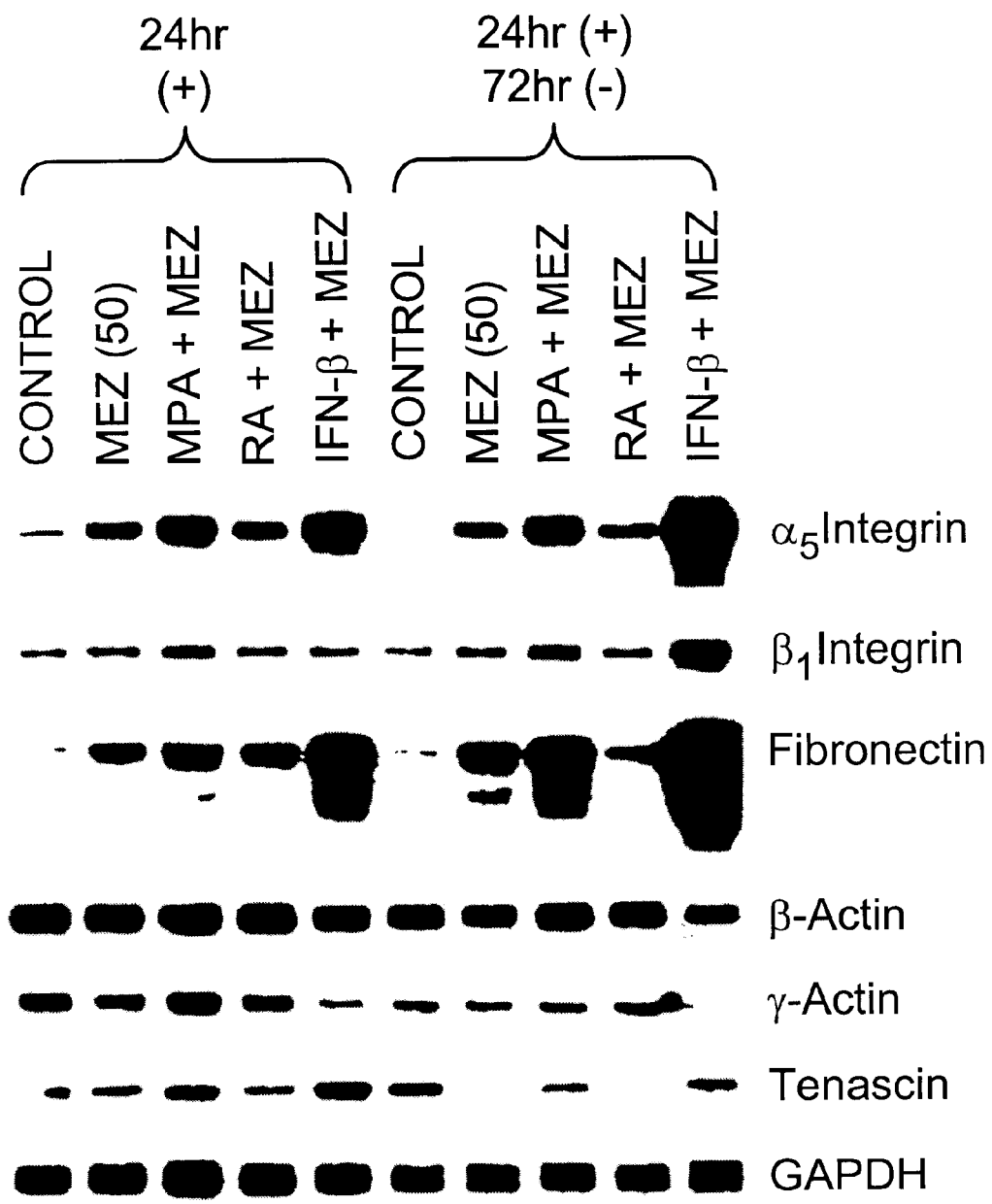
FIG. 5 Effect on gene expression in H0-1 cells of continuous and transient exposure to agents, inducing a reversible commitment to differentiation or terminal cell differentiation. Experimental details are described in the legend to FIG. 3 and in Materials and Methods of the first series of experiments.

Chances in the Expression of Extracellular and Extracellular Matrix Receptor Genes During Reversible and Irreversible Growth Suppression (Terminal Cell Differentiation) in H0-1 Cell Terminal differentiation in H0-1 cells induced by IFN-β+MEZ is associated with morphologic changes resulting in the formation of dendrite-like processes and specific biochemical changes, that is, enhanced tyrosinase activity and melanin synthesis (6). Similar morphologic and biochemical changes are induced in H0-1 cells by MEZ (6, 8) and MPA (11). Studies were conducted to determine the possible relationship between these morphologic and biochemical changes and the expression of genes encoding extracellular matrix molecules (fibronectin and tenascin), receptors for extracellular matrix proteins ($\alpha_5$ integrin and $\beta_1$ integrin), and cytoskeleton proteins (β-actin and γ-actin). When treated for 96 h, fibronectin expression was increased under all treatment protocols, with IFN-β and RA being the least effective agents in inducing enhanced fibronectin mRNA in H0-1 cells (i.e. signals were only detected after long exposures of Northern blots) (FIG. 4 and data not shown). The most effective single agents resulting in enhanced fibronectin expression were IFN-γ and MPA, whereas MEZ was less potent in inducing enhanced fibronectin expression (FIG. 4). Large increases in fibronectin expression were also observed in H0-1 cells grown for 96 h in the combination of IFN-β+IFN-γ, IFN-β+MEZ, MPA+MEZ, and RA+MEZ. IFN-β+MEZ was more effective than MPA+MEZ, RA+MEZ, or a high dose of MEZ in inducing enhanced fibronectin expression after 24-h treatment (FIG. 5). IFN-β+MEZ also enhanced fibronectin expression to a greater extent than MPA+MEZ, RA+MEZ, and a high dose of MEZ after removing this combination of inducers and growth for 72 h in medium devoid of the inducing agents (FIG. 5).

Expression of the tenascin gene in H0-1 cells treated with the various differentiation-inducing and growth-suppressing agents was more complex than fibronectin (FIGS. 4 and 5). Growth of H0-1 cells for 96 h in the presence of IFN-β, MEZ, RA, IFN-β+MEZ, or RA+MEZ resulted in decreased tenascin expression whereas IFN-γ, MPA, and IFN-β+IFN-α resulted in enhanced tenascin expression (FIG. 4). Ninety-six-hour treatment with IFN-γ, alone or in combination with IFN-β, resulted in the greatest increase in tenascin expression. In contrast, after a 24-h treatment, tenascin expression was not significantly altered by a high dose of MEZ or RA+MEZ, whereas a small increase in tenascin expression was found in IFN-β+MEZ- and MPA+MEZ-treated cultures (FIG. 5). When cultures were treated for 24 h with inducer and then grown for 72 h in the absence of inducer, decreased expression of tenascin was observed in high-dose MEZ- and RA+MEZ-treated cultures, whereas only small reductions in tenascin expression were apparent in MPA+MEZ- or IFN-β+MEZ-treated H0-1 cells (FIG. 5).

Changes were also observed in the expression of matrix receptor genes for extracellular matrix proteins, $\alpha_5$-integrin, $\beta_1$-integrin in H0-1 cells grown for (1) 24 h in the presence of the inducer(s), (2) 24 h in inducer(s) followed by 72 h in the absence of inducer(s), or (3) continuously in inducer(s) for 96 h (FIGS. 4 and 5). Increases were observed in $\alpha_5$ integrin expression in H0-1 cells treated for 96 h with IFN-β+IFN-γ, IFN-β+MEZ, MPA+MEZ and, to a lesser extent, with RA+MEZ (FIG. 4). Increased $\alpha_5$ integrin expression was also apparent in H0-1 cells treated continuously for 24 hrs or treated for 24 hrs followed by 72 hr growth in the absence of inducer(s) to a high dose of MEZ, MPA+MEZ, RA+MEZ, or IFN-β+MEZ. In contrast, $\alpha_5$ integrin expressed was reduced in cultures treated with RA for 96 h. In the case of the $\beta_1$ integrin, upregulation after 96-h treatment was apparent in cells treated with IFN-γ, IFN-β+MEZ, MPA+MEZ, and RA+MEZ (FIG. 4). The most effective inducer of both $\alpha_5$ and $\beta_1$ integrin expression in H0-1 cells was IFN-β+MEZ (FIGS. 4 and 5). The level of upregulation was greater for $\alpha_5$ integrin than the $\beta_1$ integrin (FIGS. 4 and 5).

The effect of the various growth-suppressing and differentiation-modulating compounds on expression of cytoskeletal genes (β-actin and γ-actin) in H0-1 cells is shown in FIGS. 4 and 5. Under most experimental conditions, only small changes were observed in β-actin and γ-actin mRNA levels. In the case of 96-h-treated cultures, both β-actin and, to a greater extent, γ-actin expression were decreased by treatment with a number of agents, resulting in growth suppression. In contrast, RA, which is not growth suppressive in H0-1 cells, did not significantly alter the expression of these cytoskeletal genes. A common change that was generally most pronounced under all three experimental protocols in H0-1 cells, that is, 24-h treatment, 24-h treatment followed by 72-h growth in the absence of inducer, or continuous treatment for 96 h, was the reduction in β-actin and γ-actin expression by IFN-β+MEZ.

Figure 6:
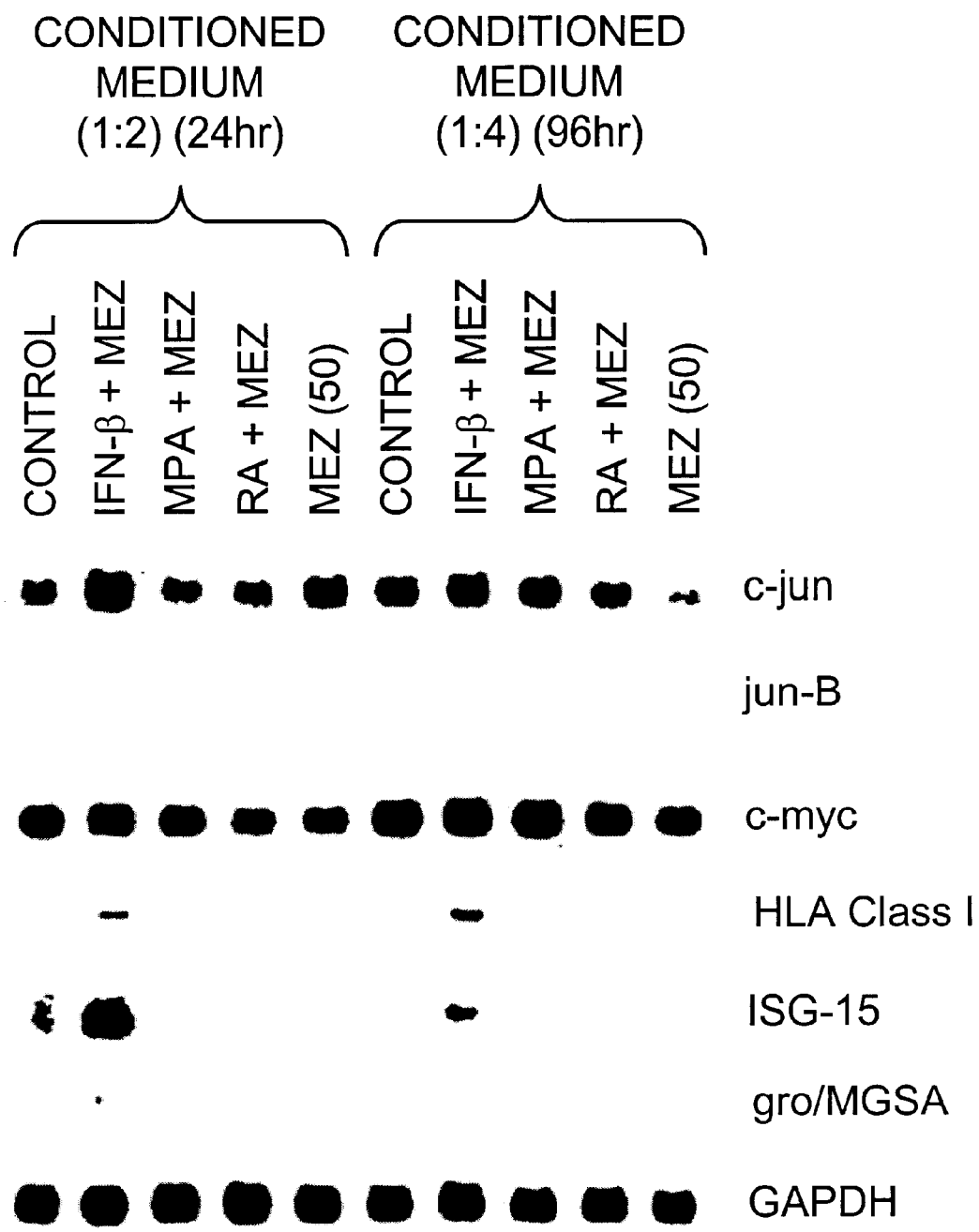
FIG. 6 Effect of conditioned medium from H0-1 cells treated with agents, resulting in a reversible commitment to differentiation or terminal cell differentiation on gene expression in naive H0-1 cells. H0-1 cells were untreated (Control) or treated for 24 h with IFN-β+MEZ (2,000 U/ml+10 ng/ml), MPA+MEZ (3.0 μM+10 ng/ml), RA+MEZ (2.5 μM+10 ng/ml), or MEZ (50) (50 ng/ml). The medium was then removed, the cultures were washed three times with serum-free medium, and grown for an additional 72 h in complete growth medium. The conditioned medium was then collected, and contaminating cells were removed by centrifugation. Conditioned medium was mixed with an equal volume of DMEM-10 (1:2), left panel CONDITIONED MEDIUM (1:2) (24 h), and applied to previously untreated (naive) H0-1 cells for 24 h. Alternatively, conditioned medium was mixed with three parts of DMEM-10 (1:4), right panel CONDITIONED MEDIUM (1:4) (96 h), and applied to previously untreated (naive) H0-1 cells for 96 h. Total RNA was isolated and analyzed by Northern blotting with the DNA probes indicated. Further details can be found in Materials and Methods of the first series of experiments.
Figure 7:
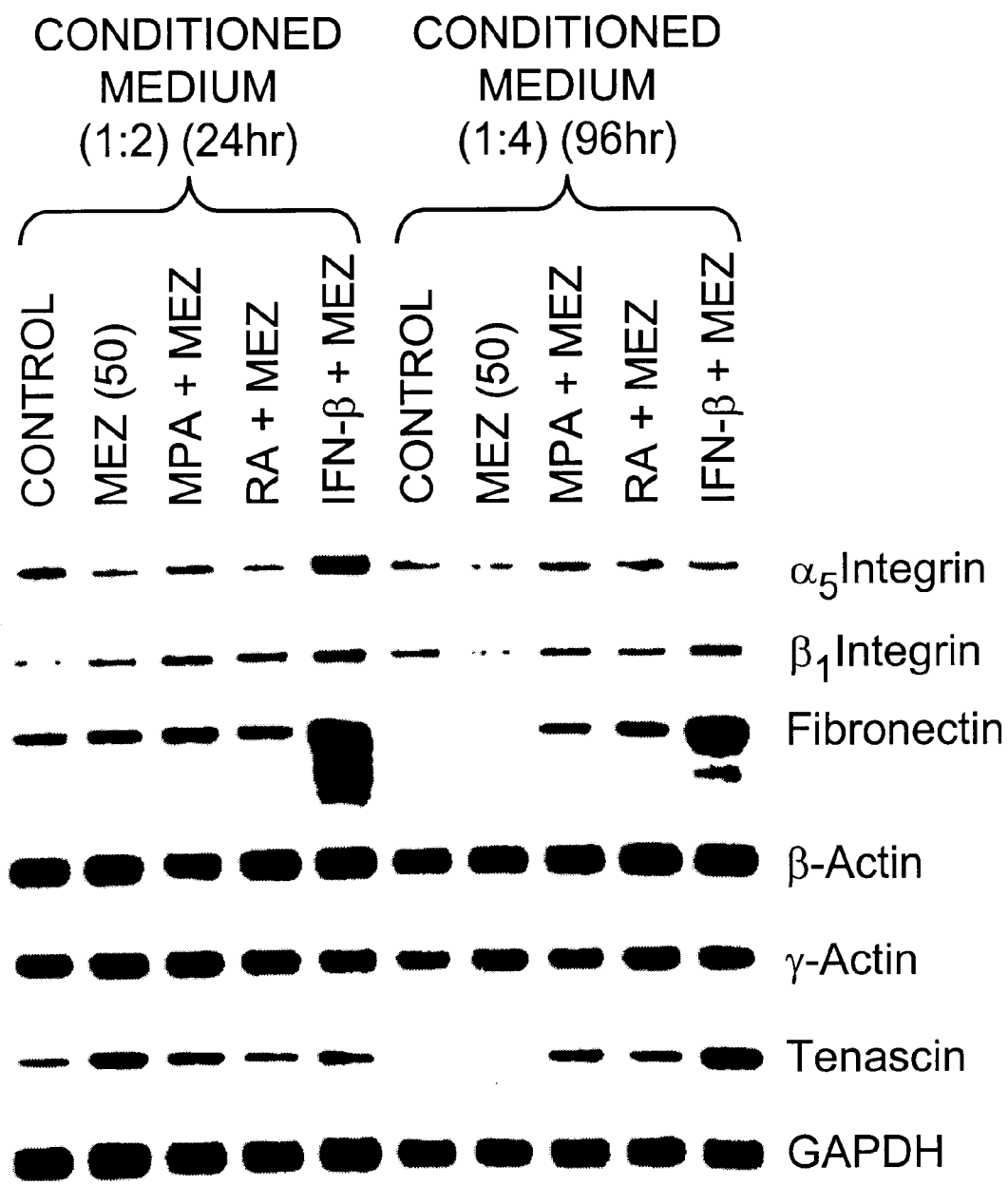
FIG. 7 Effect of conditioned medium from H0-1 cells treated with agents, resulting in a reversible commitment to differentiation or terminal cell differentiation on extracellular matrix, extracellular matrix receptor, and cytoskeletal gene expression in naive H0-1 cells. Experimental details are as described in the legend to FIG. 6 and in Materials and Methods of the first series of experiments.

Modulation of Gene Expression in H0-1 Cells by Conditioned Medium Obtained from Differentiation-Inducer-Treated H0-1 Cells The studies described previously demonstrated that interferon-responsive genes and the gro/MGSA gene were activated during the process of reversible and irreversible differentiation in H0-1 cells. They further suggested the possibility of an involvement of autocrine-feedback pathways in the differentiation process (FIGS. 2 and 3). To determine directly if H0-1 cells treated with agents inducing a reversible commitment to differentiation (a high dose of MEZ, RA+MEZ, and MPA+MEZ) and/or terminal cell differentiation (IFN-β+MEZ) secrete factor(s) that can modulate gene expression in H0-1 cells, conditioned medium was collected from cells treated for 24 h with the inducer followed by growth for 72 h in the absence of inducer (FIGS. 6 and 7). H0-1 cells were grown in an equal volume of conditioned medium plus and equal volume of DMEM-10 (1:2) for 24 h or with 1 vol of conditioned medium plus 3 vol of DMEM-10 (1:4) for 96 h. Total cytoplasmic RNA was then isolated and analyzed by Northern blotting for the expression of a series of early growth response, interferon responsive, extracellular matrix, extracellular matrix receptor, and cytoskeletal genes (FIGS. 6 and 7). With the exception of fibronectin and small increases in $\beta_1$ integrin expression, treatment for 24 h with 1:2 conditioned medium obtained from the other experimental conditions (which result in a reversible commitment to differentiation) did not alter or induce expression of the genes tested, including c-jun, jun-B, c-myc, gro/MGSA, HLA Class I antigen, ISG-15, $\alpha_5$ integrin, β-actin, γ-actin, or tenascin. Exposure of H0-1 cells for 96 h to 1:4 conditioned medium obtained from IFN-β+MEZ-treated H0-1 cells also enhanced fibronectin, HLA Class I antigen, $\beta_1$ integrin and tenascin expression, as well as inducing ISG-15 expression. With the exception of fibronectin and tenascin, which were enhanced by 1:4 conditioned medium obtained from 24-h treated IFN-β+MEZ, MPA+MEZ, RA+MEZ treated cultures, no modification in the expression of the various genes was apparent using 1:4 conditioned medium from any of the experimental procedures.

The H0-1 human melanoma cell line can be chemically induced to reversibly express specific markers of differentiation or to undergo terminal cell differentiation. The present study was undertaken to determine which specific programs of gene expression are modified as a consequence of these cellular alterations. Inductions of terminal differentiation, and, to a lesser extent, reversible differentiation, was associated with changes in the expression specific immediate early response, interferon-responsive, cytokine-responsive, extracellular matrix, and extracellular matrix receptor genes. In addition, conditioned medium obtained from H0-1 cells treated with IFN-β+MEZ also resulted in similar changes in gene expression in naive H0-1 cells as those observed following direct exposure to the chemical inducers of terminal differentiation. These results indicate that common gene-expression changes are associated with both the reversible and irreversible induction of differentiation in H0-1 cells. In addition, the terminal differentiation process is correlated with the activation of several autocrine pathways involving both IFN-β and gro/MGSA.

Immediate early response genes, such as c-myc, c-fos, c-jun, jun-B, and jun-D, have been shown to be involved in the regulation of growth and/or differentiation in other model systems [33–35]. In the case of c-myc, a reduction in expression of this gene is observed in many cell types either induced to terminally differentiate or under conditions resulting in a reduction in cellular growth without the induction of differentiation-related genes (36–40). A direct role of c-myc expression in regulating differentiation in a variety of model cell culture systems has also been demonstrated using c-myc antisense constructs or oligomers (41–45). In specific systems, the downregulation of c-myc expression by antisense constructs or oligomers has been shown to result in differentiation and growth suppression in the absence of inducing agents (45–48). Induction of both reversible differentiation and, to a greater extent, terminal differentiation in H0-1 cells resulted in decreased c-myc expression. Downregulation of c-myc expression was independent of growth suppression, as indicated by the enhanced expression of c-myc in IFN-β+IFN-γ treated cells, even though this combination of agents resulted in maximum growth suppression without the induction of any morphologic or biochemical markers of melanoma differentiation. Based on the temporal relationship and the magnitude of c-myc downregulation by the various inducing agents, continued suppression of c-myc expression may be required for the induction of terminal differentiation in H0-1 cells. Studies using antisense c-myc constructs should prove valuable in directly addressing the relationship between c-myc expression and terminal differentiation in H0-1 cells.

Two immediate early response genes, c-fos and c-jun, code for transcription factors involved in nuclear signal transduction (35, 46, 47). Expression of these genes can be induced by many external stimuli, including cytokines, growth factors, serum, phorbol esters, neurotransmitters, and viral infection (35, 46, 47). The proteins c-fos and c-jun can form a heterodimer as part of the AP-1 transcription-factor complex that binds efficiently to AP-1 sites (TGA$_G$/$_C$TCA) in DNA (35, 46, 47). Previous studies have indicated that both the c-jun and c-fos genes are activated during monocytic differentiation induced by TPA, macrophage colony-stimulating factor (M-CSF), and okadaic acid (48–50). Elevation of AP-1 activity also has been demonstrated during the induction of differentiation of F9 embryonal carcinoma stem cells by RA (51). In contrast the transcriptional enhancing activity of c-jun, jun-B (which is induced by a number of external stimuli that also induce c-jun) functions as a negative regulator of several genes normally activated by c-jun (52, 53). In the process of monocytic differentiation induced by TPA in human cells, jun-B gene transcription, steady-state mRNA levels, and mRNA stability are enhanced (54). Similarly, jun-B expression is enhanced during the process of monocytic differentiation induced in murine cells by serum-free conditioned medium from mouse lungs (55). Induction of growth suppression and both reversible and irreversible differentiation in H0-1 cells are unaltered at later time points. Unlike TPA-induced monocytic differentiation (48, 54), induction of jun-B expression by IFN-β+MEZ in H0-1 cells is regulated only at the transcriptional level (56). These data indicate that enhanced expressions of c-jun and jun-B in H0-1 cells is not directly related to the induction of terminal differentiation in H0-1 cells. A sustained elevation of c-jun and jun-B expression, however, may be components of the differentiation program in H0-1 cells.

The process of cellular differentiation is frequently associated with profound changes in cellular morphology that are related to cell—cell and cell-extracellular matrix interactions as well as the expression of cell growth and cytoskeletal genes (57). In addition, cell shape and cell-extracellular matrix interactions also play important roles in the process of tumorigenesis and metastasis (58, 59). Transformed cells often exhibit reductions in fibronectin expression as well as decreases in expression of specific integrin genes, which encode receptors for extracellular matrix proteins (60, 61). Of particular recent interest is the $\alpha_5\beta_1$ integrin complex that appears to be the major receptor for fibronectin (62). Decreases in $\alpha_5$ $\beta_1$ expression have been found in oncogenically transformed cells (60) and overexpression of the combination of $\alpha_5$ and $\beta_1$ integrin cDNA in Chinese hamster ovary (CHO) cells results in a direct suppression of the transformed phenotype (61). Agents that induced reversible differentiation (MPA+MEZ and RA+MEZ), irreversible differentiation (IFN-$\beta$+MEZ), and increased growth suppression without inducing markers of differentiation (IFN-$\beta$+IFN-$\gamma$) in H0-1 cells enhanced fibronectin, $\alpha_5$ integrin, and $\beta_1$ integrin expression. These findings suggest that the specific combinations of cytokines, such as IFN-$\beta$+IFN-$\gamma$, resulting in growth suppression and combinations of agents that induce either a reversible commitment to differentiation or terminal differentiation in H0-1 cells, can directly modify extracellular matrix and extracellular matrix receptor gene expression. The changes induced in these genes by these agents reflect a more normal, as opposed to the original, transformed cellular phenotype. In this context, it is also worth commenting on changes induced tenascin expression as a consequence of treatment with the various differentiation-inducing and/or growth-suppressing agents. Tenascin is an extracellular-matrix protein expressed (or prominently expressed) in specialized embryonic tissues, cells of neuroectodermal origin, and tumors (63). In general, tenascin is expressed at higher levels in undifferentiated vs. differentiated tumors (63). H0-1 cells express tenascin, and its level of expression is increased by IFN-$\gamma$, alone or in combination with IFN-$\beta$, whereas its expression is reduced by treatment with IFN-$\beta$, MEZ, or RA or by continuous growth in the combination of IFN-$\beta$+MEZ or RA +MEZ. These results provide further evidence that the continuous treatment of H0-1 cells for 96 h with specific differentiation-inducing agents can result in acquisition of a more differentiated cellular phenotype by these human melanoma cells.

Studies analyzing the mechanism of growth arrest during the process of differentiation in hematopoietic cells have implicated IFN-$\beta$ as an autocrine growth inhibitor important in this process (39, 64, 65). Supporting evidence for the involvement of autocrine IFN-$\beta$ in the differentiation process of hematopoietic cells include (1) the ability of IFN-$\beta$ antibody, but not IFN-$\alpha$ antibody, to partially block the reduction in c-myc mRNA and growth inhibition associated with the differentiation process; (2) the induction of interferon regulatory factor 1 (IRF-1), which is a positive transcription factor for expression of the IFN-$\beta$ gene, during the myeloid differentiation process; (3) the ability of IRF-1 antisense oligomers to partially block growth inhibition associated with IL-6 and leukemia inhibitory factor induction of differentiation; and (4) the induction of type I interferon (IFN-$\alpha$/$\beta$) gene expression during terminal differentiation in hematopoietic cells (39, 64, 65). A potential IFN-$\beta$ autocrine loop in the induction of specific programs of reversible and irreversible differentiation in human melanoma cells is also suggested by the experiments described in this article. Reversible differentiation, resulting from treatment with MPA+MEZ and RA+MEZ, and terminal cell differentiation, resulting from growth in IFN-$\beta$+MEZ, results in the enhanced expression of type I interferon-responsive genes, including HLA Class I antigen, ISG-15, and ISG-54. These same gene expression changes occur in H0-1 cells treated with conditioned medium obtained from IFN-$\beta$+MEZ treated H0-1 cells. In addition, conditioned medium induces growth suppression in H0-1 cells and IFN-$\beta$ antibodies partially block the induction by conditioned medium of ISG-15 in H0-1 cells (56). Attempts to quantitate IFN-$\beta$ in conditioned medium form inducer-treated H0-1 cells have not been successful (66). A possible reason for the lack of quantifiable IFN-$\beta$ in H0-1 inducer-treated conditioned medium could be the presence of INF-$\beta$ below the sensitivity of detection of the assay system, that is, level of IFN-$\beta$ below 2 U/ml. In this respect, the differentiating H0-1 system may be similar to hematopoietic cells induced to terminally differentiate by treatment with various inducers that also produce small quantities of high specific-activity autocrine IFN-$\beta$ (39). Further studies are required to characterize the putative autocrine IFN-$\beta$ produced by differentiating human melanoma cells and to determine its potential role in both the reversible commitment to differentiation and terminal differentiation in human melanoma cells. The present studies support the hypothesis that autocrine IFN-$\beta$ may also contribute to the differentiation process in solid tumors.

Analysis of gene expression changes resulting from exposure to IFN-$\beta$+MEZ and conditioned medium from H0-1 cells treated with these inducers suggests the presence of additional autocrine factors produced during the differentiating process in H0-1 cells. One of these putative autocrine factors is the previously identified melanoma growth factor termed MGSA (67). MGSA has been identified in the serum-free growth medium obtained from low-density cultures of the human malignant cell line Hs294T (67). The gene for MGSA has been cloned (68) and the deduced amino acid sequence for human MGSA is identical to that of the human "gro" cDNA isolated by Anisowicz et al. (69), now referred to as gro/MGSA. gro/MGSA is secreted by ~70% of primary cell cultures derived from human melanoma biopsies and by a majority of benign nevus cells with chromosomal abnormalities, whereas benign nevus cells with a normal karyotype are negative for MGSA production (70, 71). The level of gro/MGSA mRNA is enhanced in human melanoma cells treated with MGSA, indicating a potential autocrine function for this molecule (68); gro-$\alpha$ and gro-$\beta$ have also been shown to be primary response genes that are induced as a result of IL-1-mediated growth arrest in human melanoma cells (72). In addition, the expression and secretion of MGSA is strongly induced in other cell types, including human endothelial cells treated with a number of agents such as IL-1, TNF, lipopolysaccharide, thrombin, or TPA (73). These observations suggest that gro/MGSA production is not restricted to human melanoma cells and, in addition to stimulating the growth of specific melanoma cells, gro/MGSA may also play a role in the inflammation process. Applicants presently demonstrate that gro/MGSA gene expression is induced in H0-1 cells during specific programs of reversible differentiation and during terminal cell differentiation. In contrast, growth arrest, without the induction of biochemical or cellular markers of differentiation, does not result in gro/MGSA induction. The ability of conditioned medium obtained from IFN-$\beta$+MEZ-treated H0-1 cells to induce gro/MGSA in naive H0-1 cells suggests that gro/MGSA may be produced during the induction of terminal cell differentiation in H0-1 cells. At present the function of gro/MGSA (which is structurally related to a number of additional genes, including platelet factor-4, $\beta$-thromboglobulin, connective tissue-activating peptide-3, and the murine KC gene) in melanoma development is not clear. The present data suggest, however, that in addition to its growth stimulatory effect on human melanoma cells, gro/MGSA may also play a role in melanoma cell differentiation.

In summary, the H0-1 cells culture system has been used to analyze the molecular changes associated with the reversible commitment to differentiation and terminal cell differentiation in human melanoma cells. Evidence is presented indicating that induction of both processes may involve overlapping gene expression changes. However, the magnitude of the changes and the persistence of the changes suggest a potential involvement of defined programs of gene expression alterations in the induction and maintenance of the terminal cells differentiation phenotype of human melanoma cells. Although their precise roles in melanoma cell growth and differentiation are not presently known, data are also presented that indicate that induction of differentiation results in the production of autocrine factors, including IFN-β and gro/MGSA. Further studies are required to define the functional significance of specific gene expression changes and specific autocrine factors in the process of terminal cells differentiation in human melanoma cells. This information will be important in understanding the process of melanoma development and evolution and may result in the identification of novel target genes and molecules that could prove useful in the therapy of this neoplastic disease. In addition, the H0-1 differentiation model system appears ideally suited for the identification and cloning of genes involved in the induction and maintenance of loss of proliferative capacity and terminal cell differentiation in human melanoma cells.

REFERENCES FOR FIRST SERIES OF EXPERIMENTS

1. Clark, W. H., Jr., The Skin. In: Rubin, E. and Farber, J. L., Eds., Pathology, Lippincott Press Inc., New York, pp. 1194–1259. 1988.
2. Waxman, S., Rossi, G. B., and Takaku, F., Eds., The Status of Differentiation Therapy of Cancer, Vol. 1, 45:1–422, Serono Symposia Pubs., Raven Press, New York, 1988.
3. Ahmed, M. A., Nielsch, U., Guarini, L., Hermo, H., Jr., and Fisher, P. B., Modulation of differentiation: a potential mechanism by which interferons induce antitumor activity. IN: Fisher, P. B., Ed., Mechanisms of Differentiation: Modulation of Differentiation by Exogenous Agents, Vol. II, CRC Press, Boca Raton, Fla., pp. 1–56, 1990.
4. Fisher, P. B. and Rowley, P. T., Regulation of growth, differentiation, and antigen expression in human tumor cells by recombinant cytokines: Applications for the differentiation therapy of human cancer. In: Waxman, S., Rossi, G. B., and Takaku, F., Eds., The Status of Differentiation Therapy of Cancer, Vol. 2, 82:201–214, Serono Symposia Pubs., Raven Press, New York, 1991.
5. Waxman, S., Rossi, G. B., and Takaku, F., Eds., The Status of Differentiation Therapy of Cancer, vol. 2, 82:1–451, Serono Symposia Pubs., Raven Press, New York, 1991.
6. Fisher, P. B., Prignoli, D. R., Hermo, H., Jr., Weinstein, I. B., and Pestka, S., Effects of combined treatment with interferon and mezerein on melanogenesis and growth in human melanoma cells, J. Interferon Res., 5:11–22, 1985.
7. Fisher, P. B., Hermo, H., Jr., Solowey, W. E., Dietrich, M. C., Edwalds, G. M., Weinstein, I. B., Langer, J. A., Pestka, S., Giacomini, P., Kusama, M., and Ferrone, S., Effect of recombinant human fibroblast interferon and mezerein on growth, differentiation, immune interferon binding and tumor associated antigen expression in human melanoma cells. Anticancer Res., 6:765–774. 1986.
8. Huberman, E., Heckman, C., and Langenbach, R., Stimulation of differentiated functions in human melanoma cells by tumor-promoting agents and dimethyl sulfoxide. Cancer Res., 39:2618–2624, 1979.
9. Guarini, L., Temponi, M., Edwalds, G. M., Vita, J. R., Fisher, P. B., and Ferrone, S., In vitro differentiation and antigenic changes in human melanoma cell lines. Cancer Immunol. Immunother., 30:363–370, 1989.
10. Guarini, L., Graham, G. M., Jiang, H., Ferrone, S., Zucker, S., and Fisher, P. B., Modulation of the antigenic phenotype of human melanoma cells by differentiation-inducing and growth-suppressing agents. Pigment Cell Res. Suppl., 2:123–131, 1992.
11. Kiguchi, K., Collart, F. R., Henning-Chub, C., and Huberman, E., Induction of cell differentiation in melanoma cells by inhibitors of IMP dehydrogenase: altered patterns of IMP dehydrogenase expression and activity. Cell Growth Differ., 1:259–270, 1990.
12. Graham, G. M., Guarini, L., Moulton, T. A., Datta, S., Ferrone, S., Giacomini, P., Kerbel, R. S., and Fisher, P. B., Potentiation of growth suppression and modulation of the antigenic phenotype in human melanoma cells by the combination of recombinant human fibroblast and immune interferon. Cancer Immunol. Immunother., 32:382–390, 1991.
13. Giovanella, B. C., Stehlin, J. S., Santamaria, C., Yim, S. O., Morgan, A. C., Williams, L. J., Leibovitz, A., Fialkow, P. Y., and Mumford, D. M., Human neoplastic and normal cells in tissue culture. I. Cell lines derived from malignant melanomas and normal melanocytes. J. Natl. Cancer Inst., 56:1131–1142, 1976.
14. Reddy, P. G., Graham, G. M., Datta, S., Guarini, L., Moulton, T. A., Jiang, H., Gottesman, M. M., Ferrone, S., and Fisher, P. S., Effect of recombinant fibroblast interferon and recombinant immune interferon on growth and the antigenic phenotype of multidrug-resistant human glioblastoma multiforme cells. J. Natl. Cancer Inst., 83:1307–1315, 1991.
15. Su, Z.-Z., Grunberger, D., and Fisher, P. B., Suppression of adenovirus type 5 E1A-mediated transformation and expression of the transformed phenotype by caffeic acid phenethyl ester (CAPE). Mol. Carcinogenesis, 4:231–242, 1991.
16. Jiang, H., Su, Z.-Z., Datta, S., Guarini, L., Waxman, S., and Fisher, P. B., Fludarabine phosphate selectively inhibits growth and modifies the antigenic phenotype of human glioblastoma multiforme cells expressing a multidrug resistance phenotype. Int. J. Oncol., 1:227–239, 1992.
17. Erba, H. P., Gunning, P., and Kedes, L., Nucleotide sequence of the human γ-cytoskeletal actin mRNA: anomalous evolution of vertebrate non-muscle actin genes. Nucleic Acid Res., 14:5275–5294, 1986.
18. Angel, P., Allegretto, E. A., Okino, S. T., Hattori, K., Boyle, W. J., Hunter, T., and Karin, M., Oncogene jun encodes a sequence-specific trans-activator similar to AP-1. Nature (London), 332:166–171, 1988.
19. Dalla-Favera, R., Martinotti, S., Gallo, R. C., Erikson, J., and Croce, C. M., Translocation and rearrangements of the c-myc oncogene locus in human undifferentiated B-cell lymphomas. Science, 219:963–967, 1983.
20. Schwarzbauer, J. W., Tamkun, J. W., Lemischka, I. R., and Hynes, R. O., Three different fibronectin mRNAs arise by alternate splicing within the coding region. Cell, 35:421–431, 1983.
21. Cochran, B. H., Reffel, A. C., and Stiles, C. D., Molecular cloning of gene sequences regulated by platelet-derived growth factor, Cell, 33:939–947, 1983.
22. Maio, M., Gulwani, B., Langer, J. A., Kerbel, R. S., Duigou, G. J., Fisher, P. B., and Ferrone, S., Modulation by interferons of HLA antigens, high molecular weight-melanoma associated antigens and intercellular adhesion molecule-1 expression by cultured melanoma cells with different metastatic potential. Cancer Res., 49:2980–2987, 1989.
23. Schreiner, C. L., Bauer, J. S., Danilov, Y. N., Hussein, S., Sczekan, M. M., and Juliano, R. L., Isolation and characterization of Chinese hamster ovary cell variants defi- 23. cient in the expression of fibronectin receptor. J. Cell Biol., 109:3157–3167, 1989.
24. DeSimone, D. W., Patel, V., and Hynes, R. O., Unpublished data.
25. Larner, A. C., Jonak, G., Cheny, Y.-S. E., Korant, B., Knight, E., and Darnell, J. E., Jr., Transcriptional induction of two genes in human cells by α-interferon. Proc. Natl. Acad. Sci. U.S.A., 81:6733–6737, 1984.
26. Ryder, K., Lau, L. F., and Nathans, D., A gene activated by growth factors is related to the oncogene v-jun. Proc. Natl. Acad. Sci. U.S.A., 85:1487–1491, 1988.
27. Gulcher, J. R., Nies, D. E., Marton, L. S., and Stafansson, K., An alternatively spliced region of the human hexabrachion contains a repeat of potential N-glycosylation sites. Proc. Natl. Acad. Sci. U.S.A., 86:1588–1592, 1989.
28. Mark, D. V., Lu, S. D., Creasey, A., Yamamoto, R., and Lin, L., Site-specific mutagenesis of the human fibroblast interferon gene. Proc. Natl. Acad. Sci. U.S.A., 81:5662–5666, 1984.
29. Kung, H.-F., Pan, Y.-C. E., Moschera, J., Tsai, K., Bekesi, F., Chang, M., Sugino, H., and Honda, S., Purification of recombinant human immune interferon. Methods Enzymol., 119:435–447, 1986.
30. Rehberg, G., Kelder, B., Hoal, E. G., and Pestka, S., Specific molecular activities of recombinant and hybrid leukocyte interferons. J. Biol. Chem., 257:11497–11502, 1982.
31. Levy, D. E., Kessler, D. S., Pine, R., Reich, N., and Darnell, J. E., Jr., Interferon-induced nuclear factors that bind a shared promoter element correlate with positive and negative control. Genes Dev., 2:383–393, 1988.
32. Schindler, C., Shuai, K., Prezioso, V. R., and Darnell, J. E., Jr., Interferon-dependent tyrosine phosphorylation of a latent cytoplasmic transcription factor. Science, 257:809–813, 1992.
33. DePinho, R. A., Schreiber-Agus, N., and Alt, F. W., Myc family oncogenes in the development of normal and neoplastic cells. In: Vande Woude, G. F., and Klein, G., Advances in Cancer Research, Academic Press, San Diego, Calif., pp. 1–38, 1991.
34. Torres, R., Schreiber-Agus, N., Morgenbesser, S. D., and DePinho, R. A., Myc and max: a putative transcriptional complex in search of a cellular target. Curr. Opinion Cell Biol., 4:468–474, 1992.
35. Kerr, L. D., Inoue, J.-i., and Verma, I. M., Signal transduction: the nuclear target. Curr. Opinion Cell. Biol., 4:496–501, 1992.
36. Lachman, H. M. and Skoultchi, A. I., Expression of c-myc changes during differentiation of mouse erythroleukemia cells. Nature, 310:249–251, 1984.
37. Einat, M., Resnitzky, D., and Kimchi, A., Close link between reduction of c-myc expression by interferon and $G_0/G_1$ arrest. Nature, 313:597–600, 1985.
38. Yarden, A., and Kimchi, A., Tumor necrosis factor reduces c-myc expression and cooperates with interferon-γ in HeLa cells. Science, 234:1419–1421, 1986.
39. Resnitzky, D., Yarden, A., Zipori, D., and Kimchi, A., Autocrine β-related interferon controls c-myc suppression and growth arrest during hematopoietic cell differentiation. Cell, 46:31–40, 1986.
40. Resnitzky, D. and Kimchi, A., Deregulated c-myc expression abrogates the interferon- and interleukin 6-mediated $G_0G_1$ cell cycle arrest but not other inhibitory responses in M1 myeloblastic cells. Cell Growth Differ., 2:33–41, 1991.
41. Grief, A. E., and Westphal, H., Antisense myc sequences induce differentiation of F9 cells. Proc. Natl. Acad. Sci. U.S.A., 85:6806–6810, 1988.
42. Holt, J. T., Redner, R. L., and Nienhuis, A. W., An oligomer complementary to c-myc mRNA inhibits proliferation of HL-60 promyelocytic cells and induces differentiation. Mol. Cell Biol., 8:963–973, 1988.
43. Prochowinik, E. W., Kukowska, J., and Rodgers, C., c-myc antisense transcripts accelerate differentiation and inhibit G1 progression in murine erythroleukemia cells. Mol. Cell Biol., 8:3683–3695, 1988.
44. Yokayama, K. and Imamoto, F., Transcriptional control of the endogenous myc protooncogene by antisense RNA. Proc. Natl. Acad. Sci. U.S.A., 84:7363–7367, 1987.
45. Freytag, S. O., Enforced expression of the c-myc oncogene inhibits cell differentiation by precluding entry into a distinct predifferentiation state in $G_0G_1$. Mol. Cell Biol., 8:1614–1624, 1988.
46. Kouzarides, T. and Ziff, E., The role of the leucine zipper in the fos-jun interaction. Nature, 336:646–651, 1988.
47. Ransone, L. J. and Verma, I. M., Nuclear protooncogenes Fos and Jun. Ann. Rev. Cell Biol., 6:539–557, 1990.
48. Sherman, M. L., Stone, R. M., Datta, R., Bernstein, S. H., and Kufe, D. W., Transcriptional and post-transcriptional regulation of c-jun expression during monocytic differentiation of human myeloid leukemic cells. J. Biol. Chem., 265:3320–3323, 1990.
49. Nakamura, T., Datta, R., Rubin, E., Nakamura, T., Hass, R., and Kufe, D., Regulation of c-jun expression during induction of monocytic differentiation by okadaic acid. Cell Growth Differs, 2:267–272, 1991.
50. Kharbanda, S., Datta, R., Rubin, E., Nakamura, T., Hass, R., and Kufe, D., Regulation of c-jun expression during induction of monocytic differentiation by okadaic acid. Cell Growth Differ., 3:391–399, 1992.
51. Yang-Yen, H.-F., Chiu, R., and Karin, M., Elevation of AP1 activity during F9 cell differentiation is due to increased c-jun transcription. New Biologist, 2:351–361, 1990.
52. Chiu, R., Angel, P., and Karin, M., Jun-B differs in its biological properties from, and is a negative regulator of, c-Jun. Cell, 59:979–986, 1989.
53. Schutte, J., Viallet, J., Nau, M., Segal, S., Fedorko, J., and Minna, J., Jun-B inhibits and c-fos stimulates and transforming and trans-activating activities of c-jun. Cell, 59:987–997, 1989.
54. Datta, R., Sherman, M. L., Stone, R. M., and Kufe, D., Expression of the jun-B gene during induction of monocytic differentiation. Cell Growth Differ., 2:43–49, 1991.
55. Lord, K. A., Hoffman-Liebermann, B., and Liebermann, D. A., Complexity of the immediate early response of myeloid cells to terminal differentiation and growth arrest includes ICAM-1, Jun-B and histone variants. Oncogene, 5:386–396, 1990.
56. Jiang, H., Su, Z,-z, and Fisher, P. B., unpublished data.
57. Ben-Ze'ev, A., Rodriguez Fernandez, J. L., Baum, G., and Gorodecki, B., Regulation of cell contacts, cell configuration, and cytoskeletal gene expression in differentiating systems. In: Fisher, P., Ed., Mechanisms of Differentiation: Modulation of Differentiation by Exogenous Agents, Vol. II, CRC Press, Boca Raton, Fla., pp. 143–173, 1990.
58. Ben-Ze'ev, A., The cytoskeleton in cancer cells. Biochem. Biophys. Acta, 780:197–212, 1985.
59. Dedhar, S., Integrins and tumor invasion. BioEssays, 12:583–590, 1990.
60. Plantefaber, L. C. and Hynes, R. O., Changes in integrin receptors on oncogenically transformed cells. Cell, 56:281–290, 1989.
61. Giancotti, F. G., and Ruoslahti, E., Elevated levels of the $\beta_5\beta_1$ fibronectin receptor suppresses the transformed phenotype of Chinese hamster ovary cells. Cell, 60:849–859, 1990.

62. Pytela, R., Pierschbacher, M. D., and Ruoslahti, E., Identification and isolation of a 140 kd cell surface glycoprotein with properties expected of a fibronectin receptor. Cell, 40:191–198, 1985.
63. Erickson, H. P. and Bourdon, M. A., Tenascin: an extracellular matrix protein prominent in specialized embryonic tissues and tumors. Ann. Rev. Cell. Biol., 5:71–92, 1989.
64. Yarden, A., Shure-Gottlieb, H., Chebath, J., Revel, M., and Kimchi, A., Autogenous production of interferon-β switches on HLA genes during differentiation of histiocytic lymphoma U937 cells. EMBO J., 3:969–973, 1984.
65. Abdollahi, A., Lord, K. A., Hoffman-Liebermann, B., and Liebermann, D. A., Interferon regulatory factor 1 is a myeloid differentiation primary response gene induced by interleukin 6 and leukemia inhibitory factor: role in growth inhibition. Cell Growth Differ., 2:401–407, 1991.
66. Schwartz, B., Pestka, S., Jiang, H., and Fisher, P. B., unpublished data.
67. Richmond, A., and Thomas, H. G., Purification of melanoma growth stimulatory activity. J. Cell. Physiol., 129:375–384, 1986.
68. Richmond, A., Balentein, E., Thomas, H. G., Flaggs, G., Barton, D. E., Spiess, J., Bordoni, R., Francke, U., and Derynck, R., Molecular characterization and chromosomal mapping of melanoma growth stimulatory activity, a growth factor structurally related to β-thromboglobulin. EMBO J., 7:2025–2033, 1988.
69. Anisowicz, A., Bardwell, L., and Sager, R., Constitutive overexpression of a growth-regulated gene in transformed Chinese hamster and human cells. Proc. Natl. Acad. Sci. U.S.A., 84:7188–7192, 1987.
70. Richmond, A., Fine, R., Murray, D., Lawson, D. H., and Priest, L., Growth factor and cytogenetic abnormalities in nevus and malignant melanoma cells. J. Invest. Dermatol., 86:295–302, 1986.
71. Richmond, A. and Thomas, H. G., Melanoma growth stimulatory activity: isolation from human melanoma tumors and characterization of tissue distribution. J. Cell. Biochem., 36:185–198, 1988.
72. Rangnekar, V. V., Waheed, S., and Rangnekar, V. M., Interleukin-1 inducible tumor growth arrest is characterized by activation of cell type-specific "early" gene expression programs. J. Biol. Chem., 267:6240–6248, 1992.
73. Wen, D., Rowland, A., and Derynck, R., Expression and secretion of gro/MGSA by stimulated human endothelial cells. EMBO J., 8:1761–1766, 1989.

Second Series of Experiments

Molecular biological approaches for the identification and cloning of genes displaying differential expression in both related and different cell types have been described (1–5). A particularly powerful procedure that has resulted in the identification of genes differentially expressed in diverse target cells is subtraction hybridization (4, 5). This approach has been successfully used to identify genes that are specifically expressed during progression of the transformed/malignant phenotype (5, 6), in cells undergoing growth arrest (7), induced by specific DNA damaging agents (8), expressed during specific stages of B cell development (9), and associated with programmed cell death (10). Subtraction hybridization is ideally suited for the identification of rare transcripts (4, 5, 9, 11, 14), or transcripts that exhibit small variations in expression between two cell types (4, 8, 11). As described in this article, subtraction hybridization is also an ideal procedure for identifying and cloning genes that are expressed at higher levels in cells induced to differentiate versus uninduced parental cells. In addition, by performing subtraction in the opposite direction, i.e., differentiation-inducer treated (Ind$^+$) from untreated control (Ind$^-$), the present protocol can also be used to identify genes that are suppressed during terminal differentiation.

Treatment of human melanoma cells with the combination of recombinant human fibroblast interferon (IFN-β) and the antileukemic compound mezerein (MEZ), results in a rapid cessation of cell growth and the induction of terminal cell differentiation, i.e., cells remain viable, but they lose proliferative capacity (15–17). Terminal cell differentiation can be induced by IFN-β plus MEZ in human melanoma cells either innately sensitive or resistant to either agent used alone (15, 16). In contrast, treatment of melanoma cells with either IFN-β or MEZ alone results in a reversible alteration in differentiation phenotypes in the human melanoma cell line H0-1. This system represents a valuable experimental model for determining which changes in gene expression are correlated directly with growth suppression as opposed to reversible differentiation and terminal cell differentiation. Applicants have presently developed a simple and effective subtraction hybridization protocol and used it to identify melanoma differentiation associated (mda) genes displaying enhanced expression in cells treated with reversible- and terminal differentiation inducing compounds. Four types of mda genes have been identified, including genes upregulated by both IFN-β and IFN-β plus MEZ, both MEZ and IFN-β plus MEZ, all three treatments and only the combination of IFN-β plus MEZ. This approach should prove amenable to other model systems resulting in the isolation of differentially expressed genes involved in important cellular processes.

Materials and Methods

Cell Line and Differentiation Induction

The human melanoma cell line H0-1 is a melanotic melanoma derived from a 49-year-old female and was used between passage 125 and 150 (16). H0-1 cells were grown in Dulbecco's modified Eagle's medium supplemented with 10% fetal bovine serum (DMEM-5) at 37° C. in a 5% $CO_{2-95}$% air humidified incubator. Cells were either untreated (Ind$^-$) or treated (Ind$^+$) with a combination of IFN-β (2000 units per ml) and MEZ (10 ng per ml) for 2, 4, 8, 12 and 24 hr. For expression studies, H0-1 cells were untreated or treated for 12 and 24 hr with IFN-β (2000 units per ml), MEZ (10 ng per ml) or IFN-β plus MEZ (2000 units per ml plus 10 ng per ml) prior to isolation of cellular RNA and Northern blotting analysis (17).

Construction of cDNA Libraries

Total cellular RNA from untreated (Ind$^-$) and IFN-β plus MEZ treated (2, 4, 8, 12 and 24 hr) (Ind$^+$) samples was isolated by the guanidinium isothiocyanate/CsCl centrifugation procedure and poly(A$^+$) RNA was selected following oligo(dT) cellulose chromatography (18). cDNA synthesis was performed using the ZAP-cDNA™ synthesis kit from Stratagene® (La Jolla, Calif.) which is based on an adaptation of the Gubler and Hoffman method (19). A primer-adapter consisting of oligo(dT) next to a unique restriction site (XhoI) was used for first strand synthesis. The double-stranded cDNAs were ligated to EcoRI adapters and then digested with the XhoI restriction endonuclease. The resultant EcoRI and XhoI cohesive ends allowed the finished cDNAs to be inserted into the λ ZAP II vector in a sense orientation with respect to the lac-Z promoter (20). The λ ZAP II vector contains pBluescript plasmid sequences flanked by bacteriophage-derived f1 sequences that facilitate in vivo conversion of the phage clones into the phagemid (20). Two cDNA libraries were constructed: a differentiation inducer-treated cDNA library (Ind⁺) (tester library); and a control uninduced cDNA library (Ind⁻) (driver library). The libraries were packaged with Gigapack II Gold Packaging Extract (Stratagene®) and amplified on PLK-F' bacterial cells (Stratagene®)

Preparation of Double-Stranded DNA from Ind⁺ Library

The Ind⁺ cDNA phagemid library was excised from λ ZAP using the mass excision procedure described by Stratagene® (La Jolla, Calif.) [21]. Briefly, $1 \times 10^7$ pfu of Ind⁺ cDNA library were mixed with $2 \times 10^8$ XL-1 Blue strain of *Escherichia coli* and $2 \times 10^8$ pfu of ExAssist helper phage in 10 mM $MgSO_4$ followed by absorption at 37° C. for 15 min (22). After the addition of 10 ml of LB medium, the phage/bacteria mixture was incubated with shaking at 37° C. for 2 hr followed by incubation at 70° C. for 20 min to heat inactivate the bacteria and the λ ZAP phage particles. After centrifugation at 4000 g for 15 min, the supernatant was transferred to a sterile polystyrene tube, and stored at 4° C. before use.

To produce double-stranded DNA, $5 \times 10^7$ pfu of the phagemids were combined with $1 \times 10^9$ SOLR strain of *Escherichia coli*, which are nonpermissive for the growth of the helper phages and therefore prevent coinfection by the helper phages (22), in 10 MM $MgSO_4$ followed by absorption at 37° C. for 15 min. The phagemids/bacteria were transferred to 250 ml LB medium containing 50 μg/ml ampicillin and incubated with shaking at 37° C. overnight. The bacteria were harvested by centrifugation, and the double-stranded phagemid DNA was isolated by the alkali lysis method (18) and purified through a QIAGEN-tip 500 column (QIAGEN Inc., Chatsworth, Calif.).

Preparation of Single-Stranded DNA from Control Ind⁻ Library

The control Ind⁻ cDNA library was excised from lambda ZAP using the mass excision procedure described above. The phagemid ($5 \times 10^7$) were combined with $1 \times 10^9$ XL-1 Blue strain of *Escherichia coli* in 10 mM $MgSO_4$ followed by absorption at 37° C. for 15 min. The phagemids/bacteria were transferred to 250 ml LB medium, and incubated with shaking at 37° C. for 2 hr. Helper phage VCS M13 (Stratagene®, La Jolla, Calif.) was added to $2 \times 10^7$ pfu/ml, and after incubation for 1 hr. kanamycin sulfate (Sigma) was added to 70 μg/ml. The bacteria were grown overnight. The phagemids were harvested and single-stranded DNAs were prepared using standard protocols (18).

Pretreatment of Double- and Single-Stranded DNA Prior to Hybridization

To excise the inserts from the vector, double-stranded DNA from the Ind⁺ cDNA library was digested with EcoRI and XhoI, and extracted with phenol and chloroform followed by ethanol precipitation (5). After centrifugation, the pellet was resuspended in distilled $H_2O$. Single-stranded DNA from Ind⁻ cDNA library was biotinylated using photoactivatable biotin (Photobiotin, Sigma, St. Louis, Mo.) (23). In a 650 μl microcentrifuge tube, 50 μl of 1 μg/μl single-stranded DNA was mixed with 50 μl of 1 μg/μl photoactivatable biotin in $H_2O$. The solution was irradiated with the tube slanted on crushed ice at a distance of 10 cm from a 300 watt sun lamp for 15 min. The DNA was further biotinylated by adding 25 μl of photoactivatable biotin to the solution which was then exposed to an additional 15 min of irradiation as described above. To remove unlinked biotin, the reaction was diluted to 200 μl with 100 mM Tris-HCl, 1 mM EDTA, pH 9.0, and extracted 3× with 2-butanol. Sodium acetate, pH 6.5 was added to a concentration of 0.3 M, and the biotinylated DNA was precipitated with two volumes of ethanol.

Subtracted Hybridization and Construction of Subtracted cDNA Library

Subtraction hybridization was performed essentially as described by Herfort and Garber (24) with minor modifications. In a 650 μl siliconized microcentrifuge tube, 400 ng of EcoRI- and XhoI-digested Ind⁺ cDNA library and 12 μg of biotinylated Ind⁻ cDNA library were mixed in 20 μl of 0.5 M NaCl, 0.05 M HEPES, pH 7.6, 0.2% (wt/vol) sodium dodecyl sulfate and 40% deionized formamide. The mixture was boiled for 5 min and incubated at 42° C. for 48 hr. The hybridization mixture was diluted to 400 μl with 0.5 M NaCl, 10 mM Tris, pH 8.0, 1 mM EDTA and then 15 μg of streptavidin (BRL®) in $H_2O$ was added, followed by incubation at room temperature for 5 min. The sample was extracted 2× with phenol/chloroform (1:1), followed by back-extraction of the organic phase with 50 μl of 0.5 M NaCl in TE buffer, pH 8.0. An additional 10 μg of streptavidin was added and phenol/chloroform extraction was repeated. After removal of excess chloroform by brief lyophilization, the final solution was diluted to 2 ml with TE buffer, pH 8.0, and passed through a Centricon 100 filter (Amicron; Danvers, Mass.) 2× as recommended by the manufacturer. The concentrated DNA solution (approximately 50 μl) was then lyophilized. The subtracted cDNAs were ligated to EcoRI- and XhoI-digested and CIAP treated arms of the λZAP II vector and packaged with Gigapack II Gold packaging extract (Stratagene®, La Jolla, Calif.). The library was then amplified using the PLK-F' bacterial cell.

Screening Subtracted cDNA Library

The mass excision of the library was performed using ExAssist helper phage as described above. The SOLR strain of *Escherichia coli* and cDNA phagemids were mixed at 37° C. for 15 min and plated onto LB plates containing ampicillin and IPTG/X-gal. White colonies were chosen at random, isolated and grown in LB medium. Plasmid minireps and restriction enzyme digestions were performed to confirm the presence of inserts. The inserts were isolated and used as robes for Northern blotting analysis (5, 25). Total cellular RNA was prepared from H0-1 cells treated with IFN-β (2000 units/ml), MEZ (10 ng/ml), and IFN-β plus MEZ (2000 units/ml plus 10 ng/ml), electrophoresed in 0.8% agarose gels and transferred to nylon membranes (Amersham, Arlington Heights, Ill.). Radiolabeled probes were generated by random oligonucleotide priming (25). Prehybridization, hybridization, posthybridization washes, and autoradiography were performed as described (5, 18, 25).

Sequencing of mda Genes

The mda clones were sequenced using double-stranded pBluescript DNA as the template. DNA sequencing was performed using the Sanger dideoxynucleotide method with sequenase (United States Biochemical Corp., Cleveland, Ohio) and T3 promoter primer (GIBCO® BRL®, Gaithersburg, Md.). This approach generates sequences from the 5' end of the inserts. Sequences were tested for homology to previously identified sequences using the GenBank FMBL database and the GCG/FASTA computer program.

Experimental Results

Subtraction hybridization represents a valuable methodology for isolating cDNA clones representing preferentially expressed mRNAs without prior knowledge of the selected gene or its encoded product (1–10). This procedure results in a substantial enrichment of differentially expressed cDNA clones and is often preferable to differential hybridization procedures using total cDNAs (4, 5, 11–14). A number of protocols have been reported for the generation of subtraction libraries [reviewed in 4]. The traditional approach involves hybridization of a first strand cDNA (tester) made from the mRNA of one cell type with mRNA (driver) prepared from a second cell type [or the first cell type treated with a specific gene modulating agent(s)] [7–9]. Single-stranded unhybridized cDNAs are then selected by hydroxylapatite column chromatography and they are used as templates for the synthesis of second-strand cDNA (7–9). However, this procedure has a number of limitations, including the requirement for RNA handling during hybridization, which can be problematic, and the limited quantity of cDNAs recovered following hybridization and column chromatography. Other subtraction hybridization protocols involve hybridization of cDNA and photobiotinylated RNA (23, 26). Problems may still arise because of the requirement for large amounts of mRNA and from manipulation of RNA during the hybridization procedure (22). Recent improvements in subtraction hybridization utilize cDNA libraries as both tester and driver nucleic acid populations (24, 27, 28). By using driver sequences present in cloned forms, the newer approaches circumvent the problems associated with insufficient quantities of mRNAs or difficulties resulting during the preparation and manipulation of mRNAs. Improvements in subtraction hybridization procedures have included: the use of phagemid subtraction hybridization (27); the use of single-stranded phagemids with directional inserts (28); and the use of double-stranded cDNA inserts as tester and single-stranded cDNAs as the driver (21).

Figure 8:
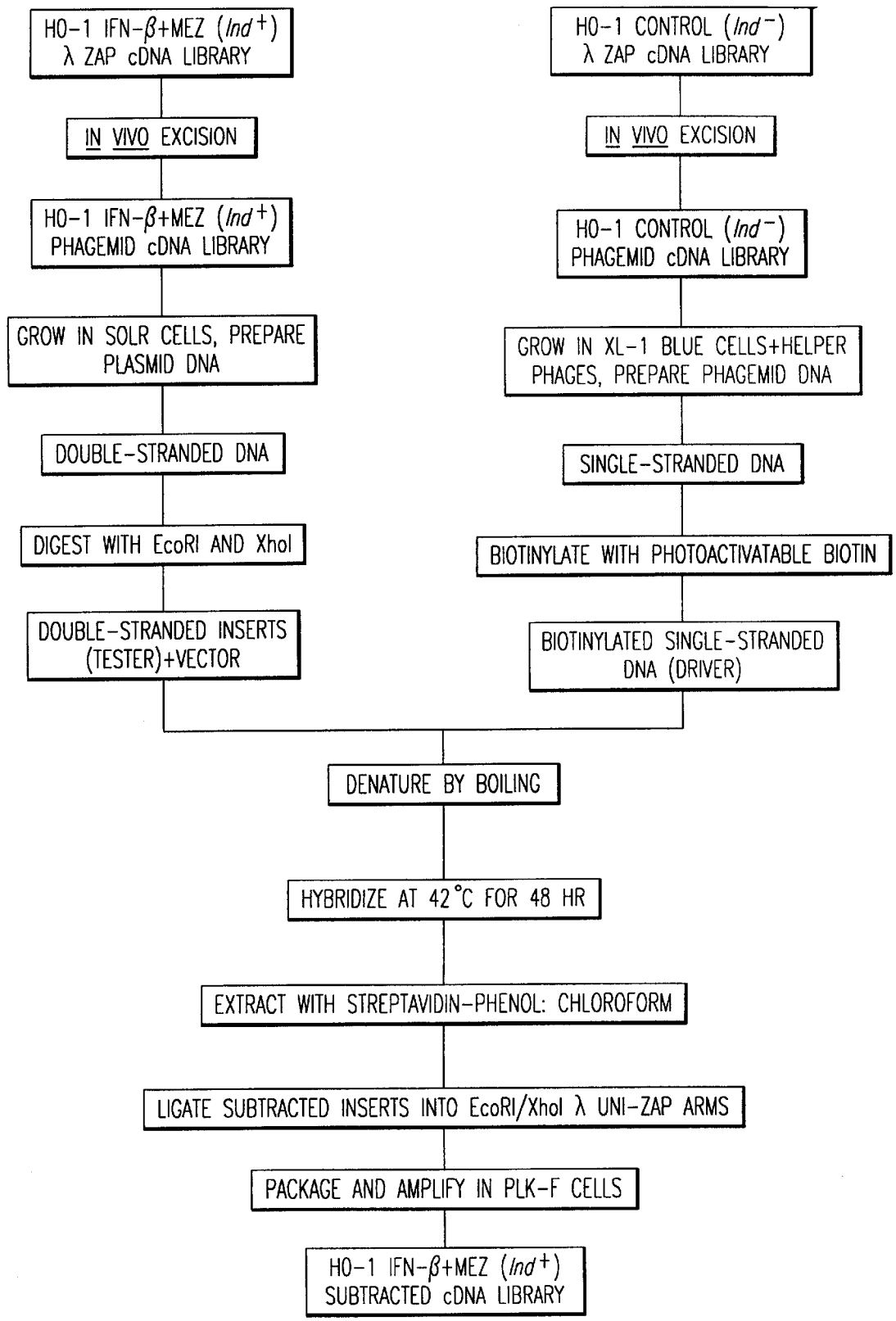
FIG. 8 Flowchart for constructing a subtractive differentiation inducer treated human melanoma cell cDNA library. cDNA libraries were constructed from differentiation inducer [IFN-β (2000 units/ml)+MEZ (10 ng/ml)] treated human melanoma (H0-1) cells (Ind$^+$) and untreated control (Ind$^−$) H0-1 cells. Using the protocols outlined, an H0-1 IFN-β+MEZ (Ind$^+$) subtracted cDNA library was constructed.

The procedure applicants have used to construct subtraction libraries involves a modification of the protocols described by Rubenstein et al. (28) and Herfort and Garber (24). This strategy is outlined in FIG. 8. Applicants' approach to subtraction library construction uses $\lambda$ phage and commercially available reagents. In other similar procedures (22, 27, 28), the end products of subtraction hybridization are either single-stranded phagemid DNA, which is converted to double-stranded DNA, or double-stranded inserts, which are ligated to plasmid vectors. These procedures have two potentially limiting drawbacks including, the lower efficiency of bacterial transformation with plasmids versus phage infection and the need for special precautions to remove the double-stranded phagemids contaminating the driver single-stranded DNA preparation. By using $\lambda$ page as vectors, these problems are easily avoided. The efficiency of phage infection of bacteria is high, often attaining levels of $10^9$ PFU/$\mu$g DNA (21). In addition, problems with contaminating plasmids in the preparation are also eliminated because they will not be packaged and transfected into bacteria. This approach, therefore, results in the construction of subtraction libraries of high titer. By employing $\lambda$ Uni-ZAP vectors which can be converted into phagemids by in vivo excision, the laborious work of subcloning the DNA inserts into plasmids is unnecessary.

cDNA libraries and subtraction libraries are prepared using the commercial ZAP-cDNA™ synthesis kit from Stratagene® (La Jolla, Calif.) (5). This product has several advantages for the construction of subtraction libraries. First, the XhoI adapter-primer permits the cDNA to be inserted into the vector in a unidirectional orientation. The efficiency of subtraction hybridization will be high if hybridization occurs only between complementary molecules in the different cDNA libraries instead of complementary molecules in the same cDNA library. This improved subtraction hybridization is achieved by using both single-stranded and double-stranded unidirectional cDNA libraries from each experimental condition. For construction of mda subtraction libraries (FIG. 8), both the H0-1 control Ind$^-$ and the IFN-$\beta$ plus MEZ treated Ind$^+$ cDNA libraries were constructed in a unidirectional manner. The efficiency of subtraction hybridization was insured by using single-stranded unidirectional Ind$^-$ cDNA as the driver. Secondly, the bacteriophage f1 origin of replication, which is present in the $\lambda$ ZAP II vector, permits excision of pBluescript II SK(–) phagemids from the bacteriophage and rescue of single-stranded DNA with the assistance of helper phage (20). The *Escherichia coli* strains XL-1 blue and SOLR, which are provided as part of the ZAP-cDNA™ kit, are very useful in preparing single-stranded and double-stranded phagemid DNA. The XL-1 blue strain is permissive for ExAssist helper phage growth, while the SOLR strain is nonpermissive (22). The phagemids are excised with ExAssist helper phage in XL-1 blue bacterial cells. The phagemids are then grown in SOLR bacterial cells for harvesting double-stranded DNA or in XL-1 blue cells with helper phages for harvesting single-stranded DNA. Using this approach, contamination of helper phage and single-stranded DNA in the double-stranded DNA preparation was minimized. Contamination could decrease the efficiency of subtraction hybridization because of the complementary binding between the single-stranded cDNA and any potentially unique sequences from the same cDNA library (tester). This could potentially result in a failure of the unique sequences to from double-stranded inserts with appropriate ends which can be ligated into the vectors. A third consideration is the commercial availability of Uni-ZAP arms which can be used as vector for the construction of subtraction libraries. Tester inserts are released from the phagemid vector by digestion with the restriction enzyme EcoRI and XhoI. After subtraction hybridization, the remaining inserts which are in the double-stranded form because of complementary hybridization are ligated in a unidirectional manner into Uni-ZAP arms because of the EcoRI and XhoI cohesive ends. This approach eliminates the requirement for additional vectors. The subtraction library is then converted into a phagemid library which can be easily manipulated for screening, sequencing, in vitro RNA transcription, and mutagenesis. Without the advent of well designed commercial kits, subtraction hybridization and subtraction library construction is both time and labor intensive. The procedure applicants describe in this article is straight forward and highly efficient in producing subtraction libraries.

Figure 9:
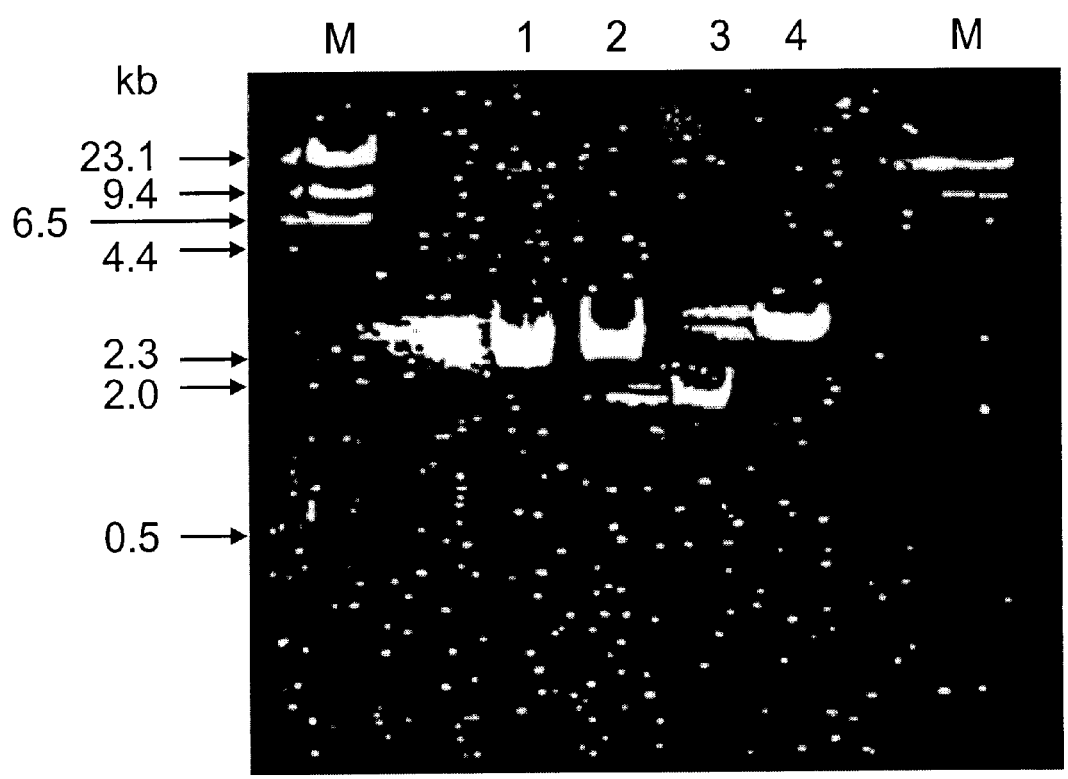
FIG. 9 Determination of the purity of the single-stranded DNA and double-stranded DNA preparations of cDNA libraries. Photograph of a 1% agarose electrophoresis gel stained with ethidium bromide and photographed under illumination with UV light. The single-stranded DNA was prepared from the control (Ind$^−$) library and double-stranded DNA from IFN-β+MEZ (Ind$^+$) library. Lane M, λ HindIII molecular weight markers; lane 1, single-stranded DNA; lane 2, single-stranded DNA digested with EcoRI and Xhol; lane 3, double-stranded DNA; lane 4, double-stranded DNA digested with EcoRI and Xhol.

Employing the approaches applicants describe above, cDNA libraries from control H0-1 cells (Ind$^+$) and H0-1 cells treated with the terminal differentiation inducing agents IFN-$\beta$ plus MEZ (Ind$^+$) have been constructed. The original titers of the cDNA libraries were $1.2\times10^6$ PFU and $1.7\times10^6$ PFU for the Ind$^-$ and Ind$^+$, respectively. The high titers obtained suggest that the cDNA libraries are representative of the mRNAs produced under the experimental conditions used. The purity of the single-stranded and double-stranded DNA was examined by digestion with the restriction endonucleases EcoRI and XhoI. Unlike double-stranded DNA, the single-stranded DNA could not be digested with the restriction endonucleases. This is demonstrated in FIG. 9, in which plasmid vector is released after digestion of double-stranded DNA but not single-stranded DNA. Four hundred ng of double-stranded DNA (tester:IND$^+$) and 12 $\mu$g of single-stranded DNA (driver:Ind$^-$) were used for subtraction hybridization. After a single-round of hybridization, the Ind$^+$ subtraction library was constructed in Uni-ZAP XR vector with an original titer of 8 to $10\times10^3$ PFU. Additional rounds of subtraction hybridization resulted in a low percentage of colonies which contained inserts. This may result because of the low concentration of potentially unique sequences remaining after the first round of subtraction hybridization. This observation indicates that the subtraction hybridization protocol applicants have utilized is very efficient and the requirement for additional subtraction hybridizations may not be necessary to identify differentially expressed genes.

Screening of subtraction libraries for differentially expressed sequences can be achieved using several procedures. In a number of studies, subtraction libraries are screened using differential hybridization techniques (7, 8, 27). However, the sensitivity of this procedure is limited by the relative abundance of the target mRNA. The enrichment of target sequences obtained in our subtractions libraries permitted the random isolation of clones for evaluation of mRNA expression in undifferentiated H0-1 cells or H0-1 cells treated with IFN-β, MEZ or IFN-β+MEZ. After in vivo excision, bacteria containing the subtraction library were plated and randomly isolated clones were used to prepare plasmids. The EcoRI/XhoI digested cDNA inserts from these clones were then used as probes for Northern blotting analysis of mRNA expression under the different experimental conditions. Among 70 cDNA clones initially analyzed, 23 clones were found to display differences in gene expression between Ind$^-$ and Ind$^+$ treated H0-1 cells. As expected, subtraction of control H0-1 cDNAs from IFN-β plus MEZ treated H0-1 cDNAs results in a series of mda genes which displayed enhanced expression after 24 hr treatment with the inducer. These included mda genes which were inducible by both IFN-β and IFN-β plus MEZ, i.e. mda-1 and mda-2; by both MEZ and IFN-β plus MEZ, i.e., mda-3; by IFN-β, MEZ and IFN-β plus MEZ, i.e., mda-4; and uniquely by IFN-β and MEZ, i.e., mda-5 and mda-6 (FIG. 10). Specific mda genes also displayed elevated expression after 96 hr exposure to IFN-β plus MEZ (data not shown).

Of the six mda genes reported in this study, only mda-3 corresponds to a previously reported gene (FIG. 11). At present, 245 bp of mda-3 have been sequenced and this cDNA shares >99% homology with the reported sequences of pLD78 (29), pAT 464 (30, 31), pAT 744 (31) and GOS19 (32-34). The pLD78 cDNA is inducible by either TPA or a T-cell mitogen, phytohemagglutinin (PHA), in human tonsilar lymphocytes (29). mda-3 is induced in H0-1 cells within 24 hr of treatment with MEZ, IFN-β plus MEZ and IFN-β plus TPA (data not shown). The sequence of the 5' flanking region of the genomic DNA encoding for the pLD78 cDNA displayed a significant homology with corresponding regions of the human interleukin 2 and immune interferon genes (29). pAT 464 and pAT 744 are inducible by TPA and PHA, with maximal induction resulting from the combination of agents, in T-cells, B-cells and the promyelocytic cell line HL-60 (31). In contrast, these cDNAs are not expressed in human fibroblasts, although as indicated in the present study a potentially similar cDNA, mda-3, is inducible in human melanoma. pAT 464 and pAT 744 share some critical amino acid similarity with a family of secreted factors including connective tissue activating factor III, platelet factor 4, an IFN-γ-induced factor, macrophage inflammatory protein and a factor chemotactic to neutrophils (3–10C, monocyte-derived neutrophil chemotactic factor, neutrophil-activating factor) (31). GOS19 genes are members of the "small inducible" family of genes, which exhibit similar exon-intron organizations and which encode secreted proteins with similar organization of cysteine and proline residues (32–34). The GOS19-1 mRNA is enhanced rapidly by the addition of both cycloheximide or lectin to cultured human blood mononuclear cells (32). This cDNA has sequence homology to the murine gene that encodes an inhibitory cytokine (MIPIα/SCI) which decreases stem cell proliferation (32). In this context, GOS19-1, which is the main GOS19 gene expressed in adult T lymphocytes, may encode a homeostatic negative regulator of marrow stem cell populations. The role of mda-3 in the process of melanoma cell growth and differentiation remains to be determined.

Studies are currently in progress to further characterize the novel mda genes, mda-1, mda-2, mda-4, mda-5, and mda-6, and determined their expression in different stages of melanoma evolution and during the induction of growth suppression, the reversible commitment to differentiation and the induction of terminal differentiation in human melanoma cells. It should be emphasized that the cDNA clones applicants have currently analyzed represent only a small percentage of the complete subtraction library. This suggests that this subtraction library has the potential for identifying and cloning additional genes involved or associated with the chemical induction of differentiation and growth suppression in human melanoma cells. In addition, by altering the driver DNA, i.e., using combinations of cDNA libraries constructed from H0-1 cells treated singularly with IFN-β and MEZ, it should be possible to further enrich for gene(s) uniquely expressed in terminally differentiated human melanoma cells, i.e. those treated with the combinations of IFN-β+MEZ.

In summary, applicants presently describe an efficient and sensitive procedure for the production of subtraction hybridized cDNA libraries which can be used for the identification and cloning of differentially expressed genes. The basic protocol utilizes biotinylated single-stranded DNA as the driver and bacteriophage as the vector and relies on the availability of commercial reagents for construction of subtraction cDNA libraries. The usefulness of the current protocol is demonstrated by the high level of enrichment obtained from genes in the subtracted library associated with the induction of differentiation of human melanoma cells, i.e., mda genes. This procedure should find wide applicability for the identification and cloning of differentially expressed genes. These can include, but are not limited to, genes displaying modified expression between closely related cell types, between disparate cell types, in cells induced to lose proliferative ability or undergo apoptosis, in cells treated with chemotherapeutic agents, and in cells induced or committed to reversible or terminal differentiation.

REFERENCES FOR THE SECOND SERIES OF EXPERIMENTS

1. Scott, M. D., Westphal, H.-H., and Rigby, R. W. J., Activation of mouse genes in transformed cells, *Cell,* 34:557–567 (1983).
2. Davis, M. M., Cohen, D. I., Nielsen, E. A., Steinmetz, M., Paul, W. E., and Hood, L. Cell-type specific cDNA probes and the murine I region: The localization and orientation of $A_a^d$, *Proc. Natl. Acad. Sci. USA,* 81:2194–2198 (1984).
3. Lee, S. W., Tomasetto, C., and Sager, R. Positive selection of candidate tumor-suppressor genes by subtractive hybridization, *Proc. Natl. Acad. Sci. USA,* 88:2825–2829 (1991).
4. Schweinfest, C. W., and Papas, T. S. Subtraction hybridization: an approach to the isolation of genes differentially expressed in cancer and other biological systems (Review), *Intl. J. Oncology,* I:499–506 (1992).
5. Reddy, P. G., Su, Z.-Z., and Fisher, P. B. Identification and cloning of genes involved in progression of transformed phenotype. In: Adolph, K. W., Ed., *Methods in Molecular*

*Genetics*, Vol. I, Academic Press, Orlando, Fla., pp. 68–102 (1993).
6. Matrisian, L. M., Bowden, G. T., Krieg, P., Furstenberger, G., Briand, J.-P., Leroy, P., and Breathnach, R. The mRNA coding for the secreted protease transin is expressed more abundantly in malignant than in benign tumors, *Proc. Natl. Acad. Sci. USA*, 83:9413–9417 (1986).
7. Schneider, C., King, R. M., and Philipson, L. Genese specifically expressed at growth arrest of mammalian cells, *Cell*, 54:787–793 (1988).
8. Fornace, A. J., Jr., Alamo, I. Jr., and Hollander, M. C. DNA damage-inducible transcripts in mammalian cells, *Proc. Natl. Acad. Sci. USA*, 85:8800–8804 (1988).
9. Yancopoulos, G. D., Oltz, E. M., Rathburn, G., Berman, J. E., Smith, R. K., Lansford, R. D., Rothman, P., Okada, A., Lee, G., Morrow, M., Kaplan, K., Prockop, S., and Alt, F. W. Isolation of coordinately regulated genes that are expressed in distinct stage of B-cell development, *Proc. Natl. Acad. Sci. USA*, 87:5759–5763 (1990).
10. Owens, G. P., Hahn, W. E, and Cohen, J. J. Identification of mRNAs associated with programmed cell death in immature thymocytes, *Mol. Cell. Biol.*, 11:4177–4188 (1991).
11. Fragnoli, J., Holbrook, N. J., and Fornace, A. J., Jr. Low-ratio hybridization subtraction, *Anal. Biochem.*, 187:364–373 (1990).
12. Frohman, M. A., Dush, M. K., and Martin, G. R. Rapid production of full-length cDNAs from rare transcripts: amplification using a single-gene specific oligonucleotide primer, *Proc. Natl. Acad. Sci. USA*, 85:8998–9002 (1988).
13. Timblin, C. J., Battey, G., and Kuehl, W. M. Application for PCR technology to subtractive cDNA cloning: Identification of genes expressed specifically in murine plasmacytoma cells, *Nucleic Acids Res.*, 18:1587–1593 (1990).
14. Wieland, I., Bolgar, G., Asouline, G., and Wigler, M. A method for difference cloning: Gene amplification following subtractive hybridization, *Proc. Natl. Acad. Sci. USA*, 87:2720–2724 (1990).
15. Fisher, P. B., Hermo, H., Jr., Solowey, W. E., Dietrich, M. C., Edwalds, G. M., Weinstein, I. B., Langer, J. A., Pestka, S., Giacomini, P., Kusama, M., and Ferrone, S. Effect of recombinant human fibroblast interferon and mezerein on growth, differentiation, immune interferon binding and tumor associated antigen expression in human melanoma cells, *Anticancer Res.*, 6:765–774 (1986).
16. Fisher, P. B., Prignoli, D. R., Hermo, H., Jr., Weinstein, I. B., and Pestka, S. Effects of combined treatment with interferon and mezerein on melanogenesis and growth in human melanoma cells, *J. Interferon Res.*, 5: 11–22 (1985).
17. Jiang, H., Su, Z.-Z., Boyd, J., and Fisher, P. B. Gene expression changes induced in human melanoma cells undergoing reversible growth suppression and terminal cell differentiation, *Mol. Cell. Different.*, 1:41–66 (1993).
18. Sambrook, J., Fritsch, E. F., and Maniatis, T., Eds., *Molecular Cloning: A Laboratory Manual*, 2nd edition, Cold Spring Harbor Lab. Press, Cold Springer Harbor, N.Y., 1989.
19. Gubler, U., and Hoffman, B. J. A simple and very effective method for generating cDNA libraries, *Gene*, 25:263–269 (1983).
20. Short, J. M., Fernandez, J. M., Sorge, J. A., and Huse, W. D. λ ZAP: A bacteriophage λ expression vector with in vivo excision properties, *Nuc. Acids Res.*, 16:7583–7600 (1988).
21. Short, J. M., and Sorge, J. A. In vivo excision properties of bacteriophage λ ZAP expression vector, *Meth. Enz.*, 216:495–508 (1992).
22. Hay, B., and Short, J. M. ExAssist™ helper phage and SOLR™ for lambda ZAP II excision, Stratagies, 5:16–18 (1992).
23. Sive, H. L., and St. John, T. A simple subtraction technique employing photoactivable biotin and phenol extraction, *Nuc. Acids Res.*, 16:10937 (1988).
24. Herfort, M. R., and Garber, A. T. Simple and Efficient subtractive hybridization screening, *BioTechniques*, 11(5):598–603 (1991).
25. Jiang, H., Su, Z.-Z., Datta, S., Guarini, L., Waxman, S., and Fisher, P. B. Fludarabine phosphate selectively inhibits growth and modifies the antigenic phenotype of human glioblastoma multiforme cells expressing a multidrug resistance phenotype, *Intl. J. Oncology*, 1:227–239 (1992).
26. Swaroop, A., Xu, J., Agarwal, N., and Weissman, S. A simple and efficient cDNA subtraction procedure: isolation of human retina-specific cDNA clones, *Nuc. Acids Res.*, 19:1954 (1991).
27. Duguid, J. R., Rohwer, R. G., and Seed, B. Isolation of cDNAs of scrapie-modulated RNAs by subtractive hybridization, *Proc. Natl. Acad. Sci. USA*, 85:5738–5742 (1988).
28. Rubenstein, J. L. R., Brice, A. E. J., Claranello, R. D., Denney, D., Proteus, M. H., and Usdin, T. B. Subtractive hybridization system using single-stranded phagemids with directional inserts, *Nuc. Acids Res.*, 18:4833–4842 (1990).
29. Obaru, K., Fukuda, M., Maeda, S., and Shimada, K. A cDNA clone used to study mRNA inducible in human tonsilar lymphocytes by a tumor promoter, *J. Biochem.*, 99:885–894 (1986).
30. Irving, S., June, C. H., Zipfel, P. F., Siebenlist, U., and Kelly, K. Mitogen-induced genes are subject to multiple pathways of regulation in the initial stages of T-cell activation, *Mol. Cell. Biol.*, 9:1034–1040 (1989).
31. Zipfel, P. F., Blake, J., Irving, S. G., Kelly, K., and Siebenlist, U. Mitogenic activation of human T cells induces two closely related genes which share structural similarities with a new family of secreted factors, *J. Immunol.*, 142:1582–1590 (1989).
32. Blum, S., Forsdyke, R. E., and Forsdyke, D. R. Three human homologs of a murine gene encoding an inhibitor of stem cell proliferation, *DNA and Cell Biol.*, 9:589–602 (1990).
33. Irving, S., Zipfel, P. F., Blake, J., McBride, O. W., Morton, C. C., Burd, P. R., Siebenlist, U., and Kelly, K. Two inflammatory mediator cytokine genes are closely linked and variably amplified on chromosome 17q, *Nucleic Acids Res.*, 18:3261–3270 (1990).
34. Nakao, M., Nomylama, H., and Shimada, K. Structures of human gene coding for cytokine LD78 and their expression, *Mol. Cell Biol.*, 10:3646–3658 (1990).

Third Series of Experiments

Development of malignant melanoma in humans, with the exception of nodular type melanoma, is a progressive process involving a discrete series of well defined stages. Although the focus of intensive scientific scrutiny, the genetic elements controlling melanocytic conversion into the various stages of the evolving melanoma have not been identified. In addition, no consistently effective therapy is currently available to treat metastatic melanoma. The long-term goal of the present proposal is to define the genes regulating melanoma growth, differentiation and progression. This information could prove valuable in elucidating potential targets for therapeutic intervention. Tumor progression in melanocytes is associated with altered patterns of normal melanocytic differentiation. Chemical induction of terminal differentiation in tumor cells represents a useful approach for reversing the negative prognosis associated with specific neoplasms. Recent studies indicate that the specific combination of recombinant human fibroblast interferon (IFN-β) and the antileukemic compound mezerein (MEZ) can reprogram human melanoma cells to undergo terminal differentiation, i.e., cells retain viability but they irreversibly lose proliferative capacity. In contrast, application of comparable doses of IFN-β or MEZ alone to human melanoma cells results in a reversible commitment to differentiation, i.e., removal of the inducing agent results in the resumption of cell growth and the loss of specific differentiation-associated properties.

Subtraction hybridization is used to identify the genotypic changes associated with induction of terminal differentiation in human melanoma cells. Using this approach, cDNAs displaying enhanced expression in melanoma cells induced to terminally differentiate versus untreated melanoma cells have been identified. Partial sequence analysis of these differentially expressed cDNAs, tentatively called melanoma differentiation associated (mda) genes, indicate that they consist of both known and previously unidentified genes. Specific mda genes may represent novel genetic elements involved in tumor cell growth and/or commitment of cells to the melanocyte lineage. The specific aims of this proposal are to characterize and determine the functional roles of the mda genes in melanoma growth, differentiation, and progression. With these aims in mind studies will be conducted to:

1) Determine the pattern and regulation of expression of the mda genes in melanocytes, nevi, radial growth phase melanoma, vertical growth phase melanoma and metastatic melanoma cells;
2) Analyze the relationship between mda gene expression and the induction of reversible commitment to differentiation, growth suppression without the induction of differentiation, DNA damage and stress responses and induction of terminal differentiation in human melanoma and other model differentiation systems;
3) Isolate full-length cDNAs of mda genes that may be involved in melanoma differentiation or progression and directly determine their potential functional role in differentiation and progression of human melanoma;
4) Isolate and characterize the promoter region of appropriate mda genes and analyze their regulation in human melanocytes, nevi and melanoma.

Experimental strategies designed to activate genes mediating a loss of proliferative capacity and the reprogramming of melanoma cells to terminally differentiate, may represent novel approaches for effective therapeutic intervention in metastatic melanoma. Elucidation of the function of the cloned mda genes should provide molecular insights into the process of melanoma differentiation and progression. In addition, specific mda genes may represent targets of clinical interest which can be exploited for suppressing the growth of metastatic melanoma and other tumorigenic cell types.

Background and Significance

Malignant melanoma epitomizes the process of tumor progression and emphasizes the selective nature of the metastatic phenotype and the growth dominant properties of metastatic cells (rev. 1 to 3). Of the numerous types of cancer developing in North American populations, melanoma is increasing at the fastest rate and it is estimated that as many as 1 in 100 currently born children may eventually develop superficial spreading type melanoma (3, 4). Although melanoma is readily curable at early stages, surgical and chemotherapeutic interventions are virtually ineffective in preventing metastatic disease and death in patients with advanced stages of malignant melanoma. These observations emphasize the need for improved therapeutic approaches to more efficaciously treat patients with metastatic melanoma.

Development of malignant melanoma in humans, with the exception of nodular type melanoma, consists of a series of sequential alterations in the evolving tumor cells (rev. 1–4). These include conversion of a normal melanocyte into a common acquired melanocytic nevus (mole), followed by the development of a dysplastic nevus, a radial growth phase (RGP) primary melanoma, a vertical growth phase (VGP) primary melanoma and ultimately a metastatic melanoma. As indicated above, although readily treatable during the early stages of development even during the VGP if the lesion is $\leq 0.76$-mm thick, currently employed techniques are not very effective (<20% survival) in preventing metastatic spread and morbidity in patients with VGP lesions >4.0-mm thickness. This experimental model system is ideally suited to evaluate the critical genetic changes that mediate both the early and late phases of melanoma evolution.

A less toxic approach to cancer therapy involves a process termed differentiation therapy (5–9). Two premises underlie this therapeutic modality. (A) Many neoplastic cells display aberrant patterns of differentiation resulting in unrestrained growth; and (B) Treatment with the appropriate agent(s) can result in the reprogramming of tumor cells to lose proliferative capacity and become terminally differentiated. Intrinsic in this hypothesis is the assumption that the genes that mediate normal differentiation in many tumor cells are not genetically defective, but rather they fail to be appropriately expressed. The successful application of differentiation therapy in specific instances may result because the appropriate genes inducing the differentiated phenotype become transcriptionally activated resulting in the production of appropriate gene products required to induce terminal cell differentiation. Applicants have tested this hypothesis using human melanoma cells (10–14). Treatment of human melanoma cells with the combination of recombinant human fibroblast interferon (IFN-α) and the antileukemic compound mezerein (MEZ) results in a rapid cessation of growth, an induction of morphological changes, an alteration in antigenic phenotype, an increase in melanin synthesis and an irreversible loss in proliferative capacity, i.e., terminal cell differentiation (10, 11, 14). IFN-β plus MEZ effectively induce terminal differentiation in human melanoma cells innately resistant to the antiproliferative effect of either agent used alone (10). In contrast, IFN-β or MEZ applied alone induce a number of similar biochemical and cellular changes in human melanoma cells, however, these changes are often reversible following removal of the inducing agent, i.e., reversible commitment to differentiation (10, 14). Although the effect of IFN-β plus MEZ toward normal human melanocytes has not been reported, Krasagakis et al. (15) did determine the effect of IFN-β plus TPA (which was present in the melanocyte growth medium) on the growth of normal human melanocytes. MEZ shares a number of in vitro properties with TPA, including its ability to replace TPA for the growth of normal melanocytes, to activate protein kinase C and to modulate cell differentiation (14, 16). In contrast to TPA, however, MEZ is a very weak tumor promoter when substituted for TPA in the initiation-promotion model of carcinogenesis on mouse skin, although it is quite potent during the second phase of tumor promotion (17, 18). When normal melanocytes are grown under optimal growth conditions, including TPA, cholera toxin, isobutylmethylxanthine and fetal bovine serum, even high doses (10,000 units/ml) of leukocyte (IFN-α), fibroblast (IFN-β) or immune (IFN-γ) interferon does not inhibit growth (15). In contrast, when grown in modified melanocyte medium not containing TPA and resulting in reduced growth potential, only IFN-β significantly inhibits proliferation. When tested in serum-free medium, all three interferon preparations are growth inhibitory toward the SKMel-28 human melanoma cell line, with IFN-β again being the most growth-suppressive (15). IFN-β has been shown to be more growth suppressive than IFN-α toward several additional human melanomas grown in serum containing medium (10). These results support the hypothesis that IFN-β may be a negative-regulator of melanocyte proliferation and malignant transformation results in an increased sensitivity to interferons (10, 15). In the case of TPA, it is an obligatory requirement for the in vitro growth of normal melanocytes, whereas TPA and MEZ are growth inhibitory toward many human melanoma cells (14–16, 19, 20).

Melanoma represents a useful experimental model to analyze the process of tumor progression (rev 1–3). Cell culture systems are available that permit the growth of normal melanocytes, nevi and melanoma cells representing different stages of tumor progression (1–3, 20–25). Analyses of the properties of cells of the melanocyte lineage indicate a number of traits that allow the different stages in melanoma evolution to be distinguished. These include: (a) morphology,; (b) life span in culture; (c) chromosomal abnormalities; (d) anchorage-independent growth; (e) tumorigenicity; (f) expression of HLA-DR (class II HLA antigens) and intercellular adhesion molecule-1 (ICAM-1) antigens; (g) response to the tumor promoting agent 12-0-tetradecanoyl-phorbol-13-acetate (TPA); (h) growth factor independence in vitro; (i) autocrine production of basic fibroblast growth factor (bFGF) and (j) growth inhibition by cytokines (rev 2, 21, 25). A limitation of the melanoma progression model, however, is the inability to obtain from the same patient who has developed a primary RGP or an early VGP melanoma (less than 0.76 mm in thickness), a genetically related more progressed melanoma. Recent studies by Dr. Kerbel and colleagues (25) suggest that by appropriate manipulation (use of matrigel) and tumor selection in nude mice, it may be possible to spontaneously progress early-stage, non- or poorly tumorigenic (in nude mice) human melanoma cell lines to a more progressed tumorigenic and metastatic state. In addition, Dr. Albino and colleagues (20) demonstrated that normal human melanocytes could be progressed to a complete melanoma phenotype and genotype following infection with a retrovirus containing the viral Ha-ras oncogene. Transformed melanocytes acquired the full spectrum of melanoma properties and displayed the same cytogenetic changes occurring during melanoma development in vivo (20). These cell lines will prove useful for evaluating the biochemical and genetic changes involved in melanoma progression. In summary, the ability to clearly define specific components of melanoma evolution will provide a valuable experimental model to define the genotypic changes mediating tumor progression.

The critical genomic changes that mediate melanoma development and progression remain to be defined. Recent studies have addressed the potential relationship between the expression of specific oncogenes, growth factor genes (in addition to basic fibroblast growth factor (bFGF)), growth factor receptor genes, protease genes and early response genes and melanoma progression (26–30). Using a panel of metastatic melanoma cell lines, steady state mRNA transcripts for several growth factors (bFGF, platelet-derived growth factor (PDGF)-A, PDGF-B, transforming growth factor (TGF)-$\beta_1$, TGF-α, melanoma growth-stimulating activity (MGSA; also called gro), interleukin (IL-1α and IL-1β) and early response (c-fos, c-jun and jun-B) genes have been found (27, 28). All of the metastatic melanoma cell lines expressed the bFGF gene and the majority of metastatic melanoma expressed c-fos, c-jun and jun-B in both serum-free and serum containing medium. With respect to the other growth factor genes tested, each metastatic melanoma displayed a pattern of expression that was specific and different (27). In contrast, two strains of normal melanocytes expressed TGF-$\beta_1$ but not bFGF, PDGF, TGF-α or MGSA mRNA at detectable levels (27). Although metastatic melanoma and normal melanocytes express c-fos, c-jun and jun-B, the expression of these transcripts in normal melanocytes was dependent on the presence of growth-promoting agents in the medium (28). In contrast, different levels of the early response genes were observed in metastatic melanoma cells grown in the presence or absence serum (28). In general, an increase in jun-B and c-fos RNA transcripts and a decrease in c-jun RNA transcripts were observed in metastatic melanomas compared to neonatal melanocytes (28). The relevance of these differences in early response gene expression in metastatic melanomas compared to neonatal melanocytes remains to be determined. In a recent study, Albino et al. (30) used PCR to determine the level of RNA transcripts for 11 different growth factors in 19 metastatic human melanoma cell lines and 14 normal human foreskin melanocyte cell lines. Transcripts for TGF-$\beta_2$ (19 of 19), TGF-α (18 of 19) and bFGF (19 of 19) were found in metastatic melanoma but not in the normal melanocytes. In contrast, TGF-$\beta_1$ and TGF-$\beta_3$ were expressed in both metastatic melanoma and normal melanocytes. The significance of these changes to melanoma progression is not apparent. These results suggest, however, that the differential expression of specific genes, i.e., bFGF, TGF-$\beta_2$, TGF-α and possibly early response genes, may contribute to or may be directly related to the metastatic melanoma phenotype.

On the basis of genetic linkage analysis of familial melanoma, cytogenetic analysis, and various molecular techniques (including RFLP analysis to identify LOH in tumor DNA samples and microcell gene transfer procedures) it is now apparent that nonrandom changes in genes on chromosomes 1, 6, 7 and 9 may contribute to the etiology of human melanoma (31–41). At this stage of analysis, at least 5 genes, mapping to chromosomes 1, 6, 7 and 9, appear to contribute to the development of malignant melanoma, and extensive tumor heterogeneity also implicates additional loci as contributors to the malignant phenotype (rev. 38, 41). A proposed model of tumor progression from melanocyte to metastatic melanoma suggests that alterations in chromosome 1 and 9 are early events in melanoma progression, whereas changes in chromosome 6 and 7 represent later stages of tumor progression (38, 41). A direct demonstration of the suppressive role of chromosome 6 in human melanoma has recently been demonstrated (37). Employing microcell mediated gene transfer, a normal human chromosome 6 was inserted into human melanoma cells (UACC-903) and shown to suppress transformed properties in vitro and tumorigenic potential in nude mice (37). Dr. Welch and colleagues have also demonstrated that insertion of a normal human chromosome 6 into the C8161 human melanoma cell line results in a suppression of metastatic potential, but not tumorigenic potential (42). The apparent discrepancy between the results of Trent et al. (37) and Welch et al. (42)

may relate to differences between UACC-903 and C8161 cells. C8161 cells exhibit both tumorigenic and metastatic properties in nude mice, whereas UACC-903 cells are tumorigenic but not metastatic in nude mice. This difference might mask the presence of a metastasis suppressor on chromosome 6 or alternatively might suggest that chromosome 6 contains both a tumor and a metastatic suppressor gene. The chromosome 6 containing C8161 cells have also been found to differ from parental C8161 cells in their biological response and in gene expression after treatment with IFN-β plus MEZ (43). Further studies are required to determine if a similar suppression of transformed and tumorigenic properties can be induced by reintroduction by microcell mediated transfer of chromosomes 1, 7 and/or 9 into melanoma cells containing abnormalities in these chromosomes. Similarly, the mechanism by which the putative melanoma suppressor gene(s) on chromosome 6, as well as suppressor gene(s) located on additional chromosomes, exert their effects on human melanoma cells and how these genes regulate tumor progression remain to be determined.

Recent studies have demonstrated the existence of at least 23 IFN-α genes and pseudogenes, all of which reside proximal to the IFN-β gene that is located on locus 9p (9p22–13) (44, 45). Nonrandom alterations in specific loci on chromosome 9 appear to be an early event in melanoma evolution. It is intriguing, therefore, that 90% (9/10) of informative melanoma DNAs have shown a reduction for one to five of the loci tested in the same region as the IFN-α/β gene (41) including a 2 to 3 megabase region on 9p21 in which a putative melanoma tumor-suppressor gene appears to be located (40). Similarly, homo- or homozygously deleted α- and β-interferon genes have been found in human acute lymphoblastic leukemias and human malignant gliomas (44–47). This observation is interesting, since interferons display antiproliferative activity toward both human melanoma and lymphoblastic leukemic cells and can be viewed therefore as tumor suppressor proteins (rev. 13). This data is compatible with the hypothesis that a tumor suppressor locus for both melanoma and leukemia is located on chromosome 9 and tumor suppression may in specific cancers involve alterations in the interferon gene region.

The mechanism by which the combination of IFN-β+MEZ induces a rapid irreversible inhibition in cellular proliferation and terminal differentiation in human melanoma cells remains to be determined. Since actinomycin D and cycloheximide can inhibit the induction of morphologic changes, growth suppression and the induction of differentiation in H0-1 cells induced by IFN-β+MEZ (49), transcriptional activation or suppression of specific gene(s) following treatment with these agents may be the primary determinants of induction of differentiation. A modified subtraction hybridization procedure was used to identify and characterize the critical genes that mediate and which are associated with the chemical induction (49). Using this approach a series of cDNAs have been identified, termed melanoma differentiation associated (mda) genes, which display enhanced expression in terminally differentiated human melanoma cells (49). Specific cDNAs have been identified which represent novel genes, i.e., their sequences have not been described previously in any of the DNA data bases. By using appropriate sense and anti-sense oligomers and expression constructs, studies will be conducted to determine the functional role of the mda genes in melanoma growth, differentiation and progression. In addition, by employing human melanoma cells representing specific stages in melanocytic evolution to metastatic melanoma it will also be possible to address the relationship between states of tumor progression and susceptibility to induction of terminal differentiation. An understanding of the process of terminal cell differentiation and the function of the mda genes could prove useful in defining the molecular basis of melanoma progression and in designing improved strategies for the therapy of malignant melanoma and other cancers.

Figure 12:
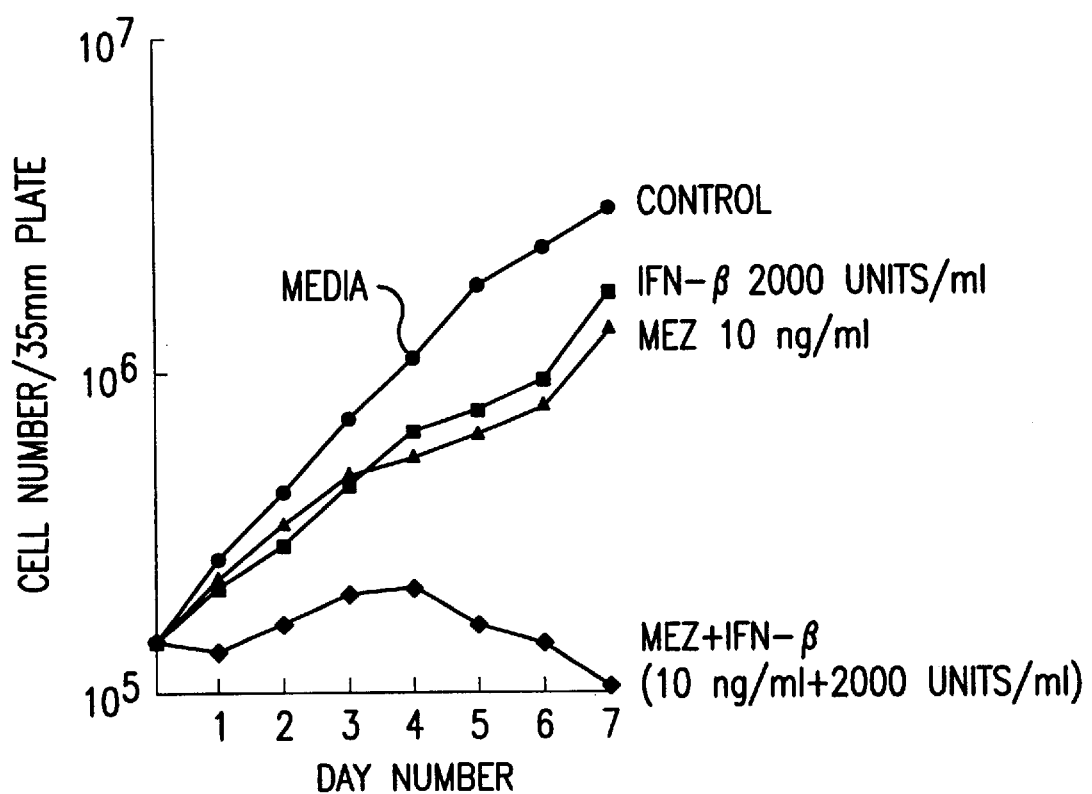
FIG. 12 Effect of IFN-β and MEZ, alone and in combination on the growth of H0-1 human melanoma cells (see third series of experiments for further details).
Figure 13:
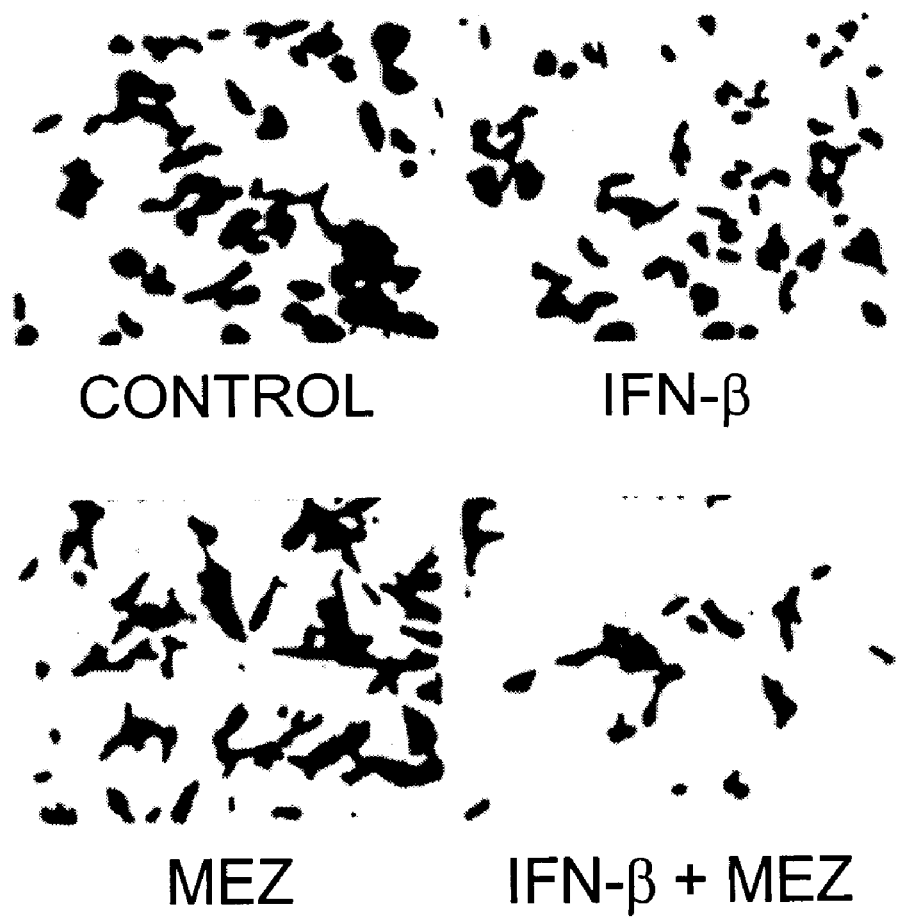
FIG. 13 Effect of IFN-β and MEZ, alone and in combination on the morphology of H0-1 human melanoma cells. Cells were treated with 2,000 units/ml of IFN-β, 10 ng/ml MEZ or the combination of agents for 24 h.

A. Induction of Terminal Differentiation in Human Melanoma Cells by IFN-β Plus MEZ As discussed in Background and Significance, a hallmark of many cancers is an inability to undergo normal programs of cellular differentiation. If this assumption is correct, and if the genetic machinery of the tumor cells could be reprogrammed to regain their commitment to normal differentiation, then appropriate external stimuli could be employed to induce a loss of proliferative capacity and terminal differentiation (5–14). In studies designed to directly test this hypothesis, applicants have successfully induced terminal differentiation in human melanoma cells with the combination of recombinant IFN-β and the anti-leukemic compound mezerein (MEZ) (10, 11, 14). In contrast, the combination of recombinant leukocyte interferon (IFN-α) and MEZ resulted in a potentiation of growth suppression, but terminal differentiation was not induced, i.e., treated cells retained proliferative capacity (10). The combination of IFN-β plus MEZ was effective in inducing terminal differentiation in human melanoma cells relatively resistant or sensitive to the growth suppressive effects of either agent employed alone (10). Induction of terminal differentiation in the human melanoma cell line H0-1 by continuous exposure for 4 or 7 days to IFN-β plus MEZ was associated with: (a) a rapid, within 24 hr, inhibition in proliferation (FIG. 12) (10, 11); (b) a profound alteration in cellular morphology (treated cells displayed dendrite-like processes) (FIG. 13) (10); and (c) an induction (in melanotic melanoma) or an increased synthesis (in melanotic melanoma) of melanin, a marker of melanoma cell differentiation (10). By employing varying doses of IFN-β and MEZ and different treatment schedules (24 hr, 4 days and/or 7 days), it has been possible to separate the chemical-induction of melanoma differentiation into three stages. These include an early completely reversible-induction phase (low doses of inducing agents for 4 or 7 days), a late partially reversible-induction phase (higher doses of inducing agents for 4 days), and an irreversible terminal-differentiation phase (specific doses of inducing agents for 24 hr, 4 days or 7 days)) (10–14).

In contrast to IFN-β plus MEZ that induces an irreversible loss in proliferative capacity and terminal differentiation in the human melanoma cell line H0-1, the combination of IFN-β plus IFN-γ induces enhanced growth suppression without terminal differentiation (12, 14, 50). In addition, IFN-β plus IFN-γ also fail to induce an increase in melanin synthesis in H0-1 cells (50).

When treated with trans retinoic acid (RA), both melanin levels and tyrosinase levels are increased in H0-1 cells, but growth is not suppressed (14, 51). Exposure to 3 $\mu$M mycophenolic acid (MPA) for 96 hr results in growth inhibition, morphologic changes, enhanced melanin synthesis and enhanced tyrosinase activity in H0-1 cells (14, 51). However, these affects are reversible when H0-1 cells treated with 3 $\mu$M MPA for 4 days are then grown in the absence of MPA for an additional 7 days (14). These results suggest that at the dose- and time-interval used, MPA (alone or in combination with MEZ) induces a reversible-induction of differentiation in H0-1 cells and not terminal differentiation. The effect of different agents on growth and the properties of H0-1 cells is summarized in Table 2 (14).

TABLE 2

| Experimental Conditions[a] | Morphology changes[b] | Melanin Synthesis[c] | Tyrosinase activity[d] |
|---|---|---|---|
| RA (2.5 μM) | − | 1+ | 2+ |
| MPA (3.0 μM) | + | 2+ | 3+ |
| MEZ (10 ng/ml) | + | 1+ | NT |
| IFN-β (2000 U/ml) | − | 1+ | NT |
| IFN-γ (2000 U/ml) | − | − | NT |
| RA + MEZ (2.5 μM + 10 ng/ml) | + | NT | NT |
| MPA + MEZ (3.0 μM + 10 ng/ml) | + | NT | NT |
| IFN-β + IFN-γ (1000 U/ml + 1000 U/ml) | − | 1+ | NT |
| IFN-β + MEZ (2000 U/ml + 10 ng/ml) | + | 4+ | NT |

| Experimental conditions[a] | Growth Suppression (reversible)[e] | Terminal cell differentiation[f] |
|---|---|---|
| RA (2.5 μM) | − | − |
| MPA (3.0 μM) | − | − |
| MEZ (10 ng/ml) | 1+ | − |
| IFN-β (2000 U/ml) | 3+ | − |
| IFN-γ (2000 U/ml) | 2+ | − |
| RA + MEZ (2.5 μM + 10 ng/ml) | 1+ | − |
| MPA + MEZ (3.0 μM + 10 ng/ml) | 3+ | − |
| IFN-β + IFN-γ (1000 U/ml + 1000 U/ml) | 4+ | − |
| IFN-β + MEZ (2000 U/ml + 10 ng/ml) | 4+[g] | + |

[a]H0-1 cells were grown for 96 hr or for 6 or 7 days (with medium changes after 3 or 4 days) in the presence of the agents indicated. For morphology, cells grown for 96 hr in the test agent were observed microscopically. For melanin synthesis, results are for 6 day assays for RA and MPA (51) or 7 day assays for MEZ, IFN-β, IFN-γ, IFN-β + IFN-γ and IFN-β + MEZ (10, 50). For tyrosinase assays, results are for 6 day assays for RA, MPA and MEZ (51). Growth suppression (reversible and terminal cell differentiation) assays, refer to cultures treated with the indicated compound(s) for 96 hr prior to cell number determination, or treated for 96 hr and then grown for 2 weeks (with medium changes every 4 days) in the absence of compound prior to cell number determination.
[b]Morphology changes refer to the development of dendrite-like processes 96 hr after growth in the indicated compound. + = presence of dendrite-like processes; − = no dendrite-like processes.
[c]Melanin assays were determined as described in refs. 10, 50, 51. Results are expressed as relative increases based on separate data presented in refs. 10, 50, 51. N.T. = not tested.
[d]Tyrosinase assays were performed as described in ref. 11. Relative increases (of a similar magnitude) were found for RA, MPA and MEZ after 6 days exposure to these agents (51). N.T. = not tested.
[e]Reversible growth suppression indicates resumption of cell growth after treatment with the indicated compound(s) for 96 hr, removal of the test agent and growth for 14 days in compound(s) free medium. Further details can be found in ref. 14. The degree of initial 96 hr growth suppression is indicated as: − = no significant change in growth (<10% reduction in growth in comparison with untreated control cultures); 1+ = ~30% reduction in growth in comparison with untreated control cultures; 2+ = ~40% reduction in growth in comparison with untreated control cultures; 3+ = ~50 to 60% reduction in growth in comparison with untreated control cultures; 4+ = ~80% reduction in growth in comparison with untreated control cultures.
[f]The combination of IFN-β + MEZ results in irreversible growth suppression.
[g]Terminal cell differentiation indicates the loss of proliferative capacity after treatment with the indicated compound(s) for 96 hr, removal of the test agent and growth for 14 days in compound(s) free medium. Further details can be found in (14).

The studies briefly described above indicate that changes in growth, morphology, melanin synthesis and tyrosinase activity can be dissociated from the induction of terminal differentiation in H0-1 melanoma cells. However, the irreversible loss of proliferative capacity and terminal differentiation resulting from treatment with IFN-β plus MEZ appear to be correlated phenomena. Employing the various agents described above it will be possible to determine which gene expression changes are related to the various components of the differentiation process in human melanoma cells.

Figure 14:
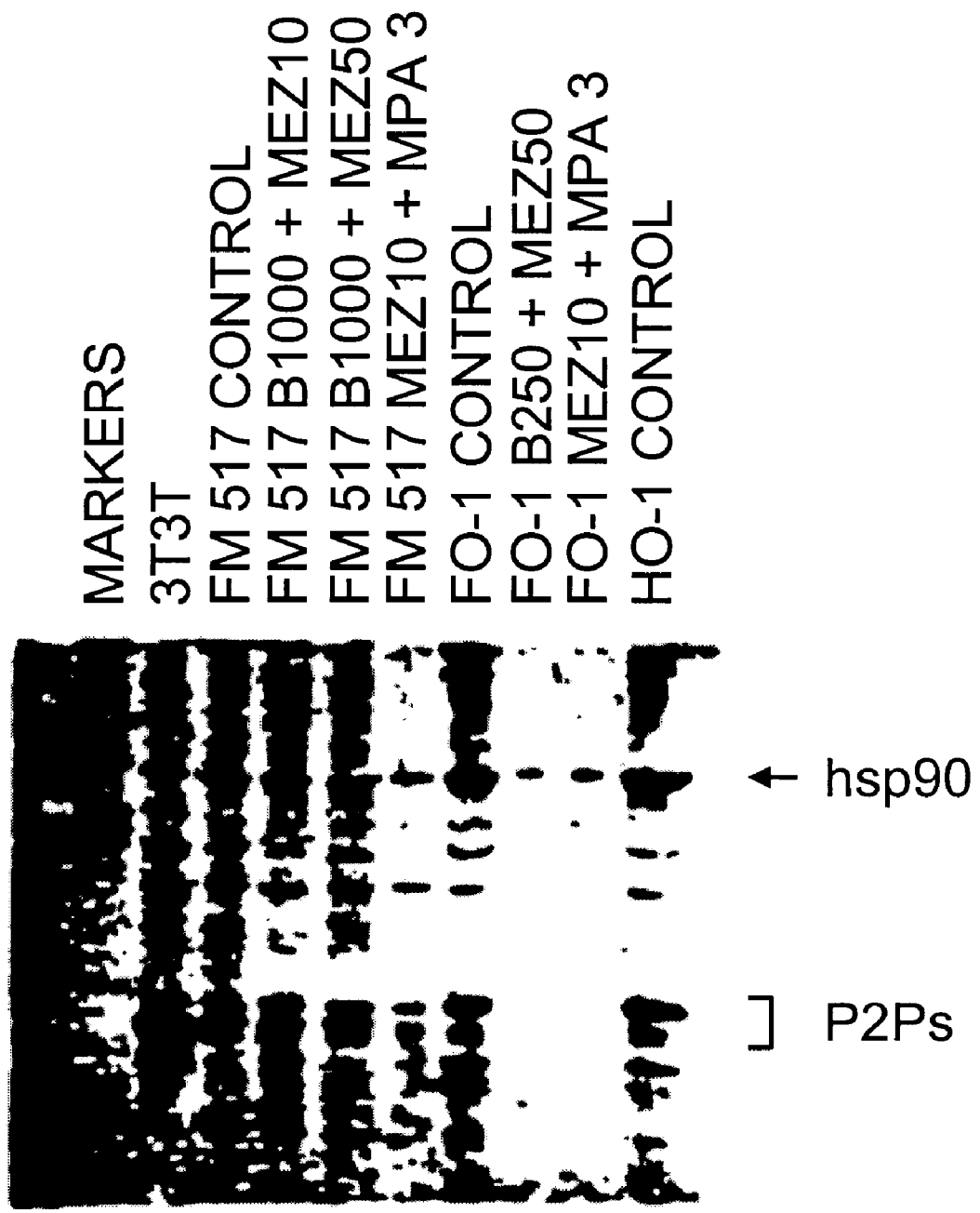
FIG. 14 Expression of proliferative sensitive proteins (P2Ps) in human melanoma cells treated with growth suppressing and differentiation inducing compounds. The combination of IFN-β+MEZ induces terminal differentiation in F0-1 human melanoma cells, but not in SV40-transformed human melanocytes. Experimental details for determining P2Ps can be found in Minoo et al. (52) and Witte and Scott (53) of the third series of experiments.

Monoclonal antibodies (MAbs) have recently been developed which recognize a series of hnRNP proteins, designated P2Ps, which display a marked reduction in both 3T3T cells and human keratinocytes induced to terminally differentiate (52, 53). In contrast, P2Ps are present in cells that have retained the ability to traverse the cell cycle, including cells reversibly growth arrested. A loss of P2Ps is also observed in cells that have irreversibly lost proliferative potential as a consequence of senescence, as well as induction of terminal differentiation (52, 53). In contrast, 3T3T cells transformed by SV40 do not undergo the terminal step of differentiation and these cells also do not show a suppression of P2P expression (52). These results support the concept that P2Ps may be directly linked to proliferative capacity of cells and may prove useful as a general marker for terminal cell differentiation. In collaboration with Dr. Robert E. Scott (University of Tennessee Medical Center, Memphis, Tenn.) applicants have begun to determine the level of P2Ps in human melanoma cells induced to terminally differentiate by exposure to IFN-β plus MEZ and MPA plus MEZ (FIG. 14). When induced to terminally differentiate, a reduction in P2Ps was apparent in several independent human melanoma cell lines (data from F0-1 human melanoma cells is shown in FIG. 14). In contrast, employing human melanocytes immortalized by the SV40 T-antigen gene (54), IFN-β plus MEZ did not induce terminal differentiation or a reduction in P2Ps, whereas MPA plus MEZ resulted in a loss of proliferative capacity and a reduction in P2Ps. In both F0-1 and FM516 SV cells, treatment with IFN-β, MEZ or MPA alone did not reduce P2Ps even though growth was suppressed (data not shown). Induction of terminal differentiation by IFN-β+MEZ in H0-1 cells resulted in a loss of P2Ps, whereas either agent employed alone did not reduce P2P levels (data not shown). Although these results are preliminary, they suggest that the chemical induction of terminal differentiation and the irreversible loss of proliferative capacity in human melanoma cells is associated with a reduction in P2Ps.

B. Gene Expression Changes Induced in Human Melanoma Cells Displaying Reversible Growth Suppression, Reversible Commitment to Differentiation and Terminal Cell Differentiation Applicants have begun to determine the spectrum of gene expression changes associated with growth suppression, morphologic alterations, increased melanin synthesis, enhanced tyrosinase activity and/or induction of terminal differentiation in human melanoma cells (12–14). The agents applicants have chosen result in reversible growth suppression, induction of melanin synthesis, morphologic alterations, enhanced tyrosinase activity, induction of a reversible commitment to differentiation or terminal differentiation with a concomitant loss of proliferative capacity in H0-1 melanoma cells (Table 2). The genes applicants have currently analyzed include: early response genes (c-fos, c-myc, c-jun, jun-B, jun-D and gro/MGSA) (14); interferon stimulated genes (ISG-15, ISG-54, HLA Class I and HLA Class II) (13, 14); cell adhesion molecules (P-cadherin, E-cadherin, N-cadherin and N-CAM) (14); extracellular matrix genes (fibronectin (FIB) and tenascin) (12, 14); cell surface proteoglycans/matrix receptors (syndecan, $\beta_1$ integrin (major FIB receptor subunit), $\alpha_5$ integrin (major FIB receptor subunit)) (14); cytoskeleton genes (tropomyosin-1, γ-actin and β-actin) (14); and a housekeeping gene (GAPDH) (14). Using the gene probes indicated above, no unique gene expression change was found which only occurred in terminally differentiated H0-1 cells. These results indicate that commitment to differentiation and terminal differentiation in H0-1 melanoma cells is associated with specific patterns of overlapping gene expression changes. As will be discussed below, an interesting change in gene expression observed in both H0-1 cells committed to differentiate and induced to terminally differentiate was the induction and enhanced expression of type I interferon responsive genes and the gro/MGSA gene. These results have led to the hypothesis that specific autocrine feedback loops may contribute or are associated with the differentiation process in human melanoma cells.

C. Changes in Cell Cycle and Early Immediate Response Genes During the Induction of Terminal Differentiation in Human Melanoma Cells As discussed above, treatment of H0-1 cells with the combination of IFN-β+MEZ results in growth suppression that is apparent by 24 hr following exposure to these inducing agents (FIG. 12) (10, 14). This system has been used to evaluate the effects of the different inducers, alone and in combination, on the expression of cell cycle regulated genes, including cdc2, cyclin A, cyclin B, histone 1, histone 4, proliferative cell nuclear antigen (PCNA), c-myc, p53 and Rb. These studies can be summarized as follows: (a) A reduction in cdc2 and histone 1 was apparent under all treatment conditions.

This effect was observed after 24 hr and was most dramatic in cells treated for 96 hr; (b) c-myc expression was marginally decreased by 24 hr treatment with MEZ and IFN-β+MEZ, whereas significant suppression was observed by 96 hr especially in IFN-β+MEZ treated H0-1 cells; (c) Both PCNA and p53 gene expression was reduced only in cells treated with IFN-β+MEZ; and (d) Rb levels remained unchanged following any of the treatment protocols. In the case of cdc2 and histone 1, IFN-β+MEZ resulted in a decreased rate of transcription of these genes. Similarly, IFN-β+MEZ decreased the stability of the cdc2 and histone 1 mRNAs. Analysis of cell cycle distribution by FACS analysis indicated that both MEZ and IFN-β+MEZ reduced the number of H0-1 cells undergoing DNA synthesis by 48-hour treatment. The most effective inhibitor of DNA synthesis in H0-1 cells was IFN-β+MEZ. These results indicate that the induction of terminal differentiation in H0-1 cells by IFN-β+MEZ is associated with a suppression in specific cell cycle related genes that occur at both a transcriptional and a postranscriptional level.

c-fos, c-jun and jun-B expression were superinduced in H0-1 cells treated with cycloheximide and IFN-β+MEZ, indicating that these genes are immediate early response genes. Differences in the temporal kinetics of induction and the mechanism of enhanced expression were apparent between these early response genes in differentiation-inducer treated H0-1 cells (55). In the case of c-fos, IFN-β+MEZ induced an increase in transcription of c-fos mRNA that was apparent after 1, 6 and 24 hr, but not after 96 hr treatment (55). In the case of c-jun, increased mRNA was apparent after 1, 6, 24 and 96-hour treatment with IFN-β+MEZ. These changes in c-jun level did not involve increased transcription, but instead resulted from an increase in half-life of the c-jun transcripts (55). In the case of jun-B, IFN-β+MEZ increased both the transcription and steady-state levels of RNA after 1- and 24-hour treatment. High levels of jun-B mRNA were also apparent in H0-1 cells induced to terminally differentiate after treatment with IFN-β+MEZ. The continued increase in c-jun and jun-B mRNA levels in terminally differentiated H0-1 cells suggests that these genes may contribute to maintenance of the terminal differentiation phenotype (55).

D. Autocrine Loops Induced in Human Melanoma Cells Treated with IFN-β Plus MEZ

As indicated above, continuous treatment with IFN-β+MEZ for 96-hour results in terminal differentiation in H0-1 human melanoma cells. This process correlates with specific patterns of gene expression changes, including the induction of two interferon stimulated genes, ISG-15 and ISG-54, and melanocyte growth stimulatory activity (gro/MGSA) (14). These observations suggested the possibility that induction of a reversible commitment to differentiation and terminal differentiation might be associated with the production of differentiation promoting factors (DPFs) (possibly including IFN-β or an IFN-β-like cytokine and melanoma growth stimulatory activity (gro/MGSA)). These DPFs could then induce by an autocrine mechanism the transcription and steady-state mRNA expression of interferon stimulated genes (ISG) and the gro/MGSA gene in H0-1 cells reversibly committed to differentiation or terminally differentiated. To further explore the relationship between treatment time and induction of differentiation and to test the autocrine hypothesis, applicants performed two types of experiments. In the first set of studies (In-Out), H0-1 cells were treated with various agents (including IFN-β+MEZ, MPA+MEZ, RA+MEZ and MEZ (at a high dose of 50 ng/ml) for 24 hr, cells were washed 2× with DMEM without FBS, DMEM containing 10% FBS was added to cultures and total cytoplasmic RNA was isolated 72 hours later. For the second set of experiments (Conditioned-Medium), cells were processed as indicated above for In-Out experiments except after 72 hour growth in the absence of inducer, medium was collected (and contaminating cells were removed by centrifugation).

Using the In-Out and Conditioned-Medium protocols it was demonstrated that: (a) At the doses employed, IFN-β+MEZ is a more potent inducer of gene expression changes and the only combination capable of inducing terminal differentiation in H0-1 cells; and (b) Conditioned medium from H0-1 cells reversibly committed to differentiate or terminally differentiated by IFN-β+MEZ induce specific programs of gene expression changes in HO-1 cells that are similar to those induced directly by the inducing agents (14). In addition, conditioned medium from IFN-β+MEZ treated HO-1 cells also induces morphologic changes and suppresses growth when added to HO-1 or FO-1 human melanoma cells (data not shown). These results support the hypothesis that induction of terminal differentiation in HO-1 melanoma cells is associated with specific changes in gene expression, some of which may be mediated by or associated with an autocrine feedback mechanism.

Figure 15:
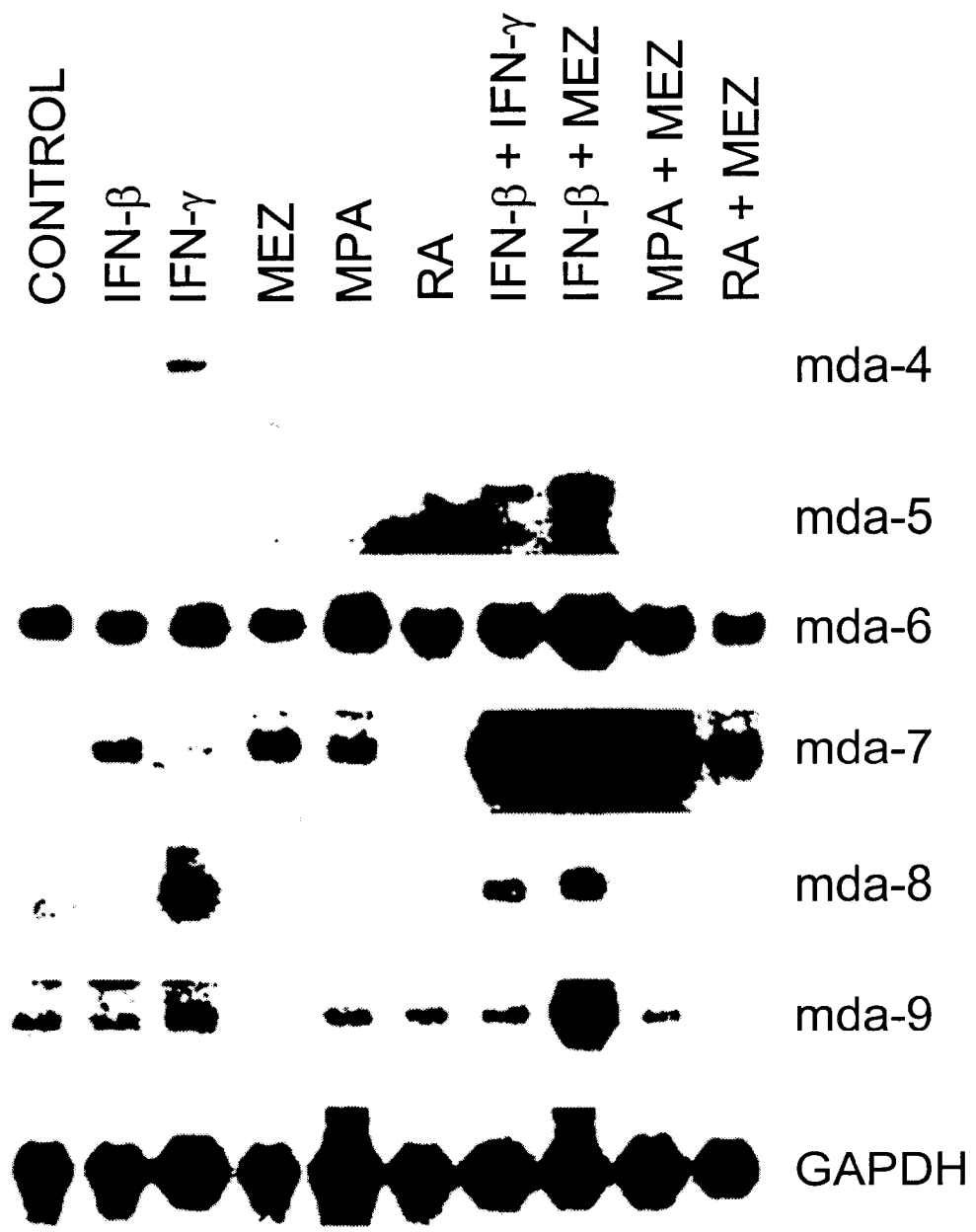
FIG. 15 Northern blot analyses of untreated and treated H0-1 cells probed with cDNA clones isolated from an H0-1 IFN-β+MEZ (Ind$^+$) subtracted cDNA library. RNA was isolated from cells treated for 96 h with the agents indicated. Concentration of agents were the same as used in FIG. 1. Experimental details can be found in Jiang and Fisher (49) and Jiang et al. (14) of the third series of experiments. IFN-β 2,000 units/ml; IFN-λ 2,000 units/ml; MEZ 10 ng/ml; MPA 3 µM; RA 2.5 µM; IFN-β+IFN-γ (1,000 units/ml of each IFN); IFN-β+MEZ (2,000 units/ml+10 ng/ml); MPA+MEZ (3 µM+10 ng/ml); RA+MEZ (2.5 µM+10 ng/ml).
Figure 16:
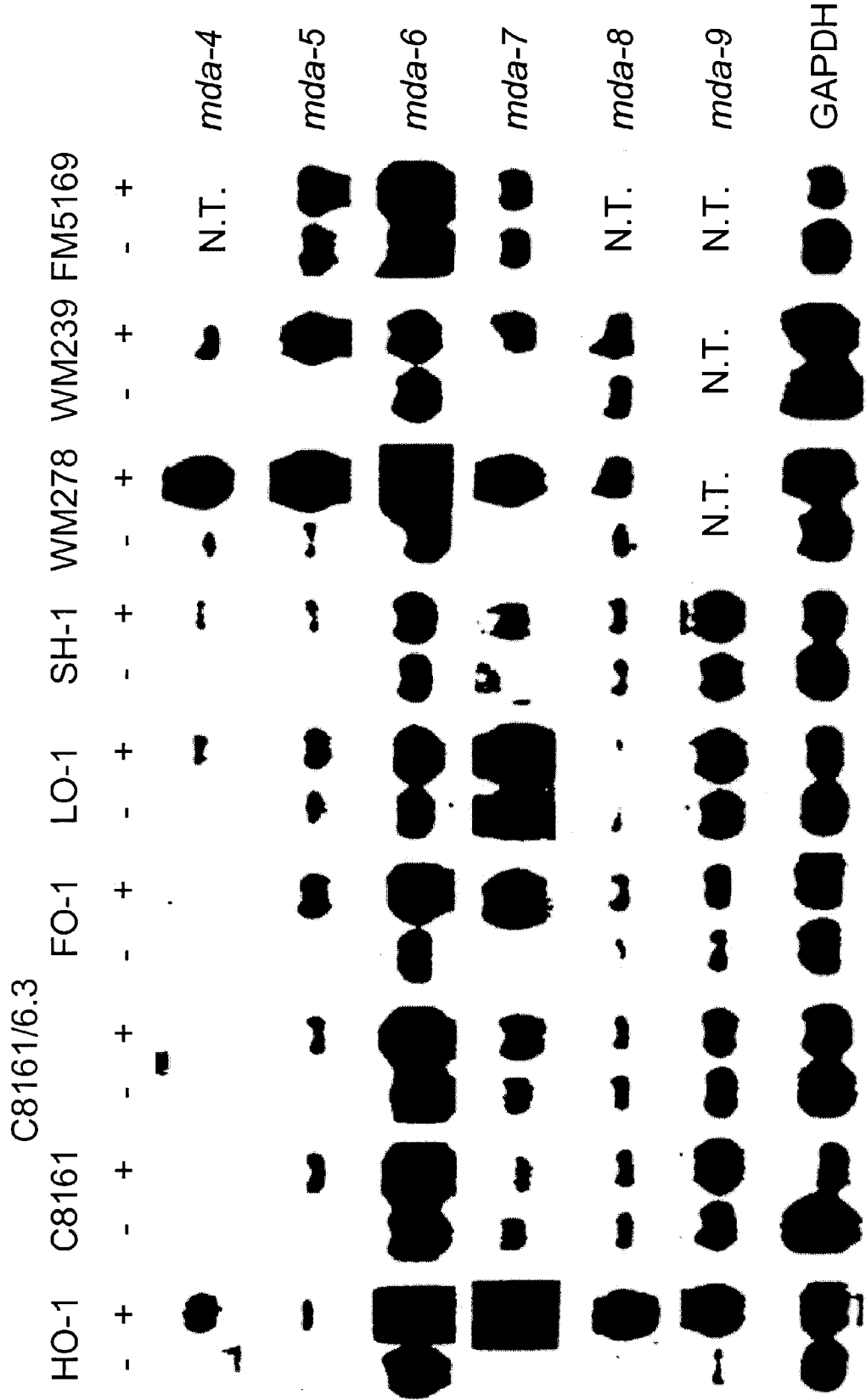
FIG. 16 Expression of mda genes in human melanomas. −=control, +=IFN-β+MEZ (2,000 units/ml±10 ng/ml).
Figure 17:
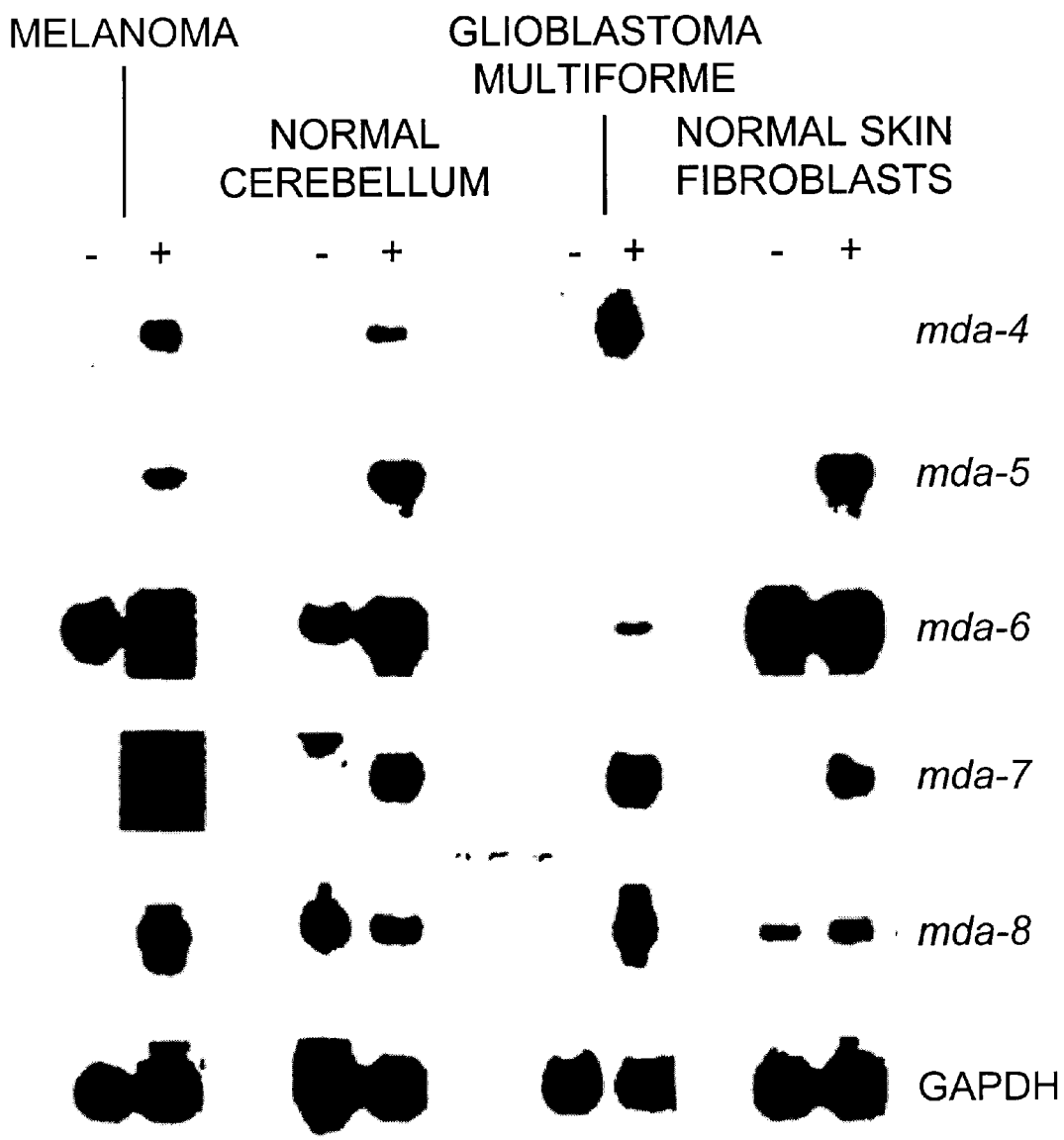
FIG. 17 Expression of mda genes in normal cerebellum, glioblastoma multiforme and normal skin fibroblasts. −=control, +=IFN-β+MEZ (2,000 units/ml+10 ng/ml).
Figure 18:
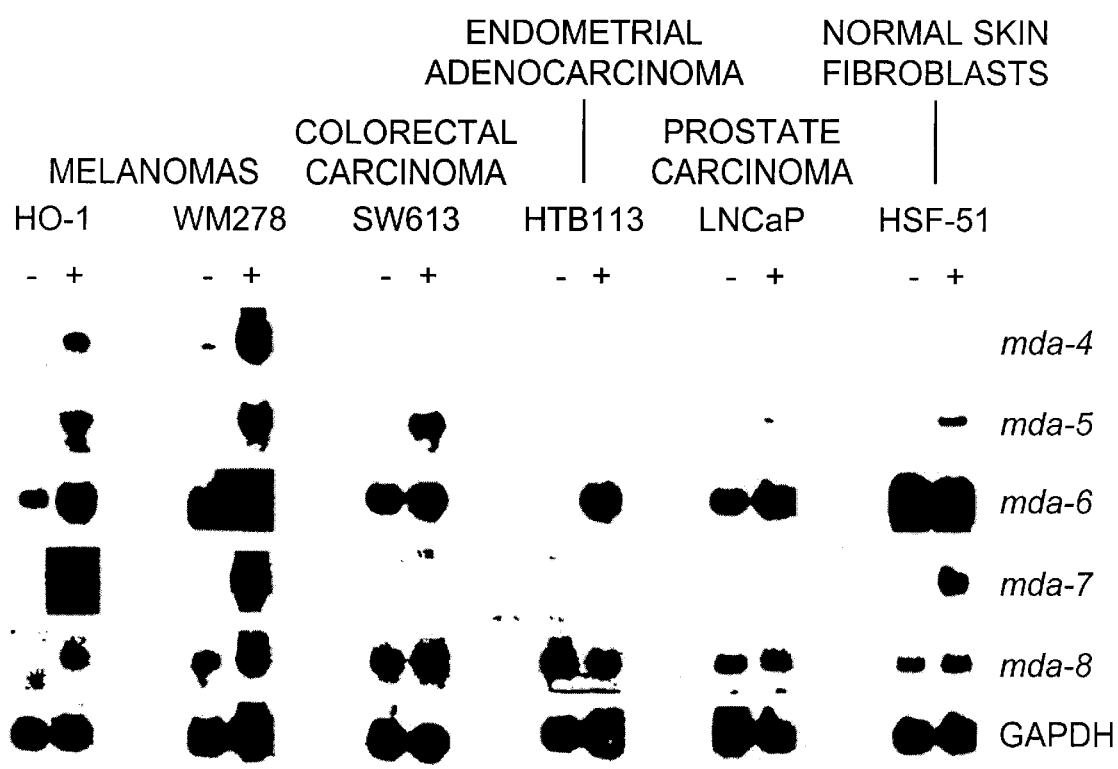
FIG. 18 Expression of mda genes in human colorectal carcinoma (SW613), endometrial adenocarcinoma (HTB113) and prostate carcinoma (LNCaP). −=control, +=IFN-β+MEZ (2,000 units/ml+10 ng/ml).
Figure 19:
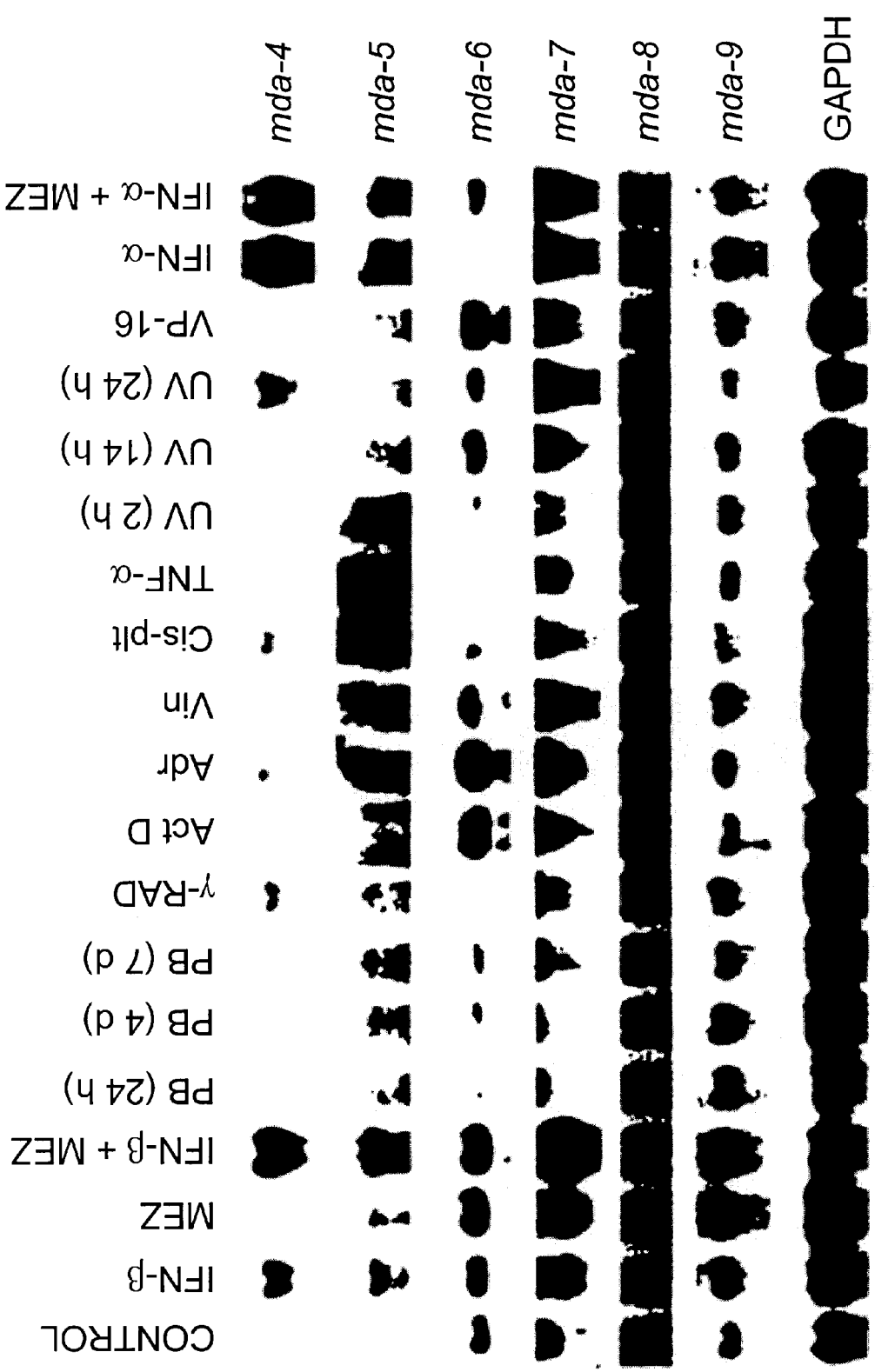
FIG. 19 Effect of various treatment protocols on mda expression in H0-1 cells. IFN-β (2,000 units/ml, 24 hours); MEZ (10 ng/ml, 24 hours); IFN-β+MEZ (2,000 units/ml+10 ng/ml, 24 hours); phenyl butyrate (PB) (4 mM, 24 hours, 4 d, 7 d); γ Rad (γ irradiation) 3 gray, 24 hours, Act D (actinomycin D) (5 µg/ml, 2 hour→24 hours assay); Adriamycin (Adr) (0.1 µg/ml, 24 hours); Vincristine (Vin) (0.1 µg/ml, 24 hours); cis-plt (cis-platinum) (0.1 µg/ml, 24 hours); TNF-α (tumor necrosis factor-α) (100 units/ml, 24 hours); UV (10 joules/mm$^2$, 2, 14 and 24 hours assay); VP-16 (5 µg/ml, 24 hours); IFN-α (2,000 units/ml, 24 hours); and IFN-α+MEZ (2,000 units/ml+10 ng/ml, 24 hours).

E. Cloning of Melanoma Differentiation Associated (mda) Genes Induced in HO-1 Melanoma Cells Treated with IFN-β Plus MEZ The ability to identify and isolate differentially expressed genes between two similar or different cell types is now readily achievable using subtraction hybridization (rev. 57, 58). A procedure for constructing subtracted libraries have been developed that is both sensitive and efficient (49). The application of this approach for the identification of genes differentially expressed in HO-1 cells treated with IFN-β plus MEZ is outlined in FIG. 8. Tester and driver cDNA libraries are directionally cloned into the commercially available λ Uni-ZAP phage vector. Subtraction hybridization is then performed between double-stranded tester DNA and single-stranded driver DNA prepared by mass excision of the libraries. The subtracted cDNAs are efficiently cloned into the λ Uni-ZAP phage vector that can be easily managed for both screening and gene characterization. The applicability of the procedure was demonstrated by the identification of cDNAs displaying enhanced expression in human melanoma cells, HO-1, induced to terminally differentiate by treatment with IFN-β+MEZ (FIG. 10). A single round of subtraction of untreated HO-1 control (Ind⁻) cDNAs from IFN-β+MEZ treated (Ind⁺) cDNAs generated a series of cDNAs displaying differential expression in untreated versus differentiation inducer-treated HO-1 cells, termed melanoma differentiation associated (mda) cDNAs. Employing the approach briefly described above, a total of 23 differentially expressed mda cDNAs have been isolated which represents only a portion of the subtracted HO-1 IFN-β+MEZ cDNA library. Partial sequence analysis of these 23 mda genes resulted in the identification of known genes, including a human TPA-inducible gene, the human apoferritin H gene, the IFP-53 (gamma-2 protein) gene, the IL-8 (monocyte-derived chemotactic factor) gene, the vimentin gene, the hnRNP A2 protein gene, human macrophage inflammatory protein (GOS19-1) and the IFN-β-inducible gene ISG-56. In addition, 6 cDNAs have been identified which do not have sequences previously reported in any of the gene data bases. As predicted based on the subtraction protocol employed, some of the mda genes are induced within 24 hours by: IFN-β and IFN-β+MEZ (e.g., mda-1 and mda-2); MEZ and IFN-β+MEZ (e.g., mda-3); IFN-β, MEZ and IFN-β+MEZ (e.g., mda-4); and only by IFN-β+MEZ (e.g., mda-5 and mda-6) (FIG. 10). A potentially important group of mda genes is represented by cDNAs displaying significantly enhanced expression in HO-1 cells treated with IFN-β+MEZ for 96 hours and displaying terminal cell differentiation, i.e., mda-5, mda-6, mda-7 and mda-9 (all representing novel genes) (FIG. 15). Additional mda cDNAs which may prove of value in understanding growth control in human melanoma cells have been identified which are expressed in both terminally differentiated HO-1 cells and HO-1 cells induced to undergo a reversible suppression in growth by treatment with IFN-β+IFN-γ, i.e., mda-4, mda-5, mda-7 and mda-8 (FIG. 15). Increased expression of a number of mda genes following treatment with IFN-β+MEZ are not restricted to HO-1 cells, since increased mda gene expression is also induced in additional human melanomas induced to terminally differentiate by treatment with IFN-β+MEZ (data not shown). The studies described above indicate the feasibility of using subtraction hybridization to identify genes that may directly mediate or represent markers of terminal differentiation in human melanoma cells.

F. Gene Expression Changes Induced in the C8161 Melanoma Cells and Chromosome 6 Microcell C8161 Hybrids Recent studies by Welch et al. (42) indicate that insertion of a normal chromosome 6 (by the microcell chromosome replacement technique) into the C8161 human melanoma cell line results in a suppression of metastatic, but not tumorigenic potential in nude mice. Treatment of C8161 cells for 4 or 7 days with IFN-β+MEZ (1000 units/ml+10 ng/ml) results in terminal cell differentiation. In contrast, under similar conditions, C8161 cells containing chromosome 6 (Clone 6.1, 6.2 and 6.3) display morphological changes and growth suppression but cells retain proliferative potential, i.e., the combination of agents induces a reversible commitment to differentiation as opposed to terminal differentiation. A lack of terminal differentiation in 6.1, 6.2 and 6.3 cells was demonstrated by removing the test agents and growth in inducer free medium (data not shown). Analysis of gene expression in parental C8161 and 6.1, 6.2 and 6.3 cells indicated differences that correlated with the presence of a normal chromosome 6. Specific differences in gene expression after 4 days incubation with IFN-β and MEZ, alone and in combination, include: (a) induction of IL-8 mRNA (which was identified as an mda cDNA in HO-1 cells treated with IFN-β+MEZ) in MEZ and IFN-β+MEZ treated C8161 cells, but not in 6.1, 6.2 or 6.3 cells; (b) induction of HLA Class I antigen mRNA by IFN-β, MEZ and IFN-β+MEZ in C8161, but only by IFN-β and IFN-β+MEZ in 6.1, 6.2 and 6.3 cells; and (c) reduced induction of ISG-15 expression in C8161 cells versus 6.1, 6.2 and 6.3 cells treated with IFN-β and IFN-β+MEZ. The studies briefly described above indicate that IFN-β+MEZ is more effective in inducing terminal differentiation in the less differentiated metastatic C8161 melanoma cells than the more differentiated 6.1, 6.2 and 6.3 cells. This model system should prove useful in determining the role of specific mda genes in expression of the tumorigenic and metastatic phenotype by human melanoma cells.

Design and Methods

A. Specific Aim #1: Determine the pattern and regulation of expression of the melanoma differentiation associated (mda) genes in melanocytes, nevi, radial growth phase melanoma, vertical growth phase melanoma and metastatic melanoma cells.

1. Rationale and General Approach

Applicants have tested the hypothesis that human melanoma cells display aberrant patterns of differentiation and by appropriate chemical treatment they can be induced to undergo an irreversible loss in proliferative capacity without a loss of viability, i.e., terminal cell differentiation (10, 11, 14). Using the combination of IFN-β+MEZ applicants have demonstrated that the reprogramming of human melanoma cells to terminally differentiate can be achieved in vitro (10, 11, 14). On the basis of a second hypothesis, i.e., terminal differentiation is associated with the selective activation of specific programs of gene expression, applicants have developed and used a modified subtraction hybridization protocol to identify genes displaying enhanced expression under conditions resulting in terminal cell differentiation (49). These studies have resulted in the cloning of a series of genes, termed melanoma differentiation associated (mda)

genes, which display such specificity. The purpose of the studies to be described below are to: (a) characterize the mda genes with respect to their level of regulation in H0-1 melanoma cells, i.e., transcriptional versus posttranscriptional mechanisms of induction; (b) determine if the expression of specific mda genes correlate with a defined stage in melanoma development; (c) continue screening our subtracted IFN-β+MEZ cDNA library to identify additional mda genes which display enhanced expression in growth arrested and terminally differentiated human melanoma cells; and (d) use additional subtraction steps to enrich for genes only expressed at high levels in H0-1 cells induced to terminally differentiate.

(a) Defining the level of regulation of mda genes in H0-1 cells treated with IFN-β+MEZ: Initial studies will focus on the mechanism by which IFN-β+MEZ increases the expression of cloned mda genes that are significantly upregulated (4- to >20-fold) by this combination of inducing agents in H0-1 cells. The genes to be analyzed will include mda-5, mda-6, mda-7, mda-8 and mda-9 described in Preliminary Studies, which represent novel IFN-β+MEZ-inducible genes not previously reported in the Gene Bank or the EMBL gene data base. The order of experiments will include: (1) determining the temporal kinetics of induction of the mda genes; (2) determining if the level of induction of specific mda genes occurs at a transcriptional level; (3) determining if any of the mda genes are immediate early (primary) response genes; and (4) determining if differentiation results in an altered stability of the mda transcripts.

(i) The screening strategy used to identify the mda genes involved Northern hybridization analysis of RNA isolated from H0-1 cells treated with IFN-β, MEZ or IFN-β+MEZ for 24 hr (49). Previous studies indicated that exposure to IFN-β+MEZ for 24 hr resulted in a number of gene expression changes also observed in H0-1 cells induced to terminally differentiate after 4 days exposure to this combination of agents (Preliminary Studies) (14). mda genes displaying increased expression in H0-1 cells after 24 hr treatment with IFN-β+MEZ were subsequently evaluated for enhanced expression after 4 days treatment with the inducers. mda-5, mda-6, mda-7, mda-8 and mda-9 genes displayed enhanced expression in H0-1 cells treated with IFN-β+MEZ for 24 or 96 hr. These results indicated that increased expression of the mda genes occurred within the first 24 hr of treatment and enhanced expression persisted during terminal cell differentiation. To determine if any of the mda genes becomes activated after a short exposure to the inducing agents, temporal kinetic studies will be performed. H0-1 cells will be treated for short-time periods (15, 30, 45, 60 and 120 min) with IFN-β, MEZ and IFN-β+MEZ, cytoplasmic RNA will be isolated, electrophoresed on 0.6% agarose gels, transferred to nylon filters and sequentially hybridized with the various mda genes and lastly with GAPDH (as a control for equal RNA levels under the various experimental conditions) (14). RNA from cells treated with the inducers will also be isolated every 2 hr over a 48 hr period to determine if any cell cycle kinetic changes occur in expression of the mda genes. An important question that also will be addressed is whether continued expression of any of the mda genes is required for maintenance of the terminal differentiation phenotype. This will be determined by analyzing RNA isolated from H0-1 cells treated with IFN-β+MEZ: continuously for 7 days (cells are terminal, but still viable); for 4 days followed by incubation in growth medium without inducers for an additional 10 days (cells remain terminal); and after 10 days in cells treated for 24 hr followed by growth in inducer-free medium (cells regain proliferative potential, i.e., they display a reversible commitment to terminal differentiation).

(ii) The studies described above will indicate if any of the mda genes is induced early after exposure to IFN-β+MEZ. To determine if IFN-β+MEZ induce expression of any of the mda genes by increasing their rates of transcription, nuclear run-on assays will be performed as described previously (55, 58, 59). Brief Description of Protocol: Nuclei will be isolated from H0-1 cells either untreated (control) or treated for 1, 6 and 24 hr with IFN-β (2000 units/ml), MEZ (10 ng/ml) or IFN-β+MEZ (2000 units/ml+10 ng/ml). RNA transcripts previously initiated by RNA polymerase II will be allowed to elongate in the presence of [$^{32}$P]UTP. Nuclear RNA will be isolated, purified by passing through a G-50 sephadex column followed by denaturing with 0.1M NaOH for 5 min on ice (55). Labeled nuclear RNA will be hybridized to nitrocellulose dot filters containing 2 μg of plasmid DNA containing the mda genes, GAPDH DNA or pBR322 DNA (negative control) which has been denatured by boiling in 0.1M NaOH for 15 min followed by dilution with cold 2M NaCl (55).

(iii) c-fos, c-jun and jun-B are immediate early (primary) response genes, i.e., induction is not dependent on new protein synthesis, but rather utilizes existing transcription factors, in IFN-β+MEZ treated H0-1 cells (55). To determine if any of the mda genes is an immediate early (primary) response gene, experiments using the protein synthesis inhibitor cycloheximide will be performed (55). Brief Description of Protocol: Approximately 2×10$^6$ H0-1 cells will be untreated or treated with IFN-β (2000 units/ml), MEZ (10 ng/ml) or IFN-β+MEZ (2000 units/ml+10 ng/ml) for 1 hr in the absence and presence of 50 μg/ml cycloheximide (added 15 min prior to any other additions) (55). Total RNA will be isolated, electrophoresed in 0.6% agarose, transferred to nitrocellulose filters and hybridized sequentially with the mda genes and lastly with GAPDH (14, 49, 60). By definition, if any of the mda genes are immediate early response genes they will be induced within 1 hour by IFN-β+MEZ in both the absence and presence of cycloheximide. Another indication that the mda genes are primary response genes would be the phenomenon of superinduction, i.e., the massive over-accumulation of immediate early response transcripts which occur when cells are treated simultaneously with an inducer and protein synthesis inhibitors (55, 61, 62).

(iv) The ability of IFN-β+MEZ to increase c-jun expression does not involve an increase in transcription, but rather results from an increase in the stability of c-jun mRNA (55). To determine if IFN-β+MEZ alters the expression of specific mda genes by a posttranscriptional mechanism, studies using the transcription inhibitor actinomycin D will be performed (55). Brief Description of Protocol: Approximately 2×10$^6$ H0-1 cells will be untreated or treated with IFN-β (2000 units/ml), MEZ (10 ng/ml) and IFN-β+MEZ (2000 units/ml+10 ng/ml) for 24 hr followed by no addition or the addition of actinomycin D (5 μg/ml) for 30 min, 1 hr, 2 hr and 3 hr prior to RNA isolation (55). The RNAs will be analyzed by Northern hybridization and probing with the different mda genes or GAPDH (14, 49, 55).

Radioautograms will be scanned using a densitometer to quantitate cellular RNA levels (55). These studies will indicate if IFN-β+MEZ can alter the stability, i.e., the half-life, of any of the mda gene transcripts.

Summary: These studies will indicate if mda-5, mda-6, mda-7, mda-8 or mda-9 are primary response genes and if their enhanced expression in human melanoma cells treated with IFN-β+MEZ results from a transcriptional and/or a posttranscriptional mechanism.

(b) Analysis of mda gene expression during the process of melanoma development: A basic tenet of our terminal differentiation hypothesis is that the mda genes may represent genes normally expressed or expressed at higher levels in melanocytes and/or in the early stages of melanoma development, i.e., nevi, early radial growth phase (RGP) primary melanoma and/or early vertical growth phase (VGP) primary melanoma. If this concept is correct, then a prediction would be that specific mda genes would display reduced expression in late VGP melanoma and metastatic melanoma versus melanocytes, nevi and early stage melanomas. Support for this hypothesis comes from preliminary studies indicating that SV40-transformed human melanocytes express high levels of mda-5, mda-6 and mda-7 mRNA in the absence and in the presence of IFN-β+MEZ (data not shown). To directly test this hypothesis applicants will analyze RNA obtained from cell cultures of melanocytes, dysplastic nevi (DN 91D, DN (MM92E)), RGP melanoma (WM 35), early VGP melanoma (WM 793, WM902b), advanced VGP melanoma (WM 983a, WM 115) and metastatic melanomas (WM 9, MeWo, SK-MEL 28, WM 239) (1, 16, 21, 22, 27) (to be supplied by Dr. Meenhard Herlyn). Applicants realize that cell cultures may not always reflect processes occurring in vivo, however, cell cultures will provide an initial indication of which mda genes to emphasize using in situ hybridization approaches with clinical specimens of melanocytes, pre-malignant skin lesions, primary melanoma and metastatic melanoma. The procedures to be used for in situ hybridization with oligonucleotide probes will be as described by Reed et al. (63) and Biroc et al. (64) (to be performed in collaboration with Dr. Anthony P. Albino, Memorial Sloan-Kettering Cancer Center, New York). In the studies by Reed et al. (63) in situ hybridization with a basic fibroblast growth factor (bFGF) oligonucleotide has been successfully used to determine differential expression of bFGF in melanocytic lineage tissue specimens. As an additional approach for determining mda gene expression in clinical specimens, RNA isolated directly from patient samples displaying different stages of melanoma evolution (to be supplied by Dr. Herlyn) will be evaluated by Northern analysis (14, 49) and where necessary to increase sensitivity of detection by RT-PCR analysis (65) for expression of the mda genes. In previous studies analyzing expression of the epidermal growth factor receptor, a wide spectrum of human central nervous system tumors obtained from patients was evaluated (66). This study clearly indicated that intact and high-quality RNA could be obtained efficiently from patient material and utilized for comparative gene expression studies.

As indicated in Background and Significance, metastatic melanoma cells are often inhibited in their growth by TPA (or MEZ), whereas the in vitro growth of normal melanocytes and nevi are stimulated by TPA (or MEZ) (1, 15, 16, 20–23). Similarly, many metastatic melanoma cell lines are growth inhibited by IFN-β (8, 13–15), whereas under optimal growth conditions normal melanocytes are not growth inhibited by IFN-β (even though TPA is incorporated in the growth medium) (15). These results indicate that progression from melanocyte to malignant melanoma involves a change in responsiveness to both TPA (or MEZ) and IFN-β. Based on these observations, it would be predicted that a stage-specific effect will be observed in melanocyte lineage cells exposed to the combination of IFN-β+MEZ. If this effect is observed, it will provide a direct test of the potential involvement of the mda genes in the process of growth inhibition and terminal differentiation resulting from treatment with IFN-β+MEZ. The melanocyte lineage cell lines, i.e., melanocyte, dysplastic nevus, RGP primary melanoma, early VGP primary melanoma, advanced VGP melanoma and metastatic melanoma (supplied by Dr. Meenhard Herlyn, Wistar Institute, Philadelphia, Pa.), will be used to directly determine: (1) if the combination of IFN-β+MEZ displays a stage-specific growth inhibitory effect and the induction of terminal differentiation; and (2) if the induction of growth suppression and/or the induction of terminal differentiation in stage-specific melanocyte lineage cells correlates with changes in the expression of specific mda genes. These studies will be conducted as described previously (10, 14). Brief Description of Protocols: For growth studies: cells will be seeded at 2.5 or $5 \times 10^4$ cells/35 mm plate; 24 hr later the medium will be changed with no additions (Control), 1000 and 2000 units/ml of IFN-β, 1, 10 and 50 ng/ml MEZ and combinations of IFN-β+MEZ; cell numbers will be determined daily (with a medium change at day 4) over a seven day period. For reversibility studies, cells will be treated for 24 hr or 4 days with the different inducers followed by growth in inducer free medium for an additional 7 to 14 days at which time cell numbers will be determined. RNA will be isolated from cells treated for 24 hr, 4 days and 7 days and analyzed by Northern blotting hybridization for expression of the mda genes as described previously (14). Biochemical markers for growth suppression and differentiation will include: an analysis of P2P levels using appropriate monoclonal antibodies and Western blotting analysis (Preliminary Studies) (52, 53); antigenic markers, such as the GD3 ganglioside and Class II MHC, and fluorescence activated cell sorter analysis as described previously (50, 67, 68); and a determination of melanin levels as described previously (69).

Studies designed to identify stage-specific effects of IFN-β+MEZ and the role of the mda genes in growth suppression and terminal cell differentiation in melanocyte lineage cells will be aided by using three recently described model systems. These will include: (A) the transformed human melanocyte cell lines 10 Wras/early and 10 Wras/late (supplied by Dr. Anthony P. Albino, Memorial-Sloan Kettering Cancer Center, NY, N.Y.) (20); (B) the metastatic human melanoma cell line C8161 and the tumorigenic but non-metastatic C8161 clones containing a normal human chromosome 6 (supplied by Dr. Dan Welch, Milton S. Hershey Medical Center, Hershey, Pa.) (42, 43); and (C) RGP or early VGP primary human melanomas (WM 35, WM 1341B and WM 793) which have been selected by injection with matrigel in nude mice for a more progressed tumorigenic and metastatic phenotype (e.g., 35-P1-N1,35-P1-N2,35-P1-N3, 1341-P1-N1, 1341-P1-N2, 1341-P2-N1 etc. (cell line: passage number; nude mouse number)) (supplied by Dr. Robert S. Kerbel, Sunnybrook Medical Center, Toronto, Canada) (25, 70). The 10 Wras/early and 10 Wras/late cells are human melanocytes transformed by a retrovirus containing the viral Ha-ras oncogene which display specific traits associated with melanoma progression (20). 10 Wras/early cells display TPA dependence, are nontumorigenic in nude mice, and express many of the antigenic markers present in normal melanocytes (20). In contrast, the 10 Wras/late cells are inhibited by TPA, tumorigenic in nude mice, contain many of the cytogenetic changes seen in metastatic melanoma (including modifications in chromosome 1, 6 and 9) and express many of the same growth factor genes as metastatic human melanoma (20). As discussed in Preliminary Studies, applicants have begun to analyze gene expression changes in IFN-β+MEZ treated C8161 cells and C8161 cells containing a microcell-transferred normal chromosome 6 (6.1, 6.2 and 6.3). Unlike C8161 cells, 6.1, 6.2 and 6.3 cells are not metastatic in nude mice (42) and they are not induced to terminally differentiate when treated with the same concentration of IFN-β+MEZ resulting in terminal differentiation in C8161 cells. 6.1, 6.2 and 6.3, therefore, may represent human melanoma cells which have been reverted to a less advanced stage in melanoma development. As discussed previously, since surgical removal of RGP or early stage VGP primary human melanomas results in a cure of this disease, it has not previously been possible to analyze more aggressive variants derived from the same early stage melanomas. Dr. Kerbel and colleagues (25) have potentially overcome this problem by injecting RGP and early VGP primary human melanomas in combination with matrigel into nude mice. Tumors which then developed were found to be tumorigenic in nude mice without the requirement for matrigel and they also acquired a "cytokine resistance phenotype" which is associated with melanoma progression (25, 70). These three cell systems should prove extremely valuable in determining if mda gene expression correlates with specific stages of melanoma progression. To test this possibility applicants will conduct similar experiments as described previously (4. A. 1. a) using these stage-specific cell lines. If our hypothesis suggesting that the response of melanocyte lineage cells to IFN-β+MEZ is stage-specific is correct, then applicants would predict that the effect of these agents on growth, mda gene expression and terminal cell differentiation would be greater in 10Wras/late vs. 10 Wras/early cells, C8161 cells vs. chromosome 6 containing C8161 clones and the more progressed vs. the less progressed RGP and early VGP primary melanoma cell lines.

Summary: These studies will indicate if a direct relationship exists between the state of progression of melanoma cells and mda gene expression. They will also indicate if the response to IFN-β+MEZ induced growth suppression, mda gene expression and terminal cell differentiation is directly related to melanoma progression.

(c) and (d) Identification of additional mda genes which display enhanced expression in growth arrested and/or terminally differentiated human melanoma cells: As indicated in Preliminary Studies (E), only a small percentage (approximately 2.5%) of our subtracted IFN-β+MEZ H0-1 library has been screened for differentially expressed genes associated with growth suppression and terminal differentiation in H0-1 cells. It is therefore conceivable that a number of additional mda genes, which still remain to be identified, are present in the subtracted IFN-β+MEZ H0-1 library. The initial subtraction hybridization approach applicants have used has resulted in the identification of cDNAs displaying enhanced expression in H0-1 cells treated with: IFN-β and IFN-β+MEZ; MEZ and IFN-β+MEZ; IFN-β, MEZ and IFN-β+MEZ; and only IFN-β+MEZ (49). To identify additional mda genes which are preferentially expressed at elevated levels in cells induced to terminally differentiate following treatment with IFN-β+MEZ applicants will perform additional subtraction hybridization steps. Brief Description of Protocol: cDNA libraries will be constructed from H0-1 cells treated with IFN-β (2000 units/ml) or MEZ (10 ng/ml) for 2, 4, 8, 12 and 24 hr as previously described (49, 57). The IFN-β and MEZ cDNA libraries will be converted into single-stranded DNA which will then be biotinylated using photoactivatable biotin and used as the Driver DNA as described previously (49). The H0-1 IFN-β+MEZ (Ind$^+$) subtracted cDNA library will be converted into double stranded DNA and the double-stranded inserts will be isolated and used as the Tester DNA (49). The Driver DNA will then be subtracted away from the Tester DNA resulting in an enriched H0-1 IFN-β+MEZ (Enriched-Ind$^+$) subtracted cDNA library (49). As an alternate approach to specifically identify genes displaying increased elevation in terminally differentiated melanoma cells, cDNA libraries will be constructed from H0-1 cells treated for 4 or 7 days with IFN-β, MEZ and IFN-β+MEZ. Subtraction hybridization will then be conducted as described (49) using these libraries to identify cDNAs only expressed at increased levels in IFN-β+MEZ-treated terminally differentiated H0-1 cells.

Summary: Additional screening of our current H0-1 IFN-β+MEZ (Ind$^+$) offers the potential of identifying more differentially expressed mda genes. By constructing additional cDNA libraries from H0-1 cells treated singularly with IFN-β or MEZ and subtracting this information away from cDNA libraries prepared from H0-1 cells treated with IFN-β+MEZ, the identification of additional mda genes displaying enhanced expression specifically in terminally differentiated melanoma cells should result.

B. Specific Aim #2: Analyze the relationship between mda gene expression and the induction of reversible commitment to differentiation, growth suppression without the induction of differentiation, DNA damage and stress responses and induction of terminal differentiation in human melanoma and other model differentiation systems.

1. Rationale and General Approach

Induction of terminal differentiation in human melanoma cells, as well as other cell types such as myoblasts, neuroblastoma and leukemic cells, is associated with an irreversible loss in proliferative ability (rev 13, 71). It is therefore reasonable to assume that some of the mda genes applicants have identified may also display enhanced expression in growth arrested melanoma (and other cell types) or melanoma cells (and other cell types) treated with various DNA damaging and chemotherapeutic agents which also induce growth-related changes. Indeed, preliminary studies indicate that mda-4, mda-5 and mda-8 exhibit increased expression in terminally differentiated H0-1 cells as well as H0-1 cells induced to undergo reversible growth suppression by treatment with IFN-β+IFN-γ (50). In addition, mda-4 also displays increased expression in H0-1 cells reversibly growth suppressed by caffeic acid phenethyl ester (72), vinblastine, tumor necrosis factor-α and X-irradiation. Additional mda genes have been identified which display enhanced expression only in H0-1 and other metastatic human melanoma cells treated with IFN-β+MEZ (i.e., they appear to be melanoma specific) or in H0-1 and dissimilar cell types induced to lose proliferative capacity, including human breast and colon carcinoma (i.e., they appear to be growth and or differentiation specific and not melanoma specific). Based on these preliminary observations, it appears that specific mda genes may be restricted to melanoma lineage cells induced to lose growth potential and become terminally differentiated, while other mda genes may represent key genes involved in growth control processes in diverse cell types. It will, therefore, be important to determine whether changes in the expression of specific mda cDNAs are restricted to human melanoma cells induced to terminally differentiate or whether they also display modified expression during other programs of terminal differentiation, DNA damage and growth arrest. The studies described below are designed to determine: (a) the spectrum of cellular changes which induce enhanced mda gene expression in human melanoma and other cell types; and (b) if induction of growth suppression and terminal differentiation in other cell types results in the enhanced expression of specific mda genes.

(a) Analysis of mda gene expression in human melanoma (and other cell types) treated with growth suppressing agents, DNA damaging agents and chemotherapeutic agents: Since terminal differentiation in H0-1 cells is associated with an irreversible loss in proliferative capacity (10, 11, 14), the mda genes applicants have identified may represent genes involved in both cell growth and terminal cell differentiation. To explore the relationship between cell growth and terminal differentiation, studies will be conducted to determine the types of agents and treatment protocols which can induce mda gene expression in human melanoma and other human cell types. The agents and treatments to be tested will include: growth suppression (incubation in reduced serum levels), heat shock, gamma irradiation, ultraviolet irradiation (UVA and UVB), carcinogenic and mutagenic agents (methyl methanesulfonate, ethyl methanesulfonate and 4-nitroquinoline-oxide), demethylating agents (5-azacytidine, phenyl butyrate), chemotherapeutic agents (vinblastine, vincristine, adriamycin, cis-platinum), tumor necrosis factor-$\alpha$, protein synthesis inhibitors (cycloheximide, puromycin, anisomycin), DNA synthesis inhibitors (amphidicolin, hydroxylurea, ara-C), transcription inhibitors (actinomycin D), topoisomerase inhibitors (camptothecin), poly-ADP-ribose inhibitors (3-aminobenzamide), protein kinase C activators (TPA, teleocidin, synthetic PKC activators (ADMB and DHI) (73–75)) and phosphatase inhibitors (calyculin, okadaic acid). Initial studies will focus on H0-1 cells. Subsequent investigations will involve other melanoma cells (representing different stages of melanoma progression) and additional human cell types (normal fibroblast and epithelial cells, neuroblastoma, glioblastoma, carcinomas (prostate, breast and colon) and sarcomas). Brief Description of Protocol: H0-1 cells (or the other experimental cell type employed) will be treated with the various agents for different time periods (ranging from 1 hr to 24 hr; or with certain treatment protocols for 4 and 7 days) and with different doses of the test treatment or agent. RNA will be isolated, electrophoresed in 0.6% agarose gels, transferred to nylon filters and hybridized sequentially with the different mda genes and lastly with GAPDH. If specific pathways appear to induce an mda gene then further biochemical studies will be conducted. For example, if PKC activators induce specific mda genes then studies will be performed using specific inactive analogs and inhibitors of PKC to determine the relationship between PKC activation and induction of gene expression. Similarly, if a treatment protocol or agent is found to induce or enhance expression of an mda gene, then subsequent studies will be conducted to determine if this change in gene expression is transcriptional or post-transcriptional (see Specific Aim #1 for experimental details).

Summary: The studies briefly outlined above will indicate if mda gene expression can be induced in H0-1, other human melanoma cells and additional human cell types, by treatment with agents which can alter growth and/or differentiation. They will provide initial information relative to potential biochemical pathways which may mediate the induction or enhanced expression of the mda genes. These experiments will also identify which mda gene(s) to use in studies (described in C. Specific Aim #3.) designed to determine the potential functional significance of mda gene expression changes in the control of growth and differentiation in human melanoma cells and other human cell types.

(b) Analysis of mda gene expression during the process of terminal differentiation in human promyelocytic leukemia (HL-60) and human skeletal muscle cultures: Specific mda genes are expressed in human melanoma and additional human cell types undergoing growth suppression with and without the induction of terminal differentiation. To explore this phenomenon further and to determine if any of the mda genes are also expressed at elevated levels in additional differentiation model systems applicants will conduct experiments using the HL-60 promyelocytic leukemic cell line (76) and human skeletal muscle cells (77, 78). TPA induces macrophage differentiation in HL-60 cells (79), whereas dimethyl sulfoxide (DMSO) results in granulocytic differentiation in HL-60 cells (80). In addition, growth of HL-60 cells in medium containing DMSO for 5 days followed by growth in TPA results in cells which switch from a granulocytic to monocytic differentiation program (81). These studies indicate that specific monocytic or granulocytic lineages can be induced in HL-60 cells by appropriate chemical manipulation. By growing HL-60 cells in incremental increases of TPA and DMSO, applicants have isolated variant populations which display a quantitative resistance to either TPA- or DMSO-induced differentiation (76). These resistant variants do not, however, display cross-resistance to other inducers, i.e., TPA induces a similar pattern of differentiation in parental HL-60 and HL-60/DMSO$^R$ cells and DMSO induces a similar pattern of differentiation in parental HL-60 and HL-60/TPA$^R$ cells. Although IFN-aA and IFN-$\beta$ induce growth suppression in parental HL-60, TPA-resistant HL-60 (HL-60/TPA$^R$) and DMSO-resistant HL-60 (HL-60/DMSO$^R$) cells, they do not induce these cells to differentiate terminally (76). However, the combination of IFN-$\alpha$A or IFN-$\beta$ and TPA results in a synergistic growth suppression and the induction of terminal differentiation in both parental and HL-60/TPA$^R$ cells (76). Similarly, the combination of IFN-$\alpha$A or IFN-$\beta$ and DMSO results in synergistic growth suppression and the induction of terminal differentiation in both parental and HL-60/DMSO$^R$ cells (76). This experimental model will prove extremely valuable in determining if a correlation exists between enhanced mda gene expression and either growth suppression or growth suppression with the induction of specific programs of terminal differentiation in human myeloblastic leukemic cells. Brief Description of Protocols: Parental HL-60, HL-60/TPA$^R$ and HL-60/DMSO$^R$ cells will be incubated with IFN-$\beta$ (2000 units/ml)±inducer (TPA at $10^{-9}$ and $10^{-6}$ M or DMSO 0.9 to 1.5%) for 1, 3 and 7 days (with fresh medium±additions added at day 4). Cell numbers and terminal differentiation (as monitored by the presence of morphologically mature cells and the ability of cells to reduce nitroblue tetrazolium (NBT) (granulocyte specific) or the production of nonspecific esterase (macrophage specific) will be determined (84). RNA will be isolated, electrophoresed in 0.6% agarose gels, transferred to nylon filters and hybridized sequentially with the different mda genes and lastly with GAPDH (14, 49). Since the induction of both growth suppression and terminal differentiation is concentration- and compound-dependent in parental HL-60 and variant HL-60 cells, the studies outlined above will indicate if a relationship exists between the degree of growth suppression and/or the induction of terminal differentiation and expression of the different mda genes in HL-60 cells.

Methods are available for the in vitro growth of myogenic muscle satellite cells obtained from normal adult human skeletal muscle (82). These cultures recapitulate normal myogenesis, a process that can be followed with specific morphologic and biochemical markers and thus provides a useful system for assessing the effects of various agents on the process of cellular differentiation in human cells (77, 78, 82). Using this model system, applicants have previously demonstrated that TPA (and related compounds) inhibit spontaneous and induced myogenesis, whereas IFN-αA enhances myogenesis (77, 78). Inhibition or enhancement of differentiation in human skeletal muscle cultures is associated with either the suppression or induction, respectively, of specific morphologic changes (development of multinucleated myotubes) and changes in creatine kinase isoenzyme transition from CK-BB to the CK-MM form (77, 78). Applicants have also developed SV40-immortalized human skeletal muscle cells which fail to undergo terminal differentiation when treated with IFN-αA (83). This experimental model will prove extremely valuable in determining if any of the mda genes are differentially expressed during the induction of terminal differentiation or growth suppression in human skeletal muscle cells. Brief Description of Protocols: Muscle cultures will be grown from human skeletal muscle biopsy specimens obtained from diagnostic evaluation (from patients of either sex and ranging from 6 months to 50 years of age) as previously described (77, 78, 82). Prior to myoblast fusion, the cells will be trypsinized and plated at $2 \times 10^6$ cells/10 cm tissue culture plate, cultures will be incubated with IFN-β (2000 units/ml) and MEZ (10 ng/ml), alone and in combination, for 1, 4 and 7 days (with an appropriate medium change at day 4). Cell numbers will be determined and differentiation will be monitored using morphologic (myoblast fusion) and biochemical (creatine kinase isoenzyme transition from CK-BB to CK-MM) criteria (77, 78, 82). RNA will be isolated, electrophoresed in 0.6% agarose gels, transferred to nylon filters and hybridized sequentially with the different mda genes and lastly with GAPDH. When only small quantities of RNA are available, RT-PCR (65) will be used to determine expression of the appropriate mda gene in early passage human skeletal myoblast cultures. In this model system, IFN-β promotes skeletal muscle differentiation whereas MEZ inhibits differentiation. By employing specific concentrations of IFN-β+ MEZ, it is possible to obtain either an enhancement in differentiation, no change in differentiation or an inhibition in differentiation (78). This system should permit a direct determination of the relationship between mda gene expression and the induction of myogenesis in human skeletal muscle cultures.

Summary: The studies described briefly above will indicate if any of applicants mda genes display altered expression during the induction of growth suppression and terminal differentiation in human myeloid leukemic cells and human skeletal muscle cells. If changes are observed, subsequent studies could be conducted to determine if the mda genes display enhanced expression in other differentiation models, including the U937 human monoblastic leukemia cell which can be induced to undergo macrophage differentiation (81), the PC12 rat pheochromocytoma cell line which can be induced to undergo neuronal differentiation (85) and human neuroblastoma cells which can be induced to differentiate terminally when treated with retinoic acid or other agents. In addition, if mda gene expression changes are observed in HL-60 cells induced to terminally differentiate, further studies would be conducted using HL-60 cells and other inducing agents which result in growth arrest without differentiation, DNA damage and apoptosis and terminal cell differentiation (with and without apoptosis). These studies would indicate which cellular and biochemical changes in HL-60 cells result in induction of specific programs of mda gene expression.

C. Specific Aim #3: Isolate full-length cDNAs of mda genes that may be involved in melanoma differentiation or progression and directly determine their potential functional role in the differentiation and progression of human melanoma.

1. Rationale and General Approach

The ability to analyze the functional significance of specific mda genes will require the isolation of full-length cDNAs. Once a full-length cDNA has been identified for a specific mda gene it can be used to: (1) produce its encoded protein using an in vitro translation system; (2) generate polyclonal antibodies specific for peptide regions of the encoded protein; (3) determine the location of the mda gene product in human melanoma cells and in tissue sections from patients; (4) determine the effect of overexpression of the mda gene on induction of growth suppression and terminal differentiation; and (5) determine the effect of blocking mda gene expression (using antisense oligomers or expression vector constructs) on the ability of IFN-β+MEZ to induce growth suppression and terminal cell differentiation. The approaches to be utilized to identify full-length mda cDNAs, in vitro translate the full-length mda cDNAs, produce antibodies against specific peptides of the encoded proteins, determine the location of the encoded proteins and to construct and analyze the effect of sense and antisense oligomers and expression vector constructs on growth and differentiation in H0-1 and other cell types is described below.

(a) Strategy for isolating full-length mda cDNAs: Rapid amplification of cDNA ends (RACE) is a procedure for amplification of nucleic acid sequences from a mRNA template between a defined internal site and an unknown sequence representing either the 3' or 5' end of the mRNA (86–88). The RACE procedure will be used to obtain the complete sequence of the full-length mda cDNAs (5' ends) using the sequences (already determined) as the templates. Two types of gene-specific primers will be synthesized: the RT primer for reverse transcription and the AMP primer for PCR amplification. The sequence of the AMP primer is located upstream of the RT primer. First strand cDNA synthesis is initiated from the RT primer. After first strand cDNA synthesis, the original mRNA template is destroyed with RNase H and unincorporated dNTPs and RT primers are separated from cDNA using Centricon spin filters (Amicon Corp.). An oligo-DA anchor sequence is then added to the 3' end of the cDNA using TdT (terminal d transferase) and dATP. PCR amplification is accomplished using the AMP primer and a mixture of oligo(dT)-adapter primer/adapter primer (1:9). The adapter primer contains a specific sequence which, in the form of dsDNA, can be recognized and digested by the restriction enzymes SalI and XhoI. Following amplification, the RACE products will be digested with specific restriction enzymes (which do not cut the cDNA internally) and cloned into an appropriate plasmid (such as pBlueScript). The clones with specific inserts will be selected by screening (using DNA filter hybridization) and multiple independent clones of each gene will be used simultaneously for DNA sequencing to eliminate possible errors in sequence determination as a result of misincorporations occurring during the PCR amplification process.

(b) Characterization of full-length mda cDNAs: Full-length mda cDNAs will be used to obtain information about the mda-encoded proteins and the potential function of these genetic elements in regulating growth and differentiation of human melanoma cells. As will be described below, in vitro translation will be used to obtain the mda-encoded proteins. Once the protein structure is determined, synthetic peptides will be constructed and used to generate antibodies specific for defined regions of the mda proteins. Antibodies will be used to determine the location of the mda proteins in melanoma and other cell types and tissue sections.

(i) Determination of protein structure and development of polyclonal antibodies specific for mda genes: Once full-length mda cDNAs have been isolated and sequenced, information will be available relative to the presence of open reading frames and the amino acid composition of the putative proteins encoded by these mda genes. To directly determine the size of the proteins encoded by the mda genes, full-length cDNAs will be subcloned into the pGEM-1 vector and transcribed in vitro using SP6 polymerase (Promega Corp., Madison, Wis.) as described (89). The in vitro transcribed RNA will be translated in a rabbit reticulocyte lysate (Amersham) in the presence of [$^{35}$S]methionine according to the manufacturer's instructions and dialyzed against 10 mM Hepes, pH 7.9, 1 mM $MgCl_2$, 1 mM dithiothreitol, 20% glycerol, 100 mM NaCl, 100 $\mu$M $ZnCl_2$ at 4° C. overnight. Protein products will be analyzed by electrophoresis in an SDS/10–20% polyacrylamide gradient gel. Based on predicted amino acid structure of the protein, i.e., hydrophobicity value, antigenicity value and turn structure based on the deduced sequences of the mda cDNA, specific amino acids will be chosen for generating synthetic peptides (75, 90). Synthetic peptides will then be used to generate polyclonal antibodies (Hazelton Laboratories, Denver, Pa. or Cappel Laboratories, Durham, N.C.). Brief Description of Protocol: The synthetic peptides will be conjugated with carrier proteins, bovine serum albumin and CGG (chicken γ-globulin) as described (90). Two and one-half mg of peptide and 5 mg of carrier protein in double-distilled water will be incubated with 20 mg of either ethyl CDI (1-ethyl-3-(3-dimethyl-aminopropyl)carbodiimide hydrochloride) (Sigma) or morpho CDI (1-cyclohexyl-3-(2-morpholinoethyl)carbodiimide metho-p-toluenesulfonate) (Sigma) in water at room temperature for 2 hours and dialyzed against PBS, pH 7.2. Rabbits will be immunized with 0.5 mg of BSA peptide (conjugated by ethyl CDI) emulsified with complete Freund's adjuvant at 2-week intervals. The antisera against peptides will then be purified by affinity chromatography coupled with CGG peptide (conjugated by morpho CDI), excluding the by-product generated in the conjugation reaction. The polyclonal antibodies will be titered (by 1:1 serial dilution, beginning with a 1:50 dilution) on human melanoma cells, either untreated or treated with IFN-β+MEZ, by ELISA assays as described previously (91).

(ii) Immunostaining of cultured cells and sectioned patient samples with anti-mda peptide antibodies: Based on preliminary studies using SV40-immortalized human melanocytes, applicants would predict that specific mda gene products would be produced at increased levels in normal melanocytes versus melanoma cells. To test this possibility and to determine if differences are apparent in specific stages of melanoma development or as a consequence of IFN-β+MEZ treatment, melanocytes, dysplastic nevi and different staged melanomas (RGP, early VGP, late VGP and metastatic) will be cultured on coverslips. Twenty four hr later, one group of cultures will receive a media change without additions and the other will receive fresh medium with 2000 units/ml of IFN-β+10 ng/ml of MEZ. After an additional 24 hr, cultures will be washed 3× with PBS followed by fixation with 3.7% formalin for 30 min (90, 91). The slides will then be washed 3× with PBS and treated with 0.2% Triton X-100/PBS for 5 min at room temperature. After extensive washing with PBS and blocking nonspecific binding sites with 2% egg albumin/PBS, the cells will be incubated with affinity purified anti-mda peptide antibody or preimmunized control sera for 30 min. The slides will then be incubated with fluorescein isothiocyanate-conjugated goat anti-rabbit immunoglobulin antibody for 30 min followed by examination with a fluorescence microscope after extensive washing with 0.1% SDS/PBS (90). Studies will also be conducted to determine if the anti-mda peptide antibodies react with melanocyte/melanoma lineage tissue. Reactivity of the anti-mda peptide antibodies toward sectioned clinical samples representing normal melanocytes, dysplastic nevi, and RGP, early VGP, late VGP and metastatic melanoma (supplied by Drs. Albino and Herlyn) (63) will be analyzed as previously described (90, 91).

(iii) Analysis of the effect of forced mda expression on growth and differentiation in human melanoma cells: A key question will be whether expression of any of the mda genes can directly inhibit melanoma growth or induce morphological, biochemical or gene expression changes associated with growth suppression and the induction of differentiation without the addition of inducer (IFN-β+MEZ). To determine the effect of overexpression of specific mda genes on growth and differentiation in human melanoma cells applicants will employ expression vectors containing full-length mda cDNAs. Full-length mda cDNAs will be cloned into an expression vector containing an inducible promoter, such as the dexamethasone (DEX)-inducible MMTV promoter, and a selectable antibiotic resistance gene, such as the neomycin resistance gene, e.g., pMAMneo construct (Clonetech). Transfer of this mda-S construct into human melanoma cells will permit the direct isolation of cells containing the specific mda-S gene and will permit regulation (by altering DEX concentrations) of the level of expression of the specific mda gene. This approach may be necessary, since continuous increased expression of specific mda genes under control of promoters such as the cytomegalovirus (CMV) or the β-actin promoter may result in loss of proliferative ability and/or terminal differentiation in human melanoma cells. By using different MTV promoter-driven constructs containing different mda genes and different antibiotic resistance genes, it will also be possible to construct melanoma cells containing several mda-S inducible gene constructs. An additional advantage of a regulatable expression vector system will be the stable nature of the cell clones and the ability to determine if transient or prolonged mda-S expression is required to induce an irreversible loss of proliferative capacity and terminal differentiation in H0-1 cells. Brief Description of Protocols: H0-1 cells (additional human melanoma cell lines or other human tumor cell lines) will be seeded at 2×10$^6$ cells/100 mm plate, 24 hr later cells will be transfected by electroporation with the mda-S construct (alone if a selectable gene is present in the construct or in conjunction with a cloned selectable gene) as described (92). Antibiotic resistant colonies will be selected and isolated as pure clones (92, 93). The presence of the inserted gene will be determined by Southern blotting and expression of the endogenous and exogenous gene will be distinguished by RNase protection assays (58, 94). The ability of DEX to enhance expression of the mda-S gene in appropriate H0-1 cell lines will be determined by growing cells in the presence or absence of the appropriate inducer ($10^{-9}$ to $10^{-5}$ M DEX or 2000 units/ml of IFN-$\beta$) for 24 hr prior to isolating and characterizing RNA expression (95). Under conditions of non-induction (absence of DEX) or induction (presence of DEX) cells containing the MMTV-inducible mda-S constructs will be evaluated for alterations in growth (10, 14), increases in melanin synthesis (10, 69), modification in cell surface antigenic phenotype (67, 68, 72), changes in the levels of P2Ps (52, 53), patterns of gene expression (14) and the induction of irreversible loss of proliferation (terminal differentiation) (10, 11, 14) using previously described protocols.

Potential Outcome of mda-S Expression Construct Studies

The studies briefly described above could result in one of three potential outcomes. First, a single mda-S construct could induce growth suppression, gene expression changes associated with differentiation and terminal cell differentiation in the absence of IFN-$\beta$+MEZ. This would provide compelling evidence that this specific mda gene is a controlling element in regulating growth and differentiation in human melanoma cells. Second, specific mda-S constructs could modify only a portion of the changes induced by IFN-$\beta$+MEZ in human melanoma cells, i.e., induce growth suppression, induce growth suppression and some markers of differentiation or induce only some of the gene expression changes associated with differentiation without affecting growth. If this occurs, then it may be possible by using a combination of mda-S constructs, which induce different components of the differentiation program in human melanoma cells, to induce a loss of proliferative capacity and terminal differentiation in human melanoma cells. Third, mda-S constructs could display no effects on growth or differentiation programs in H0-1 cells. This result would of course be the least informative outcome. It would suggest that the specific mda-S constructs tested are not controlling elements in melanoma differentiation, although these genes may be altered during the induction of growth suppression and terminal differentiation in human melanoma cells by IFN-$\beta$+MEZ.

(iv) Analysis of the effect of antisense oligomers and expression vector constructs on growth and differentiation in human melanoma cells: Antisense RNA is an effective approach for interfering with the expression of specific target genes (96). The antisense transcript has a sequence complementary to the target mRNA and can presumably anneal to the mRNA and disrupt normal processing or translation (96). Mechanism(s) by which antisense constructs inhibit gene functions include: a direct interference in translation by binding to the ribosomal assembly (translation initiation) site and/or coding regions; stimulation of mRNA degradation by RNase H which specifically cleaves double-stranded RNA hybrids; and blocking translocation of the mRNA from the nucleus into the cytoplasm (96). Previous studies have demonstrated that antisense constructs or oliogodeoxyribonucleotides (oligomers) of specific genes, such as c-myc and Egr-1, can modulate cell growth and/or differentiation (84, 97–101). To determine the effect of blocking mda gene expression on growth and differentiation in human melanoma cells applicants will conduct experiments using antisense oligomers and expression vectors containing antisense constructs.

In the first set of experiments applicants will determine if oligomers complementary to specific regions of the mda genes can induce growth suppression and/or changes in the expression of genes previously shown to be altered in H0-1 cells treated with IFN-$\beta$+MEZ, i.e., c-myc, IL-8, FIB, MGSA/gro, ISG-15, c-jun and jun-B (14, 55). As indicated above, antisense oligomers have been employed successfully to alter cell physiology in a number of cell lines and they have been shown to affect the expression of many genes (rev. 102, 103). mda-gene specific oligomers complementary to the translation initiation sites or 5'-coding regions will be synthesized with phosphorothioate modification (phosphorothioate oligodeoxynucleotide) to increase nuclease resistance (96, 102, 103). Although unmodified oligomers have been utilized in many laboratories, they can be degraded rapidly by nucleases present in serum-supplemented medium (96, 102). Since experiments with H0-1 and the other cell types will utilize serum-containing medium, applicants will use phosphorothioate oligodeoxynucleotides as opposed to unmodified oligomers. Brief Description of Protocols: For growth studies, H0-1 cells (or other test cell lines) will be seeded at $2.5 \times 10^4$ cells/35 mm tissue culture plate and 24 hr later fresh medium with IFN-$\beta$+MEZ (2000 units/ml+10 ng/ml), various concentrations (1 to 200 $\mu$M) of the 3',5'-phosphorothioate end-capped mda antisense oligomer complementary to several target sequences of the 5' region of the mda gene (20 bases in length) (mda-AS oligomer) or the combination of IFN-$\beta$+MEZ and the mda-AS oligomer will be added. As appropriate controls, cultures will also receive similar concentrations of a 5',3'-phosphorothioate end-capped mda sense oligomer (mda-S oligomer) or the mda-S oligomer plus IFN-$\beta$+MEZ (65, 84, 104). Cell numbers will be determined daily over a 7 day period (with medium changes with the appropriate additions every 48 hr) to identify the correct mda-AS oligomer to use and the concentration of mda-AS oligomer required to block the effect of IFN-$\beta$+MEZ on growth inhibition in H0-1 cells. If an appropriate mda-AS oligomer is identified it will be used for subsequent studies to determine the effect of this mda-AS oligomer on gene expression (14) and biochemical (10, 52, 53, 69) and immunological changes (67, 68, 72) induced in H0-1 cells treated with IFN-$\beta$+MEZ. For gene expression studies, H0-1 cells (or other test cell lines) will be seeded at $2.5 \times 10^6$ cells/100 mm tissue culture plate and the appropriate concentration of mda-AS or mda-S oligomer will be added 24 hr later. RNA will be isolated after an additional 24 hr or 96 hr (with a medium change after 48 hr), electrophoresed in 0.6% agarose gels, transferred to nylon filters and hybridized sequentially with c-myc, c-jun, jun-B, ISG-15, MGSA/gro, IL-8, FIB and lastly with GAPDH (14). Assays will also be conducted to determine if mda-AS oligomers can prevent or diminish the biochemical, immunological and/or cellular changes induced in H0-1 cells by the combination of IFN-$\beta$+MEZ. Parameters to be monitored, by previously described techniques, include morphology (10), melanin synthesis (10, 69), antigenic expression (67, 68, 72) and levels of P2Ps (52, 53). Possible Outcome of Studies: The experiments described above could produce one of three possible outcomes. First, specific mda-AS oligomers could inhibit the ability of IFN-β+MEZ to induce growth suppression, gene expression changes associated with differentiation and terminal cell differentiation. Second, specific mda-AS oligomers could modify only a portion of the changes induced by IFN-β+MEZ in H0-1 cells, i.e., reverse growth suppression, reverse both growth suppression and terminal differentiation or reverse only some of the gene expression changes. Third, specific mda-AS oligomers could display no effect on the growth suppression or the differentiation program induced by IFN-β+MEZ.

A positive result using mda-AS oligomers in blocking specific cellular and biochemical changes in H0-1 cells treated with IFN-β+MEZ would provide strong evidence for a relationship between expression of a specific mda gene and a defined component of the differentiation process. However, a negative effect of a specific mda-AS gene could occur for many reasons including lack of stability of the antisense oligomer, inadequate quantity of the antisense oligomer or the requirement for the expression of multiple mda genes in the differentiation process. To further explore the effect of mda-AS gene expression in inhibiting chemical induction of differentiation in human melanoma cells experiments will also be conducted using mda-AS cDNAs (mda cDNAs cloned in an antisense orientation) in expression vector constructs. Since one question applicants intend to address is the relationship between levels of expression and tissue specific expression of specific mda-AS cDNAs and cellular phenotype, applicants will use several expression vector constructs under the transcriptional control of different promoters. The constructs to be used should result in high level targeted, constitutive or inducible transcriptional control of the mda-AS cDNAs. The same mda-AS cDNA will be cloned into an expression vector containing a promoter which will permit: high levels of constitutive expression (β-actin promoter (84, 94)); enhanced expression after interferon treatment (interferon responsive sequence (IRS) promoter (pTKO-1) (105); inducible expression in the presence of dexamethasone-(MMTV) inducible promoter (93, 106); or expression in melanocyte/melanoma lineage cells (tyrosinase promoter (107)). In addition, by using different selectable genes, i.e., neomycin, histidinol, hygromycin etc., either present in the expression vector construct or by cotransfection (93) it will be possible to construct human melanoma cells which contain several mda-AS cDNAs. In summary, the use of different promoters will permit a direct evaluation of constitutive, inducible and cell-lineage specific (targeted) expression of the mda-AS cDNA on growth and differentiation in human melanoma and other cell types. If expression of a specific mda-AS cDNA inhibits the ability of IFN-β+MEZ to induce growth suppression, changes in gene expression and terminal differentiation in H0-1 and other human melanoma cells, this would provide strong evidence for a direct relationship between expression of this mda cDNA and the growth and differentiation process in human melanoma cells. Brief Description of Protocols: H0-1 cells (additional human melanoma cell lines or other human tumor cell lines) will be seeded at $2 \times 10^6$ cells/100 mm plate, 24 hours later cells will be transfected by electroporation with the mda-AS construct (alone if a selectable gene is present in the construct or in conjunction with a cloned selectable gene) as described (92, 93). Antibiotic resistant colonies will be selected and isolated as pure clones (92, 93). The presence of the inserted gene will be determined by Southern blotting and expression of the endogenous and exogenous gene will be distinguished by RNase protection assays (58, 94). The ability of interferon or dexamethasone to enhance antisense in a pTKO-1 (interferon inducible promoter) or a pMAMneo (DEX inducible) construct, respectively, will be determined by growing cells in the presence or absence of the appropriate inducer ($10^{-9}$ to $10^{-5}$ M DEX or 2000 units/ml of IFN-β) for 24 hours prior to isolating and characterizing RNA expression (95, 105). Similar cellular (growth and morphology), biochemical (melanin and P2P levels), immunological (antigenic expression) and molecular (gene expression) parameters as used to study mda-S constructs will be used to study mda-AS constructs.

Summary: These studies will provide important information about the mda encoded gene products and they will indicate if perturbations in the expression of specific mda genes can directly modify growth or the differentiation process in human melanoma cells.

D. Specific Aim #4: Isolate and characterize the promoter region of mda genes and analyze their regulation in human melanocytes, nevi and melanoma.

1. Rationale and General Approach

In order to elucidate the mechanism underlying the transcriptional regulation of the mda genes it will be necessary to analyze the promoter regions of these genes. This will be important for studies aimed at determining regulatory control of the mda genes including chemical induction, autoregulation, tissue specific regulation and developmental regulation. Once the appropriate promoters of the mda genes have been isolated, studies can be conducted to identify relevant trans-regulatory factors (nuclear proteins) which bind to specific cis-regulatory elements and activate or repress the expression of the mda genes. The experiments outlined below are designed to: [a] clone the promoter region of specific mda genes and analyze their function in untreated and IFN-β+MEZ treated melanoma cells; [b] identify cis-regulatory elements in the promoter region of specific mda genes which are responsible for IFN-β+MEZ induction in human melanoma cells; and [c] identify and characterize trans-regulatory elements which activate (or repress) expression of the mda genes.

(a) Cloning the promoter region of the mda genes and testing their function in untreated and IFN-β+MEZ treated human melanoma cells: To isolate the promoter region of the mda gene a human genomic library will be constructed by partial digestion of H0-1 human melanoma genomic DNA with the restriction enzyme Sau3AI and then ligation into dephosphorylated vectors (phage or cosmid vectors) (92). Using the mda cDNA gene to screen the library, clones will be identified which contain both the mda gene and its 5' and 3' regions (92). Since the insert in a phage or cosmid vector is too large to analyze (i.e., 10 to 30 Kb) and the structure and size of the genomic DNA for the mda genes are not known, the inserts will be subcloned (to an approximate size of 2 Kb) in order to identify the potential promoter region (92). Two types of probes will be used for subcloning: one containing the coding region of the mda gene and the other a synthetic oligonucleotide (a 20 mer) complementary to the sequence located in the 5' non-translated region of the mda gene. The genomic DNA containing the mda gene in phage or cosmid vector will be digested with a series of restriction enzymes, electrophoresed on 0.8% agarose gels and transferred to nylon filters (92, 108). This Southern blot will then be probed with the coding region of the mda gene and the synthetic oligonucleotide. This double probing method will permit a more effective identification of the promoter region than utilizing a single probe. Putative promoter inserts of approximately 2 Kb in size will be subcloned into various CAT expression vector constructs (including pSVOCAT, pUVOCAT or pChlorAce) for later functional analysis (92, 108, 109).

The putative promoter region of the mda genes will be sequenced by the Sanger dideoxynucleotide procedure (110). The transcription start site (+1) will be determined by primer extension as described previously (108, 111). Dried total RNA samples of H0-1 melanoma cells with or without treatment with IFN-β+MEZ will be resuspended in 20 µl of 10 mM PIPES (pH 6.4)-400 mM NaCl containing 5'-end $^{32}$P-labeled oligonucleotides (a 25 mer, complementary to the 5'-untranslated region of the mda gene) made by the T4 nucleotide kinase method. After 3 hr incubation at 60° C., 80 µl of 50 mM Tris-HCl (pH8.2)-5 mM $MgCl_{2-10}$ mM dithiothreitol-5 mM deoxyguanosine nucleoside triphosphates-25 µl of dactinomycin per ml containing 10 U of avian myeloblastosis virus reverse transcriptase will be added and the primer extension reaction will be allowed to proceed for 1 hr at 42° C. Following phenol-chloroform extraction and ethanol precipitation, samples will be electrophoresed on 6%. acrylamide-8 M urea sequencing gels (108, 111). From the length of the extended products, the transcription initiation site of the mda gene can be determined.

To functionally analyze the various mda promoters, appropriate pmdaCAT constructs will be transfected into melanoma cells by the $CaPO_4$ method or electroporation (Gene Pulser, Bio-Rad) as previously described (93, 108, 109). Cell extracts will be prepared 48 hr after transfection by washing cells 3x with PBS, pelleting manually resuspended cells and lysing cells by three cycles of freeze-thawing. The CAT reaction will then be performed by adding 55 µl of cell extracts into a reaction mixture consisting of 5 µl of $^{14}$C-chloramphenicol, 70 µl of 1 M Tris-HCl (pH8.0) and 20 µl of 4 mM butyryl CoA (108, 109). After incubation at 37° C. for 2 hr, the reaction mixture will be extracted with ethyl acetate or xylene and CAT activity will be determined either by scintillation counting or by TLC (108, 109). If CAT expression can be detected in specific pmdaCAT construct transfected human melanoma cells after treatment with IFN-β+MEZ, but not in untreated cultures, this would indicate that the promoter region of the specific mda gene contains appropriate cis-acting elements responsive to induction by IFN-β+MEZ. If no induction is apparent, further subcloning and screening of cosmid or phage clones would be performed until an mda promoter of sufficient length to mediate CAT induction in differentiation inducer-treated human melanoma cells is obtained. A potentially useful series of CAT constructs have been developed by United States Biochemical (Cleveland, Ohio), referred to as the pChlorAce series. The basic plasmid pChlorAce-B does not contain a eucaryotic promoter or enhancer sequences and is therefore dependent on incorporation of a functional promoter upstream from the CAT gene for expression of CAT activity. The construct, pChlorAce-E, contains an enhancer sequence permitting a direct test of a functional promoter CAT-junction for testing mda promoter sequences. The promoter containing plasmid, pChlorAce-P, incorporates an SV40 promoter upstream from the CAT gene allowing the insertion of enhancer elements in both orientations upstream or downstream from the promoter-CAT transcriptional unit. It will be possible by inserting different parts of the mda gene into the pChlorAce-P construct to directly identify the enhancer component of the mda gene. The control plasmid, pChlorAce-C contains both the promoter and enhancer and can function as an internal standard for comparing promoter and enhancer strengths.

An important question will be whether specific mda genes display tissue- and developmental-specific expression. Once specific mda promoters are identified they can be used to address this issue. mda-CAT constructs will be tested for levels of expression in untreated and IFN-β+MEZ-treated normal human melanocytes, dysplastic nevi and RGP, early VGP, late VGP and metastatic melanomas. Experiments will also be performed to determine if the mda promoters can function in either untreated or IFN-β+MEZ-treated non-melanocyte/melanoma lineage cells. Positive expression in specific target cells would suggest that the appropriate regulatory proteins are either constitutively present or inducible in these cells.

(b) Identifying cis-elements in the mda promoter responsible for induction by IFN-β+MEZ in human melanoma cells: Once a functional mda promoter has been identified studies will be conducted to locate cis-elements responsible for induction of expression by IFN-β+MEZ. The approach to be used will involve the construction and evaluation for CAT inducible activity of a series of 5'-deletion mutants, 3'-deletion mutants, internal-deletion mutants and linker-scanning mutants of the mda promoter regions. The details for constructing the 5'-deletion, 3'-deletion and internal-deletion mutants and screening for CAT activity has been described previously (108, 109). Linker-scanning mutants will be constructed by combining 5'- and 31-deleted mda promoter sequences after filling gap regions with a linker DNA sequence (such as an EcoRI linker) (92). The structure of the various mutants will be determined by sequence analysis (95, 110). Since the promoter region for the mda gene is located in front of the CAT reporter gene in the various pmdaCAT constructs, the CAT activity for each construct can be measured using liquid scintillation and/or TLC (108, 109). This will permit a direct comparison of CAT transcriptional activity of the mutant promoter to that of the unmodified mda promoter. These studies will result in the identification of specific cis-regulatory elements responsible for IFN-β+MEZ induction of enhanced mda gene expression in human melanoma cells.

(c) Identifying trans-acting nuclear proteins induced by IFN-β+MEZ which mediate transcriptional enhancing activity of mda genes in human melanoma cells: The current view on regulation of eucaryotic gene expression suggests that trans-acting proteins bind to specific sites within cis-elements of a promoter region resulting in transcriptional activation (rev in 112, 113). Studies employing various mutant mda promoter CAT constructs will provide information relative to cis-regulatory elements mediating activity of the mda promoters. Experiments will be performed to identify trans-acting factors (nuclear proteins) and determine where these factors interact with cis-regulatory elements. To achieve this goal, two types of studies will be performed, one involving DNase-I footprinting (methylation interference) assays (108, 109) and the second involving gel retardation (gel shift) assays (109, 114).

For DNase-I footprinting assays nuclear extracts from human melanoma cells, untreated or treated with IFN-β+MEZ, will be prepared as described previously (109, 113, 115). DNase-I footprinting assays will be performed as described (108, 109). The cis-element (approximately 200 bp) for IFN-β+MEZ induction, identified from the experiments described above, will be terminally labeled with $^{32}$P and incubated with crude nuclear extracts from untreated or IFN-β+MEZ treated human melanoma cells using the protocols described previously (108, 109). The reaction mixture which has been digested with DNase-I enzyme will be terminated and the digested products will be analyzed on an 8% sequencing gel (108, 109). The differential protection between nuclear extracts from induced and uninduced human melanoma cells will provide relevant information concerning the involvement of trans-acting factors in activation and the location of specific sequences in the cis-regulatory elements of the mda promoter mediating this activation. If differential protection is not detected using this approach, the sensitivity of the procedure can be improved by using different sized DNA fragments from the mda promoter region or by using partially purified nuclear extracts (109).

As a second approach for investigating the interaction between cis-acting elements in the mda promoter and trans-acting factors in mediating transcriptional control, gel shift assays will be performed as described previously (109, 114). For this assay, $^{32}$P-labeled cis-elements will be incubated with nuclear extracts from untreated or IFN-β+MEZ treated human melanoma cells and reaction mixtures will be resolved on 5 or 8% polyacrylamide gels (109, 114). After autoradiography, the pattern of retarded DNAs on the gel will provide information concerning the interaction between trans-acting factors and specific regions of the cis-elements in the mda promoters. Non-labeled cis-elements (self-competition) will be added as a competitor to duplicate samples to eliminate the possibility of non-specific binding and to confirm that the interaction is really conferred by the trans-acting factor. To begin to identify the trans-acting factors, different non-labeled DNAs (for example TATA, CAT, TRE, Sp-I binding site, NFkB, CREB, TRE, TBP, etc.) can be used as competitors in the gel shift assay to determine the relationship between the trans-acting factors and other previously identified transcriptional regulators.

Summary: These studies will result in the identification and cloning of the mda promoter region, the identification of cis-regulatory elements in the mda promoters and the identification of trans-regulatory elements which activate (or repress) expression of mda genes.

F. Future Studies: The currently proposed research will result in the characterization of specific genes which may be involved in or mediate growth control, response to chemotherapeutic and DNA damaging agents and terminal differentiation in human melanoma cells. Once appropriate mda genes are identified they can subsequently be used to directly test their functional role in development and melanocyte/melanoma biology. Experiments can also be performed to define the role of these genes in non-melanoma target cells and additional programs of differentiation. Future studies which also are not within the scope of the present proposal would include: (a) evaluation of the effect of specific mda-S and mda-AS constructs on the growth (tumorigenic and metastatic potential) and differentiation of human melanoma (and other tumor cell types) grown in vivo in nude mice; (b) generation of transgenic mice displaying both tissue and non-tissue specific overexpression of individual or combinations of mda genes to evaluate the effect of modified mda expression on development; and (c) homologous recombination-mediated gene targeting techniques to produce mice with specific mda null mutations to evaluate the effect of lack of expression of specific mda genes on tissue and embryo development.

REFERENCES OF THE THIRD SERIES OF EXPERIMENTS

1. Herlyn, M., Human melanoma: development and progression. Cancer Metastasis Rev. 9:101–112, 1990.
2. Kerbel, R. S., Growth dominance of the metastatic cancer cell: cellular and molecular aspects. Adv. Cancer. Res. 55:87–132, 1990.
3. Clark, W., Tumor progression and the nature of cancer. Br. J. Cancer 64:631–644, 1991.
4. Clark, W. H., Jr, The Skin. In: Rubin, E & Farber, J L, Eds, Pathology, Lippincott Press Inc., New York, pp. 1194–1259, 1988.
5. Sachs L., Control of normal cell differentiation and the phenotypic reversion of malignancy in myeloid cells. Nature 274: 535–539, 1978.
6. Jimenez, J. J. & Yunis, A. A., Tumor cell rejection through terminal cell differentiation. Science 238: 1278–1280, 1987.
7. Waxman S., Rossi, G. B. & Takaku, F. (eds.), The Status of Differentiation Therapy of Cancer, vol I, Serono Symposia Pubs, 45:1–422, Raven Press, NY, 1988.
8. Fisher, P. B. & Rowley, P. T., Regulation of growth, differentiation, and antigen expression in human tumor cells by recombinant cytokines: applications for the differentiation therapy of human cancer. In: The Status of Differentiation Therapy of Cancer, vol II, Waxman S., Rossi, G. B. & Takaku, F. (eds.), Serono Symposia Pubs, Raven Press, NY, 82:201–214, 1991.
9. Waxman, S., Rossi, G. B. & Takaku, F. (eds.), In: The Status of Differentiation Therapy of Cancer, vol II, Serono Symposia Pubs, Raven Press, NY, 85:1–451, 1991.
10. Fisher, P. B., Prignoli, D. R., Hermo, H. Jr., Weinstein, I. B. & Pestka, S., Effects of combined treatment with interferon and mezerein on melanogenesis and growth in human melanoma cells. J. Interferon Res. 5:11–22, 1985.
11. Fisher, P. B., Hermo H, Jr., Solowey, W. E., Dietrich, M. C., Edwalds, G. M., Weinstein, I. B., Langer, J. A., Pestka, S., Giacomini, P., Kusama, M. & Ferrone, S., Effect of recombinant human fibroblast interferon and mezerein on growth, differentiation, immune interferon binding and tumor associated antigen expression in human melanoma cells. Anticancer Res. 6:765–774, 1986.
12. Ahmed, M. A., Guarini, L., Ferrone, S. & Fisher, P. B., Induction of differentiation in human melanoma cells by the combination of different classes of interferons or interferon plus mezerein. Ann. NY Acad. Sci. 567:328–333, 1989.
13. Ahmed, M. A., Nielsch, U., Guarini, L., Hermo, H. Jr. & Fisher, P. B., Modulation of differentiation: a potential mechanism by which interferons induce antitumor activity. In: Mechanisms of Differentiation: Modulation of Differentiation by Exogenous Agents, Fisher, P. B. (ed.), vol II, pp 1–56, CRC Press Inc, Boca Raton, Fla., 1990.
14. Jiang, H., Su, Z. Z., Boyd, J. & Fisher, P. B., Gene expression changes induced in human melanoma cells undergoing reversible growth suppression and terminal cell differentiation. Mol. Cell Differentiation 1:41–66, 1993.
15. Krasagakis, K., Garbe, C., Kruger, S. & Orfanos, E., Effects of interferons on cultured human melanocytes in vitro: interferon-beta but not -alpha or -gamma inhibit proliferation and all interferons significantly modulate the cell phenotype. J. Invest. Dermatol. 97:364–372, 1991.
16. Herlyn, M., Mancianti, M. L., Janbrosic, J., Bolen, J. B. & Koprowski, H., Regulatory factors that determine growth and phenotype of normal human melanocytes. Exp. Cell Res. 179:322–331, 1988.
17. Mufson, R. A., Fischer, S. M., Verma, A. K., Gleason, G. L., Slaga, T. J. & Boutwell, R. K., Effects of 12-O-tetradecanoylphorbol-13-acetate and mezerein on epidermal ornithine decarboxylase activity, isoproterenol-stimulated levels of cyclic adenosine 3′:5′-monophosphate, and induction of mouse skin tumors in vivo. Cancer Res. 39:4791–4796, 1979.
18. Slaga, T. J., Fischer, S. M., Nelson, K. & Gleason, G. L., Studies on the mechanism of skin tumor promotion:

19. Huberman, E., Heckman, C. & Langenbach, R., Stimulation of differentiated functions in human melanoma cells by tumor-promoting agents and dimethyl sulfoxide. Cancer Res. 39:2618–2624, 1979.
20. Albino, A. P., Sozzi, G., Nanus, D. M., Jhanwar, S. C. & Houghton, A. N., Malignant transformation of human melanocytes: induction of a complete melanoma phenotype and genotype. Oncogene 7:2315–2321, 1992.
21. Herlyn, M., Kath, R., Williams, N., Valyi-Nagy, I. & Rodeck, M., Growth-regulatory factors for normal, premalignant and malignant human cell in vitro. Adv. Cancer Res. 54:213–234, 1989.
22. Rodeck, U., Herlyn, M., Menssen, H. D., Furlanetto, R. W. & Koprowski, H., Metastatic but not primary melanoma cell lines grow in vitro independently of exogenous growth factors. Int. J. Cancer 40:687–690, 1987.
23. Halaban, R., Kwon, B. S., Ghosh, S., Bovis, P. D. & Baird A., bFGF as an autocrine growth factor for human melanomas. Oncogene Res 3:177–186, 1988.
24. Cornil, I., Theodorescu, D., Man, S., Herlyn, M., Jambrosic, J. & Kerbel, R. S., Fibroblast cell interactions with human melanoma cells affect tumor cell growth as a function of tumor progression. Proc. Natl. Acad. Sci. USA 88:6028–6032, 1991.
25. Kobayashi, H., Man, S., MacDougall, J. R., Graham, C. H., Lu, C. & Kerbel, R. S., Development of 'multicytokine resistance' during human melanoma progression: analysis using tumorigenic variants of low-grade early-stage human melanomas. Amer. J, Pathol., in submission, 1993.
26. Albino, A. P., The role of oncogenes and growth factors in progressive melanoma-genesis. Pigment Cell Res. Suppl. 2:199–218, 1992.
27. Rodeck, U., Melber, K., Kath, R. E., Menssen, H-D, Varello, M., Atkinson, B. & Herlyn, M., Constitutive expression of multiple growth factor genes by melanoma cells but not normal melanocytes. J Invest. Dermatology 97:20–26, 1991.
28. Yamanishi, D. T., Buckmeier, J. A. & Meyskens, F. L., Jr, Expression of c-jun, jun-B, and c-fos proto-oncogenes in human primary melanocytes and metastatic melanomas. J. Invest. Dermatology 97:349–353, 1991.
29. Chenevix-Trench, G., Martin, N. G. & Ellem, K. A. O., Gene expression in melanoma cell lines and cultured melanocytesL correlation between levels of c-src-1, c-myc and p53. Oncogene 5: 1187–1193, 1990.
30. Albino, A. P., Davis B M & Nanus D M, Induction of growth factor RNA expression in human malignant melanoma: markers of transformation. Cancer Res. 51:4815–4820, 1991.
31. Limon, J., Dal Cin, P., Sait, S. N. J., Karakousis, C. & Sandberg, A. A., Chromosome changes in metastatic human melanoma. Cancer Genetics Cytogenetics 30:201–211, 1988.
32. Parmiter, A. H., Balaban, G., Herlyn, M., Clark, W. H. Jr. & Nowell, P. C., A t(1;19) chromosome translocation in three cases of human malignant melanoma. Cancer Res. 46:1526–1529, 1988.
33. Pedersen, M. I. & Wang, N., Chromosomal evolution in the progression and metastasis of human malignant melanoma: a multiple lesion study. Cancer Genetics Cytogenetics 41:185–201, 1989.
34. Dracopoli, N. C., Alhadeff, B., Houghton, A. N. & Old, L. J., Loss of heterozygosity at autosomal and X-linked loci during tumor progression in a patient with melanoma. Cancer Res. 47:3995–4000, 1987.
35. Cowan, J. M., Halaban, R. & Francke, U., Cytogenetic analysis of melanocytes from premalignant nevi and melanomas. J. Natl. Cancer Inst. 80:1159–1164, 1988.
36. Dracopoli, N. C., Harnett, P., Bale, S. J., Stanger, B. Z., Tucker, M. A., Housman, D. E. & Kefford, R. F., Loss of alleles from the distal short arm of chromosome 1 occurs late in melanoma tumor progression. Proc. Natl. Acad. Sci. USA 86:4614–4618, 1989.
37. Trent, J. M., Stanbridge, E. J., McBride, H. L., Meese, E. U., Casey, G., Araujo, D. E., Witkowski, C. M. & Nagle R, B., Tumorigenicity in human melanoma cell lines controlled by introduction of human chromosome 6. Science 247:568–571 (1990).
38. Trent, J. M., Cytogenetics of human malignant melanoma. Cancer Metastasis Rev, 10:103–113, 1991.
39. Cannon-Albright, L. A., Goldgar, D. E., Meyer, L. J., Lewis, C. M., Anderson, D. E., Fountain, J. W., Hegi, M. E., Wiseman, R. W., Petty, E. M., Bale, A. E., Olopade, O. I., Diaz, M. O., Kwiatkowski, D. J., Piepkorn, W., Zone, J. J. & Skolnick, M. H., Assignment of a locus for familial melanoma, MLM, to chromosome 9p13–p22. Science 258:1148–1152, 1992.
40. Fountain, J. W., Karayiorgou, M., Ernstoff, M. S., Kirkwood, J. M., Vlock, D. R., Titus-Ernstoff, L., Bouchard, B., Vijayasaradhi, S., Houghton, A. N., Lahti, J., Kidd, V. J., Housman, D. E. & Dracopoli, N. C. Homozygous deletions within human chromosome band 9p21 in melanoma. Proc. Natl. Acad. Sci. USA 89:10557–10561, 1992.
41. Fountain, J. W., Bale, S. J., Housman, D. E. & Dracopoli, N. C., Genetics of melanoma. Cancer Surveys 9:645–671, 1990.
42. Welch, D. R., Chen, P., Miele, M. E., McGary, C. T., Bower, J. M., Stanbridge, E. J. & Weissman, C., Microcell-mediated transfer of chromosome 6 into metastatic human C8161 melanoma cells suppresses metastasis but does not inhibit tumorigenicity. Oncogene, in press, 1993.
43. Lin, J., Jiang, H., Su, Z-z, Welch, D. R. & Fisher, P. B., Gene expression changes induced during differentiation in human melanoma cells containing a microcell inserted normal chromosome 6. Manuscript in preparation, 1993.
44. Henco, K., Brosius, J., Fujisawa, A., Fujisawa, J-I., Haynes, J. R., Hochstadt, J., Koviacic, T., Pasek, M., Schambock, A., Schmid, J., Todokoro, K., Walchli, M., Nagata, S. & Weissman, C., Structural relationship of human interferon alpha genes and pseudogenes. J. Mol. Biol. 185:227–260, 1985.
45. Diaz, M. O., Ziemin, S., LeBeau, M. M., Pitha, P., Smith, C. D., Chilcote, R. R. & Rowley, J. D., Homozygous deletion of the α- and $β_1$-interferon genes in human leukemia and derived cell lines. Proc. Natl. Acad. Sci. USA 85:5259–5263, 1988.
46. Diaz, M. O., Rubin, C. M., Harden, A., Ziemen, S., Larson, R. A., LeBeau, M. M. &Rowley, J. D., Deletions of interferon genes in acute lymphocytic leukemia. New England J. Med. 322:77–82, 1990.
47. Miyakoshi, J., Dobler, K. D., Allalunis-Turner, J., McKean, J. D. S., Petruk, K., Allen, P. B. R., Aronyk, K. N., Weir, B., Huyser-Wierenga, D., Fultun, D., Urtasun, R. C. & Day, R. S. III, Absence of IFNA and IFNB genes from human malignant glioma cell lines and lack of correlation with cellular sensitivity to interferons. Cancer Res. 50:278–283, 1990.
48. Jiang, H. H. & Fisher, P. B., Induction of terminal differentiation in human melanoma cells by the combination of recombinant fibroblast interferon and mezerein involves transcriptional modulation of specific genes. Manuscript in preparation, 1993.
49. Jiang, H. H. & Fisher, P. B., Use of a sensitive and efficient subraction hybridization protocol for the identification of genes differentially regulated during the induction of differentiation in human melanoma cells. Mol. Cell Different., in press, 1993.
50. Graham, G. M., Guarini, L., Moulton, T. A., Datta, S., Ferrone, S., Giacomini, P., Kerbel, R. S. & Fisher, P. B., Potentiation of growth suppression and modulation of the antigenic phenotype in human melanoma cells by the combination of recombinant human fibroblast and immune interferon. Cancer Immunol. Immunother. 32:382–390, 1991.
51. Kiguchi, K., Collart, F. R., Henning-Chubb, C. & Huberman, E., Induction of differentiation in melanoma cells by inhibitors of IMP dehydrogenase: altered patterns of IMP dehydrogenase expression and activity. Cell Growth & Differ. 1:259–270, 1990.
52. Minoo, P., Sullivan W., Solomon, L. R., Martin, T. E., Toft, D. O. & Scott, R. E., Loss of proliferative potential during terminal differentiation coincides with decreased abundance of a subset of heterogeneous ribonuclear proteins. J. Cell Biol. 109:1937–1946, 1989.
53. Witte, M. M. & Scott, R. E., Repression of two proliferation proteins during senescence and terminal differentiation in normal and SV40 transfected human keratinocytes: P2Ps and SC40 large T-antigen. Mol. Cell Differ, 2:185–195, 1993.
54. Melber, K., Zhu, G. & Diamond, L., SV40-transformed human melanocyte sensitivity growth inhibition by the phorbol ester 12-O-tetradecanoylphorbol-13-acetate. Cancer Res. 49:3650–3655, 1989.
55. Jiang, H., Waxman, S. & Fisher, P. B., Regulation of c-fos, c-jun, and jun-B gene expression in human melanoma cells induced to terminally differentiate. Mol Cell Differ. 1(2):197–214, 1993.
56. Schweinfest, C. W. & Papas, T. S., Subtraction hybridization: an approach to the isolation of genes differentially expressed in cancer and other biological systems (Review). Int. J. Cancer 1:499–506, 1992.
57. Reddy, P.G., Su, Z. Z. & Fisher, P. B., Identification and cloning of genes involved in progression of transformed phenotype. In: Methods in Molecular Genetics, vol 1, Adolph, K. W. (ed.), Academic Press, pp 68–102, Orlando, Fla., 1993.
58. Duigou, G. J., Babiss, L. E., Iman, D. S., Shay, J. W. & Fisher, P. B., Suppression of the progression phenotype in somatic cell hybrids occurs in the absence of altered type 5 adenovirus gene expression. Mol. Cell. Biol. 10:2027–2034, 1990.
59. Su, Z. Z., Austin, V. A., Zimmer, S. G. & Fisher, P. B., Defining the critical gene expression changes associated with expression and suppression of the tumorigenic and metastatic phenotype in Ha-ras-transformed cloned rat embryo fibroblasts. Oncogene, 8:1211–1219, 1993.
60. Jiang, H., Su, Z. Z., Datta, S., Guarini, L., Waxman, S. & Fisher, P. B., Fludarabine phosphate selectively inhibits growth and modifies the anitgenic phenotype of human glioblastoma multiforme cells expressing a multidrug resistance phenotype. Int. J. Oncol 1:227–239, 1992.
61. Lau, L. F. & Nathans, D., Expression of a set of growth-related immediate early genes in BALB/c3T3 cells: coordinate regulation with c-fos and c-myc. Proc. Natl. Acad. Sci. USA 84:1182–1186, 1986.
62. Kouzarides, T. & Ziff, E., The role of the leucine zipper in fos-jun interaction. Nature 336:646–651, 1988.
63. Reed, J. A., McNutt, N. S. & Albino, A. P., Differential expression of basic fibroblast growth factor (bFGF) in melanocytic lesions demonstrated by in situ hybridization: implications for tumor progression. Amer. J. Pathology, in submission, 1993.
64. Biroc, S. L., Murphy-Erdosh, C., Fisher, J. M. & Payan, D. G., The use of $^{32}$P-labeled oligonucleotides for in situ hybridization of vertebrate embryo frozen sections. Bio-Technique 15:250–254, 1993.
65. Abdollahi, A., Lord, K. A., Hoffman-Liebermann, B. & Liebermann, D. A., Interferon regulatory factor 1 is a myeloid differentiation primary response gene induced by interleukin 6 and leukemia inhibitory factor: role in growth inhibtion. Cell Growth & Different. 2:401–407, 1991.
66. Bruce, J. N., Duigou, G. J. & Fisher, P. B., Expression of the epidermal growth factor receptor in human central nervous system tumors. In: Molecular Diagnostics of Human Cancer, Furth, M. & Greaves, M. (Eds), Cancer Cell, vol 7, pp 363–370, Cold Spring Harbor Press Inc, NY, 1989.
67. Guarini, L., Temponi, M., Edwalds, G. M., Vita, J. R., Fisher, P. B. & Ferrone, S., In vitro differentiation and antigenic changes in human melanoma cell lines. Cancer Immunol Immunother 30:363–370, 1989.
68. Guarini, L., Graham, G. M., Jiang, H., Ferrone, S., Zucker, S. & Fisher, P. B., Modulation of the antigenic phenotype of human melanoma cells by differentiation-inducing and growth-suppressing agents. Pigment Cell Res. Suppl. 2:123–131, 1992.
69. Fisher, P. B., Babiss, L. E. & Miranda, A. F., Measurement of the effect of interferons on cellular differentiation in murine and human melanoma cultures. In: Methods Enzymol, Interferons, Pestka, S. (ed.), 119:611–618, Academic Press, Orlando, Fla., 1986.
70. MacDougall, J. R., Kobayashi, H. & Kerbel, R. S., Responsiveness of normal/dysplastic melanocytes and melanoma cells from different lesional stages of disease progression to the growth inhibitory effects of TGF-β. Mol. Cell Differentiation 1:21–40, 1993.
71. Fisher, P. B. & Grant, S., Effects of interferon on differentiation in normal and tumor cells. Pharmacol. Therapeut. 27:143–166, 1985.
72. Guarini, L., Su, Z.z., Zucker, S., Lin, J., Grunberger, D. & Fisher, P. B., Inhibition of growth and modulation of antigenic phenotype in human melanoma and glioblastoma multiforme cells by caffeic acid phenethyl ester (CAPE). Cell Mol. Biol. 38:513–527, 1992.
73. Wender, P. A., Konrad, F. K., Sharkey, N. A., Dell'Aquila. M. L. & Blumberg, P. C., Analysis of the phorbol ester pharmacore on protein kinase C as a guide to the rational design of new classes of analogs. Proc. Natl. Acad. Sci. USA. 83:4214–4219, 1986.
74. Leon, J. A., Gutierrez, M. C., Jiang, H., Estabrook, A., Waxman, S. & Fisher, P. B., Modulation of the antigenic phenotype of human breast carcinoma cells by modifiers of protein kinase C activity and recombinant human interferons. Cancer Immunol. Immunother. 35:315–324, 1992.
75. Leon, J. A., Goldstein, N. I. & Fisher, P. B., New approaches for the development and application of monoclonal antibodies for the diagnosis and therapy of human cancer. Pharmacol. Therap., in press, 1993.
76. Grant, S., Bhalla, K., Weinstein, I. B., Pestka, S., Mileno, M. D. & Fisher, P. B., Recombinant human interferon sensitizes resistant myeloid leukemic cells to induction of terminal differentiation. Biochem. Biophys. Res. Commun. 130:379–388, 1985.

77. Fisher, P. B., Miranda, A. F., Mufson, R. A., Weinstein, L. S., Fujiki, H., Sugimura, T. & Weinstein, I. B. Effects of teleocidin and the phorbol ester tumor promoters on cell transformation, differentiation and phospholipid metabolism. Cancer Res. 42:2829–2835, 1982.

78. Fisher, P. B., Miranda, A. F., Babiss, L. E., Pestka, S. & Weinstein, I. B. Opposing effects of interferon produced in bacteria and of tumor promoters on myogenesis in human myoblast cultures. Proc. Natl. Acad. Sci. USA 80:2961–2965, 1983.

79. Rovera, G., Santoli, D. & Damansky, C. Human promyelocytic leukemia cells in culture differentiate into macrophage-like cells when treated with phorbol diester. Proc. Natl. Acad. Sci. USA 76: 2779–2803, 1979.

80. Collins, S. J., Ruscetti, F. W., Ruscetti, R. E., Gallagher, R. & Gallo, R. C. Terminal differentiation of human promyelocytic leukemia cells induced by dimethyl sulfoxide and other polar compounds. Proc. Natl. Acad. Sci. USA 75:2458–2462, 1978.

81. Liebermann, D., Hoffman-Liebermann, B. & Sachs, L. Regulation of gene expression by tumor promoters. II. Control of cell shape and developmental programs for macrophages and granulocytes in human myeloid leukemic cells. Int. J. Cancer 28:285–291, 1981.

82. Miranda, A. F., DiMauro, S. & Somer, H. Isoenzymes as markers of differentiation. In: Muscle Regeneration, DiMauro, S. (Ed.), pp 453–473, Raven Press, NY, 1979.

83. Miranda, A. F., Babiss, L. E. & Fisher, P. B. Transformation of human skeletal muscle cells by simian virus 40 (SV40). Proc. Natl. Acad. Sci. USA 80:6581–6585, 1983.

84. Nguyen, H. Q., Hoffman-Liebermann, B. & Liebermann, D. A. The zinc finger transcription factor Egr-1 is essential for and restricts differentiation along the macrophage lineage. Cell 72:197–209, 1993.

85. Batistatou, A. & Greene, L. A. Induction of sulfated glycoprotein-2 (SGP-2) gene in PC12 cells by NGF and other treatments. Mol. Cell. Differen. 1:81–97, 1993.

86. Frohman, M. A., Dush, M. K. & Martin, G. R. Rapid production of full-length cDNAs from rare transcripts: amplification using a single gene-specific oligonucleotide primer. Proc. Natl. Acad. Sci. USA 85:8998–9002, 1988.

87. Loh, E. Y., Elliott, J. F., Cwirla, S., Lanier, L. L. & Davis, M. M. Polymerase chain reaction with single-sided specificity: Analysis of T cell receptor δ chain. Science 243:217–220, 1989.

88. Ohara, O., Dorit, R. L. & Gilbert, W. One-sided polymerase chain reaction: the amplification of cDNA. Proc. Natl. Acad. Sci. USA 86:5673–5677, 1989.

89. Krieg, P. & Melton, D. A. Functional messenger RNA, are produced by SP6 in vitro transcription of cloned cDNAs. Nucleic Acids Res. 12:7057–7070, 1984.

90. Tagawa, M., Sakamoto, T., Shigemoto, K., Matsubara. H., Tamura, Y., Ito, T., Nakamura, I., Okitsu, A., Imai, K. & Taniguchi, M. Expression of novel DNA-binding protein with zinc finger structure in various tumor cells. J. Biol. Chem. 265:20021–20026, 1990.

91. Goldstein, N. I., Nagle, R., Villar, H., Hersch, E. & Fisher, P. B. Isolation and characterization of a human monoclonal antibody which reacts with breast and colorectal carcinoma. Anticancer Res. 10:1491–1500, 1990.

92. Sambrook, J., Fritsch, E. F. & Maniatis, T. In: Molecular Cloning: A Laboratory Manual, 2nd edition, Cold Spring Harbor Laboratories Press, Cold Spring Harbor, N.Y., 1989.

93. Su, Z. z., Grunberger. D. & Fisher. P. B. Suppression of adenovirus type 5 E1A-mediated transformation and expression of the transformed phenotype by caffeic acid phenyl ester (CAPE). Mol. Carcinogenesis 4:231–242, 1991.

94. Duigou, G. J., Su, Z. z., Babiss, L. E., Driscoll, B., Fung, Y-K. T. & Fisher, P. B. Analysis of viral and cellular gene expression during progression and suppression of the transformed phenotype in type 5 adenovirus-transformed rat embryo cells. Oncogene 6:1813–1824, 1991.

95. Su, Z. Z., Leon, J. A., Jiang, H., Austin, V. N., Zimmer, S. G. & Fisher, P. B. Wild-type adenovirus 5 transforming genes function as transdominant suppressors of oncogenesis in mutant adenovirus type 5 transformed rat embryo fibroblast cells. Cancer Res. 53:1929–1938, 1993.

96. Neckers, L., Whitesell, L., Rosolen, A. & Geselowitz, D. A. Antisense inhibition of oncogene expression. Crit. Rev. Oncog. 3:175–231, 1992.

97. Grief, A. E. & Westphal, H. Antisense Myc sequences induce differentiation of F9 cells. Proc. Natl. Acad. Sci. USA 85:6806–6810, 1988.

98. Holt, J. T., Redner, R. L. & Nienhuis, A. W. An oligomer complementary to c-myc mRNA inhibits proliferation of HL-60 promyelocytic cells and induces differentiation. Mol. Cell. Biol. 8:963–973, 1988.

99. Prochownik, E. V., Kukowska, J. & Rogers, C. c-myc antisense transcripts accelerate differentiation and inhibit G1 progression in murine erythroleukemia cells. Mol. Cell. Biol. 8:3683–3695, 1988.

100. Yokoyama, K. & Imamoto, F. Transcriptional control of the endogenous MYC protooncogene by antisense RNA. Proc. Natl. Acad. Sci. USA 84:7363–7367, 1987.

101. Freytag, S. O. Enforced expression of c-myc oncogene inhibits cell differentiation by precluding entry into a distinct predifferentiation state in G0/G1. Mol. Cell. Biol. 8:1614–1624, 1988.

102. Toulme, J-J & Helene, C. Antimessenger oligodeoxyribonucleotides: an alternative to antisense RNA for artificial regulation of gene expression—a review. Gene 72:51–58, 1988.

103. Stein, C. A. & Cheng, Y-C. Antisense oligonucleotides as therapeutic agents—is the bullet really magical? Science 261:1004–1012, 1993.

104. Jaskulski, D., DeRiel, J. K., Mercer, E. M., Calabretta, B., & Baserga, R. Inhibition of cellular proliferation by antisense oligonucleotides to PCNA cyclin. Science 240:1544–1546, 1988.

105. Deiss, L. P. and Kimchi, A. A genetic tool used to identify thioredoxin as a mediator of a growth inhibitory signal. Science 252:117–120, 1991.

106. Izant, J. G. & Weintraub, H. Constitutive and conditional suppression of exogenous and endogeneous genes by anti-sense RNA. Science 229:345–352, 1985.

107. Vile, R. G. & Hart, I. R. In vitro and in vivo targeting of gene expression to melanoma cells. Cancer Res. 53:962–967, 1993.

108. Shen, R., Chen, Y., Huang, L., Vitale, E. & Solursh, M. Characterization of the human HOX-7 promoter and its regulation by retinoic acid. Genes Develop, in submission, 1993.

109. Shen, R., Goswami, S. K., Mascareno, E., Kumar, A. & Siddiqui, M. A. Q. Tissue-specific transcription of the cardiac myosin light-chain 2 gene is regulated by an upstream repressor element. Mol. Cell. Biol. 11:1676–1685, 1991.

110. Sanger, F., Nicklen, S. & Coulson, A. R. DNA sequencing with chain-terminating inhibitors. Proc. Natl. Acad. Sci. USA 74:5463–5467, 1977.

111. McKnight, S. L. & Kingsbury, R. Transcriptional control signals of a eukaryotic protein-coding gene. Science 217:316–324, 1982.

112. Maniatis, T., Goodbourn, S. & Fischer, A. Regulation of inducible and tissue-specific gene expression. Science 236:1237–1244, 1987.

113. Ptashne, M. How eukaryotic transcriptional activators work. Nature 335:683–689, 1988.
114. Su, Z. Z., Shen, R., O'Brian, C. A. & Fisher, P. B. Induction of transformation progression in type 5 adenovirus-transformed rat embryo cells by a cloned protein kinase C $\beta_1$ gene and reversal of progression by 5-azacytidine. Oncogene, in press, 1993.
115. Dignam, J. D., Levbovitz, R. M. & Roeder, R. G. Accurate transcription initiation by RNApolymerase II in a soluble extract from isolated mammalian nuclei. Nuc. Acids Res. 11:1475–1489, 1982.

Fourth Series of Experiments mda-1: Novel gene which displays increased expression in IFN-β and IFN-β+MEZ treated H0-1 cells after 24 hours. Decreased expression occurs in H0-1 cells treated with IFN-β+MEZ for 96 hours. (HJ 3-13).

```
TGGACTTGTGTTCTGACTAGAACTCAACATGTTACTAGGCACATGTGTCATGTCT        (SEQ. ID NO: 8)

CAGGTCAGTGCTGTGACAGAATTGATACGAGAGAAATGTCGCTTATGCTATCACT

GATCTACACATGTCTGATAGATAGTCAGATACAGATGATGAGGAATCT mda-2:
GAATTCAGTGAACTCTTTTCTCATTCTCTTTGTTTTGTGGCACTTCACAATGTAG        (SEQ ID NO: 9)

AGGAAAAAACCAAATGACCGCACTGTGATGTGAATGGCACCGAAGTCAGATGAGT

ATCCTGTAGGTCACCTGCAGCCTGGCTTGCCACTTGTCTTAACTCTGAATATTTC

ATTTCAAAGGTGCTAAAATCTGAAATCTGCTAGTGTGAACTTGCTCTACTCTCTG

AATGATTCAATCCTATTCATACTATCTTGTAGATATATCAACTAAAAAAA.
```

Properties of mda-4

This cDNA is novel (analysis of various gene data bases indicates that the sequence of mda-4 is 68.5% homologous to the human interferon gamma induced protein).

Expression in H0-1 Human Melanoma Cells

Increased expression after 24 hour treatment of H0-1 cells with recombinant human fibroblast interferon (IFN-β) (2,000 units/ml), mezerein (MEZ) (10 ng/ml) and to a greater extend with the combination of IFN-β+MEZ (2,000 units/ml+10 ng/ml). Analysis of terminally differentiated H0-1 cells, i.e., H0-1 cells treated with the combination of IFN-β+MEZ (2,000 units/ml+10 ng/ml) for 96 hours, indicate continued increased expression in IFN-β+MEZ treated H0-1 cells.

Increased expression in H0-1 cells after 96 hour exposure to immune interferon (IFN-γ) (2,000 units/ml) and IFN-β+IFN-γ (1,000 units/ml+1,000 units/ml) (note: this combination of agents results in a similar degree of growth suppression in H0-1 cells as does IFN-β+MEZ. However, growth suppression is reversible with the combination of interferons, whereas it is irreversible with the combination of IFN-β+MEZ).

mda-4 represents a novel IFN-γ-inducible gene which is also induced during terminal cell differentiation in H0-1 cells. Could prove useful as a gene marker for immune interferon response and as a gene marker for terminal differentiation in human melanoma cells.

Expression in Additional Human Melanoma Cells

Increased expression of mda-4 results after a 24 hour treatment with IFN-β+MEZ in H0-1, L0-1, SH-1, WM278 and WM239 human melanoma cells. Mda-4 is not expressed or inducible in the melanotic F0-1 human melanoma cell or in the C8161 human melanoma cells or C8161/6.3 cells (a C8161 human melanoma cell clone containing an inserted normal human chromosome 6: These cells are tumorigenic in nude mice, but unlike parental C8161 cells, they are non-metastatic).

Mda-4 displays increased expression in additional human melanoma cells besides the human melanoma cell from which it was cloned, i.e., H0-1 after 24 hour treatment with IFN-β+MEZ.

Expression in Normal Cerebellum, a Central Nervous System Tumor (Glioblastoma Multiforme) (GBM) and Normal Skin Fibroblast Cell Lines Mda-4 is not expressed de novo in normal cerebellum, GBM or normal skin fibroblasts. However, it is inducible in both normal cerebellum and GBM, but not in normal skin fibroblasts, following a 24 hour treatment with IFN-β+MEZ.

Mda-4 is susceptible to induction by IFN-β+MEZ in human cerebellum and GBM cultures, but not in normal human skin fibroblasts.

Expression in Colorectal Carcinoma (SW613), Endometrial Adenocarcinoma (HTB113) and Prostate Carcinoma (LNCaP)

Mda-4 is not expressed de novo in various carcinoma cells and it is not inducible in these cells following a 24 hour treatment with IFN-β+MEZ. Mda-4 is not expressed in human carcinoma cells.

Effect of Various Treatment Protocols on Expression in H0-1 Cells

A 24 hour treatment with IFN-β (2,000 units/ml), IFN-α (2,000 units/ml), IFN-α+MEZ (2,000 units/ml+10 ng/ml), IFN-α+MEZ (2,000 units/ml+10 ng/ml), cis-platinum (0.1 µg/ml), gamma irradiation (treated with 3 gray and analyzed after 24 hours). In addition, treatment with UV (10 joules/mm$^2$ and assayed 24 hours later) results in increased expression in H0-1 cells.

No or only a small change in expression is observed in H0-1 cells treated with MEZ (10 ng/ml; 24 hours or 96 hours), IFN-β (2,000 units/ml; 96 hours), phenyl butyrate (PB) (4 mM; treated for 24 hours, 4 days or 7 days), mycophenolic acid (MPA) (3 µM; 96 hours), trans retinoic acid (RA) (2.5 µM; 24 hours), MPA+MEZ (3 µM+10 ng/ml; 96 hours), RA+MEZ (2.5 µM; 96 hours), actinomycin D (5 µg/ml for 2 hours, assayed after 24 hours), adriamycin (0.1 µg/ml; 24 hours), vincristine (0.1 µg/ml; 24 hours), TNF-α (100 units/ml; 24 hours) or VP-16 (5 µg/ml; 24 hours).

mda-4 is a novel gene which displays the following properties: 1) it is inducible in H0-1 cells during terminal differentiation (treatment with IFN-β+MEZ for 96 hours) and following 96 hour treatment with recombinant gamma interferon (alone or in combination with IFN-β); 2) it is inducible by IFN-β+MEZ in a series of human melanomas in addition to H0-1, normal cerebellum and GBM cells, but it is not expressed or inducible by IFN-β+MEZ in normal skin fibroblasts or three different types of carcinomas (colorectal, endometrial adenocarcinoma or prostate carcinoma); and 3) increased expression is induced in HO-1 cells treated with specific DNA damaging agents (cis-platinum, gamma irradiation and UV irradiation).

This gene represents a cytokine-, DNA damage-, and chemotherapy-(cis-platinum) and terminal differentiation-inducible gene possibly restricted to cells of neuroectodermal origin (melanoma and central nervous system). mda-4 may prove useful: 1) as a marker for specific tissue lineage's (i.e., neuroectodermal) (diagnostic applications); 2) to monitor response to DNA damage (induced by gamma irradiation and UV irradiation) and treatment with chemotherapeutic agents which work in a similar manner as cis-platinum (diagnostic applications); 3) to assay for types I (IFN-α and IFN-β) and type II (IFN-γ) interferon in biological fluids (diagnostic applications); and 4) to identify compounds which have the capacity to induce terminal differentiation in human melanoma cells (drug screening programs to identify new chemotherapeutic agents). Once full-length cDNAs are isolated, this gene (used in a sense orientation in an appropriate expression vector) may prove useful in inhibiting growth and inducing terminal differentiation in human melanomas and specific central nervous system tumors (GBM) (therapeutic applications). Antisense constructs of specific regions of this gene could also prove useful in preventing damage to normal tissue (e.g., bone marrow) treated with differentiation inducing and specific chemotherapeutic and DNA damaging agents (therapeutic applications).

mda-4

Expression in Additional Human Melanoma Cells

Increased expression of this gene occurs in HO-1, C8161, C8161/6.3 (a C8161 human melanoma cell clone containing an inserted normal human chromosome 6: These cells are tumorigenic in nude mice, but unlike parental C8161 cells they are non-metastatic), F0-1, L0-1, SH-1, WM278 and WM239 human melanoma cells treated with IFN-β+MEZ for 24 hours. This gene is constitutively expressed in immortalized human melanocytes FM5169 (transformed by SV40). Some upregulation is observed in FM5169 following IFN-β+MEZ treatment for 24 hours.

Expression of mda-5 is increased by IFN-β+MEZ in 7 additional human melanoma cells besides the human melanoma cell it was cloned from i.e., HO-1. In addition, this gene is expressed in melanocytes and its expression is increased to a lesser degree than in most human melanomas following a 24 hour treatment with IFN-β+MEZ.

Expression in Normal Cerebellum, a Central Nervous System Tumor (Glioblastoma Multiforme) (GBM) and Normal Skin Fibroblast Cell Lines mda-5 is express de novo at low levels in normal cerebellum, but not in GBM or normal skin fibroblasts. However, expression is increased in normal cerebellum (>10-fold) and expression is induced in GBM (small induction) and normal skin fibroblasts (good induction) following a 24 hour treatment with IFN-β+MEZ.

This gene is susceptible to modulation by IFN-β+MEZ in human cerebellum, GBM and normal human skin fibroblasts. Differential de novo and inducible expression is seen

```
TTCTTCTTTGTAAAAGTTTTTAATACACTGCTGAAAGATAAATTCATTCCAAAGA  (SEQ ID NO: 10)

GAATAATTATATAGCAAGATATTATCGGCACAGTGGTTTCTTAGAGGTAAATAGCG

CCTCACGTGTGTTAGATGCTGAATCTGACCAAA.
```

Properties of mda-5

This cDNA is novel (it has sequence homology to a *Homo sapiens* putatively transcribed partial sequence; Accession number Z20545; from the UK-HGMP, MRC Human Genome Mapping Project Resource, Centre Clinical Research Centre, Watford Road, Harrow, Middlesex, HA1 England)

Expression in HO-1 Human Melanoma Cells

Increased expression after 24 hour treatment of HO-1 cells with recombinant human fibroblast interferon (IFN-β) (2,000 units/ml), and to a greater extent with IFN-β+MEZ (2,000 units/ml+10 ng/ml) in combination.

Analysis of terminally differentiated HO-1 cells, i.e., HO-1 cells treated with the combination of IFN-β+MEZ (2,000 units/ml+10 ng/ml) for 96 hours, indicate continued increased expression in IFN-β+MEZ treated HO-1 cells.

Enhanced expression of mda-5 is also observed, albeit to a lesser extend, in HO-1 cells treated for 96 hours with immune interferon (IFN-γ) (2,000 units/ml) and in 96 hours IFN-β+IFN-γ (1,000 units/ml+1,000 units/ml) treated HO-1 cells (greater increased than with IFN-γ alone) (note: this combination of agents results in a similar degree of growth suppression in HO-1 cells as does IFN-β+MEZ. However, growth suppression is reversible with this combination of interferons, whereas it is irreversible with the combination of IFN-β+MEZ).

mda-5 represents a novel IFN-γ-inducible gene which also displays increased expression during terminal cell differentiation in HO-1 cells. This gene could prove useful as a marker for immune interferon response and as a marker for terminal differentiation in human melanoma cells.

in normal cerebellum cells versus GBM, with normal cerebellum displaying both higher de novo and inducible expression.

Expression in Colorectal Carcinoma (SW613), Endometrial Adenocarcinoma (HTB113) and Prostate Carcinoma (LNCaP)

mda-5 is not expressed de novo in colorectal carcinoma (SW613) and endometrial adenocarcinoma (HTB113), whereas it is expressed at low levels in prostate carcinoma (LNCaP).

Following a 24 hour treatment with IFN-β+MEZ, mda-5 expression is induced at high levels in colorectal carcinoma (SW613) cells, but no expression is seen in endometrial adenocarcinoma (HTB113).

In the case of human prostate (LNCaP), IFN-β+MEZ treatment for 24 hours results in a 2- to 3-fold increase in mRNA expression.

This gene displays a differential pattern of both de novo and inducible expression in different human carcinomas.

Effect of Various Treatment Protocols on Expression in HO-1 Cells

A 24 hour treatment with IFN-β (2,000 units/ml), IFN-α (2,000 units/ml), IFN-β+MEZ (2,000 units/ml+10 ng/ml) and IFN-α+MEZ (2,000 units/ml+10 ng/ml) results in increased expression in HO-1 cells.

mda-5 is induced after 96 hour treatment with IFN-γ and IFN-β+IFN-γ. Highest level of expression is observed in HO-1 cells treated with IFN-β+MEZ for 24 or 96 hours. Very low induction after 96 hour treatment with IFN-β (2,000 units/ml).

No change in expression is observed in H0-1 cells treated with MEZ (10 ng/ml) (24 or 96 hours), MPA (3 μM; 96 hours), RA (2.5 μM; 96 hours), MPA+MEZ (3 μM+10 ng/ml; 96 hours), RA+MEZ (2.5 μM+10 ng/ml; 96 hours), phenyl butyrate (PB) (4 mM PB for 24 hours, 4 days or 7 days), cis-platinum (0.1 μg/ml; 24 hours), gamma irradiation (treated with 3 gray and analyzed after 24 hours), UV (10 joules/mm², assayed 24 hours later), actinomycin D (5 μg/ml for 2 hours, assayed 24 hours later), adriamycin (0.1 μg/ml; 24 hours), vincristine (0.1 μg/ml; 24 hours), cis-platinum (0.1 μg/ml; 24 hours), TNF-α (100 units/ml; 24 hours) or VP-16 (5 μg/ml; 24 hours).

mda-5 is a novel gene which displays the following properties: 1) it is inducible during terminal differentiation (treatment with IFN-β+MEZ for 96 hours) and following treatment for 96 hours with recombinant gamma interferon (alone or in combination with IFN-β); 2) treatment for 24 hours with IFN-β+MEZ results in increased expression in all human melanomas tested and in an SV40-immortalized human melanocyte; 3) it is highly inducible by IFN-β+MEZ within 24 hours in normal cerebellum and normal skin fibroblast cells, but it is only weakly inducible in GBM; 4) it is differentially inducible in three different types of carcinomas (with induction greatest in colorectal, low induction in prostate carcinoma and no induction in endometrial adenocarcinoma); and 5) increased expression is induced in H0-1 cells treated with both type I interferon (IFN-α and IFN-β) and type II interferon (IFN-γ) (IFN-β is more effective than IFN-α when used at an equivalent dose in enhancing expression of this gene).

This gene represents a cytokine- and terminal differentiation-inducible gene displaying increased expression in all melanomas, in select carcinomas, in normal skin fibroblasts and in both normal cerebellum and GBM. mda-5 may be useful: 1) as a marker for specific tissue lineages and for distinguishing tumors of similar histotype (i.e., carcinomas) (diagnostic applications; 2) to monitor response to type I and II interferon treatment (diagnostic applications; and 3) to identify compounds which have the capacity to induce terminal differentiation in human melanoma cells (drug screening programs to identify new differentiation-inducing agents). Once full-length cDNAs are isolated, this gene (used in a sense orientation in an appropriate expression vector) may prove useful in inhibiting growth and inducing terminal differentiation in human melanomas and other classes of tumors (therapeutic applications).

mda-5

```
CTGCAAAAGAAGTGTGCCGACTATAAATAAATGGTGAAATCATCTGCAAATGTGG    (SEQ ID NO: 11)

CCAGGCTTGGGGAACAATGATGGTGCACAAAGGCTTAGATTTGCCTTGTCTCAAA

ATAAGGAATTTTGTAGTGGTTTCAAAATATCACAAGAACGTACAAGTGGTAGATA

CTATCACATTCACTGACTATCAGAGTCG

ACAAACCAGTGATTCCCCTTCCTCAGATACTGGGACTAACAGCTTCACCTGGTGT    (SEQ. ID NO: 12)

TGGAGGGGCCACGAAGCAAGCCAAAGCTGAAGAACACATTTTAAAACTATGTGCC

TATCTTGATGCATTTACTATTAAAACTGTTAAAGAAAACCTTGATCAACTGAAAA

ACCAAATACAGGAGCATGCAAGAAGTTTGCCATTGCAGATGCAACCAGAGAAGAT

CCATTTAAAGAGAAACTTCTAGAAATAATGACAAGGATTCAAACTTATTGTCAAA

TGAGTCCAATGTCAGATTTTGGACTC.
```

Properties of mda-6 mda-6 is identical to WAF1, CIP1, SDI1 that encodes a Mr.21,000 protein (p21) that is an inhibitor of cyclin dependent kinases.

Expression on H0-1 Human Melanoma Cells

Increased expression after 24 hour treatment of H0-1 cells with recombinant human fibroblast interferon (IFN-β) (2,000 units/ml), MEZ (10 ng/ml) and to the greatest extent with IFN-β+MEZ (2,000 units/ml+10 ng/ml) in combination.

Analysis of terminally differentiated H0-1 cells, i.e., H0-1 cells treated with the combination of IFN-β+MEZ (2,000 units/ml+10 ng/ml) for 96 hours indicate continued increased expression in IFN-β+MEZ treated H0-1 cells; and (b) no significant or reduced alteration in expression after 96 hour treatment in H0-1 cells treated with IFN-β (2,000 units/ml), IFN-γ (2,000 units/ml), MEZ (10 ng/ml), mycophenolic acid (MPA) (3 μM) (induces growth suppression increased melanin synthesis and morphology changes, but not terminal differentiation in H0-1 cells) trans retinoic acid (RA) (2.5 μM) (increases melanin synthesis and tyrosinase activity, but does not alter growth, morphology or induce terminal differentiation in human melanoma cells), IFN-β+IFN-γ (1,000 units/ml+1,000 units/ml) (growth suppressive without inducing markers of differentiation), MPA+MEZ (3 μM+10 ng/ml) (reversible growth suppression and induction of differentiation markers in H0-1 cells) and RA+MEZ (2.5 μM+10 ng/ml) (growth suppression and reversible induction of differentiation markers without inducing terminal cell differentiation).

mda-6 represents a novel gene which is enhanced in H0-1 cells by IFN-β+MEZ (which induces terminal differentiation) but not to the same extent by agents inducing growth suppression or various markers of differentiation. It could prove useful as a marker for the induction of terminal differentiation in human melanoma cells.

Expression in Additional Human Melanoma Cells

Variable increases in expression of this gene occur in H0-1, C8161, C8161/6.3 (a C8161 human melanoma cell clone containing an inserted normal human chromosome 6: These cells are tumorigenic in nude mice, but unlike parental C8161 cells they are non-metastatic), F0-1, L0-1, SH-1, WM278 and WM239 human melanoma cells treated with IFN-β+MEZ for 24 hours. This gene is constitutively expressed in immortalized human melanocytes FM516-SV (transformed by SV40). Some upregulation is also observed in FM516-SV following IFN-β+MEZ treatment for 24 hours.

Expression of mda-6 is increased by IFN-β+MEZ in 7 additional human melanoma cells besides the human melanoma cell it was cloned from, i.e., H0-1. In addition, this gene is expressed in melanocytes and its expression is increased following a 24 hour treatment with IFN-β+MEZ.

Expression in Normal Cerebellum, a Central Nervous System Tumor (Glioblastoma Multiforme) (GBM) and Normal Skin Fibroblast Cell Lines mda-6 is expressed de novo at high levels in normal cerebellum and normal skin fibroblasts. mda-6 is not expressed at significant levels in GBM cells. mda-6 expression is increased in normal cerebellum (>10-fold) and expression is induced in GBM following a 24 hour treatment with IFN-β+MEZ. mda-6 expression is not altered in normal human skin fibroblasts after a 24 hour treatment with IFN-β+MEZ.

This gene is susceptible to modulation by IFN-β+MEZ in human cerebellum and GBM. In contrast, this gene is expressed and no change in expression is seen following treatment in normal human skin fibroblasts. Differential de novo and inducible expression is also apparent in normal cerebellum cells versus GBM, with normal cerebellum displaying higher de novo expression. This gene could be a component of growth control in central nervous system glial cells (including normal cerebellum cells), which is repressed in malignant GBM cells.

Expression in Colorectal Carcinoma (SW613), Endometrial Adenocarcinoma (HTB112) and Prostate Carcinoma (LNCaP)

mda-6 is expressed at high levels de novo in colorectal carcinoma (SW613) and prostate carcinoma (LNCaP). mda-6 de novo expression in endometrial adenocarcinoma (HTB113) is low. Treatment for 24 hours with IFN-β+MEZ does not significantly alter mda-6 expression in colorectal carcinoma (SW613) or prostate carcinoma (LNCaP). Treatment for 24 hours with IFN-β+MEZ induces mda-6 expression in endometrial adenocarcinoma (HTB113) to a similar level as in colorectal and prostate carcinomas.

mda-6 displays a differential pattern of both de novo and inducible expression in different human carcinomas. De novo expression is low in endometrial adenocarcinoma and high in colorectal and prostate carcinoma. Inducible expression following treatment with IFN-β+MEZ is only observed in endometrial adenocarcinoma cells.

Effect of Various Treatment Protocols on Expression in H0-1 Cells

Treatment with IFN-β (2,000 units/ml; 24 hours), MEZ (10 ng/ml; 24 hours), IFN-β+MEZ (2,000 units/ml+10 ng/ml; 24 hours), actinomycin D (5 µg/ml; 2 hour treatment followed by 24 hour growth), adriamycin (0.1 µg/ml; 24 hour) and VP-16 (5 µg/ml; 24 hour) results in increased expression in H0-1 cells. Highest level of induction observed in H0-1 cells treated with IFN-β+MEZ for 24 hours or 96 hours; and actinomycin D, adriamycin and VP-16 treated for 24 hours.

Decreased expression of mda-6 is observed in H0-1 cells treated with phenyl butyrate (PB) (4 mM) (24 hours, 4 or 7 days), cis-platinum (0.1 µg/ml; 24 hours), UV (10 joules/mm$^2$; 2 hours after treatment), gamma irradiation (3 gray; assayed after 24 hours), IFN-α (2,000 units/ml; 24 hours) and TNF-α (100 units/ml; 24 hours).

No change in mda-6 expression observed in H0-1 cells treated with UV (10 joules/mm$^2$) and assayed after 14 or 24 hours and in H0-1 cells treated for 24 hours with IFN-α+MEZ (2,000 units/ml+10 ng/ml), or vincristine (0.1 µg/ml; 24 hours).

mda-6 is a novel gene which displays the following properties: 1) its expression is increased during terminal differentiation (treatment with IFN-β+MEZ for 96 hours); 2) treatment for 24 hours with IFN-β+MEZ results in variable increases in its expression in all human melanomas tested and in an SV40-immortalized human melanocyte; 3) it is expressed in early stage melanomas (radial and early vertical growth phase melanomas), but not or at reduced levels in more advanced melanomas (metastatic melanomas); 4) it is expressed de novo and highly inducible by IFN-β+MEZ within 24 hours in normal cerebellum; 5) it is not expressed de novo in GBM and only marginally induced in GBM after 24 hour treatment with IFN-β+MEZ; 6) high levels of de novo expression are seen in normal skin fibroblasts, colorectal carcinoma (SW613) and prostate carcinoma (LNCaP), but IFN-β+MEZ treatment does not significantly alter expression; 7) endometrial adenocarcinoma (HTB113) cells display low levels of expression of this gene, whereas IFN-β+MEZ treatment for 24 hours results in high levels of expression; 8) expression is increased in H0-1 cells treated with actinomycin D, adriamycin and VP-16; 9) expression is reduced in H0-1 cells treated with phenyl butyrate, gamma irradiation, cis-platinum and TNF-α; and 10) expression is highest in normal melanocytes and a dysplastic nevus and reduced in radial growth phase (RGP) and vertical growth phase (VGP) primary melanomas and lowest in metastatic melanoma; 11) expression is reduced as a function of tumorigenic progression in Matrigel-progressed RGP and early VGP primary melanoma: 12) expression is low in tumorigenic and metastatic C8161 human melanoma cells and increased in three independent C8161 clones containing an inserted normal chromosome 6 that are tumorigenic but not metastatic: 13) an immediate early response gene i.e., induced in the presence of cyclohexmide, in human promyelocytic leukemia. HL-60 cells induced to differentiate into monocytes and macrophages (treatment with 12-O-tetradecanoyl-phorbol-13-acetate (TPA) or vitamin D3) or granulocytes (treatment with all-trans retinoic acid (RA) or dimethyl sulfoxide (DMSO)); 14) induced as a function of growth arrest and differentiation in human neuroblastoma cells by treatment with the combination of phenylacetate and RA; and 15) induced during the induction of differentiation and growth arrest in human histiocytic lymphoma, U-937, cells by treatment with TPA.

mda-6 represents a terminal differentiation-regulated gene displaying increased expression in all melanomas tested, in specific carcinomas, in normal cerebellum cells and in GBM cells treated with IFN-β+MEZ. mda-6 is also induced during the induction of monocyte/macrophage and granulocyte differentiation in human promyelocytic leukemia (HL-60) cells; differentiation in human neuroblastoma cells; and differentiation in histiocytic lymphoma (U-937) cells. This gene also displays increased expression in cells treated with specific chemotherapeutic agents, including adriamycin and VP-16. In contrast, expression of mda-6 is decreased following treatment with gamma irradiation, the demethylating anticancer agent phenyl butyrate, the cytokine TNF-α and the chemotherapeutic agent cis-platinum. mda-6 may be useful: 1) as a marker for specific tissue lineages and for distinguishing tumors of similar histotype (i.e., carcinomas, astrocytomas) (diagnostic applications); 2) to monitor response to topoisomerase inhibitors such as VP-16 and specific chemotherapeutic agents which function in a similar manner as adriamycin and cis-platinum (drug screening programs to identify new chemotherapeutic agents); 3) to identify compounds which have the capacity to induce terminal differentiation in human melanoma cells myeloid leukemic cells, histiocytic lymphoma and neuroblastoma (drug screening programs to identify new differentiation-inducing and chemotherapeutic agents); and 4) to monitor states of tumor progression, i.e., only expressed or expressed at higher levels in less aggressive and early stage cancers. Once full-length cDNAs are isolated, this gene (used in a sense orientation in an appropriate expression vector) may also prove useful in inhibiting growth and inducing terminal differentiation in human melanomas and other classes of tumors (therapeutic applications). Overexpression of this gene in specific cell types (such as bone marrow cells) may also result in a decreased sensitivity of these cells to various DNA damaging agents and chemotherapeutic agents (therapeutic applications). This could prove useful in protecting bone marrow cells from damage induced by radiation and chemotherapy (therapeutic applications). Similarly, use of antisense constructs may also result in a decreased sensitivity to growth suppression in normal cells induced by specific classes of DNA damaging and therapeutic agents (therapeutic applications). This gene may also prove useful in the classification of more advanced astrocytomas (such as GBM) from less advanced earlier stages of astrocytomas (diagnostic applications). This gene may also prove useful in distinguishing between early stage (early radial growth phase, early vertical growth phase) melanoma and late stage (late vertical growth phase, metastatic) melanoma (diagnostic applications).

mda-6

Expression in Additional Human Melanoma Cells

Increased expression of mda-7 occurs in H0-1, C8161, C8161/6.3 (a C8161 human melanoma cell clone containing an inserted normal human chromosome 6: These cells are tumorigenic in nude mice, but unlike parental C8161 cells they are non-metastatic), F0-1, L0-1, SH-1, WM278 and WM239 human melanoma cells treated with IFN-β+MEZ for 24 hours. This gene is constitutively expressed in immortalized human melanocytes FM5169 (transformed by SV40). However, no increase in expression is observed in FM5169 following IFN-β+MEZ treatment for 24 hours.

mda-7 is either variably expressed or variably induced in all human melanoma cells treated with IFN-β+MEZ. In contrast, although this gene is expressed in melanocytes, no change in expression is observed following a 24 hour treatment with IFN-β+MEZ.

Expression in Normal Cerebellum, a Central Nervous System Tumor (Glioblastoma Multiforme) (GBM) and Normal Skin Fibroblast Cell Lines mda-7 is not expressed de novo in normal cerebellum, GBM or normal skin fibroblasts.

Expression of mda-7 is induced in normal cerebellum, GBM and normal skin fibroblasts following a 24 hour treatment with IFN-β+MEZ.

mda-7 is not expressed de novo but is susceptible to induction by IFN-β+MEZ in human cerebellum, GBM and normal human skin fibroblasts.

```
ATGCCACGTGGGCTCATATGGGGCTGGGAGTAGTTGTCTTTCCTGGCACTAACGT   (SEQ ID NO: 13)

TGAGCCCCTGGAGGCACTGAAGTGCTTAGTGTACTTGGAGTATTGGGGTCTGACC

CAAACACCTTCCAGCTCCTGTAACATACTGGCCTGGACTGTTTTCTCTCGCGCCT

CCCCATGTGCTCCTGGTTCCCGTTTCCTCCACCTAGACTGTAAACCTCTCGCA.

CCTGCAGTCCTGGAAGCGCGAGGGCCTCAAACGCGCTCTACATCTTCTGCCTTAG   (SEQ ID NO: 14)

TCTCAGTTTGCGTGTCTTAATTATTATTTGTGTTTTAATTTAAACACCTCCTCAT

GTACATACCCTGGCCGCCCCCTGCCCCCCAGCCTCTCGGATTAGAATTATTTAAA

CAAAAACTAGGCGGTTGAATGAGAGGTTCCTATGAGTACTGGGCATTTTTATTTT

ATGAAATACTATTTAAAGCCTCCTCATCCCATGTTCTCCTTTTCCTCTCTCCCGG

AGTT.
```

Properties of mda-7 mda-7 is a novel cDNA (it has no sequence homology with previously reported genes in the various DNA data bases).

Expression in H0-1 Human Melanoma Cells

Increased expression of mda-7 after 24 hour treatment of H0-1 cells with recombinant human fibroblast interferon (IFN-β) (2000 units/ml), MEZ (10 ng/ml) and to the greatest extent with IFN-β+MEZ (2000 units/ml+10 ng/ml).

Increased expression of mda-7 is observed in H0-1 cells treated for 96 hours with IFN-β (2000 units/ml), MEZ (10 ng/ml), MPA (3 μM), IFN-β+IFN-γ (1000 units/ml+1000 units/ml), IFN-β+MEZ (2000 units/ml+10 ng/ml), MPA+MEZ (3 μM+10 ng/ml) and RA+MEZ (2.5 μM+10 ng/ml). Maximum induction is observed with IFN-β+MEZ followed by MPA+MEZ and IFN-β+IFN-γ.

The relative level of mda-7 induction correlates with the degree of growth suppression observed H0-1 cells treated with the various growth and differentiation modulating agents. The greatest increase in expression is observed in cells induced to irreversibly lose proliferative capacity and become terminally differentiated by treatment with IFN-β+MEZ.

Expression in Colorectal Carcinoma (SW613), Endometrial Adenocarcinoma (HTB113) and Prostate Carcinoma (LNCaP)

mda-7 is not expressed de novo in colorectal carcinoma (SW613), endometrial adenocarcinoma (HTB113) or prostate carcinoma (LNCaP).

mda-7 is not induced in colorectal carcinoma (SW613), endometrial adenocarcinoma (HTB113) or prostate carcinoma (LNCaP) cells following a 24 hour treatment with IFN-β+MEZ.

This gene is neither expressed de novo or inducible by IFN-β+MEZ in human carcinomas.

Effect of Various Treatment Protocols on Expression in H0-1 Cells

Treatment with IFN-β (2000 units/ml; 24 hours), MEZ (10 ng/ml; 24 hours), IFN-β+MEZ (2000 units/ml+10 ng/ml; 24 hours and 96 hours), IFN-α+MEZ (2000 units/ml+10 ng/ml; 24 hours), adriamycin (0.1 μg/ml; 24 hours), vincristine (0.1 μg/ml; 24 hours), and UV (10 joules/mm$^2$ and assayed 24 hours later) results in increased mda-7 expression in H0-1 cells. mda-7 is also induced after 96 hour treatment with MPA (3 μM), IFN-β+IFN-γ (1000 units/ml+

1000 units/ml), MPA+MEZ (3 µM+10 ng/ml) and RA+MEZ (2.5 µM+10 ng/ml). Highest level of expression observed in H0-1 cells treated with IFN-β+MEZ for 24 or 96 hours.

No induction in mda-7 expression is observed in H0-1 cells treated with IFN-α (2000 units/ml; 24 hours), IFN-γ (2000 unit/ml; 96 hours), phenyl butyrate (4 mM PB for 24 hours, 4 days or 7 days), cis-platinum (0.1 µg/ml; 24 hours), gamma irradiation (treated with 3 gray and analyzed after 24 hours), actinomycin D (5 µg/ml for 2 hours, assayed 24 hours later), TNF-α (100 units/ml; 24 hours) or VP-16 (5 µg/ml; 24 hours).

mda-7 is a growth and differentiation and sensescence-regulated novel gene which displays the following properties: 1) it is inducible during terminal differentiation (treatment with IFN-β+MEZ for 96 hours) and following treatment for 96 hours with many growth modulating and differentiation inducing agents; 2) treatment for 24 hours with IFN-β+MEZ results in increased expression in all human melanomas tested, but not in an SV40-immortalized human melanocyte; 3) it is not expressed de novo but it is highly inducible by IFN-β+MEZ within 24 hours in normal cerebellum, GBM and normal skin fibroblast cells; 4) it is not expressed or inducible in colorectal, endometrial or prostate carcinomas; 5) increased expression is induced in H0-1 cells treated with adriamycin, vincristine and UV irradiation; and 6) it is not expressed in growing human neuroblastoma cells but it is inducible following growth suppression and the induction of terminal differentiation; 7) it is not expressed in human promyeloctyic leukemia (HL-60 and human histiocytic lymphoma (U-937) cells but it is induced following the induction of growth arrest and terminal differentiation; and 8) it is not expressed in actively growing human cells but it is induced during cellular senescence.

mda-7 is a novel growth- and terminal differentiation-regulatable gene displaying increased expression in all melanomas (but not in melanocytes), and in normal skin fibroblasts and in both normal cerebellum and GBM cells treated with IFN-β+MEZ. In contrast, mda-7 is not expressed or induced in a series of carcinomas. mda-7 may be useful: 1) as a marker for specific tissue lineage's (i.e., melanomas from keratinocytes) (diagnostic applications); 2) in distinguishing fibroblasts (inducible with IFN-β+MEZ) from carcinomas (non-inducible with IFN-β+MEZ) (diagnostic applications); 3) for the identification of agents capable of inducing growth suppression and various components of the differentiation process (including terminal differentiation) in human melanomas (drug screening programs to identify new differentiation-inducing and chemotherapeutic agents); and 4) distinguishing melanocytes, and perhaps nevi, from early and late stage melanoma cells (diagnostic applications). Once full-length cDNAs are isolated, this gene (used in a sense orientation in an appropriate expression vector) may also prove useful in inhibiting growth and inducing terminal differentiation in human melanomas (therapeutic applications).

mda-7

Properties of mda-8 mda-8 is a novel cDNA (it has no sequence homology with previously reported genes in the various DNA data bases)

Expression in H0-1 Human Melanoma Cells

Increased expression of mda-8 results in H0-1 cells after 24 hour treatment with the combination of IFN-β+MEZ (2000 units/ml+10 ng/ml).

Analysis of terminally differentiated H0-1 cells, i.e., H0-1 cells treated with the combination of IFN-β+MEZ (2000 units/ml+10 ng/ml) for 96 hours indicate continued increased expression of mda-8.

Treatment of H0-1 cells for 96 hours with immune interferon (IFN-γ) (2000 units/ml) or IFN-β+IFN-γ (1000 units/ml+1000 units/ml) results in enhanced mda-8 expression. The level of increased mda-8 expression at 96 hour is similar in IFN-γ, IFN-β+IFN-γ and IFN-β+MEZ treated H0-1 cells. (Note: The combination of IFN-β+IFN-γ results in a similar degree of growth suppression at 96 hour in H0-1 cells as does IFN-β+MEZ. However, growth expression is reversible with the combination of interferons, whereas it is irreversible with the combination of IFN-β+MEZ).

mda-8 is a novel IFN-γ-inducible gene which also displays increased expression during terminal cell differentiation in H0-1 human melanoma cells. mda-8 could prove useful as a marker for immune interferon response and a marker for terminal differentiation in human melanoma cells.

Expression in Additional Human Melanoma Cells

Increased expression of mda-8 occurs in H0-1, C8161 and WM278 human melanoma cells treated for 24 hours with IFN-β+MEZ (2000 units/ml+10 ng/ml).

No change in expression of mda-8 is seen in additional human melanomas treated for 24 hours with IFN-β+MEZ, including C8161/6.3 (a C8161 human melanoma cell clone containing an inserted normal human chromosome 6: These cells are tumorigenic in nude mice, but unlike parental C8161 cells they are non-metastatic), F0-1, L0-1, SH-1, and WM239.

Expression of this gene is increased by IFN-β+MEZ in specific human melanoma cells.

Expression in Normal Cerebellum, a Central Nervous System Tumor (Glioblastoma Multiforme) (GBM) and Normal Skin Fibroblast Cell Lines mda-8 is expressed de novo in normal cerebellum, but not in GBM.

mda-8 is expressed de novo in normal skin fibroblasts.

Growth for 24 hours in IFN-β+MEZ (2000 units/ml+10 ng/ml) results in marginal changes in mda-8 expression in normal cerebellum and normal skin fibroblasts.

Expression of mda-8 is induced at high levels in GBM cells following a 24 hour exposure to IFN-β+MEZ.

This gene is expressed de novo in both normal cerebellum and normal skin fibroblasts, but not in GBM. This gene is induced by IFN-β+MEZ in human GBM, but expression is not altered in normal cerebellum cells and normal skin fibroblasts.

```
CAGAATATTGTGCCCCATGCTTCTTTACCCCTCACAATCCTTGCCACAGTGTGGG  (SEQ ID NO: 15)

CAGTGGATGGGTGCTTAGTAAGTACTTAATAAACTGTGGTGCTTTTTTTGGCCTG

TCTTTGGATTGTTAAAAAACAGAGAGGGATGCTTGGATGTAAACTGAACTTCAGA

GCATGAAATCACACTGTCTCTGATATCT.
```

Expression in Colorectal Carcinoma (SW613), Endometrial Adenocarcinoma (HTB113) and Prostate Carcinoma (LNCaP)

mda-8 is expressed de novo in colorectal carcinoma (SW613), endometrial adenocarcinoma (HTB113) and prostate carcinoma (LNCaP).

Following a 24 hour treatment with IFN-β+MEZ, expression of mda-8 is unaffected in colorectal carcinoma (SW613), endometrial adenocarcinoma (HTB113) and prostate carcinoma (LNCaP) cells.

mda-8 is expressed de novo in the three types of carcinomas. mda-8 gene expression is not altered in the three carcinomas after treatment for 24 hours with IFN-β+MEZ.

Effect of Various Treatment Protocols on Expression in H0-1 Cells

Increased expression of mda-8 results after treatment with IFN-β (2000 units/ml; 24 hours), actinomycin D (5 μg/ml for 2 hours, assayed 24 hours later), adriamycin (0.1 μg/ml; 24 hours), cis-platinum (0.1 μg/ml; 24 hours) and UV (10 joules/mm$^2$, assayed 2, 14 and 24 hours later).

A 96 hour treatment with IFN-γ (2000 units/ml), IFN-β+MEZ (2000 units/ml) and IFN-β+IFN-γ (1000 units+1000 units) results in increased mda-8 expression.

No change in expression of mda-8 is observed in H0-1 cells treated with MEZ (10 ng/ml; 24 or 96 hours), IFN-β (2000 units/ml; 24 or 96 hours), MPA (3 μM; 96 hours), RA (2.5 μM; 96 hours), MPA+MEZ (3 μM+10 ng/ml; 96 hours), RA+MEZ (2.5 μM+10 ng/ml), phenyl butyrate (4 mM PB for 24 hours, 4 days or 7 days), gamma irradiation (treated with 3 gray and analyzed after 24 hours), vincristine (0.1 μg/ml; 24 hours), TNF-α (100 units/ml; 24 hours), VP-16 (5 μg/ml; 24 hours), IFN-α (2000 units/ml) or IFN-α+MEZ (2000 units/ml+10 ng/ml).

mda-8 is a novel gene which displays the following properties: 1) it is inducible during terminal differentiation (treatment with IFN-β+MEZ for 96 hours) and following treatment for 96 hours with recombinant gamma interferon (alone or in combination with IFN-β); 2) treatment for 24 hours with IFN-β+MEZ results in increased expression in only select human melanomas; 3) it is expressed de novo in normal cerebellum, normal skin fibroblasts, colorectal carcinoma (SW613), endometrial adenocarcinoma (HTB113) and prostate carcinoma (LNCaP), but not in GBM; 4) treatment with IFN-β+MEZ for 24 hours results in no change in expression in normal cerebellum, normal skin fibroblasts, colorectal carcinoma (SW613), endometrial adenocarcinoma (HTB113) and prostate carcinoma (LNCaP); 5) treatment for 24 hours with IFN-β+MEZ induces expression in GBM cells; and 6) increased expression is induced in H0-1 cells treated with actinomycin D, adriamycin, cis-platinum and UV irradiation.

mda-8 is a cytokine- and terminal differentiation-responsive gene displaying increased expression in specific human melanomas and GBM cells treated with IFN-β+MEZ (also inducible in H0-1 after 96 hour treatment with IFN-γ and IFN-γ+IFN-β). Enhanced expression is also apparent in H0-1 human melanoma cells treated with the transcription inhibitor actinomycin D, the chemotherapeutic agents adriamycin and cis-platinum and UV irradiation. mda-8 may be useful: 1) as a marker for distinguishing between normal glial cells and malignant astrocytomas (such as GBM) (diagnostic applications); 2) to monitor response to type II interferon treatment (diagnostic applications); and 3) to identify compounds which have the capacity to induce terminal differentiation, induce similar cytotoxic effects as adriamycin, cis-platinum and UV irradiation (drug screening programs to identify new differentiation-inducing and chemotherapeutic agents). Once full-length cDNAs are isolated, this gene (used in a sense orientation in an appropriate expression vector) may prove useful in inhibiting growth and inducing terminal differentiation in specific human melanomas and glioblastoma multiforme tumors (therapeutic applications).

mda-8

```
TTAAAGTTTGCCCTTGTGCTAAAGTGCCAGTGTATGTATGTTATACTTGATTTGG  (SEQ ID NO: 16)

TTGTAAACTATATTTCAAAGTAAACCCTAGTGTAATAAGTTTTATAACTAAAAAG

GTTTAAGCTGCTAAAACTATTTTTAAGAGATGTGAAATCGAGTATGGGACTATCT

TTTTTTCCTCCTCTAAA.
```

Properties of mda-9 mda-9 is a novel cDNA (it displays sequence homology to human transforming growth factor-β (TGF-β) mRNA, 55.1% homology in 138 bp; GB-Pr:Humtgfbc).

Expression in H0-1 Human Melanoma Cells

Increased expression of mda-9 occurs after 24 hour treatment of H0-1 cells with the combination of IFN-β+MEZ (2000 units/ml+10 ng/ml).

Increased expression of mda-9 persists in terminally differentiated H0-1 cells, i.e., H0-1 cells treated with the combination of IFN-β+MEZ (2000 units/ml+10 ng/ml) for 96 hours.

mda-9 is a novel gene (with homology to TGF-β) which displays increased expression in terminally differentiated H0-1 human melanoma cells.

Expression in Additional Human Melanoma Cells

Variable increases in expression of mda-9 occurs in H0-1 and C8161 human melanoma cells treated for 24 hours with IFN-β+MEZ (2000 units/ml+10 ng/ml).

The level of expression of mda-9 decreases in SH-1 cells treated for 24 hours with IFN-β+MEZ (2000 units/ml+10 μg/ml).

No change in mda-9 expression results in F0-1, L0-1 or C8161/6.3 cells (a C8161 human melanoma cell clone containing an inserted normal human chromosome 6: These cells are tumorigenic in nude mice, but unlike parental C8161 cells they are non-metastatic).

Expression of mda-9 is increased by IFN-β+MEZ in specific human melanoma cells. The lack of enhanced expression in C8161/6.3 cells treated with IFN-β+MEZ, whereas parental C8161 cells do show an increase, suggests that modulation of this gene may correlate with more advanced stages of melanoma development (i.e., melanoma cells with metastatic potential).

Effect of Various Treatment Protocols on Expression in H0-1 Cells

Increased expression of mda-9 is observed in H0-1 cells treated with IFN-β (2000 units/ml; 24 hours), MEZ (10 ng/ml; 24 hours), IFN-β+MEZ (2000 units/ml+10 ng/ml; 24 and 96 hours), phenyl butyrate (4 mM PB for 24 hours, 4 days or 7 days), gamma irradiation (treated with 3 gray and analyzed after 24 hours), TNF-α (100 units/ml; 24 hours), IFN-α (2000 units/ml), IFN-α+MEZ (200 units/ml+10 ng/ml), VP-16 (5 μg/ml; 24 hours) or UV (10 joules/mm$^2$, assayed 2 or 14 hours later).

No change in mda-9 expression is observed in H0-1 cells treated with actinomycin D (5 μg/ml for 2 hours, assayed 24 hours later), UV (10 joules/mm$^2$ assayed 24 hours later), cis-platinum (0.1 μg/ml; 24 hours), vincristine (0.1 μg/ml; 24 hours), IFN-β (2000 units/ml; 96 hours), IFN-γ (2000 units/ml; 96 hours), MEZ (10 ng/ml; 96 hours), MPA (3 μM; 96 hours), RA (2.5 μM; 96 hours), IFN-β+IFN-γ (1000 units/ml+1000 units/ml; 96 hours), MPA+MEZ (3 μM+10 ng/ml; 96 hours) or RA+MEZ (2.5 μM+10 ng/ml).

mda-9 is a novel gene with sequence homology to TGF-β which displays the following properties: 1) it is inducible during terminal differentiation (treatment with is IFN-β+MEZ for 96 hours) in H0-1 human melanoma cells; 2) treatment for 24 hours with IFN-β+MEZ results in increased expression in several human melanomas; 3) treatment for 24 hours with IFN-β+MEZ results in increased expression in the tumorigenic and metastatic human melanoma C8161, but not in C8161/6.3 which is tumorigenic but not metastatic; and 4) increased expression is induced in H0-1 cells treated with a number of agents including phenyl butyrate, gamma irradiation, TNF-α, UV irradiation (after 2 and 14 hours, but not after 24 hours), IFN-α and IFN-α+MEZ.

mda-9 is a terminal differentiation-responsive gene displaying increased expression in several human melanomas treated with IFN-β+MEZ. Enhanced expression is induced by IFN-β+MEZ in the tumorigenic and metastatic human melanoma cell C8161, but not its reverted derivative C8161/6.3 (which retains tumorigenicity, but has lost metastatic potential). Increased expression is also apparent in H0-1 human melanoma cells treated with the demethylating anti-cancer agent phenyl butyrate, the cytokine TNF-α, gamma irradiation and UV irradiation.

mda-9 may be useful: 1) as a marker for distinguishing between early stage and more progressed human melanoma (diagnostic applications); and 2) to identify compounds which have the capacity to induce terminal differentiation and to induce specific patterns of DNA damage as induced by UV irradiation and gamma irradiation (drug screening programs to identify new differentiation-inducing and chemotherapeutic agents). Once full-length cDNAs are isolated, this gene (used in a sense orientation in an appropriate expression vector) may also prove useful in inhibiting growth and inducing terminal differentiation in specific human melanomas (therapeutic applications). When used in an antisense orientation, expression of this gene might allow normal cells (such as bone marrow cells) to be engineered to be resistant to cytotoxicity induced by specific chemotherapeutic agents and gamma irradiation (therapeutic applications).

mda-9

```
AAAACTTTCAAGAGATTTACTGACTTTCCTAGAATAGTTTCTCTACTGGAAACCT  (SEQ ID NO: 17)
GATGCTTTTATAAGCCATTGTGATTAGGATGACTGTTACAGGCTTAGCTTTGTGT
GAAAACCAGTCACCTTTCTCCTAGGTAATGAGTAGTGCTGTTCATATTACTTTAG
TTCTATAGCATACTCGATCTTTAACATGCTATCATAGTACATTAGATGATG.
```

Additional mda Genes Isolated Using Subtraction Hybridization from H0-1 Human Melanoma Cells Treated with IFN-β+MEZ mda-1: Novel gene which displays increased expression in IFN-β and IFN-β+MEZ treated H0-1 cells after 24 hours (HP 2-36). (Jiang and Fisher, Molecular and Cellular Differentiation, 1 (3), in press, 1993).

mda-2: Novel gene which displays increased expression in IFN-β and IFN-β+MEZ treated H0-1 cells after 24 hours (HP-3-31). (Jiang and Fisher, Molecular and Cellular Differentiation, 1 (3), in press, 1993).

mda-3: Increased expression in MEZ and IFN-β+MEZ treated H0-1 cells after 24 hours (HP 2-4). (Identical to Human GOS 19-1 mRNA, cytokine (Gb-Pr:Hummipla), human TPA-inducible mRNA, pLD78 (GB-Pr:Humpld78). (Jiang and Fisher, Molecular and Cellular Differentiation, 1 (3), in press, 1993).

mda-11: Novel gene which displays increased expression in IFN-β+MEZ treated H0-1 cells after 24 hours. (HJ 2-78). (87.2% identity to the rat ribosomal protein IF116).

```
CGCACGTCACCCACCTTCCGGCGGCCGAAGACACTGCGACTCCGGAGACAGCCCA  (Seq. ID NO: 18)
AATATCCTCGGAAGAGCGCTCCCAGGAGAAACAAGCTTGACCACTATGCTATCAT
CAAGTTTCCGCTGACCACTGAGTCTGCCATGAAGAAGATAGAAGACAACAACACA
CTTGTGTTCATTGTGGATGTTAAAGCCAACAAGCACCAGATTAACAGCTGTGAGA
GCTGTATGACATTGATGTGCAGTACACCTGATCGTCT.
``` mda-12: Gene which displays increased expression in IFN-β+MEZ treated H0-1 cells after 24 hours. (HP 3-8). (Identical to Human GOS19-3 mRNA (Gb-Humcpgcus2), LD78A (Gb-Pr:Humld78a).

mda-13: Gene which displays increased expression in IFN-β and IFN-β+MEZ treated H0-1 cells after 24 hours. (HP S-7). (Identical to interferon stimulated gene-56 (ISG56), an IFN-β inducible gene).

mda-14: Gene which displays increased expression in IFN-β+MEZ treated H0-1 cells after 24 hours. (HP 2-59 and HP 3-114, same gene isolated independently two times).

(Identical to interleukin-8 (IL-8) (Gb-Un:M28130), human mRNA for MDNCF (monocyte derived neutrophil chemotactic factor) (Gb-Pr:Nummdncf).

```
TAAAAAAATTCATTCTCTGTGGTATCCAAGAATCAGTGAAGATGCCAGTGAAACT    (Seq. ID NO: 19)

TCAAGCAAATCTACTTCAACACTTCATGTATTGTGTGGGTCTGTTGTAGGGTTGC

CAGATGCAATACAAGATTCCTGGTTAAATTTGAATTTCAGTAAACAATGAATAGT

TTTTCATTGTACATGAAATATCAGAACATACTTATATGTAAGTATATTATTGATG

ACAAACACAATATTTAATATA.
``` mda-15: Gene which displays increased expression in IFN-β+MEZ treated H0-1 cells after 24 hours (HP 2-64). (Identical to vimentin, intermediate filament protein (Gb-Pr:Humviment).

mda-16: Gene which displays increased expression in IFN-β+MEZ treated H0-1 cells after 24 hours. (HP 2-18). (Identical to human apoferritin H gene (Gb-Pr:Humferg2).

mda-17: Gene which displays increased expression in IFN-β+MEZ treated H0-1 cells after 24 hours. (HP 2-40). (Identical to IFP-53 (Gb Pr:Humifp), IFN-inducible gamma 2 protein (Gb-Huminfig).

```
GGGGGTGAAACTTTCCAGTTTACTGAACTCCAGACCATGCATGTAGTCCACTCCA    (SEQ ID NO: 20)

GAAATCATGCTCGCTTCCTTGGCACACAGTGTTCTCCTGCCAAATGACCCTAGAC

CCTCTGTCCTGCAGAGTCAGGGTGGCTTTTACCCTGACTGTGTCGATGCAGAGTC

TGCTCGACAGAT.
``` mda-18: Gene which displays increased expression to IFN-β+MEZ treated H0-1 cells after 24 hours (HP 2-45). (Identical to hnRNP A1 protein (Gb-Pr:Humrnpa1), RNA binding protein (Gb-Pr:Humhnrnpa).

```
TACGATCAGACTGTTACATTTAGCAATCAACAGCATGGGCGAAAAAAAAAAATC    (Seq. ID No. 21)

TACTTAAAACCCTTTGTTGGAATGCTTTACACTTTCCACAGAACAGAAACTAAAA

TAACTGTTTACATTAGTCACAATACAGTCTCGA.
```

Fifth Series of Experiments

The carcinogenic process often proceeds through a series of interrelated stages and is regulated by multiple genetic changes and environmental factors (1–6). Although the specific events controlling each component of this multistep process remain to be defined, a recurrent theme in many cancer cells is an aberrant pattern of differentiation (7–10). In addition, as cancer cells evolve, ultimately developing new phenotypes or an increased expression of pre-existing transformation-related phenotypes, the degree of expression of differentiation associated traits is often further diminished. Malignant melanoma epitomizes the process of tumor progression and emphasizes the selective nature of the metastatic phenotype and the growth dominant properties of metastatic cells (11–14). Of the numerous types of cancer developing in North American populations, melanoma is increasing at the fastest rate and it is estimated that as many as 1 in 100 currently born children may eventually develop superficial spreading type melanoma (11). Although melanoma is readily curable at early stages, surgical and chemo- therapeutic interventions are virtually ineffective in preventing metastatic disease and death in patients with advanced stages of malignant melanoma. These observations emphasize the need for improved therapeutic approaches to more efficaciously treat patients with metastatic melanoma.

Figure 20:
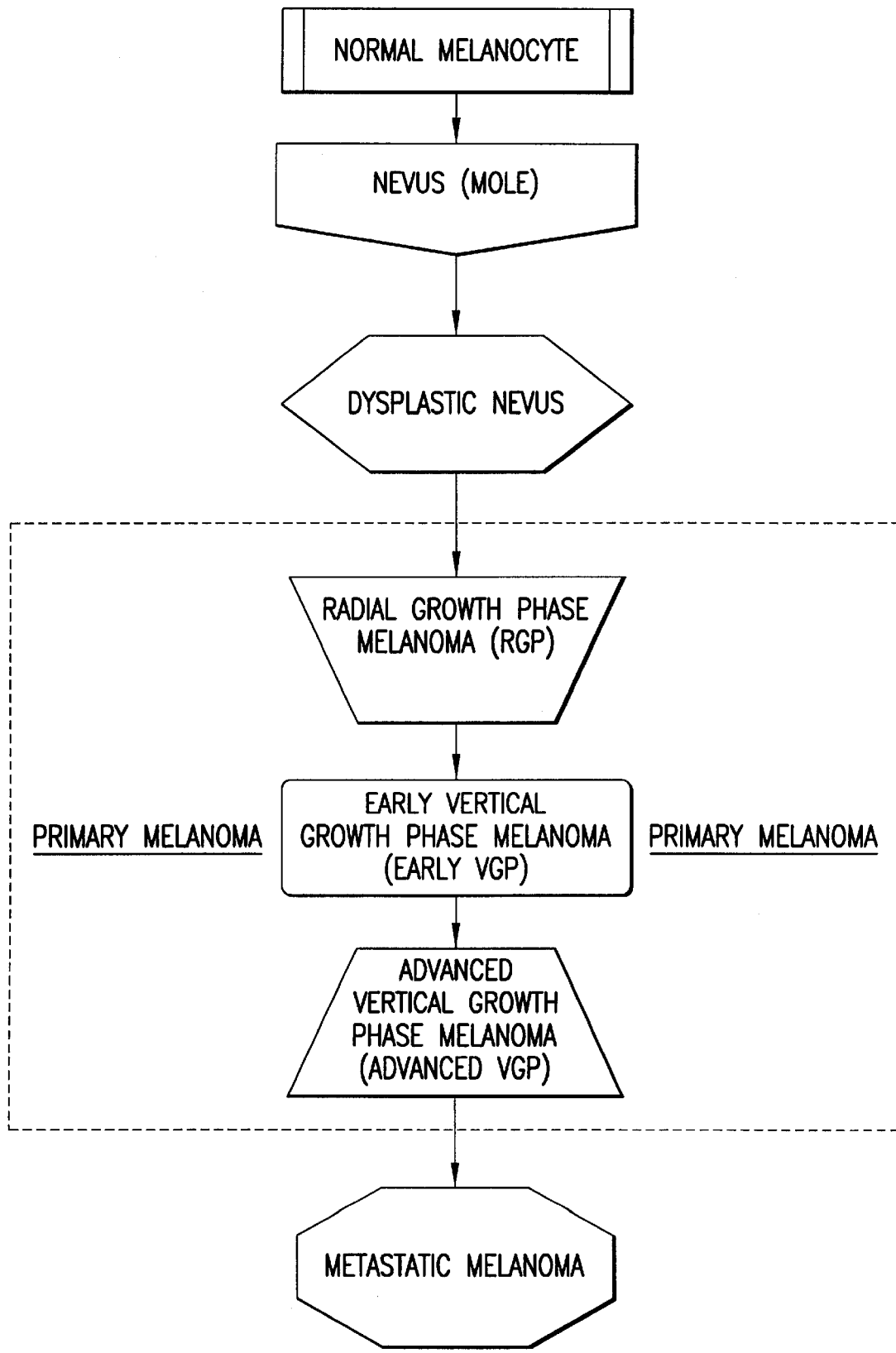
FIG. 20. Stages in the development of metastatic melanoma.
Figure 21D:
FIGS. 21A–H. Effect of recombinant human IFN-β and mezerein (MEZ) used alone and in combination on the morphology of H0-1 and B0-2 human melanoma cells (X150). (A) Control H0-1 cells 24 h postplating. (B) H0-1 cells exposed to 2,000 units/ml IFN-β for 24 h. (C) H0-1 cells exposed to 10 ng/ml MEZ for 24 h. (D) H0-1 cells exposed to 2,000 units/ml IFN-β and 10 ng/ml MEZ for 24 h. (E) Control B0-2 cells 24 h postplating. (F) B0-2 cells exposed to 2,000 units/ml IFN-β for 24 h. (G) B0-2 cells exposed to 10 ng/ml MEZ for 24 h. (H) B0-2 cells exposed to 2000 units/ml IFN-β and 10 ng/ml MEZ for 24 h. Data from reference [18] of the fifth series of experiments.
Figure 21C:
Figure 21B:
Figure 21A:
Figure 21H:
Figure 21G:
Figure 21F:
Figure 21E:

Development of malignant melanoma in humans, with the exception of nodular type melanoma, consists of a series of sequential alterations in the evolving tumor cells (11–15). These include conversion of a normal melanocyte into a common acquired melanocytic nevus (mole), followed by the development of a dysplastic nevus, a radial growth phase (RGP) primary melanoma, a vertical growth phase (VGP) primary melanoma and ultimately a metastatic melanoma (FIG. 20). Although readily treatable during the early stages of development, even during the VGP if the lesion is ≦0.76-mm thick, currently employed techniques are not very effective (<20% survival) in preventing metastatic spread and morbidity in patients with VGP lesions >4.0-mm thickness (11). This exceptional model system is ideally suited to evaluate the critical gene expression changes that mediate both the early and late phases of melanoma evolution.

A potentially less toxic approach to cancer therapy involves a process termed differentiation therapy (7, 9, 10, 16, 17). Two premises underlie this therapeutic modality. (A) Many types of neoplastic cells display aberrant patterns of differentiation resulting in unrestrained growth; and (B) Treatment with the appropriate agent(s) can result in the reprogramming of tumor cells to lose proliferative capacity and become terminally differentiated. Intrinsic in this hypothesis is the assumption that the genes that mediate normal differentiation in many tumor cells are not genetically defective, but rather they fail to be expressed appropriately. The successful application of differentiation therapy in specific instances may result because the appropriate genes inducing the differentiated phenotype become transcriptionally activated resulting in the production of necessary gene products required to induce terminal cell differentiation. Applicants have tested this hypothesis using human melanoma cells (8, 10, 18–23). Treatment of human melanoma cells with the combination of recombinant human fibroblast interferon (IFN-β) and the antileukemic compound mezerein (MEZ) results in a rapid cessation of growth, an induction of morphological changes, an alteration in antigenic phenotype, an increase in melanin synthesis and an irreversible loss in proliferative capacity, i.e., terminal cell differentiation (18, 21, 23). In contrast, treatment of the same melanoma cells with equivalent doses of either IFN-β or MEZ alone results in specific differentiation-related and immunologically-related changes and growth suppression, but terminal differentiation does not occur (18, 21, 24–34).

This invention summarizes the results of applicants' analysis of the process of reversible and irreversible (terminal) differentiation in human melanoma cells. By using the technique of subtraction hybridization a series of novel genes, termed melanoma differentiation associated (mda), have been identified that display enhanced expression during differentiation and growth arrest in human melanoma cells. These newly identified mda genes should prove useful in defining the molecular basis of human melanoma growth, differentiation and transformation progression.

Dissecting the Processes of Growth Control and Differentiation in Human Melanoma Cells The process of terminal differentiation in H0-1 cells involves a number of changes in cellular phenotype and gene expression (18, 21, 23, 35). Biochemical and cellular changes include growth suppression, changes in melanin synthesis (biochemical differentiation) and modified antigenic properties (immunologic differentiation) (18, 21, 23, 29, 34, 35). The ability to define the relationship between the different components of growth and differentiation and the corresponding gene expression changes induced in human melanoma cells has been assisted by the identification of specific compounds that induce different components of these processes (FIGS. 21A–H) (18, 21, 23, 33, 36).

Figure 22:
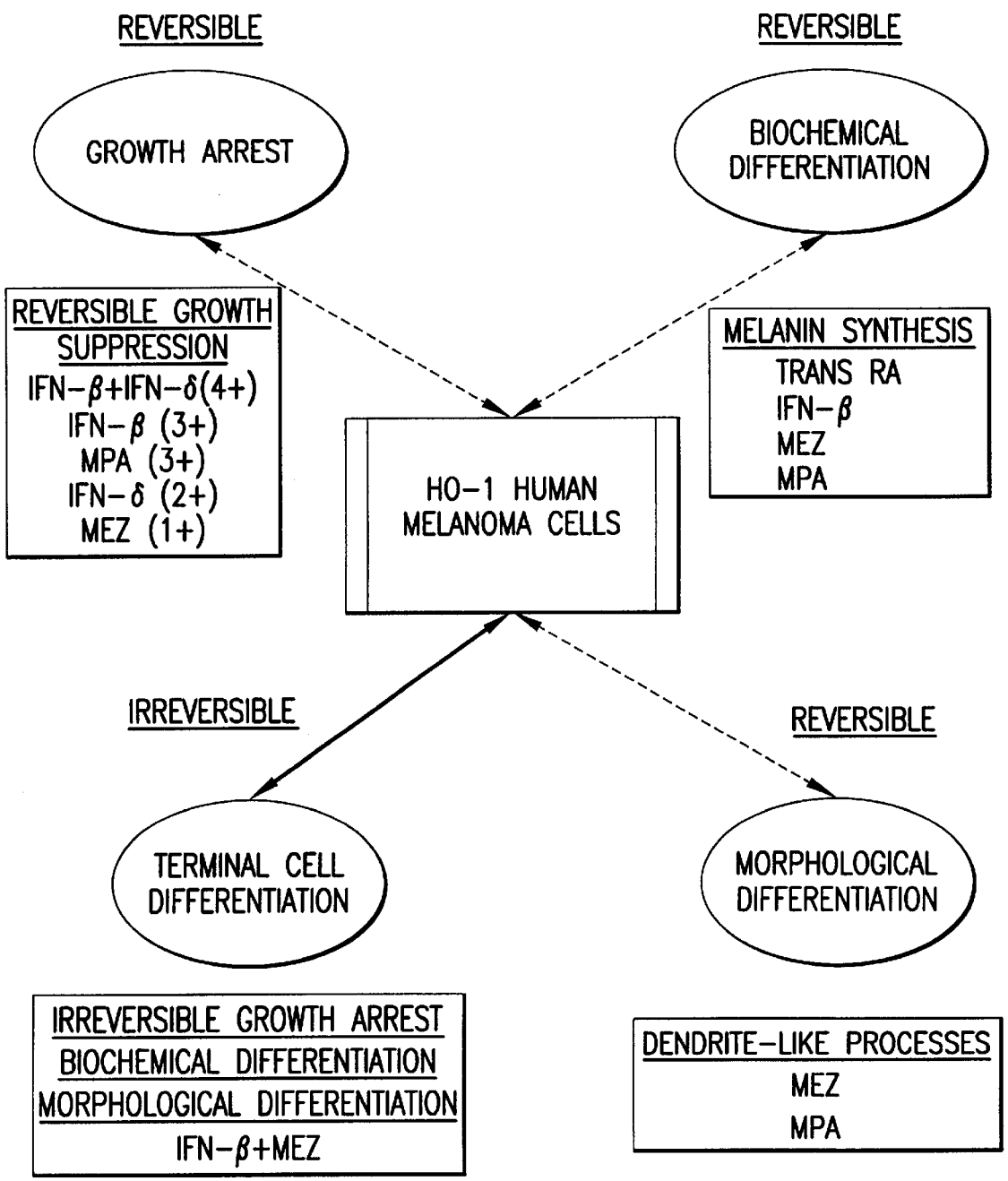
FIG. 22 Components of the differentiation process in H0-1 human melanoma cells. Abbreviations: IFN-β: recombinant human fibroblast interferon; IFN-γ: recombinant immune interferon; MPA: mycophenolic acid; MEZ: mezerein; Trans RA: trans retinoic acid. Relative growth suppression: 4+=~80% reduction in growth in comparison with untreated control cultures; 3+=~50 to 60% reduction in growth in comparison with untreated control cultures; 2+=~40% reduction in growth in comparison with untreated control cultures; 1+=~30% reduction in growth comparison with untreated control cultures.

Growth of H0-1 cells in the combination of IFN-β plus recombinant immune interferon (IFN-γ) results in a similar level of growth suppression after 96 hr as does the combination of IFN-β+MEZ (23, 33). However, this combination of interferons induces reversible growth arrest and it does not cause an increase in melanin synthesis above that induced by IFN-β alone (33). This specific combination of agents permits a dissociation between reversible growth suppression and induction of irreversible growth suppression and terminal differentiation. Treatment of H0-1 cells with compounds such as all-trans retinoic acid (RA), mycophenolic acid (MPA), IFN-β and MEZ results in a reversible increase in melanin synthesis, i.e., reversible biochemical differentiation (FIGS. 21A–H) (23, 36). However, although MPA, IFN-β and MEZ induce growth suppression, RA increases melanin and tyrosinase levels without altering H0-1 growth (23, 26]. These results indicate that RA can be used to identify gene expression changes correlating directly with increased melanin synthesis in the absence of growth suppression. Additional compounds that have proven of interest, include MPA and MEZ that induce morphologic differentiation in H0-1 cells (FIG. 22). These changes in H0-1 cells are also reversible following growth in the absence of the inducing agent. The only currently available combination of agents that can irreversibly induce the spectrum of differentiation changes resulting in terminal cell differentiation in H0-1 cells is IFN-β+MEZ (18, 21, 23).

Gene Expression Changes Induced in Human Melanoma Cells During Reversible Growth Suppression and Terminal Cell Differentiation As discussed briefly above, treatment of H0-1 cells with a number of agents, either independently or in combination, can result in reversible growth suppression and the reversible expression of differentiation-associated changes or terminal cell differentiation (23). A key question is the nature of the gene expression changes that correlate with these modifications in H0-1 phenotype. To begin to address this issue, studies have focused on genes involved in early stages of growth response (c-fos, c-myc, c-jun, jun-B and jun-D), in cytokine response (interferon stimulated gene-15 (ISG-15), ISG-54, HLA Class I antigen, HLA Class II antigen, melanoma growth stimulatory activity (gro/MGSA)), in the extracellular matrix (fibronectin and tenascin), as receptors for extracellular matrix proteins ($\alpha_5$ integrin and $\beta_1$ integrin), and as cytoskeletal proteins β-actin and γ-actin) (23, 25). The pattern of gene expression changes occurring in terminally differentiated H0-1 cells is shown in Table 3. Analysis of the expression of similar genes in cells undergoing reversible growth arrest indicates that none of these changes are unique to terminally differentiated H0-1 cells (23, 25). Instead, these specific changes in gene expression appear to correlate with various aspects of the differentiation and growth arrest program induced in H0-1 cells by the various compounds.

TABLE 3

Gene Expression Changes Observed in Terminally Differentiated H0-1 Cells

| Increased Expression | Decreased Expression | No Change in Expression |
|---|---|---|
| c-jun | c-myc | c-fos |
| jun-B | cyclin A | RB |
| HLA Class I | cyclin B | N-cadherin |
| ISG-15 | tenascin | |
| ISG-54 | γ-actin | |
| gro/MGSA | β-actin | |
| $\alpha_5$ integrin | cdc 2 | |
| $\beta_1$ integrin | histone H1 | |
| fibronectin | histone H4 | |

H0-1 cells were grown for 96 hr in the presence of 2000 units/ml IFN-β and 10 ng/ml MEZ prior to isolation of total RNA and analysis of gene expression by Northern blotting analysis (23). Cells remain viable under these conditions, but they irreversibly lose proliferative ability (18, 23).

Autocrine Factors Involved in Gene Expression Changes Induced in Human Melanoma Cells During Reversible Growth Suppression and Terminal Cell Differentiation A potentially important mediator of growth arrest during differentiation in hematopoietic cells is autocrine IFN-β (37–39). Evidence suggesting a link between autocrine IFN-β and differentiation in hematopoietic cells include: (a) the observation that IFN-β neutralizing antibodies can partially abrogate the reduction in c-myc levels and growth suppression occurring during hematopoietic differentiation; (b) the induction of interferon regulatory factor 1 (IRF-1) during myeloid differentiation; (c) the partial reversal by IRF-1 antisense oligomers of growth inhibition and the induction of differentiation induced in leukemic cells by interleukin-6 and leukemia inhibitory factor; and (d) the induction of specific type I interferon (IFN-α/β) gene expression during terminal differentiation in hematopoietic cells (37–39).

Enhanced expression of interferon responsive-genes and the gro/MGSA gene occurs in H0-1 cells during the processes of reversible and irreversible differentiation (23). These observations suggest that autocrine-feedback pathways could contribute to the gene expression changes observed during the differentiation process. To directly test for this possibility, H0-1 cells were treated with various inducing agents for 24 hr, cultures were washed free of inducers and then grown for 72 hr in medium lacking the inducing compounds. The conditioned medium from these cells was collected and tested for its ability to induce gene expression changes in naive H0-1 cells (23). Conditioned medium obtained from cells treated with IFN-β+MEZ induced growth suppression and a number of gene expression changes also apparent in inducer-treated H0-1 cells (23, 40). These include, enhanced c-jun, $\alpha_5$ integrin and fibronectin expression and induction of jun-B, HLA Class I, ISG-15, and gro/MGSA expression (23). These observations suggest two autocrine loops may be associated with differentiation in H0-1 cells, one involving an autocrine IFN-β and the other an autocrine gro/MGSA. Support for the IFN-β autocrine loop is indicated by the ability of IFN-β antibodies to partially neutralize ISG-15 induction by conditioned medium and the direct induction of the IFN-β gene as monitored by RT-PCR by conditioned medium (40). However, conditioned medium from IFN-β+MEZ-treated H0-1 cells does not induce terminal differentiation in H0-1 cells (40). Similarly, additional agents that induce reversible growth arrest and differentiation also produce conditioned medium that can induce type I interferon responsive genes in naive H0-1 cells. These results suggest that specific autocrine loops may also contribute to growth inhibition and the differentiation process in solid tumors such as human melanoma.

Identification of Genes Differentially Expressed During the Processes of Differentiation and Growth Suppression in Human Melanoma Cells To directly identify genes displaying differential expression in human melanoma cells induced to terminally differentiate applicants have used a modified subtraction hybridization approach (FIG. 8) (41). cDNA libraries were prepared from poly (A+) RNA obtained from untreated H0-1 cells (Ind⁻ cDNA library; driver cDNA library), and H0-1 cells treated with IFN-β+MEZ for 2, 4 8, 12 and 24 (Ind⁺ cDNA library; tester cDNA library). Tester and driver cDNA libraries were directionally cloned into the commercially available λ Uni-ZAP phage vector. Subtraction hybridization was then performed between double-stranded tester DNA and single-stranded driver DNA prepared by mass excision of the libraries. The subtracted cDNAs were efficiently cloned into the λ Uni-ZAP phage vector, which permits easy manipulation for both screening and gene characterization. A single round of subtraction of untreated H0-1 control (Ind⁻) cDNAs from IFN-β+MEZ-treated (Ind⁺) cDNAs resulted in the identification of a series of cDNAs displaying differential expression in untreated versus differentiation inducer-treated H0-1 cells. These cDNAs are referred to as melanoma differentiation associated (mda) cDNAs. Initially 70 cDNA clones were analyzed and 23 clones were found to display differences in gene expression between Ind⁻- and Ind⁺-treated H0-1 cells (41). As anticipated, subtraction of control H0-1 cDNAs from IFN-β+MEZ-treated H0-1 cDNAs resulted in a series of MDA genes that displayed enhanced expression after 24-h treatment with the various inducers. These included genes displaying enhanced expression in H0-1 cells treated with both IFN-β and IFN-β+MEZ (mda-1 and mda-2), MEZ and IFN-β+MEZ (mda-3), IFN-β,MEZ and IFN-β+MEZ (mda-4) and uniquely by IFN-β+MEZ (mda-5 and mda-6) (FIG. 10) (41). Of these six mda genes, only mda-3 originally represented a previously identified gene, GOS-19-1 (41). Analysis of eight additional human melanoma cell lines indicates that specific mda genes also display enhanced expression following a 24-h treatment with IFN-β+MEZ (data not shown).

The studies described above indicate that specific mda genes exhibit elevated expression in H0-1 cells after 24-h treatment with appropriate inducing agents. Studies were performed to monitor mda expression in H0-1 cells treated with IFN-β, MEZ or IFN-β+MEZ for 96-h (FIG. 15). Additionally, the pattern of expression of specific mda genes under experimental conditions inducing reversible growth suppression (IFN-β+IFN-γ, IFN-β, IFN-γ, MEZ, MPA, MPA+MEZ, RA+MEZ), increased melanin synthesis (IFN-β, MEZ, MPA, RA, IFN-β+MEZ, MPA+MEZ, RA+MEZ), increased melanin synthesis (IFN-β,MEZ, MPA, RA, IFN-β+MEZ, MPA+MEZ, RA+MEZ), morphological changes (MPA, MEZ, IFN-β+MEZ, MPA+MEZ, RA+MEZ) or terminal cell differentiation (IFN-β+MEZ) was determined. These experiments indicate continuous elevated expression of mda-4, mda-5, mda-6 (p21), mda-7, mda-8 and mda-9 in terminally differentiated H0-1 cells (FIG. 15). A differential pattern of expression of the mda genes was observed in H0-1 cells treated with the various differentiation and growth modulating agents. Three of the mda cDNAs, mda-4, mda-5 and mda-8, displayed overlapping induction profiles in H0-1 cells. These genes displayed elevated expression in H0-1 cells treated for 96 hr with IFN-β+MEZ, IFN-γ or IFN-β+IFN-γ (FIG. 15). These cDNAs, which have not been previously described in any DNA data base, may correspond to new classes of cytokine-responsive genes. This possibility is currently under investigation. Expression of mda-7 was increased in H0-1 cells treated for 96 h with agents inducing growth arrest, including IFN-β, MEZ, MPA, IFN-β+IFN-γ, IFN-β+MEZ, MPA+MEZ, RA+MEZ. The degree of increase in mda-7 expression was greatest in H0-1 cells treated with IFN-β+MEZ that also induces terminal cell differentiation. Treatment of H0-1 cells for 96 hr with RA does not induce growth changes or induce mda-7 expression. Similarly, IFN-γ that only marginally inhibits H0-1 growth also does not result in significant mda-7 expression. In the case of mda-9, increased expression in H0-1 cells was only apparent in terminally differentiated cells treated with IFN-β+MEZ (FIG. 15). Further studies are in progress to isolate full-length cDNAs for the various novel mda genes and to analyze their expression during the processes of growth and differentiation in human melanoma and other human cell types.

The Melanoma Differentiation Associated Gene-6 (mda-6) is the Cyclin-Dependent Kinase Inhibitor, p21

Cell-cycle regulation results from the ordered activation of a series of related enzymes referred to as cyclindependent kinases (CDKs) (42). In normal cells, CDKs are predominantly found in multiple quaternary complexes, consisting of CDK, a cyclin, proliferating cell nuclear antigen (PCNA) and the p21 protein (43, 44). p21 controls CDK activity, thereby affecting cell-cycle control and growth in mammalian cells (43–50). Using human glioblastoma cells containing an inducible wild-type p53 tumor suppressor gene and subtraction hybridization, a gene called WAF1 (wild-type p53-activated fragment 1) that encodes an $M_r21,000$ protein was identified (49, 50). WAF1 is the same p21-encoding gene identified using the two-hybrid system as a potent CDK inhibitor, referred to as CPI1 (Cdk-interacting protein 1) (46). p.21 levels have been shown to increase in senescent cells (gene referred to as sdi-1; senescent cell-derived inhibitor) (51) and overexpression of p21 inhibits the growth of tumor cells (46, 49, 51). Treatment of wild-type p53 containing cells with DNA damaging agents results in elevated wild-type p53 protein and increased p21 levels (51). In this context, p21 may directly contribute to $G_1$ growth arrest and apoptosis resulting in specific target cells after induction of DNA damage (51). Recent studies also demonstrate that p21 can: directly inhibit PCNA-dependent DNA replication in the absence of a cyclin/CDK; and inhibit the ability of PCNA to activate DNA polymerase δ by directly interacting with PCNA (52). These studies indicate that p21 is an important component of growth control, cell-cycle progression, DNA replication and the repair of damaged DNA.

Sequence analysis of mda-6 indicates that it is the CDK inhibitor p21 (41) (FIG. 23A+B; GenBank accession number U09579). The cloning of this gene from a differentiation-inducer treated human melanoma library, indicates that mda-6 (p21) may contribute to the induction of growth arrest observed in terminally differentiated human melanoma cells. Like WAF1, mda-6 is also induced in human melanoma cells following DNA damage resulting from treatment with methyl methanesulfonate (53). In human melanoma, mda-6 expression is increased during terminal differentiation, rapidly induced by incubation in serum free medium and enhanced in cells grown to high saturation densities (53). Several lines of evidence indicate that the expression of mda-6 inversely correlates with melanoma progression (53). These include: (A) the presence of higher levels of mda-6 in actively growing melanocytes and nevi and reduced levels in radial and early vertical growth phase primary melanomas as well as metastatic human melanomas (53); (B) decreased expression of mda-6 in early vertical growth phase primary human melanoma cells selected for autonomous or enhanced tumor formation in nude mice (53, 54); and (C) increased levels of mda-6 mRNA in metastatic human melanoma cells displaying a loss of metastatic potential resulting following introduction of a normal chromosome 6 (53, 55). Taken together, these recent studies indicate that p21 (mda-6/WAF1/CIP1/CAP20/sdi-1) may function as a negative regulator of melanoma growth, progression and metastasis.

CDK inhibitors, in addition to p21, have also been identified (56–59). These include: a 16-kDa protein, $p16^{Ink4}$ (inhibitor of cyclin-dependent kinase 4), that specifically inhibits cyclin D/Cdk4 (56); a 27-kDa inhibitory protein, $p27^{Kip1}$ (kinase inhibitory protein 1), induced in transforming growth factor-β-arrested and contact-inhibited cells (57, 58); and a 28-kDa protein, $p28^{Ick}$ (inhibitor of cyclin-dependent kinase), that binds to and inhibits the kinase activity of preformed Cdk/cyclin complexes in human cells (59). It is not presently known if any or all of these CDK inhibitors contribute to the process of differentiation inducer-mediated growth arrest and terminal cell differentiation in human melanoma.

Summary and Perspectives

It is now possible to reprogram cultured human melanoma cells to an earlier stage in their development by treatment with the appropriate inducing agents. This process, an important component of differentiation therapy, can result in a rapid loss of proliferative potential and terminal differentiation in these cancer cells. By using the appropriate inducers, it is possible to manipulate specific components of the differentiation program in a reversible or irreversible (terminal cell differentiation) manner. This capability results in a powerful model system permitting the systematic dissection of the roles of specific genes and biochemical pathways in regulating growth, differentiation and oncogenic potential in human melanoma cells. The combination of IFN-β+MEZ induces an irreversible loss of growth potential and terminal cell differentiation in human melanoma cells. At comparable concentrations, IFN-β or MEZ alone induce certain components of the differentiation process, but they do not induce an irreversible loss of growth potential or terminal differentiation. The process of terminal differentiation in human melanoma cells treated with IFN-β+MEZ involves specific biochemical, structural, immunological and gene expression alterations.

Figure 24:
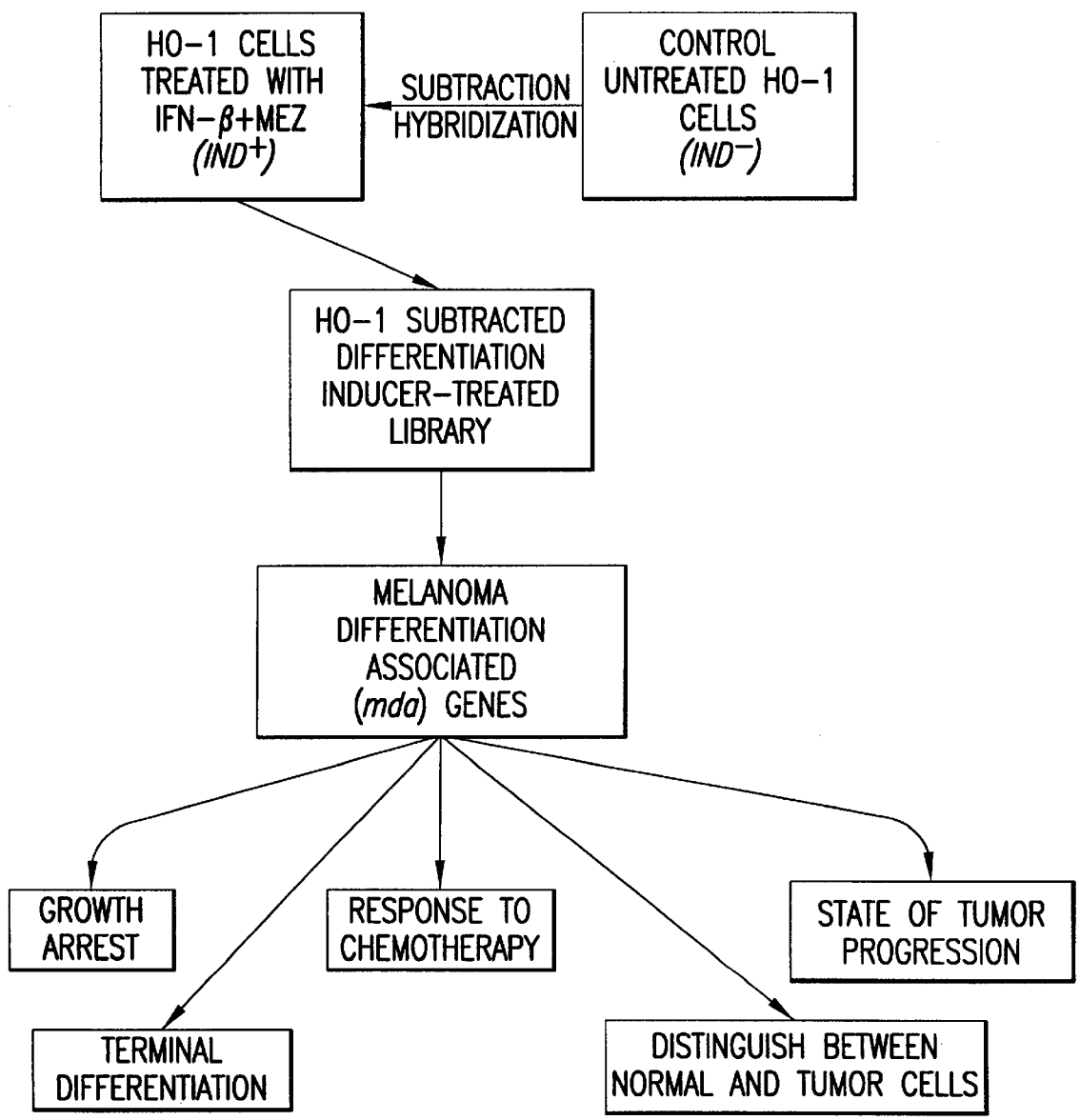
FIG. 24 Cellular changes mediating enhanced expression of certain mda genes and differential expression of particular mda genes during tumor progression and in normal versus tumor-derived cell types. Specific mda genes have been identified that display enhanced expression during treatment with agents that induce growth suppression, DNA damage (including chemotherapeutic agents that function by different mechanisms) and/or terminal differentiation. Additional mda genes have also been shown to display differential expression as a function of tumor progression and in matched sets of normal versus tumor-derived human cells.
Figure 25A:
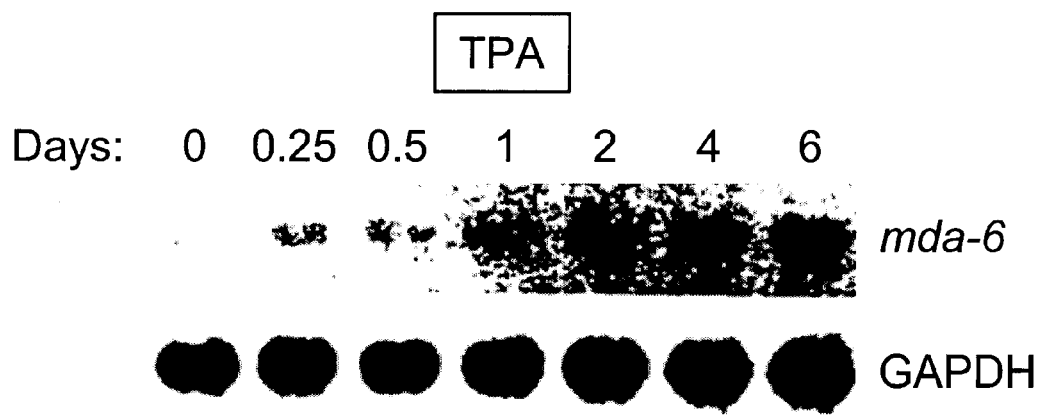
FIGS. 25A–B Induction of mda-6 (WAF1/CIP1/SDI1) expression in HL-60 cells by TPA and RA. Total cytoplasmic RNA was isolated from HL-60 cells treated with TPA (3 nM) for 0.25, 0.5, 1, 2, 4 or 6 d and from HL-60 cells treated with RA (1 µM) for 0.5, 1, 2, 4 or 6 d. A 10-µg aliquot of RNA was run on a 1.0% agarose gel and transferred to a nylon filter. Blots were hybridized with a multi-prime $^{32}$P-labeled mda-6 gene probe. Filters were stripped and rehybridized with a multiprime $^{32}$P-labeled GAPDH probe.
Figure 25B:
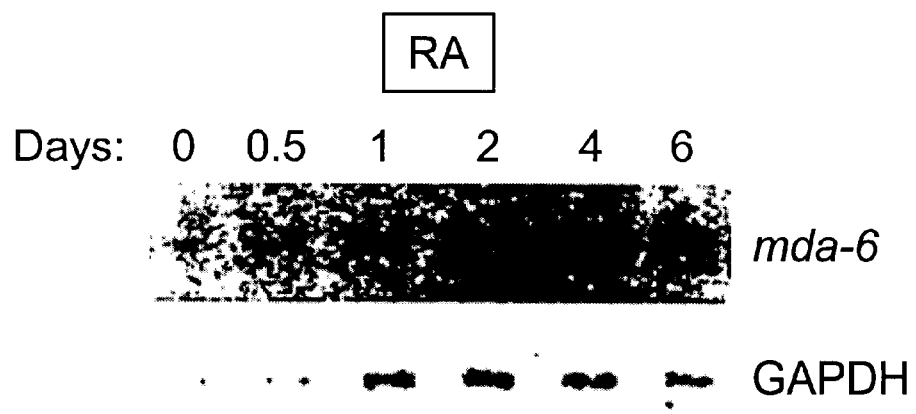

To identify the critical gene expression changes associated with and controlling terminal differentiation in human melanoma cells applicants have used a modified subtraction hybridization protocol. This approach has resulted in the identification of a series of melanoma differentiation associated (mda) genes, including both previously identified and novel, that display elevated expression in human melanoma cells treated with differentiation and growth suppressing agents. One of the mda genes, mda-6, is identical to the cyclin-dependent kinase inhibitor p21 (also referred to as WAF1, CAP20, CIP1, and sdi-1). Initial studies using a panel of unique mda genes indicate that increased expression of specific mda genes' results following treatment with agents inducing growth arrest and terminal differentiation as well as defined classes of DNA damaging and chemotherapeutic agents (FIG. 24). Specific mda genes also display differential expression as a function of human melanoma progression, in normal versus tumor-derived cells of neuroectodermal origins and in additional cell differentiation model systems.

Future studies using the mda genes should prove valuable in defining the molecular determinants mediating growth control, tumor progression, response to chemotherapy and terminal cell differentiation in human melanoma and other tumors. The mda genes will also prove useful as part of a simple genetic screen for identifying and monitoring agents inducing specific DNA damage pathways and for identifying agents capable of inducing terminal differentiation in cancer cells. This information should prove important in developing improved therapeutic modalities for metastatic melanoma and for additional human malignancies.

REFERENCES OF THE FIFTH SERIES OF EXPERIMENTS

1. Fisher, P. B., Enhancement of viral transformation and expression of the transformed phenotype by tumor promoters. In: Slaga, T. J., Ed., Tumor Promotion and Cocarcinogenesis In Vitro, Mechanisms of Tumor Promotion, CRC Press, Inc., Boca Raton, Fla., pp. 57–123, 1984.
2. Weinstein, I. B., The origins of human cancer: molecular mechanisms of carcinogenesis and their implications for cancer prevention and treatment. Cancer Res., 48: 4135–4143, 1988.
3. Bishop, J. M., Molecular themes in oncogenesis, Cell, 64: 235–248, 1991.
4. Vogelstein, B., and Kinzler, K. W., The multistep nature of cancer. Trends Genet., 9: 138–141, 1991.
5. Liotta, L. A., Steeg, P. G., and Stetler-Stevenson, W. G., Cancer metastasis and angiogenesis: and imbalance of positive and negative regulation. Cell, 64: 327–336, 1991.
6. Knudson, A. G., Antioncogenes and human cancer. Proc. Natl. Acad. Sci. U.S.A., 90 10914–10921, 1993.
7. Waxman, S. Rossi, G. B., and Takaku, F. Eds., The Status of Differentiation Therapy, vol. I, Raven Press, NY, 1988.
8. Ahmed, M. A., Nielsch, U., Guarini, L. Hermo, H., Jr., and Fisher, P. B., Modulation of differentiation: a potential mechanism by which interferons induce antitumor activity. In: Fisher, P. B., Ed., Mechanisms of Differentiation: Modulation of Differentiation by Exogenous Agents, vol. II, CRC Press Inc., Boca Raton, Fla., pp. 1–56, 1990.
9. Waxman, S. Rossi, G. B., and Takaku, F., Eds., The Status of Differentiation Therapy, vol. II, Raven Press, NY, 1991.
10. Fisher, P. B., and Rowley, P. T., Regulation of growth, differentiation and antigen expression in human tumor cells by recombinant cytokines: applications for the differentiation therapy of cancer. In: Waxman S., Rossi, G. B., and Takaku, F. (Eds.) The Status of Differentiation Therapy of Cancer, vol. II, Raven Press, NY, pp. 201–213, 1991.
11. Clark, W., Tumor progression and the nature of cancer. Br. J. Cancer, 64: 631–644, 1991.
12. Kerbel, R. S., Growth dominance and the metastatic cancer cell: cellular and molecular aspects. Adv. Cancer Res., 55:87–132, 1990.
13. Herlyn, M., Human melanoma: development and progression. Cancer Metastasis Rev., 9: 101–112, 1990.
14. Lu, C., and Kerbel R. S., Cytokines, growth factors and the loss of negative growth controls in the progression of human cutaneous malignant melanoma. Current Opinion Oncology, 6: 212–220, 1994.
15. Herlyn, M., Kath, R., Williams, N., Valyi-Nagy, I., and Rodeck, U., Growth-regulatory factors for normal, premalignant and malignant human cells in vitro. Adv. Cancer Res., 54: 213–234, 1989.
16. Sachs, L. Control of normal cell differentiation and the phenotypic reversion of malignancy in myeloid cells. Nature, 274: 535–539, 1978.
17. Jiminez, J. J., and Yunis, A. A., Tumor cell rejection through terminal cell differentiation. Science, 238: 1278–1280, 1987.
18. Fisher, P. B., Prignoli, D. R., Hermo, H., Jr., Weinstein, I. B., and Pestka, S., Effects of combined treatment with interferon and mezerein on melanogenesis and growth in human melanoma cells. J. Interferon Res., 5: 11–22, 1985.
19. Fisher, P. B., and Grant, S. Effects of interferon on differentiation in normal and tumor cells. Pharmacol. Therapeut., 27: 143–166, 1985.
20. Fisher, P. B., Hermo, H., Jr., Pestka, S., and Weinstein, I. B., Modulation of differentiation in murine and human melanoma cells by interferon and phorbol ester tumor promoters. In: Bagnara, J., Klaus, S. N., Paul, E., and Schartl, M., Eds., Pigment Cell 1985: Biological, Molecular and Clinical Aspects of Pigmentation, Univ. of Tokyo Press, Tokyo, pp. 325–332, 1985.
21. Fisher, P. B., Hermo, H., Jr., Solowey, W. E., Dietrich, M. C., Edwalds, G. M., Weinstein, I. B., Langer, J. A., Pestka, S., Giacomini, P., Kusama, M., and Ferrone, S., Effect of recombinant human fibroblast interferon and mezerein on growth, differentiation, immune interferon binding and tumor associated antigen expression in human melanoma cells. Anticancer Res., 6: 765–774, 1986.
22. Ahmed, M. A., Guarini, L., Ferrone, S., and Fisher, P. B., Induction of differentiation in human melanoma cells by the combination of different classes interferons or interferon plus mezerein. N.Y. Acad. Sci., 567: 328–333, 1989.
23. Jiang, H., Su, Z.-z., Boyd, J., and Fisher, P. B., Gene expression changes associated with reversible growth suppression and the induction of terminal differentiation in human melanoma cells. Mol. Cell. Different., 1 (1): 41–66, 1993.
24. Giacomini, P., Aguzzi, A., Pestka, S., Fisher, P. B., and Ferrone, S., Modulation by recombinant DNA leukocyte ($\alpha$) and fibroblast ($\beta$) interferons of the expression and shedding of HLA and tumor associated antigens by human melanoma cells. J. Immunolo., 133: 1649–1655, 1984.
25. Giacomini, P., Imberti, L., Aguzzi, A., Fisher, P. B., Trinchieri, G., and Ferrone, S., Immunochemical analysis of the modulation of human melanoma associated antigens by DNA recombinant immune interferon. J. Immunol., 135: 2887–2894, 1985.
26. Giacomini, P., Gambari, R., Barbieri, R., Nistico, P., Tecce, R., Pestka, S., Gustafsson, K., Natali, P. G., and Fisher, P. B., Regulation of the antigenic phenotype of human melanoma cells by recombinant interferons. Anticancer Res., 6: 877–884, 1986.
27. Giacomini, P., Fisher, P. B., Duigou, G. J., Gambari, R., and Natali, P. G., Regulation of class II MHC gene expression by interferons: insights into the mechanism of action of interferon. Anticancer Res., 8: 1153–1162, 1988.
28. Maio, M., Gulwani, B., Tombesi, S., Langer, J. A., Duigou, G. J., Kerbel, R. S., Fisher, P. B., and Ferrone, S., Differential induction by immune interferon of the gene products of the HLA-D region on the melanoma cell line MeWo and its metastatic variant MeM 50–10. J. Immunol., 141: 913–920, 1988.
29. Guarini, L., Temponi, M., Edwalds, G. M., Vita, J. R., Fisher, P. B., and Ferrone S., In vitro differentiation and antigenic changes in human melanoma cell lines. Cancer Immunol. Immunother., 30: 363–370, 1989.
30. Maio, M., Gulwani, B., Langer, J. A., Kerbel, R. S., Duigou, G. J., Fisher, P. B., and Ferrone, S., Modulation by interferons of HLA antigens, high molecular weight-melanoma associated antigens and intercellular adhesion molecule-1 expression by cultured melanoma cells with different metastatic potential. Cancer Res., 49: 2980–2987, 1989.
31. Giacomini, P., Fraioli, R., Nistico, P., Tecce, R., Nicotra, M. R., De Filippo, F., Fisher, P. B., and Natali, P. G., Modulation of the antigenic phenotype of early passage human melanoma cells derived from multiple autologous metastases by recombinant human leukocyte, fibroblast and immune interferons. Int. J. Cancer, 46: 539–545, 1990.
32. Nistico, P., Tecce, R., Giacomini, P., De Filippo, F., Fisher, P. B., and Natali, P. G., Effect of recombinant human leukocyte, fibroblast, and immune interferons on expression of class I and II MHC and Ii chain in early passage human melanoma cells. Cancer Res., 50: 7422–7429, 1990.
33. Graham, G. M., Guarini, L., Moulton, T. A., Datta, S., Ferrone, S., Giacomini, P., Kerbel, R. S. and Fisher, P. B., Potentiation of growth suppression and modulation of the antigenic phenotype in human melanoma cells by the combination of recombinant human fibroblast and immune interferon. Cancer Immunol. Immunotherap., 32: 382–390, 1991.
34. Guarini, L., Graham, G. M., Jiang, H., Ferrone, S., Zucker, S., and Fisher, P. B., Modulation of the antigenic phenotype of human melanoma cells by differentiation-inducing and growth-suppressing agents. Pigment Cell Res. Suppl., 2: 123–131, 1992.
35. Jiang, H., Waxman, S., and Fisher, P. B., Regulation of c-fos, c-jun and jun-B gene expression in human melanoma cells induced to terminally differentiate. Mol. Cell. Different., 1: 197–214, 1993.
36. Kiguchi, K., Collart, F. R., Henning-Chub, C., and Huberman, E., Induction of cell differentiation in melanoma cells by inhibitors of IMP dehydrogenase: altered patterns of IMP dehydrogenase expression and activity. Cell Growth Different., 1:259–270, 1990.
37. Yarden, A., Shure-Gottlieb, H., Chebath, J., Revel, M., and Kimchi, A., Autogenous production of interferon-$\beta$ 38. Resnitzky, D., Yarden, A., Zipori, D., and Kimchi, A., Autocrine β-related interferon controls c-myc suppression and growth arrest during hematopoietic cell differentiation. Cell, 46:31–40, 1986.
39. Abdollahi, A., Lord, K. A., Hoffman-Liebermann, B., and Liebermann, D. A., Interferon regulatory factor 1 is a myeloid differentiation primary response gene induced by interleukin 6 and leukemia inhibitory factor: role in growth inhibition. Cell Growth Different., 2: 401–407, 1991.
40. Young, S.-m., Jiang, H., Mariano, T., Petska, S., and Fisher, P. B., Manuscript in preparation, 1994.
41. Jiang, H., and Fisher, P. B., Use of a sensitive and efficient subtraction hybridization protocol for the identification of genes differentially regulated during the induction of differentiation in human melanoma cells. Mol. Cell. Different., 1 (3): 285–299, 1993.
42. Sherr, C. J., Mammalian $G_1$ cyclins. Cell 73: 1059–1065, 1993.
43. Xiong, Y., Zhang, H., and Beach, D., D type cyclins associate with multiple protein kinases and the DNA replication and repair factor PCNA. Cell 71: 505–514, 1992.
44. Xiong, Y., Zhang, H., and Beach D., Subunit rearrangement of the cyclin-dependent kinases is associated with cellular transformation. Genes and Develop., 7: 1572–1583, 1993.
45. Gu, Y., Turck, C. W., and Morgan, D. O., Inhibition of CDK2 activity in vivo by an associated 20K regulatory subunit. Nature, 366: 707–710, 1993.
46. Harper, J. W., Adami, G. R., Wei, N., Keyomarsi, K., and Elledge, S. J., The p21 Cdk-interacting protein Cip1 is a potent inhibitor of G1 cyclin-dependent kinases. Cell, 75: 895–816, 1993.
47. Xiong, Y. Hannon, G. J., Zhang, H., Casso, D., Kobayashi, R., and Beach, D., p21 is a universal inhibitor of cyclin kinases. Nature, 366: 701–704, 1993.
48. Dulic, V., Kaufmann, W. K., Wilson, S. J., Tisty, T. D., Lees, E., Harper, J. W., Elledge, S. J., and Reed, S. I., p53-Dependent inhibition of cyclin-dependent kinase activities in human fibroblasts during radiation-induced G1 arrest. Cell, 76: 1013–1023, 1994.
49. El-Deiry, W. S. Tokino, T., Velculescu, V. E., Levy, D. B., Parsons, R., Trent, J. M., Lin, D., Mercer, W. E., Kinzlet, K. W., and Vogelstein, B., WAF1, a potential mediator of p53 tumor suppression. Cell, 75: 817–825, 1993.
50. El-Deiry, W. S., Harper, J. W., O'Connor, P. M., Velculescu, V. E., Canman, C. E., Jackman, J., Pietenpol, J. A., Burrell, M., Hill, D. E., Wang, Y., Wilman, K. G., Mercer, W. E., Kastan, M. B., Kohn, K. W., Elledge, S. J., Kinzler, K. W., and Vogelstein, B., WAF1/CIP1 is induced in p53-mediated $G_1$ arrest and apoptosis. Cancer Res., 54: 1169–1174, 1994.
51. Noda, A., Ning, Y., Venable, S. F., Pereira-Smith, O. M., and Smith J. R., Cloning of senescent cell-derived inhibitors of DNA synthesis using an expression screen. Exp. Cell Res., 211: 90–98, 1994.
52. Waga, S., Hannon, G. J., Beach, D., and Stillman, B., The p21 inhibitor of cyclin-dependent kinases controls DNA replication by interaction with PCNA. Nature, 369: 574–578, 1994.
53. Jiang, H., Lin, J., Herlyn, M., Kerbel, R. S., Weissman, B. E., Welch, D. R., and Fisher, P. B., mda-6, WAF1/CIP1, is a melanoma differentiation-associated gene displaying differential expression during growth, differentiation and progression in human melanoma. Proc. Natl. Acad. Sci. USA, in submission, 1994.
54. Kobayashi, H., Man, S., MacDougall, J. R., Graham, C. H., Lu, C., and Kerbel, R. S., Development of 'multicytokine resistance' during human melanoma progression: analysis using tumorigenic variants of low-grade early-stage human melanomas. Amer. J. Pathol., 144: 776–786, 1994.
55. Welch, D. R., Chen, P., Miele, M. E., McGary, C. T., Bower, J. M., Stanbridge, E. J., and Weissman, B. E., Microcell-mediated transfer of chromosome 6 into metastatic human C8161 melanoma cells suppresses metastasis but does not inhibit tumorigenicity. Oncogene, 9: 255–262, 1994.
56. Serono, M., Hannon, G. J., and Beach, D., A new regulatory motif in cell-cycle control causing specific inhibition of cyclin D/CDK4. Nature, 366: 704–707, 1993.
57. Polyak, C., Kato, J., Solomon, M. J., Sherr, C. J., Massague, J., Roberts, J., and Koff, A., p27Kip1, a cyclin-Cdk inhibitor, links transforming growth factor-beta and contact inhibition to cell cycle arrest. Genes and Development, 8: 9–22, 1994.
58. Singerland, J. M., Hengst, L., Pan, C.-H, Alexander, D., Stampfer, M. R., and Reed, S. I., A novel inhibitor of cyclin-Cdk activity detected in transforming growth factor-β-arrested epithelial cells. Mol. Cell. Biol., 14: 3683–3694, 1994.
59. Hengst, L., Dulic, V., Slingerland, J. M., Less, E., and Reed, S. I., A cell cycle-regulated inhibitor of cyclin-dependent kinases. Proc. Natl. Acad. Sci. USA, 91: 5291–5295, 1994.

Sixth Series of Experiments

The multistep carcinogenic process is often characterized by discrete changes in cellular phenotype, including resistance to normal growth inhibitory controls and aberrant patterns of differentiation (Fisher & Rowley, 1991; Knudson, 1993; Hoffman & Liebermann, 1994; Jiang et al., 1994). Treatment of specific cancers with differentiation modulating agents can result in a suppression of growth and the induction of a more mature differentiated phenotype (Sachs, 1978; Jimenez & Yunis, 1987; Waxman et al., 1988, 1991; Fisher & Rowley, 1991; Lotan, 1993). The mechanism underlying these profound effects on cellular physiology are not currently known. In the case of human melanoma, the combination of recombinant fibroblast interferon (IFN-β) and the antileukemic compound mezerein (MEZ) results in an irreversible loss of proliferative capacity and terminal cell differentiation (Fisher et al., 1985; Jiang et al., 1993). This model system, combined with subtraction hybridization, is being used to define the molecular basis of growth control and cancer cell differentiation (Jiang & Fisher, 1993; Jiang et al., 1994). Using a differentiation-induction plus subtraction hybridization approach, a series of differentially expressed cDNAs, termed melanoma differentiation associated (mda) genes, have been identified that display enhanced expression as a function of growth suppression and terminal cell differentiation (Jiang & Fisher, 1993; Jiang et al., 1994).

The human p21 cyclin-dependent kinase (Cdk)-interacting protein CIP1 (Xiong et al., 1993b); Harper et al., 1993), and the mouse CAP20 homologue (Gu et al., 1993), is a ubiquitous inhibitor of cyclin kinases and an integral component of cell cycle control. This gene is identical to the WAF1 (wild-type (wt) p53 activated factor-1) gene identified following induction by wt p53 protein expression in a human glioblastoma multiforme cell line (El-Deiry et al., 1993). p21 has also been independently cloned as a consequence of induction of senescence in normal human foreskin fibroblast cells, SDI1 (senescent cell-derived inhibitor-1) (Noda et al., 1994), and during the process of terminal cell differentiation in human melanoma cells, mda-6 (Jiang and Fisher, 1993; Jiang et al., 1994). p21 is a nuclear localized protein that is inducted by DNA damage and during apoptosis in specific cell types as a function of wt p53 activation (El-Deiry et al., 1993, 1994). These studies suggest that p21 may be an important downstream mediator of wt p53-induced growth control in mammalian cells (El-Deiry et al., 1993, 1994). Somewhat paradoxical data indicates that WAF1/CIP1 is induced as an immediate-early gene following mitogenic stimulation of growth arrested cells in a p53-independent manner (Michieli et al., 1994). Applicants presently demonstrate that mda-6 (WAF1/CIP1/SDI1) expression is also induced by mechanistically diverse acting agents resulting in macrophage/monocyte (TPA and Vit D3) or granulocyte (RA and DMSO) differentiation in human promyelocytic leukemia cells (Collins, 1987), HL-60, that lack endogenous p53 genes (Wolf and Rotter, 1985). Using differentiation-resistant variants (Homma et al., 1986; Mitchell et al., 1986), a direct correlation is found between the early induction of mda-6 expression and the onset of specific programs of differentiation in HL-60 cells. Applicants' results indicate that sustained p21 expression can be maintained in the absence of wt p53 protein and elevated levels of p21 (WAF1/CIP1/SDI1) mRNA and protein correlate with growth suppression and differentiation induction in a p53-independent manner in HL-60 cells.

Experimental Results

Figure 26A:
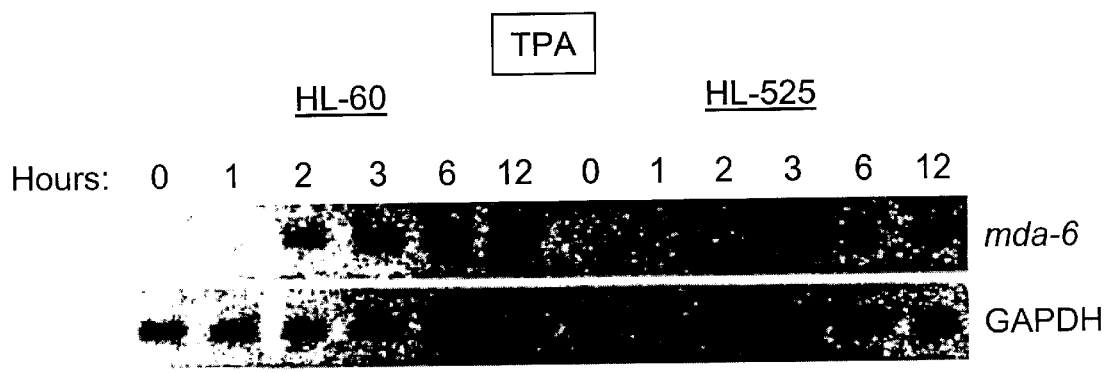
FIGS. 26A–C Early induction of mda-6 (WAF1/CIP1/SDI1) expression in HL-60 and TPA-resistant HL-60 (HL-525) cells treated with TPA, RA and Vit D3. Cells were treated with TPA (3 nM), RA (1 µM) or Vit D3 (400 nM) for 1, 2, 3, 6 or 12 h. RNA was isolated and analyzed by RT-PCR using appropriate mda-6 or GAPDH specific primers as described in the Materials and methods.
Figure 26B:
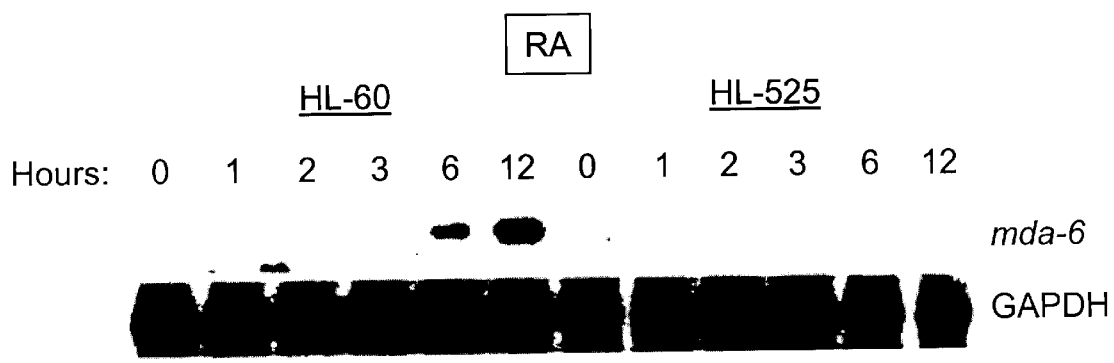
Figure 26C:
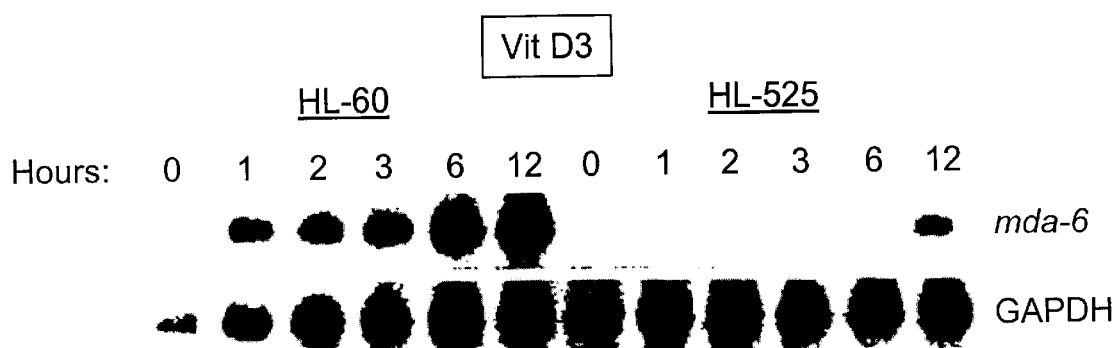

Treatment with Diverse Acting Differentiation Inducing Agents Results in Increased mda-6 (WAF1/CIP1/SDI1) Expression in HL-60 Cells HL-60 is a differentiation competent myeloid leukemia cell line that can be induced to differentiate along both monocytic and granulocytic lineages following exposure to the appropriate inducing agents (Gallagher et al., 1979; Huberman & Callaham, 1979; Breitman et al., 1980; Collins 1987). Treatment of HL-60 cells with TPA, that commit these cells to a macrophage-like lineage (Lotem & Sachs, 1979; Rovera et al., 1979), induces mda-6 expression as detected by both Northern blotting (FIGS. 25A–B) and RT-PCR (FIGS. 26A–C). Induced expression following TPA treatment (3 nM) occurs within 2 h of exposure and elevated mda-6 levels persist in terminally differentiated HL-60 cells (FIGS. 25A–B and 27A–C). Similarly, Vit D3 (400 nM), that also commits HL-60 cells to a monocyte-macrophage-like lineage (Miyaura et al., 1981; Tanaka et al., 1982), induces mda-6 within 1 h of treatment and elevated expression continues in terminally differentiated HL-60 cells (FIGS. 26A–C and 27A–C). Induction of a granulocyte-like phenotype in HL-60 cells by RA (Breitman et al., 1980) or DMSO (Collins et al., 1978) also induces mda-6 mRNA production. In the case of RA (1 $\mu$M), induction of mda-6 is apparent within 3 h and expression remains elevated 6 days post-RA treatment (FIGS. 25A–B, 26A–C and 27A–C). DMSO (1%) also induces mda-6 by 3 h and augmented expression persists at day 5 when cells are terminally differentiated (data not shown). These results indicate that induction of both macrophage/monocyte and granulocyte differentiation pathways in human myeloid leukemia HL-60 cells results in the induction of mda-6 expression. In addition, mda-6 expression is induced during the early commitment stage of HL-60 differentiation and persists in terminally differentiated cells.

Figure 28:
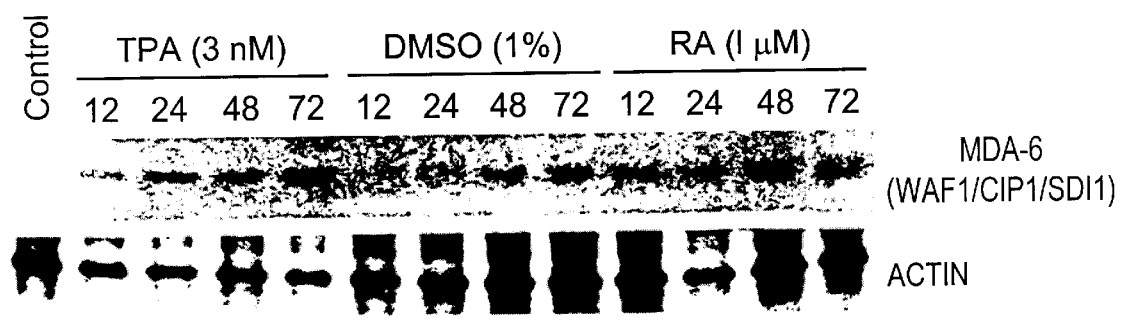
FIG. 28 Induction of the MDA-6 (WAF1/CIP1/SDI1) encoded protein p21 in HL-60 cells treated with TPA, DMSO and RA. Lysates from untreated HL-60 (control) and HL-60 cells treated with TPA (3 nM), DMSO (1%) or RA (1 µM) for 12, 24, 48 and 72 h were immunoprecipitated with WAF1/CIP1 (MDA-6) polyclonal antibody or actin monoclonal antibody as described in Materials and methods. The size of the MDA-6 protein is 21 kDa and the size of the Actin protein is 42 kDa.

To determine if the elevation in mda-6 expression with an increase in MDA-6 (WAF1/CIP1/SDI1) protein, HL-60 cells were labeled for 4 h with $^{35}$S-methionine after 12, 24, 48 and 72 h treatment with TPA (3 nM), DMSO (1%) or RA (1 $\mu$M) and lysates were immunoprecipitated using WAF1/CIP1 antibody (FIG. 28). As a control for protein loading, the level of ACTIN protein was determined by immunoprecipitation. Although no MDA-6 protein was detected in HL-60 cells, 12 h treatment with TPA or RA resulted in immunologically reactive MDA-6 protein. In 1% DMSO treated HL-60, MDA-6 protein was first apparent by 48 h. The levels of MDA-6 protein increased in a temporal manner with all three inducers and the highest levels were apparent at 72 h. The most active inducer of MDA-6 protein, as well as the most active growth suppressing agent, was TPA. Polyclonal antibodies prepared against N-terminal peptide regions of MDA-6 also immunoprecipitated MDA-6 from differentiation inducer treated HL-60 cells and human melanoma cells. In contrast, using a monoclonal antibody (PAb 421) that reacts with both wild-type and mutant p53, no reactive protein was detected after immunoprecipitation of $^{35}$S-methionine labeled lysates prepared from HL-60 cells and TPA-, DMSO- or RA-treated HL-60 cells (data not shown). These results provide direct evidence that induction of elevated mda-6 mRNA expression in differentiation inducer-treated HL-60 cells results in elevated MDA-6 protein levels in the absence of p53 protein.

Induction of mda-6 Expression is Altered in Differentiation-resistant HL-60 Variants The availability of variants of HL-60 cells displaying resistance to TPA-induced growth suppression and differentiation (Murao et al., 1983; Fisher et al., 1984; Anderson et al., 1985; Mitchell et al., 1986; Homma et al., 1986, 1988; Tonetti et al., 1992) provides a valuable experimental model to evaluate the potential involvement of mda-6 in these processes. By continuously growing HL-60 cells in gradually increasing concentrations of TPA (up to 3 $\mu$M), the TPA-resistant HL-60 variant HL-525 was developed (Homma et al., 1986; Mitchell et al., 1986). These cells were used to determine the kinetics of mda-6 expression as a function of short term (1 through 12 h) and long-term (1 through 6 d) treatment with TPA, Vit D3 and RA. As anticipated, HL-525 cells demonstrate a suppressed response to mda-6 induction following TPA treatment (FIGS. 26A–C). Parental HL-60 cells treated with 3 nM TPA show mda-6 expression within 2 h, whereas induction in HL-525 cells is not apparent until 12 h treatment (FIGS. 26A–C and 27A–C). Vit D3 (400 nm) treatment of HL-60 parental cells results in mda-6 expression after 1 h with a continued increase over the 12 h test period (FIGS. 26A–C). In HL-525 cells, mda-6 expression is observed by 2 h following Vit D3 treatment and the level of expression in the variant cells after 12 h exposure to 400 nM Vit D3 is lower than seen in HL-60 cells similarly treated for 1 h. RA (1 $\mu$M) induces mda-6 expression after 3 h in HL-60 cells and the level of mda-6 expression increases over the 12 h test period. In contrast, no induction of mda-6 is apparent in RA-treated HL-525 cells by 12 h. These results indicate that the TPA-resistant HL-525 cells differ from HL-60 cells with respect to the early induction of mda-6. This defective early induction of mda-6 in HL-525 cells is most evident following RA or TPA treatment, whereas Vit D3 results in a reduced capacity to induce mda-6 that is less dramatic than with the other inducers. Since these studies involve separate RT-PCR reactions, direct quantitation is difficult, however, it appears that both the early kinetics of induction and the final level of induction of mda-6 are reduced in HL-525 cells in comparison with HL-60 parental cells. These observations are supported by Northern blotting analyses of similar samples (data not shown).

Figure 27A:
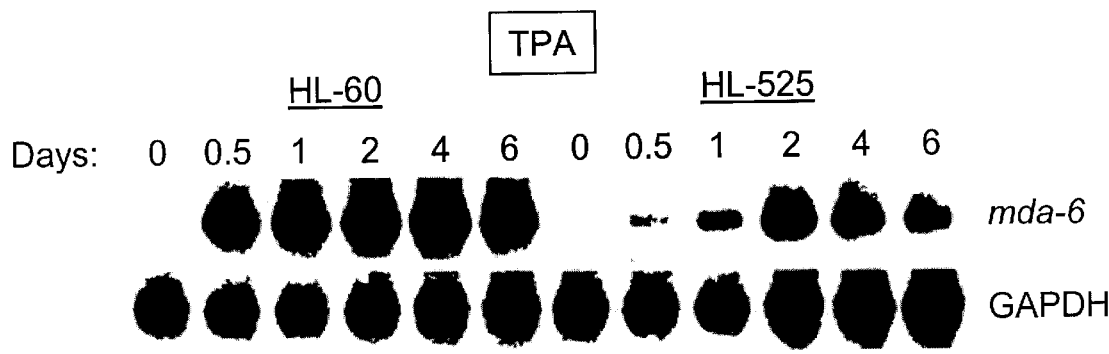
FIGS. 27A–C Induction of mda-6 (WAF1/CIP1/SDI1) expression in HL-60 and TPA-resistant HL-60 (HL-525) cells after extended incubation with TPA, RA and Vit D3. Cells were treated with TPA (3 nM), RA (1 µM) or Vit D3 (400 nM) for 0.5, 1, 2, 4 or 6 d. RNA was isolated and analyzed by RT-PCR using appropriate mda-6 or GAPDH specific primers as described in the Materials and methods.
Figure 27B:
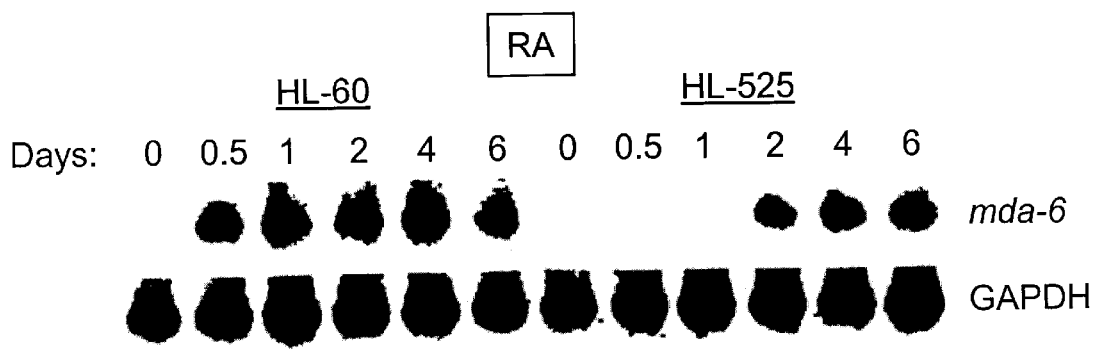
Figure 27C:
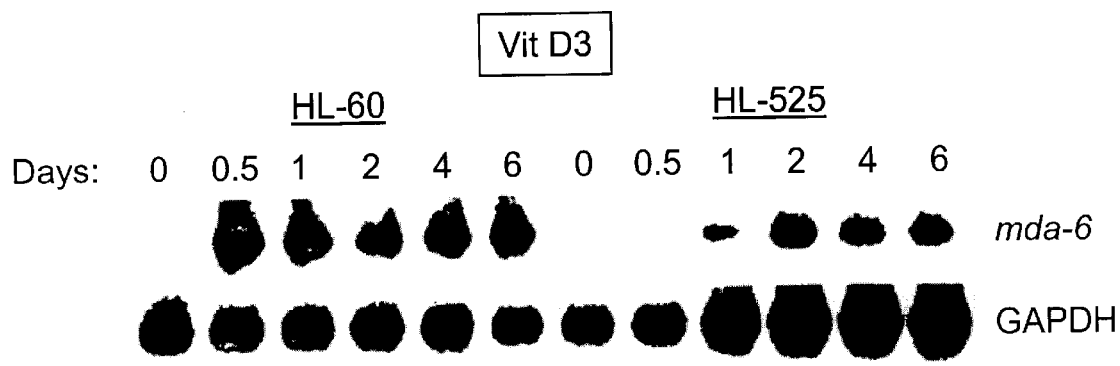

RT-PCR analyses were used to determine the effect of extended treatment times (12 h to 6 d) on induction of mda-6 in HL-60 and HL-525 cells (FIGS. 27A–C). With the three inducers, mda-6 expression in HL-60 cells was apparent during all of the extended treatment times. In the case of HL-525, mda-6 expression was also induced at all of the time points by TPA and Vit D3. On the basis of direct quantitation and an adjustment for amplification of GAPDH, the levels of mda-6 induction in TPA- and Vit D3-treated HL-525 cells appear to be lower than in similarly treated HL-60 cells (FIGS. 27A–C). However, since RT-PCR assay employed is not quantitative (no internal GAPDH control was used in the same amplification reaction), further studies using quantitative RT-PCR and Northern blotting will be required to verify this conclusion. In the case of RA treated HL-525 variant cells, a delay in induction of mda-6 is evident, i.e. expression is not detected until 2 d post-treatment (FIGS. 27A–C). These results suggest that the HL-525 TPA-resistant variant may also display an attenuated response to mda-6 expression following extended treatments with RA and Vit D3 as well as TPA.

Previous studies indicate that a 6 d growth of HL-60 cells is strongly inhibited (60 to 98% reduction in cell number relative to control) by 3 nM TPA, 1 µM RA and 400 nM Vit D3 with TPA being the most effective of the group (Murao et al., 1983 and data not shown). In the HL-525 variant, only a slight reduction (less than 5%) in growth is observed after treatment with TPA or Vit D3. Treatment with 1 µM RA for 6 d results in a 35% reduction in cell numbers. These results indicate that the TPA-resistant variant displays some cross-resistance to the growth suppressive effects of RA and it is relatively refractive to the dose of Vit D3 used for the present studies. Analysis of OKM1 reactivity, which reacts with human blood monocytes and granulocytes (Foon et al., 1982), in HL-60 indicates that both TPA and Vit D3 are similarly active, while RA displays a somewhat reduced activity (Table 4). In HL-60 cells, an increase in OKM1 positive cells is seen with all of the inducers over time, with maximum induction observed at 6 d with TPA and Vit D3 and by 4 d with RA. In contrast, HL-525 cells treated with TPA do not display a significant increase in OKM1 positive cells, whereas RA induces a small effect at 6 d and Vit D3 is an effective inducer of OKM1 reactivity at both 4 and 6 d. These observations indicate that the effects of Vit D3 on growth suppression and induction of differentiation are not directly correlated processes in HL-525 cells, whereas growth suppression and induction of differentiation are related changes in Vit D3 treated HL-60 parental cells.

TABLE 4

OKM1 reactivity in HL-60 and HL-525 cells treated with differentiation inducers

| Cell type | Inducer | Days of induction | | |
|---|---|---|---|---|
| | | 2 | 4 | 6 |
| HL-60 | | | | |
| | Untreated | 3 | 5 | 12 |
| | TPA | 55 | 81 | 95 |
| | RA | 49 | 76 | 77 |
| | Vit D3 | — | 88 | 95 |
| HL-525 | | | | |
| | Untreated | 5 | 3 | 5 |
| | TPA | — | 8 | 4 |
| | RA | — | 10 | 13 |
| | Vit D3 | — | 84 | 80 |

Figure 29A:
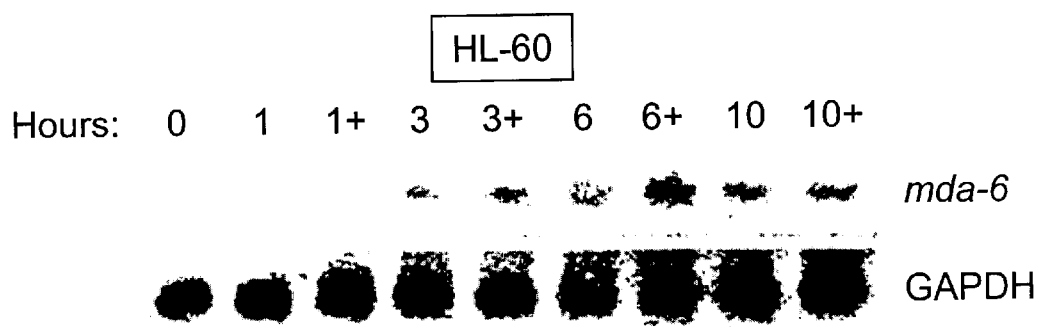
FIGS. 29A–B Effect of CHX on the induction of mda-6 in HL-60 and TPA-resistant HL-60 (HL-525) cells. Cells were treated with CHX (10 µg/ml) for 1, 3, 6 or 10 h or with CHX (10 µg/ml) plus TPA (3 nM) for 1+, 3+, 6+ or 10+h. RNA was isolated and analyzed by RT-PCR using appropriate mda-6 or GAPDH specific primers as described in the Materials and methods in the sixth series of experiments.
Figure 29B:
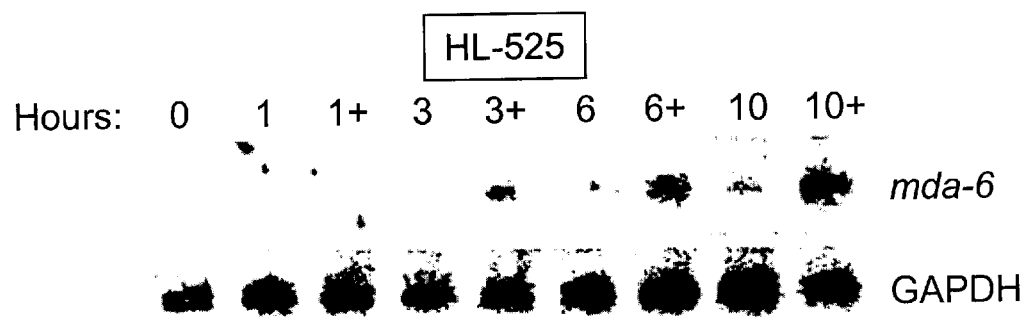

Cells were seeded into 100-mm Petri dishes at $1.5 \times 10^5$ cells/ml and TPA (3 nM), RA (1 µM) or Vit D3 (400 nM) added 12 h later. OKM1 reactivity was assessed at the indicated times as described in Materials and methods. Results are expressed as percent OKMI positive cells.
— = Not determined.

mda-6 is an Immediate-early Gene Induced in HL-60 Cells in the Presence of Cycloheximide To determine if the induction of mda-6 expression requires continuous protein synthesis, the effect of the protein synthesis inhibitor cycloheximide (CHX) on de novo and TPA-induced mda-6 expression was determined (FIGS. 29A–B). Treatment of HL-60 cells with CHX for 1, 3, 6 or 10 h results in the induction of mda-6. In addition, the relative level of mda-6 induction is unaffected when HL-60 cells are simultaneously treated with TPA and CHX. In HL-525 cells, CHX also induces mda-6 expression, but the level of induction is lower than in HL-60 parental cells. In contrast, when HL-525 cells are treated with both CHX and TPA, mda-6 expression is increase (superinduction) to a greater extent than with CHX alone (FIGS. 29A–B). These results indicated that mda-6 is an immediate-early response gene in HL-60 cells and induction does not require ongoing protein synthesis. The ability of CHX alone to induce mda-6 expression in HL-60 and to a lesser extent in HL-525 cells suggests that mda-6 expression may be controlled by an unstable suppressor. In the case of HL-525, inhibition in TPA-induced differentiation may be related to alterations in the levels of this unstable suppressor.

Experimental Discussion

Terminal differentiation in diverse cell types occurring either spontaneously or as a consequence of treatment with specific inducing agents correlates with an irreversible loss of proliferative potential (Sachs, 1978; Jimenez & Yunis, 1987; Waxman et al., 1988; 1991; Fisher & Rowley, 1991; Hoffman & Liebermann, 1994). The specific gene expression changes and proteins that mediate growth arrest and induction of differentiation in the majority of differentiation models remain to be defined. Using subtraction hybridization and agents capable of inducing terminal cell differentiation in human melanoma cells, mda genes have been identified whose expression directly correlate with growth arrest and terminal cell differentiation (Jiang & Fisher, 1993; Jiang et al., 1994). One such gene, mda-6 is identical to WAF1/CIP1/CAP20/SDI1 that encodes the ubiquitous inhibitor of cyclin-dependent kinases, p21 (Jiang & Fisher, 1993; Jiang et al., 1994). A direct effect of p21 on growth has been demonstrated by transfecting expression constructs into mammalian cells (El-Deiry et al., 1993; Harper et al., 1993; Jiang et al., in preparation). Although induction of p21 expression was initially considered to be dependent upon wild-type p53 protein (El-Deiry et al., 1993, 1994), recent studies suggest that this assumption must be reevaluated (Michieli et al., 1994). These include the ability of mitogens to transiently stimulate p21 expression in quiescent fibroblasts from p53 knock out mice lacking p53 protein (Michieli et al., 1994) and the decreased expression of p53 mRNA and protein but the increased expression of mda-6 mRNA and protein in terminally differentiated human melanoma cells (Jiang et al., in preparation). In the present study, definitive evidence is presented that p21 (mda-6/WAF1/CIP1/CAP20/SDI1) is an immediate-early response gene that is induced in the absence of p53 protein as a function of growth arrest and induction of differentiation in HL-60 cells. The ability of diverse inducers, including TPA and Vit D3 that produce monocyte and macrophage differentiation and RA and DMSO that elicit granulocyte differentiation, to stimulate p21 mRNA synthesis and p21 protein in HL-60 cells defines this early genotypic change as an important component of growth arrest and terminal differentiation in myeloid leukemic cells.

Previous studies have demonstrated that TPA-resistant variants of HL-60 cells, isolated in the absence of mutagenesis, display a number of biochemical and cellular traits that distinguish them from parental TPA-sensitive HL-60 cells (Murao et al., 1983; Fisher et al., 1984; Anderson et al., 1985; Homma et al., 1988; Tonetti et al., 1992). TPA-resistant HL-60 variant cells, such as HL-525, display altered protein kinase C (PKC) isozyme profiles, including the absence of PKC-β and possibly a δ-like PKC gene expression (Tonetti et al., 1992). TPA resistance in HL-60 cells is associated with decreased fluidity of either the inner leaflet of the plasma membrane and/or of the cytosolic organellar membranes (Fisher et al., 1984). A striking biochemical difference between HL-60 and TPA-resistant HL-60 variants is the inability of the latter cell type to translocate PKC from the cytosol to the membrane fraction following TPA treatment (Homma et al., 1986). TPA-resistant HL-60 variants also display modifications in protein phosphorylation patterns after TPA treatment (Homma et al., 1988) and altered responses in immediate-early gene expression following TPA treatment (Tonetti et al., 1992). Of most direct relevance to the present study is the observation by Tonetti et al. (1992) that the HL-525 variant displays an attenuated response to TPA induction of immediate-early genes, including c-fos, c-jun and jun-B. The level of c-fos and jun-B induction is substantially greater in TPA-treated HL-60 parental cells and in the TPA-sensitive HL-60 clone, HL-205, than in two TPA-resistant clones, HL-525 and HL-534. In the case of c-jun, TPA fails to induce this gene expression change in HL-525 or HL-534 cells, whereas induction is apparent in HL-60 and HL-205 cells by 9 h post-treatment with TPA (Tonetti et al., 1992).

In the present study, applicants demonstrate that the TPA-resistant variant HL-525 displays a diminished response to TPA-induction of mda-6 in comparison with HL-60 cells (FIGS. 26A–C and 27A–C). The HL-525 cells likewise differ from HL-60 cells in the induction of mda-6 following treatment with Vit D3 and RA (FIGS. 26A–C and 27A–C). With both of these agents, the temporal pattern of induction and the magnitude of induction of mda-6 are diminished in HL-525 cells. The TPA-resistant HL-525 variant also displays a reduced susceptibility to growth arrest following treatment with Vit D3 and RA, whereas Vit D3 still has the capacity to induce differentiation as monitored by OKT1 reactivity (Table 4). These findings indicate that these two phenomena, i.e., growth arrest and differentiation, are dissociable processes in HL-525 cells. Unlike TPA- and RA-treated HL-525 cells, Vit D3 treated cells show early induction of mda-6 (after 2 h treatment) (FIGS. 26A–C). Although further studies are required, it is tempting to speculate that the early induction of mda-6 by Vit D3 may be a primary determinant committing HL-525 cells to differentiate, whereas the absence of sufficient accumulated levels of p21 protein, encoded by mda-6, in long-term treated cultures (6 d) precludes growth arrest.

CHX induces mda-6 in HL-60 cells and the ability of TPA to induce mda-6 expression is not inhibited by CHX indicating that mda-6 is an immediate-early response gene. In HL-525 cells, CHX induces mda-6 less effectively than in HL-60 cells, whereas the combination of CHX and TPA results in a superinduction of mda-6 in this TPA-resistant variant (FIGS. 29A–B). These observations and previous investigations support the hypothesis that the HL-525 variant cells may be defective in signal transduction processes, possibly involving PKC-β and a δ-like PKC gene, that prevent or reduce the induction of immediate-early response genes, including c-fos, c-jun, jun-B and p21. The lower levels of the immediate-early response genes following TPA treatment may then impede the induction of subsequent cellular genes involved in the initiation of terminal differentiation in HL-525 cells. Induction of the immediate-early gene p21 during the commitment phase of HL-60 differentiation may be an important component in initiating differentiation, whereas a continued elevation of p21 may be required for growth arrest and maintenance of terminal differentiation in HL-60 cells. In the case of the HL-525 variant, treatment with TPA does not induce the early induction of p21 and it may not generate sufficiently high levels of p21 to produce sustained growth arrest.

Recent studies are providing new insights into the mode of action of p21. The p21 protein was originally identified as part of quaternary cyclin D complexes in human diploid fibroblasts, that also possess cyclin-dependent kinases (CDK) and proliferating cell nuclear antigen (PCNA) (Xiong et al., 1992). Subsequent studies demonstrated that p21 and PCNA can form multiple quaternary complexes with all cyclins and CDKs in normal human fibroblasts, but not in virally transformed cells (Xiong et al., 1993a). p21 has also been shown to associate with and inhibit the activity of all cyclin-CDK enzymes (Xiong et al., 1993b; Harper et al., 1993; Gu et al., 1993). Recent experiments demonstrate that p21 can directly complex with and inhibit PCNA suggesting that this protein may be a critical regulator of DNA replication, DNA repair and cell cycle machinery (Waga et al., 1994). The importance of p21 in cell cycle and growth control has been reinforced by the independent isolation of this gene by virtue of its induction by the tumor suppressor p53 [WAF1, (El-Deiry et al., 1993)], as a direct regulator of CDK2 using the two-hybrid screening technique [CIP1, Harper et al., 1993), as a cDNA from senescent cells with the ability to inhibit the ability of young cells to enter S phase after overexpression following transient transfection [SDI1, (Noda et al., 1994)] and as a differentially expressed differentiation related cDNA isolated from a human melanoma cell library using subtraction hybridization (mda-6, Jiang & Fisher, 1993; Jiang et al., 1994). The level of p21 has been shown to vary depending on the specific stage of the cell cycle (Li et al., 1994). In IMR90 normal diploid fibroblast cells released from serum starvation, the levels of p21 are maximum immediately after serum stimulation, start to decrease as cells reach the G1/S boundary, display lowest levels during S phase, and increase again as cells leave the S phase and enter the G2 and M phase (Li et al., 1994). These observations indicate that p21 may contribute to both the G1/S and the G2/M checkpoint pathways. The interaction of p21 with cyclin and CDK during the cell cycle is not random, but rather occurs when the specific cyclin-CDK enzyme is reputed to function (Li et al., 1994). Moreover, the increased level of p21 in quiescent and terminally differentiated cells suggests that this protein may play a crucial role in preventing these cells from re-entering the cell cycle, an absolute requirement for terminal differentiation.

In summary, the ability of different inducers of growth suppression and terminal differentiation to induce p21 early in the differentiation process and the persistence of elevated levels of p21 after terminal differentiation in the p53 negative HL-60 cell line indicates an important role for this inhibitor of cyclin-dependent kinases in differentiation. Further support for an involvement of p21 in growth control and differentiation is indicated by the ability of structurally diverse inducers of differentiation to induce p21 expression and growth arrest in additional cell lines, including human melanomas (Jiang & Fisher, 1993; Jiang et al., 1994) and human neuroblastomas (Jiang et al., in preparation). Moreover, the diminished ability of specific inducers of differentiation to produce growth arrest and differentiation in the TPA-resistant HL-525 variant also correlates with a reduced early and sustained induction of p21. Further studies to determine if forced expression of p21, using inducible expression vectors, are sufficient to induce an irreversible loss in proliferative capacity and terminal differentiation in HL-60 cells, and other differentiation competent cell culture systems, appears warranted and are currently in progress. These experiments will permit a direct functional evaluation of p21 in regulating both cellular growth and differentiation in the absence and presence of wild-type p53.

Materials and Methods

Cells and Culture Conditions

HL-60 cells were originally provided by Dr. R. C. Gallo (National Cancer Institute, Bethesda, Md.) (Collins et al., 1978; Huberman & Callaham, 1979). HL-60 cells designated HL-525 were derived by cloning HL-60 cells after subculturing 102 times in the presence of increasing concentrations (up to 3 $\mu$M) of TPA at 5- to 8-day intervals (Homma et al., 1986; Mitchell et al., 1986). The HL-525 cell variant displays a stable phenotype with regards to resistance to induction of cell differentiation by TPA for at least 50 to 60 subcultures (200 to 300 cell generations). Prior to the experiments described in this study, the HL-525 cells were subcultured more than 20 times in the absence of TPA. Cells were grown in 100-mm tissue culture dishes in RPMI 1640 medium supplemented with 20% fetal bovine serum, penicillin (100 units/ml) and streptomycin (100 $\mu$g/ml) (Grand Island Biological Co., NY) at 37° C. in an atmosphere of 5% $CO_2$ in air in a humidified incubator. The 1,25-$(OH)_2D_3$(Vit D3) and TPA were dissolved in a final concentration of 0.01% DMSO, and all-trans retinoic acid (RA) was dissolved in 0.1% DMSO in culture medium. DMSO at these concentrations did not affect cell growth or the expression of the various differentiation markers. Control cultures were treated with DMSO at a final concentration of 0.1% in culture medium. For experiments designed to test the effect of DMSO on HL-60 and HL-525 cells, DMSO was added to tissue culture medium at a final concentration of 1%. Stock solutions of CHX (10 mg/ml) were prepared in culture medium. CHX was added at a final concentration of 10 $\mu$g/ml. To examine a requirement for protein synthesis on mda-6 gene expression, HL-60 or HL-525 cells were seeded into 150 mm Petri dishes (5×10$^5$ cells/ml) in 30 ml of medium. CHX was added to a final concentration of 10 $\mu$g/ml 15 min prior to the addition of TPA to 3 nM. Cells were harvested at various times after addition of TPA for subsequent RNA isolation and analysis.

Measurement of Differentiation and Growth

Cell counts were determined by hemocytometer chamber counting. Immunofluorescence tests for reactivity with the OKM1 antibody (Ortho Pharmaceutical Corp., Raritan, N.J.) were performed as previously described (Murao et al., 1983).

RNA Isolation, Northern Blotting and RT-PCR

RNA was purified by centrifugation through a CsCl cushion as described by Chirgwin et al. (1979). Ten $\mu$g of RNA was denatured with glyoxal/DMSO, electrophoresed on 1.0% agarose gels, transferred to nylon membranes, hybridized to a $^{32}$p-labeled mda-6 probe (Jiang and Fisher, 1993) and then after stripping the membrane hybridized to a $^{32}$p-labeled rat GAPDH probe (Fort et al., 1985), as described previously (Reddy et at., 1991; Su et al., 1991; Jiang et al., 1992). Following hybridization, the filters were washed and exposed for autoradiography (Reddy et al., 1991; Su et al., 1991; Jiang et al., 1992). mda-6 and GAPDH gene expression were also determined by reverse transcription-polymerase chain reaction (RT-PCR) as described (Adollahi et al. 1991; Lin et al., 1994). Total cytoplasmic RNA was treated with 0.5 units DNase (Boehringer-Mannheim Biochemicals)/$\mu$g RNA in 15% glycerol, 10 mM Tris, pH 7.5, 2.5 mM $MgCl_2$, 0.1 mM EDTA, 80 mN KC1, 1 mM $CaCl_2$ and 1 unit/ml RNasin (Promega) at 30° C. for 10 min. RNA was extracted with phenol-chloroform, precipitated with sodium acetate/ethanol and RNA pellets were resuspended in diethylpyrocarbonate-treated $H_2O$. One $\mu$g of total RNA was reverse transcribed with 200 units of murine leukemia virus reverse transcriptase (Bethesda Research Laboratories) in 20 $\mu$l containing 1 mM deoxyribonucleotide triphosphates, 4 mM $MgCl_2$, 10 mM Tris, pH 8.3, 50 mM KCl, 0.001% gelatin and 0.2 $\mu$g oligo-dT primer. Samples were diluted to 100 $\mu$l with buffer containing 0.2 mM deoxyribonucleotide triphosphates, 2 mM $MgCl_2$, 10 mM Tris, pH 8.3, 50 mM KCl and 0.001% gelatin. Fifty pmol of each primer, 1.5 units Taq DNA polymerase Perkin-Elmer Cetus) were added and samples were covered with mineral oil, heated at 95° C. for 5 mm and subjected to 20 cycles of PCR in a Perkin-Elmer Thermal Cycler using 2 mm denaturation at 95° C., 1 mm annealing at 55° C. and 4 mm polymerization at 72° C. After extraction with chloroform, 20 $\mu$g of products were electrophoresed, blotted onto nylon filters and hybridized with an mda-6 or GAPDH specific probe. The template primers for mda-6 were 5' to 3' CTCCAAGTACACTAAGCACT (SEQ ID NO:22) and TAGTTCTACCTCAGGCAGCT (GenBank accession number U09579) (SEQ ID. NO:23) and the template primers for human GAPDH were 5' to 3' CATGGCCTCCAAGGAGTAAGA (SEQ ID. NO:24) and CGTCTTCACCACCATGGAGAA (GenBank accession number J02642) (SEQ ID NO:25).

Immunoprecipitation Analyses

Immunoprecipitation analyses were performed as described previously (Duigou et al., 1991; Su et al. 1993). Logarithmically growing HL-60 cells were either untreated or treated for 12, 24, 48 or 72 h with TPA (3 mM), RA (1 $\mu$M) or DMSO (1%) in 10-cm plates. Cultures were starved of methionine for 1 h at 37° C. in methionine-free medium, cells were concentrated by pelleting and labeled for 4 h at 37° C. in 1 ml of the same medium with 100 $\mu$Ci of [$^{35}$S] (NEN; Express $^{35}$S). After labeling, the cells were washed twice with ice-cold phosphate-buffered saline and lysed for 1 h on ice by the addition of RIPC (20 mM Tris-base, pH 7.5, 500 mM NaCl, 0.05% Nonidet P-40, 100 $\mu$g/ml phenylmethylsulfonyl fluoride and 0.02% sodium azide). The lysate was clarified by centrifugation in an Eppendorf microfuge at 10,000×g for 10 min at 4° C. Samples containing 4×10$^6$ counts were incubated with 2 $\mu$g of WAF1/CIP1 (C-19) (Santa Cruz Biotechnology) (or MDA-6 peptide-derived) rabbit polyclonal IgG or actin monoclonal antibody (Oncogene Sciences) with rocking at 4° C. for 24 h. The next day, 30 $\mu$l (packed volume) of protein G-agarose (Oncogene Sciences) was added to each tube, and incubation with rocking at 4° C. continued for another hour. The protein G pellets were then washed five times with 1 ml of ice-cold RIPC:phosphate-buffered saline (1:1, v/v). Thirty $\mu$l of sodium dodecyl sulfate-polyacrylamide gel electrophoresis buffer were added to the pellets, and the sample was heated at 87° C. for 3 min. The samples were loaded onto an 10% polyacrylamide gel and run overnight at 40 V. The gel contained Rainbow protein markers (Amersham) for sizing. Gels were fixed with 10% acetic acid plus 10% methanol for 30 min, incubated in DMSO for 30 min, incubated with 10% 2,5-diphenyloxazole in DMSO for 30 min, washed three times with cold water (10 min each), dried and exposed to film.

REFERENCES OF THE SIXTH SERIES OF EXPERIMENTS

Adollahi, A., Lord, K. A., Hoffman-Liebermann, B. & Liebermann, D. A. (1991). Cell Growth Different., 2, 401–407.

Anderson, N. L., Gemmell, M. A., Coussens, P. M., Murao, S.-i. & Huberman, E. (1985). Cancer Res., 45, 4955–4962.

Breitman, T. R., Delonic, S. E. & Collins, S. J. (1980). Proc. Natl. Acad. Sci. USA, 77, 2936–2940.

Chirgwin, J. M., Przybyla, A. E., MacDonald, R. J. & Rutter, R. J. (1970). Biochemistry, 18, 5294–5299.

Collins, S. J. (1987). Blood, 70, 1233–1234.

Collins, S. J., Ruscetti, F. W., Ruscetti, R. E., Gallagher, R. & Gallo, R. (1978). Proc. Natl. Acad. Sci. U.S.A., 75, 2458–2462.

Duigou, G. J., Su, Z.-z., Babiss, L. E., Driscoll, B., Fung, Y.-K. T. & Fisher, P. B. (1991). Oncogene, 6, 1813–1824.

El-Deiry, W. S., Harper, J. W., O'Connor, P. M., Velculescu, V. E., Canman, C. E., Jackman, J., Pietenpol, J. A., Burrell, M., Hill, D. E., Wang, Y., Wiman, K. G., Mercer, W. E., Kastan, M. B., Kohn, K. W., Elledge, S. J., Kinzler, K. W. & Vogelstein, B. (1994). Cancer Res., 54, 1169–1174.

El-Deiry, W. S., Tokino, T., Velculescu, V. E., Levy, D. B., Parsons, R., Trent, J. M., Lin, D., Mercer, W. E., Kinzler, K. W. & Vogelstein, B. (1993). Cell, 75, 817–825.

Fisher, P. B. & Rowley, P. T. (1991). Status of Differentiation Therapy of Cancer, Waxman, S., Rossi, G. B. & Takaku, F. (eds.). Raven Press, Inc.: New York. pp. 201–213.

Fisher, P. B., Prignoli, D. R., Hermo, H., Jr., Weinstein, I. B. & Pestka, S. (1985). J. Interferon Res., 5, 11–22.

Fisher, P. B., Schachter, D., Abbott, R. E, Callaham, M. F. & Huberman, E. (1984). Cancer Res., 44, 5550–5554.

Foon, K. A., Schroff, R. W. & Gale, R. P. (1982). Blood, 60, 1–19.

Fort, P., Marty, L., Piechaczyk, M., Sabrouty, S. E., Dani, C., Jeanteur. P. & Blanchard, J. M. (1985). Nucleic Acids Res., 13, 1431–1442.

Gallagher, R., Collins, S., Trujillo, J., McCredie, K., Ahearn, M., Tsai, S., Metzgar, R., Aulakh, G., Ting, R., Ruscetti, F. & Gallo, R. (1979). Blood, 54, 713–733.

Gu, Y., Turck, C. W. & Morgan, D. O. (1993). Nature, 366, 707–710.

Harper, J. W., Adami, G. R., Wei, N., Keyomarsi, K. & Elledge, S. J. (1993). Cell, 75, 805–816.

Hoffman, B. & Liebermann, D. (1994). Oncogene, 9, 1807–1812.

Homma, Y., Gemmell, M. A. & Huberman, E. (1988). Cancer Res., 48, 2744–2748.

Homma, Y., Henning-Chubb, C. B. & Huberman, E. (1986). Proc. Natl. Acad. Sci. USA, 83, 7316–7319.

Huberman, E. & Callaham, M. F. (1979). Proc. Natl. Acad. Sci. USA, 76, 1293–1297.

Jiang, H. & Fisher, P. B. (1993). Mol. Cell. Different., 1 (3), 285–299.

Jiang, H., Lin, J. & Fisher, P. B. (1994). Mol. Cell. Different., 2 (3), in press.

Jiang, H., Su, Z.-z., Boyd, J. & Fisher, P. B. (1993). Mol. Cell. Different. 1 (1), 41–66.

Jiang, H., Su, Z.-z., Datta, S., Guarini, L., Waxman, S. & Fisher, P. B. (1992). Intl. J. Oncology, 1, 227–239.

Jimenez, J. J. & Yunis, A. A. (1987). Science, 238, 1278–1280.

Knudson, A. G. (1993). Proc. Natl. Acad. Sci., USA, 90, 10914–10921.

Li, Y., Jenkins, C. W., Nichols, M. A. & Xiong, Y. (1994). Oncogene, 9, 2261–2268.

Lin, J., Su, Z.-z., Grunberger, D., Zimmer, S. G. & Fisher, P. B. (1994). Intl. J. Oncology, 5, 5–15.

Lotan, R. (1993). Retinoids in Oncology, Hong, W. K. & Lotan, R. (eds.), Marcel Dekker, Inc.: New York pp. 43–72.

Lotem, J. & Sachs, L. (1979). Proc. Natl. Acad. Sci. USA, 76, 5158–5162.

Michieli, P., Chedid, M., Lin, D., Pierce, J. H., Mercer, W. E. & Givol, D. (1994). Cancel Res., 54, 3391–3395.

Mitchell, R. H., Henning-Chubb, C. B., Huberman, E. & Verma, I. M. (1986). Cell, 45, 497–504.

Miyaura, D., Abe, E., Kuribayashi, T., Tanaka, H., Konno, K., Nishii, Y. & Suda, T. (1981). Biochem. Biophys. Res. Commun., 102, 937–943.

Murao, S.-i., Gemmell, M. A., Callaham, M. F., Anderson, N. L. & Huberman, E. (1983). Cancer Res., 43, 4989–4996.

Noda, A., Ning, Y., Venable, S. F., Pereira-Smith, O. M. & Smith, J. R. (1994). Exp. Cell. Res., 211, 90–98.

Reddy, P. G., Graham, G. M., Datta, S., Guarini, L., Moulton, T. A., Jiang, H., Gottesman, M. M., Ferrone, S. & Fisher P. B. (1991). J. Natl. Cancer Inst., 83, 1307–1315.

Rovera, G., Santoli, D. & Damsky, C. (1979). Proc. Natl. Acad. Sci. U.S.A., 76, 2779–2803.

Sachs, L. (1978). Nature, 274, 535–539.

Su, Z.-z., Grunberger, D. & Fisher, P. B. (1991). Mol. Carcinog., 4, 231–242.

Su, Z.-z., Leon, J. A., Jiang, H., Austin, V. A., Zimmer, S. G. & Fisher, P. B. (1993). Cancer Res., 53, 1929–1938.

Tanaka, H., Abe, E., Miyaura, C., Kuribayashi, T., Konno, K., Nishii, Y. & Suda, T. (1982). Biochem. J., 204, 713–719.

Tonetti, D. A., Horio, M., Collart, F. R. & Huberman, E. (1992). Cell Growth Different., 3, 739–745.

Waga, S., Hannon, G. J., Beach, D. & Stillman, B. (1994). Nature, 369, 574–578.

Waxman, S., Rossi, G. B. & Takaku, F. (eds.) (1988). The Status of Differentiation Therapy, vol. I, Raven Press, Inc.: New York.

Waxman, S., Rossi, G. B. & Takaku, F. (eds.) (1991). The Status of Differentiation Therapy, vol. II, Raven Press, Inc.: New York.

Wolf, D. & Rotter, V. (1985). Proc. Natl. Acad. Sci. USA, 82, 790–794.

Xiong, Y., Zhang, H. & Beach, D. (1993a). Genes & Develop., 7, 1572–1583.

Xiong, Y., Hannon, G. J., Zhang, H., Casso, D., Kobayashi, R. & Beach, D. (1993b). Nature, 366, 701–704.

Xiong, Y., Zhang, H. & Beach, D. (1992). Cell, 71, 505–514.

Seventh Series of Experiments

The combination of recombinant human fibroblast interferon (IFN-$\beta$) and the antileukemic compound mezerein (MEZ) induces terminal differentiation with an irreversible loss of proliferative capacity in human melanoma cells. Using subtraction hybridization, cDNAs were identified that display enhanced expression in terminally differentiated and growth arrested human melanoma cells (Jiang and Fisher, 1993; Jiang et al., 1994). A specific melanoma differentiation-associated (mda) cDNA, mda-6, is described whose expression inversely correlates with melanoma progression and growth. mda-6 is identical to WAF1/CIP1/SDI1 that encodes the $M_r$ 21,000 protein (p21) that is an inhibitor of cyclin-dependent kinases. Actively growing normal melanocyte, SV40-immortalized human melanocyte and dysplastic nevus cell lines synthesize elevated levels of mda-6 mRNA; whereas, actively proliferating radial and early vertical growth phase primary melanomas as well as metastatic human melanoma cells produce reduced levels of mda-6 mRNA. Treatment of primary and metastatic human melanoma cells with IFN-β+MEZ results in growth inhibition and an increase in mda-6 expression. mda-6 expression also increases when human melanoma cells are grown to high saturation densities or when grown in serum-free medium. Using anti-p53 and anti-p21 antibodies, an inverse correlation is found between p53 and p21 protein levels during growth arrest and differentiation. Induction of growth arrest and terminal differentiation in H0-1 human melanoma cells by IFN-+MEZ results in a temporal decrease in wild-type p53 protein levels with a corresponding increase in p21 levels. In the Matrigel-assisted melanoma progression model, mda-6 expression decreases in early vertical growth phase primary human melanoma cells selected for autonomous or enhanced tumor formation in nude mice. In metastatic human melanoma cells displaying a loss of metastatic potential resulting following introduction of a normal human chromosome 6, mda-6 mRNA levels increase. Taken together, these studies indicate that mda-6 (p21) may function as a negative regulator of melanoma growth, progression and metastasis.

Development of malignant melanoma in humans, with the exception of nodular type melanoma, often consists of a series of sequential alterations in the evolving tumor cells (for reviews see: Kerbel, 1990; Herlyn, 1990; Clark, 1991). These changes may include conversion of a normal melanocyte into a common acquired melanocytic nevus (mole), followed by the development of a dysplastic nevus, a radial growth phase (RGP) primary melanoma, a vertical growth phase (VGP) melanoma and ultimately a metastatic melanoma. Melanomas are readily treatable during the early stages of development; however currently employed therapies are not very effective (<20% survival) in preventing metastatic spread and morbidity in patients with VGP lesions >4.0-mm thickness. These observations indicate an imperative for improved therapeutic modalities for treating patients with this malignancy.

A potentially less toxic strategy for cancer therapy involves a procedure termed "differentiation therapy" (Sachs, 1978; Jimenez & Yunis, 1987; Waxman et al., 1988, 1991; Fisher & Rowley, 1991; Lotan, 1993; Jiang et al., 1994a). An essential premise underlying this approach is that specific cancers have reversible defects in normal programs of differentiation and growth control. By using specific single or combinations of agents, it has been possible to slow or stop proliferation of cancer cells and correspondingly increase expression of differentiation-associated properties (for reviews see: Waxman et al., 1988, 1991; Fisher & Rowley, 1991; Lotan, 1993; Jiang et al., 1994a).

Treatment of human melanoma cells with IFN-β+MEZ results in rapid, irreversible loss of proliferative capacity, an induction of specific changes in gene expression, a modification in cell surface antigenic profile and terminal cell differentiation (Fisher et al., 1985, 1986; Guarini et al., 1989, 1992; Graham et al., 1991; Jiang & Fisher, 1993; Jiang et al., 1993, 1994a). The ability of IFN-β+MEZ to induce terminal differentiation in human melanoma cells is hypothesized to be a consequence of activation by these agents of genes that negatively control melanoma growth and induce differentiation. Two predictions arise from this model: specific genes involved in growth control and differentiation in human melanoma cells are expressed at diminished levels in melanoma versus their normal melanocyte counterpart; and the combination of IFN-β+MEZ can induce enhanced expression of specific melanoma differentiation associated (mda) genes, growth suppression and terminal cell differentiation (Jiang & Fisher, 1993; Jiang et al., 1994a). To test these possibilities and to directly identify and clone genes that would fulfill this scheme, a modified subtraction hybridization approach was used that employed the human melanoma cell line H0-1 treated with IFN-β+MEZ (Jiang & Fisher, 1993). Using this strategy a series of melanoma differentiation associated (mda) genes were cloned that display enhanced expression in H0-1 human melanoma cells treated with IFN-β+MEZ (Jiang & Fisher, 1993; Jiang et al., 1994a). mda-6 encodes the cyclin dependent kinase inhibitor protein, p21 (Jiang et al., 1994a, 1994b). p21 has been cloned by a number of laboratories by virtue of its ability to interact with and inhibit cyclin dependent kinases (CIP1: cyclin-dependent kinase (CDK)-interacting protein-1) (Harper et al., 1993), its induction by wild-type p53 (WAF1; wild-type (wt) p53 activated factor-1) (El-Deiry et al., 1993), its induction during senescence (SDI1; senescent cell-derived inhibitor-1) (Noda et al., 1994) and its induction as a function of growth arrest and terminal differentiation in human melanoma cells (mda-6; melanoma differentiation associated gene-6) (Jiang & Fisher, 1993; Jiang et al., 1994a). Although originally assumed to be dependent on wt p53 for induction (El-Deiry et al., 1993, 1994), recent studies indicate that p21 can also be induced in a p53-independent manner (Michieli et al., 1994; Jiang et al., 1994b; Steinman et al., 1994). In the present study, applicants demonstrate that the levels of p21 protein increase as the levels of wt p53 protein decrease during IFN-β+MEZ induction of growth suppression and terminal differentiation in H0-1 human melanoma cells. These results reveal a novel association between p21 and p53 in the process of melanoma growth and differentiation. Moreover, applicants show a relationship between expression of mda-6 and melanoma evolution, differentiation and growth. These results provide a direct link between alterations in p21 expression and cancer progression.

Experimental Results

Increased mda-6 Expression in Human Melanoma Cells During Growth Inhibition and Terminal Cell Differentiation To define the molecular basis by which IFN-β+MEZ induces irreversible growth arrest and terminal differentiation in human melanoma cells applicants used the technique of subtraction hybridization with uninduced and differentiation inducer treated H0-1 human melanoma cDNA libraries (Jiang & Fisher, 1993). Using this strategy, an mda-6 cDNA was identified in a differentiation inducer (IFN-β+MEZ) treated subtracted H0-1 human melanoma library that displays differential expression as a function of IFN-β+MEZ induced growth arrest and terminal differentiation (Jiang & Fisher, 1993; Jiang et al., 1994a). By screening a differentiation inducer-treated H0-1 cDNA library (Jiang & Fisher, 1993) and using rapid amplification of cDNA ends (RACE) (Frohman et al., 1988; Loh et al., 1989; Ohara et al., 1989) a full-length mda-6 cDNA was cloned (Jiang et al., 1994a). mda-6 contains the same open reading frame as WAF1 (El-Deiry et al., 1993), CIP1 (Harper et al., 1993), CAP20 (Gu et al., 1993) and SDI1(Noda et al., 1994) (FIG. 30). These genes encode the ubiquitous inhibitor of cyclin dependent kinases, p21.

Figure 32:
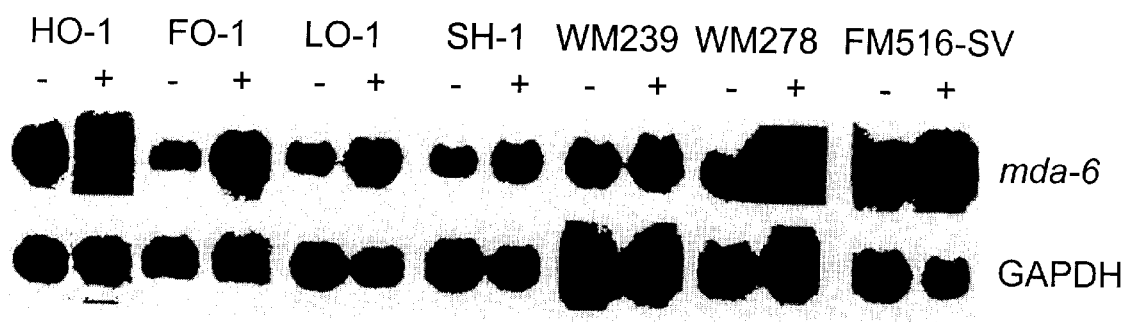
FIG. 32 Effect of IFN-β+MEZ on mda-6 (p21) expression in human melanoma cells and an SV40-transformed human melanocyte culture. High-density melanoma cells (H0-1, F0-1, L0-1, SH-1, WM239 and WM278) and logarithmically growing low-density SV40-transformed human melanocytes (SV516-SV) were treated with IFN-β (2000 units/ml)+MEZ (10 ng/ml) for 24 hr, total RNA was isolated and analyzed by Northern blotting (Jiang & Fisher, 1993; Jiang et al., 1993). Filters were probed with mda-6 then stripped and probed with GAPDH as described (Jiang & Fisher, 1993; Jiang et al., 1993).

Treatment of actively growing H0-1 cells for 24 h with IFN-β+MEZ results in increased mda-6 mRNA levels and growth inhibition (Fisher et al., 1985; Jiang & Fisher, 1993; Jiang et al., 1993) (FIGS. 31A–E). In contrast, treatment of H0-1 cells with either IFN-β or MEZ for 24 h results in a smaller induction of mda-6 expression and reduced growth inhibition (Fisher et al., 1985; Jiang & Fisher, 1993; Jiang et al., 1993). Enhanced mda-6 expression and terminal cell differentiation are also produced in additional human melanoma cells treated with IFN-β+MEZ, including F0-1, SH-1, L0-1, WM-239 and WM-278 (FIG. 32). mda-6 is expressed at higher de novo levels in a low-density SV40-transformed human melanocyte culture (FM516-SV) (Melber et al., 1989) than in low-density and the majority of high-density melanoma cultures (FIG. 32 and data not shown). mda-6 levels are increased and melanoma growth is inhibited after 24 h treatment with IFN-β+MEZ and 96 h treatment with the inducers results in terminal differentiation in the human melanoma cultures (FIG. 32 and data not shown). In contrast, although mda-6 expression is enhanced by 24 h in IFN-β+MEZ-treated FM516-SV cells, growth is only marginally reduced ($\leq 15\%$) (FIG. 32 and data not shown). Unlike human melanoma cells, 96 h exposure of FM516-SV cells to IFN-β+MEZ does not result in terminal differentiation in the majority of treated cells (data not shown).

Elevated mda-6 expression persists in H0-1 cells, and other melanoma cells, induced to terminally differentiate by continuous exposure to IFN-β+MEZ for 96 h, whereas H0-1 cells, and additional melanoma cultures, treated singly with IFN-β or MEZ for 96 h recover from growth suppression and contain similar levels of mda-6 as control cells (FIGS. 31A–E and data not shown). Previous studies indicate that growth of H0-1 cells for 24 h in IFN-β+MEZ or MEZ, but not IFN-β, followed by removal of the inducing agent(s) and growth for an additional 72 h in complete medium results in sustained growth inhibition (Jiang et al., 1993). Under these experimental conditions, mda-6 expression remains elevated with both types of treatment with the highest expression occurring with IFN-β+MEZ that also induces the greatest residual growth inhibition (Jiang et al., 1993) (FIGS. 31A–E).

Even without treatment with differentiation-inducing agents, H0-1 cells grown to high density (FIGS. 31A–E) or grown in the absence of serum (FIGS. 31A–E) express elevated levels of mda-6 mRNA. The induction of enhanced mda-6 mRNA levels is rapid, occurring within 15 min treatment (FIGS. 31A–E). Elevated mda-6 expression is also evident in IFN-β+MEZ treated H0-1 cells simultaneously culured in the presence of cycloheximide (data not shown) and following a 2 h exposure to 25 μg/ml of the alkylating carcinogen, methyl methanesulfonate (data not shown). These observations suggest a direct relationship between mda-6 expression and growth suppression in human melanoma cells.

Inverse Relationship Between p21 and Wild-type p53 Levels During Growth Arrest and Differentiation in H0-1 Human Melanoma Cells Treatment of H0-1 cells with IFN-β+MEZ results in rapid growth arrest, that is apparent within 24 h (Fisher et al., 1985; Jiang et al., 1993). In contrast, IFN-β and MEZ alone result in smaller changes in growth in H0-1 cells (Fisher et al., 1985; Jiang et al., 1993). Analysis of p53 mRNA levels in IFN-β, MEZ and IFN-β+MEZ treated H0-1 cells indicate no significant change after 24 h, but significant inhibition is observed in p53 expression that is maximum in IFN-β+MEZ (96 h) treated terminally differentiated H0-1 cells (Jiang et al., in preparation). MEZ also induces a reduction in p53 mRNA levels in 96 h treated H0-1 cells, whereas no change in p53 mRNA occurs in H0-1 cells treated with IFN-β for 96 h (Jiang et al., in preparation). Since the kinetics of suppression in p53 gene expression is the opposite of that observed with mda-6 expression in differentiation inducer treated H0-1 cells, experiments were conducted to determine the effects of growth suppression and terminal differentiation on p53 and p21 protein levels.

Immunoprecipitation analysis of p53 under conditions preventing protein denaturization (<1% SDS) with monoclonal antibodies Ab1 (PAb421; Oncogene Sciences), that identifies both wild-type and mutant p53, and Ab3 (PAb240; Oncogene Sciences) that recognizes mutant p53, indicate that H0-1 cells contain a wild-type p53 protein (data not shown). A wild-type p53 protein is also present in a number of other cell types evaluated in the present study, including FM516-SV, L0-1, SH-1 and F0-1, whereas WM239 cells contain a mutant p53 (data not shown). To rule out potential artifacts, immunoprecipitation studies with Ab1 and Ab3 were performed with labeled extracts from cell lines with known p53 status, including MeWo (previously shown to contain a mutant p53 by sequence analysis) (Loganzo et al., 1994), Saos-2 (p53-null phenotype), human skin fibroblasts (wild-type p53) and SW480 colon carcinoma cells (mutant p53) (data not shown). The current results are in agreement with several recent studies (Volkenandt et al., 1991; Castresana et al., 1993; Greenblatt et al., 1994; Montano et al., 1994; Loganzo et al., 1994) indicating that p53 mutations are rare in human melanoma and the majority of human melanomas contain a wild-type as opposed to a mutant p53 protein.

Figure 33:
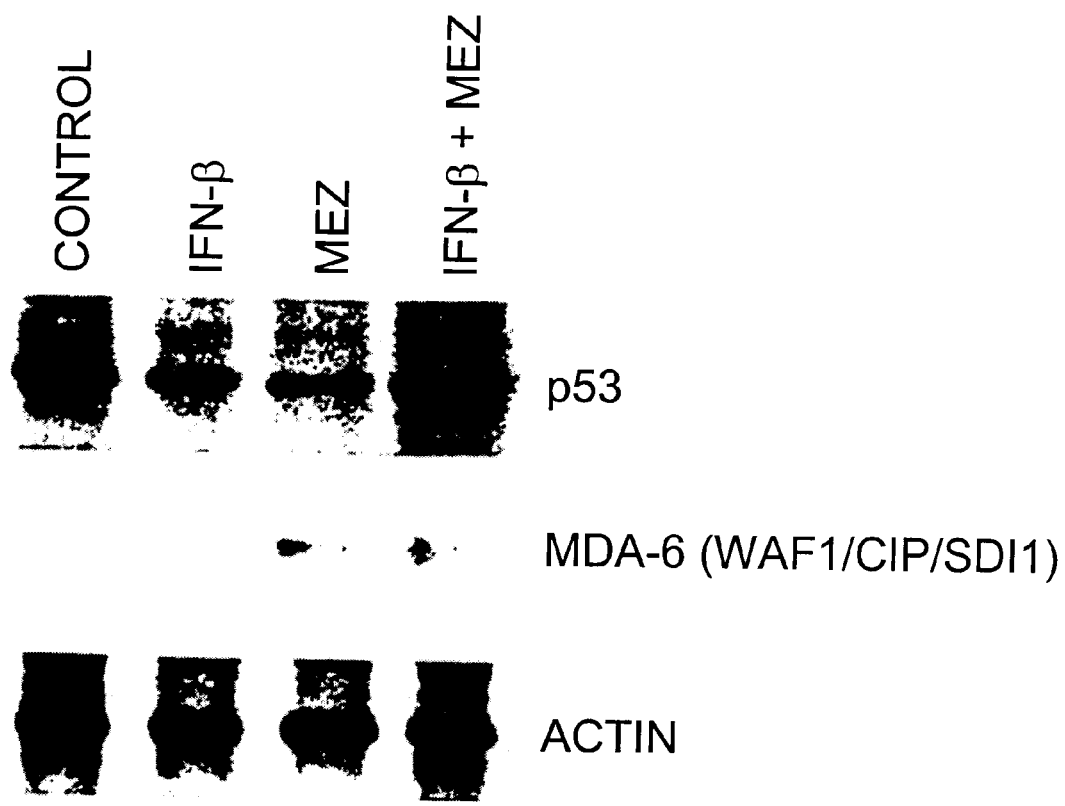
FIG. 33 Effect of 24 h treatment of H0-1 cells with IFN-β, MEZ and IFN-β+MEZ on p53 and p21 levels. Lysates from untreated (control) and H0-1 cells treated with IFN-β (2000 units/ml), MEZ (10 ng/ml) or IFN-β+MEZ (2000 units/ml+10 ng/ml) for 24 h were immunoprecipitated with p53 monoclonal antibody Ab1 (PAb421), p21 (WAF1/CIP1) polyclonal antibody or an actin monoclonal antibody as described in Materials and methods in the seventh series of experiments.
Figure 34:
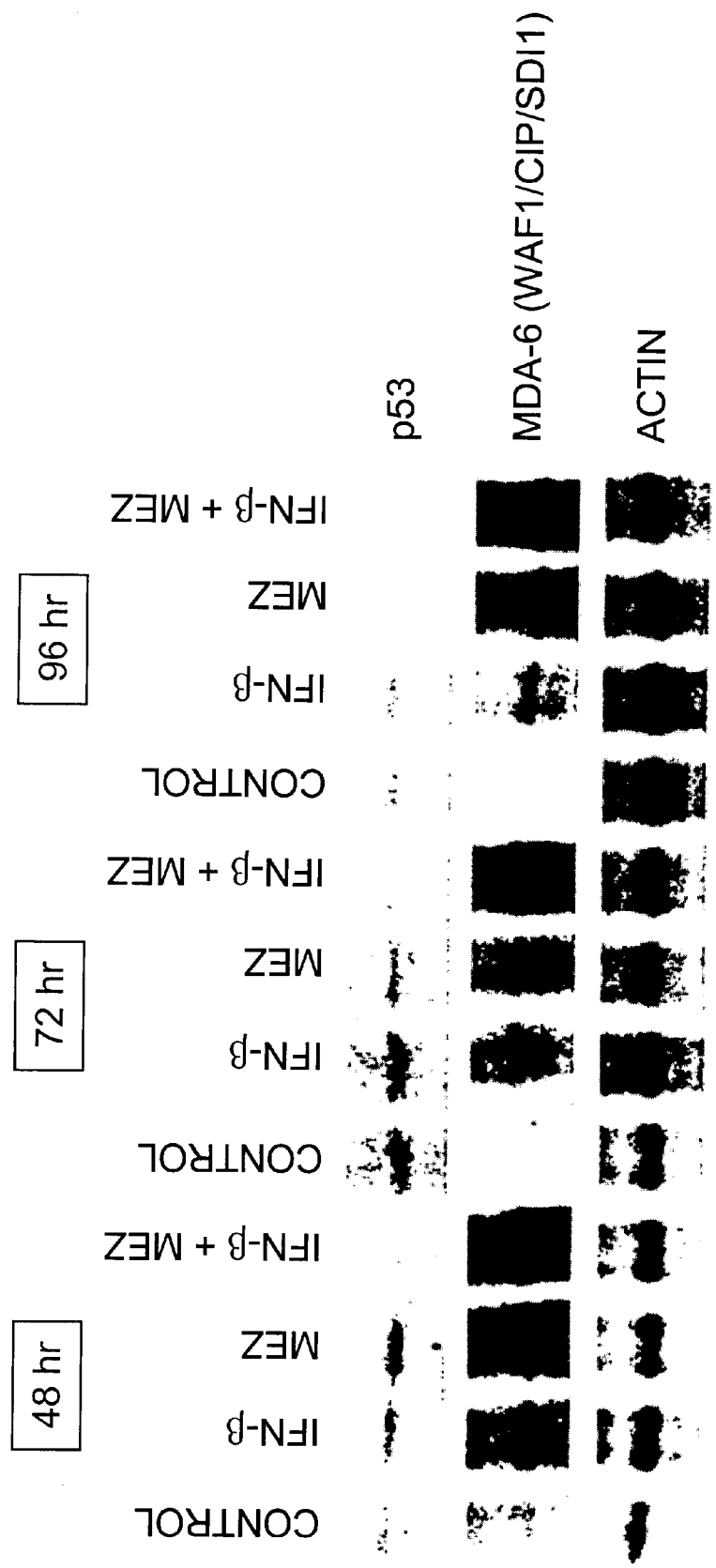
FIG. 34 Expression of p53 and p21 as a function of growth arrest and terminal differentiation in H0-1 cells. Lysates from untreated (control) and H0-1 cells treated with IFN-β (2000 units/ml), MEZ (10 ng/ml) or IFN-β+MEZ (2000 units/ml+10 ng/ml) for 48, 72 and 96 h were immunoprecipitated with p53 monoclonal antibody Ab1 (PAb421), p21 (WAF1/CIP1) polyclonal antibody or an actin monoclonal antibody as described in Materials and methods in the seventh series of experiments.

To determine the effect of the various inducing agents on p53 and p21 protein levels the following experiment was performed. H0-1 cells were grown in inducer-free medium (control), IFN-β (2000 units/ml), MEZ (10 ng/ml) or IFN-β+MEZ (2000 units/ml+10 ng/ml) for 24, 48, 72 or 96 h, cells were labeled with $^{35}$S-methionine and cell lysates were prepared and analyzed by immunoprecipitation analyses using Ab1 (PAb421), p21 (WAF1/CIP1, Santa Cruz Biotechnology; and rabbit polyclonal antibodies prepared against mda-6 peptides) and actin (Oncogene Sciences Inc.) (FIGS. 33 and 34). As observed with mRNA levels, no significant change in wild-type p53 protein occurs in H0-1 cells treated for 24 h with IFN-β, MEZ or IFN-β+MEZ (FIG. 33). In contrast, p21 mRNA and protein are induced in H0-1 cells, with IFN-β+MEZ>MEZ>IFN-β (FIGS. 31A–E and 33). As seen with mRNA levels, the concentration of wild-type p53 protein decreases and p21 protein increases over a 96 h period in MEZ and IFN-β+MEZ treated H0-1 cells (FIG. 34). Increases in p21 protein are also seen in H0-1 cells treated with IFN-β for 48, 72 or 96 h, whereas no change in wild-type p53 protein occurs over the same period in similarly treated cells (FIG. 34). These results indicate that induction of p21 can occur without increases in wild-type p53 protein (IFN-β treated cells) and elevated levels of p21 under conditions of residual growth arrest and/or terminal differentiation correlate with a reduction in wild-type p53 protein in H0-1 melanoma cells.

Figure 35:
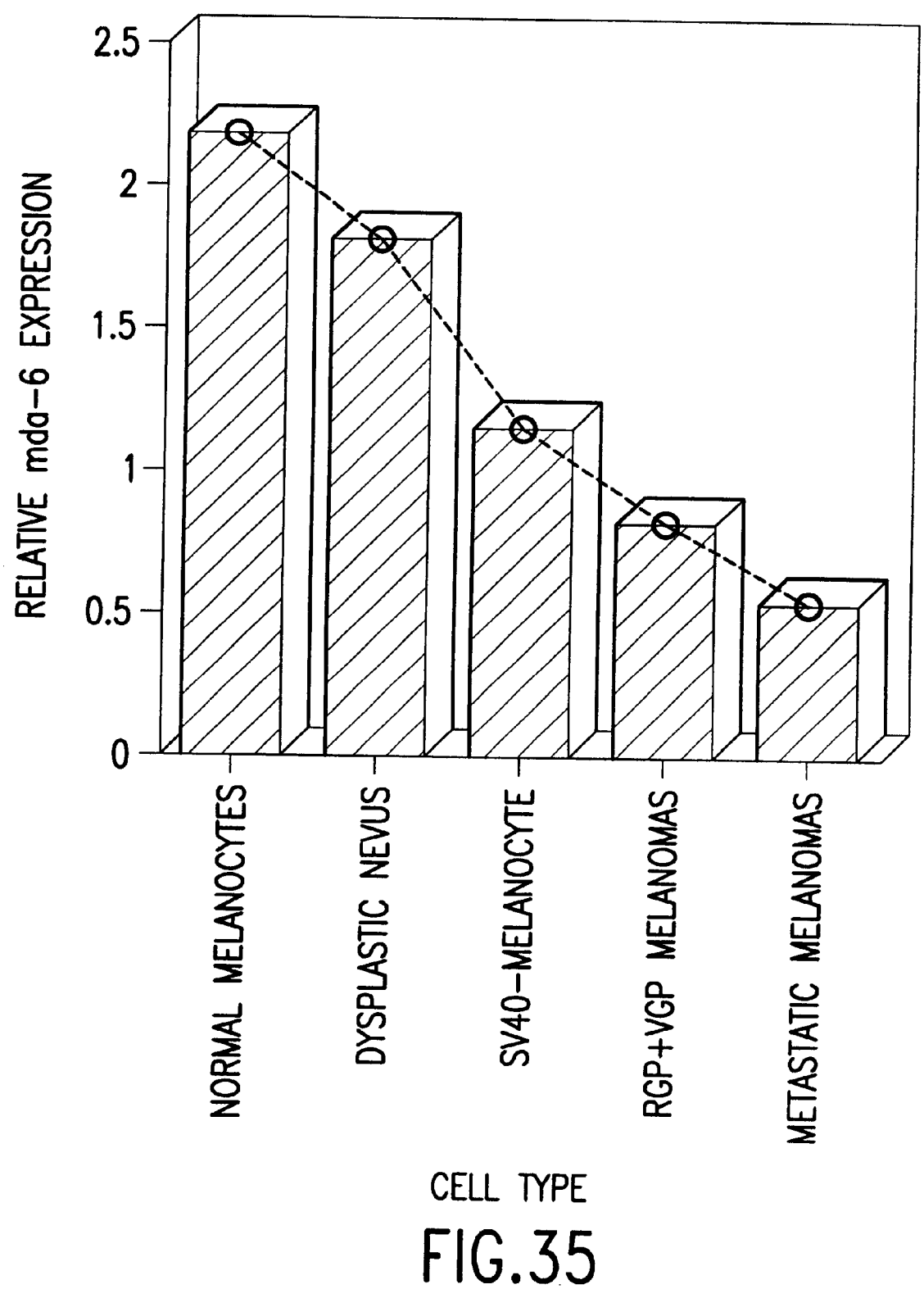
FIG. 35 Relative expression of mda-6 during melanoma progression. The level of mda-6 relative to GAPDH was determined by quantitative (comparative) RT-PCR in actively growing cells. RGP: radial growth phase primary melanoma. VGP: vertical growth phase primary melanoma. Results represent average for: 5 melanocyte cultures, one dysplastic nevus culture, one SV40-transformed immortalized melanocyte culture, one RGP and four early VGP primary melanomas and six metastatic melanomas.

Inverse Relationship Between mda-6 Expression and Evolution from Normal Melanocyte to Metastatic Melanoma A prediction of applicants' melanoma aberrant differentiation model is that normal melanocytes should express elevated levels of specific mda genes with progressively less expression in primary and metastatic melanoma cells. As shown in FIG. 32, the level of mda-6 is higher in an actively growing low-density SV40-transformed human melanocyte culture (FM516-SV) than in corresponding high-density proliferating human melanoma cells. The level of mda-6 is variably increased in all of the melanomas treated with IFN-β+MEZ (FIG. 32). Induction of mda-6 occurs in logarithmically growing FM516-SV cells treated with IFN-β+MEZ. However, only the melanoma cells become terminally differentiated following growth for 96 h in IFN-β+MEZ (data not shown). To evaluate mda-6 levels as a function of melanoma evolution, mda-6 and GAPDH (internal RNA expression standard) levels were determined by comparative RT-PCR in actively growing melanocytes (5 samples), a dysplastic nevus (1 sample), an SV40-transformed immortalized melanocyte culture (1 sample), RGP (1 sample) and early VGP (4 samples) primary melanomas and metastatic melanomas (6 samples) (FIG. 35). The highest levels of mda-6 are found in actively growing melanocytes and the dysplastic nevus and the lowest relative levels of mda-6 are present in primary and metastatic melanomas. The difference in relative mda-6 expression (as a function of GAPDH expression) determined by comparative RT-PCR indicates that actively growing normal melanocytes express on average >4-fold more mda-6 than actively growing metastatic melanoma cells (P<0.01). These results suggest an inverse correlation between levels of mda-6 expression and human melanoma evolution.

Figure 36:
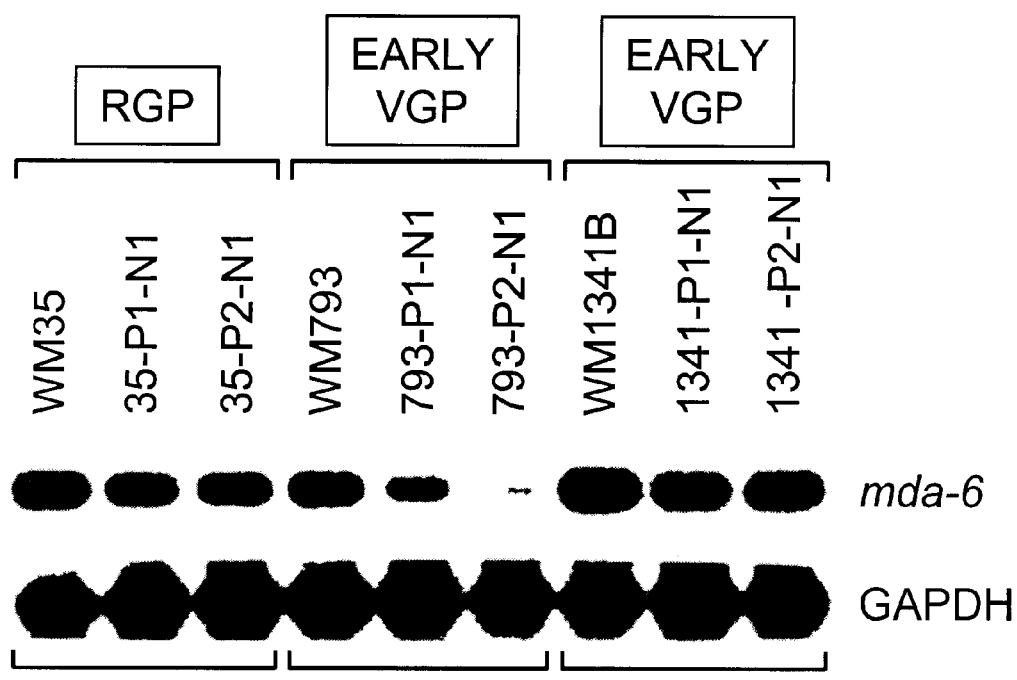
FIG. 36 Expression of mda-6 (p21) as a function of Matrigel-mediated progression in primary human melanomas. The level of mda-6 and GAPDH was determined by RT-PCR for the indicated actively proliferating cell lines. P1 and P2 refers to the first and second passage, respectively, through nude mice of RGP or early VGP melanoma cells in combination with Matrigel.

Reduced Expression of mda-6 in Matrigel-progressed Primary Human Melanoma Cultures The ability to study human melanoma progression by comparison of sequentially obtained cell lines established from the same patient is very limited since removal of the vast majority of RGP or thin VGP primary melanomas results in cure (Herlyn, 1990; Kerbel, 1990; Clark, 1991). Consequently, the derivation of genetically related variants from such tumors that express a biologically more aggressive phenotype must be obtained under experimental selections. One such method is "Matrigel-assisted" tumorigenic growth (Kobayashi et al., 1994). For example, the early stage primary melanoma cell lines known as WM35, WM1341B and WM793 are non or poorly tumorigenic in nude mice in comparison to the great majority of advanced stage human melanomas (Kobayashi et al., 1994). However, co-injection of the early stage cell lines with Matrigel, a reconstituted basement membrane extract permits rapid tumor growth in nude mice and the derivation of sublines that will readily grow as solid tumors in secondary nude mouse recipients, even in the absence of Matrigel co-injection (Kobayashi et al., 1994). These tumorigenic Matrigel progressed sublines can be compared to the non/poorly tumorigenic parental cell lines for various properties such as relative mda-6 expression. As shown in FIG. 36, the level of mda-6 as determined by RT-PCR in Matrigel progressed sublines of WM35, WM1341B and WM793 are variably reduced in comparison with the original patient-derived cell lines. The relative degree of suppression in mda-6 is greatest in the WM793 series, that also display a more progressed phenotype as indicated by a low-level of de novo tumorigenic potential in nude mice in the absence of Matrigel (Kobayashi et al., 1994). The smallest reduction in expression occurs in the Matrigel-progressed WM35 RGP primary melanoma cells (FIG. 36). Treatment of parental and Matrigel-progressed RGP and early VGP melanomas with IFN-β+MEZ results in increased mda-6 expression (determined by Northern blotting) and growth suppression (data not shown). These observations provide further support for an inverse relationship between mda-6 expression and human melanoma progression and melanoma growth.

Increased Expression of mda-6 in C8161 Cells Containing a Normal Human Chromosome 6

Figure 37:
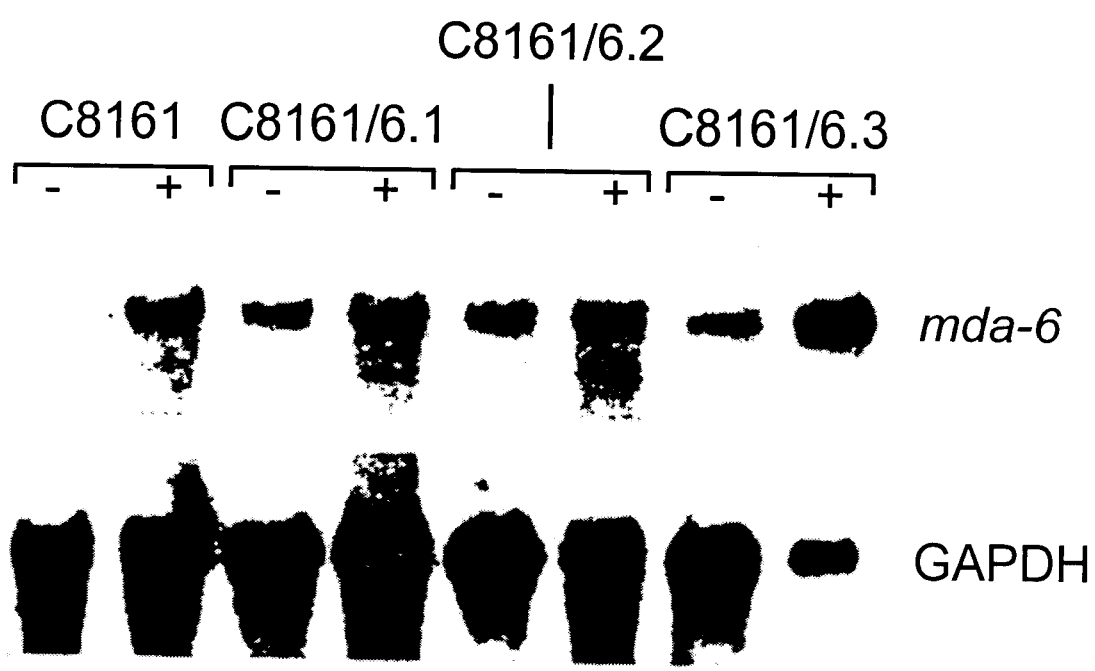
FIG. 37 Northern blot analysis of mda-6 (p21) expression in C8161 human melanoma and chromosome 6 containing C8161 human melanoma subclones. Levels of mda-6 and GAPDH mRNAs were determined in actively growing untreated cells (−) and cells treated for 96 hr with IFN-β+MEZ (1000 units/ml+10 ng/ml) as described (Jiang & Fisher, 1993; Jiang et al., 1994a).
Figure 39:
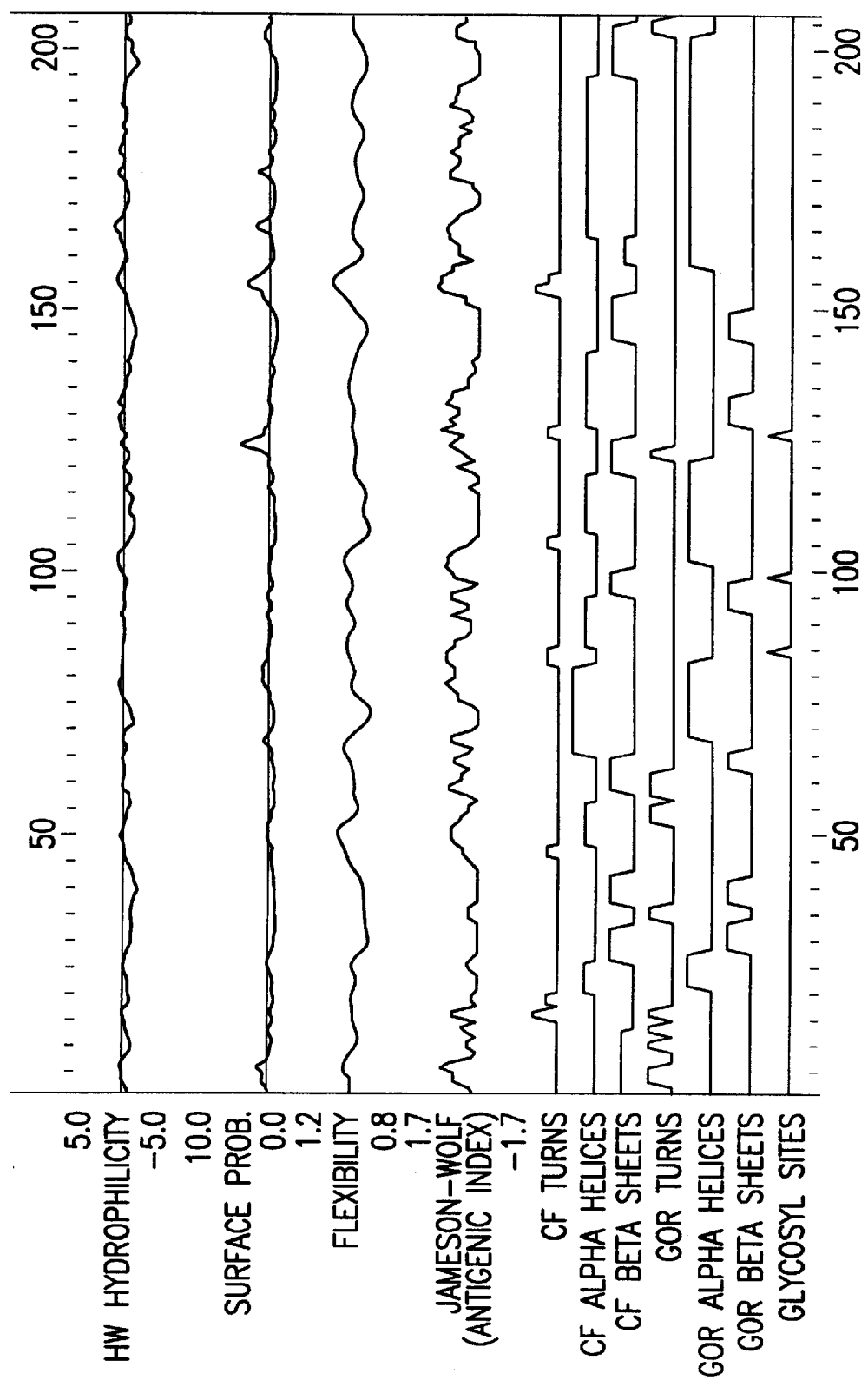
FIG. 39 Properties and structure of the mda-7 encoded gene product as predicted by GCG/Plotstructure program.
Figure 40:
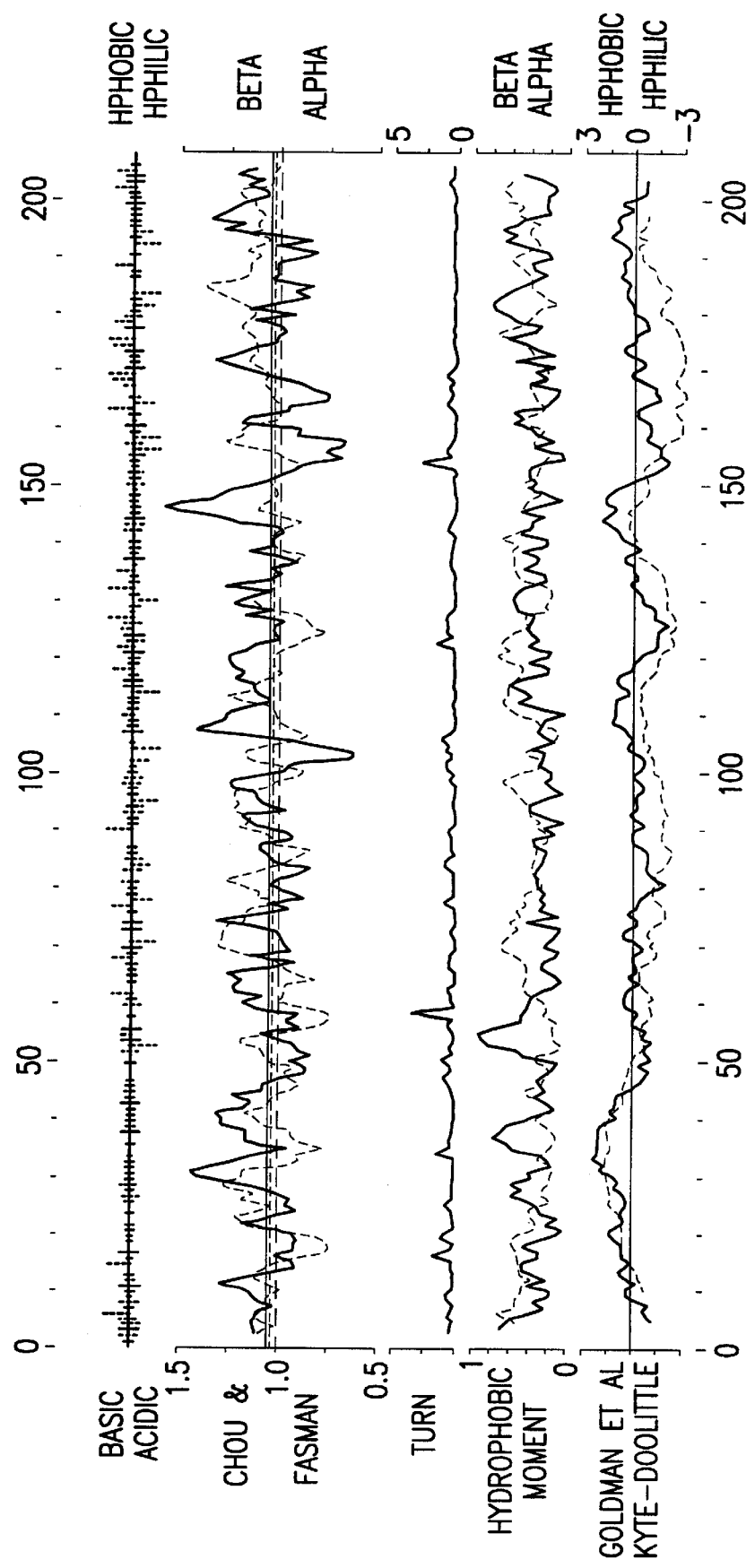
FIG. 40 Hydrophobic analysis and structural predictions of the mda-7 encoded gene product by GCG/Pepplot program. A potential transmembrane domain is predicted using this program.
Figure 41:
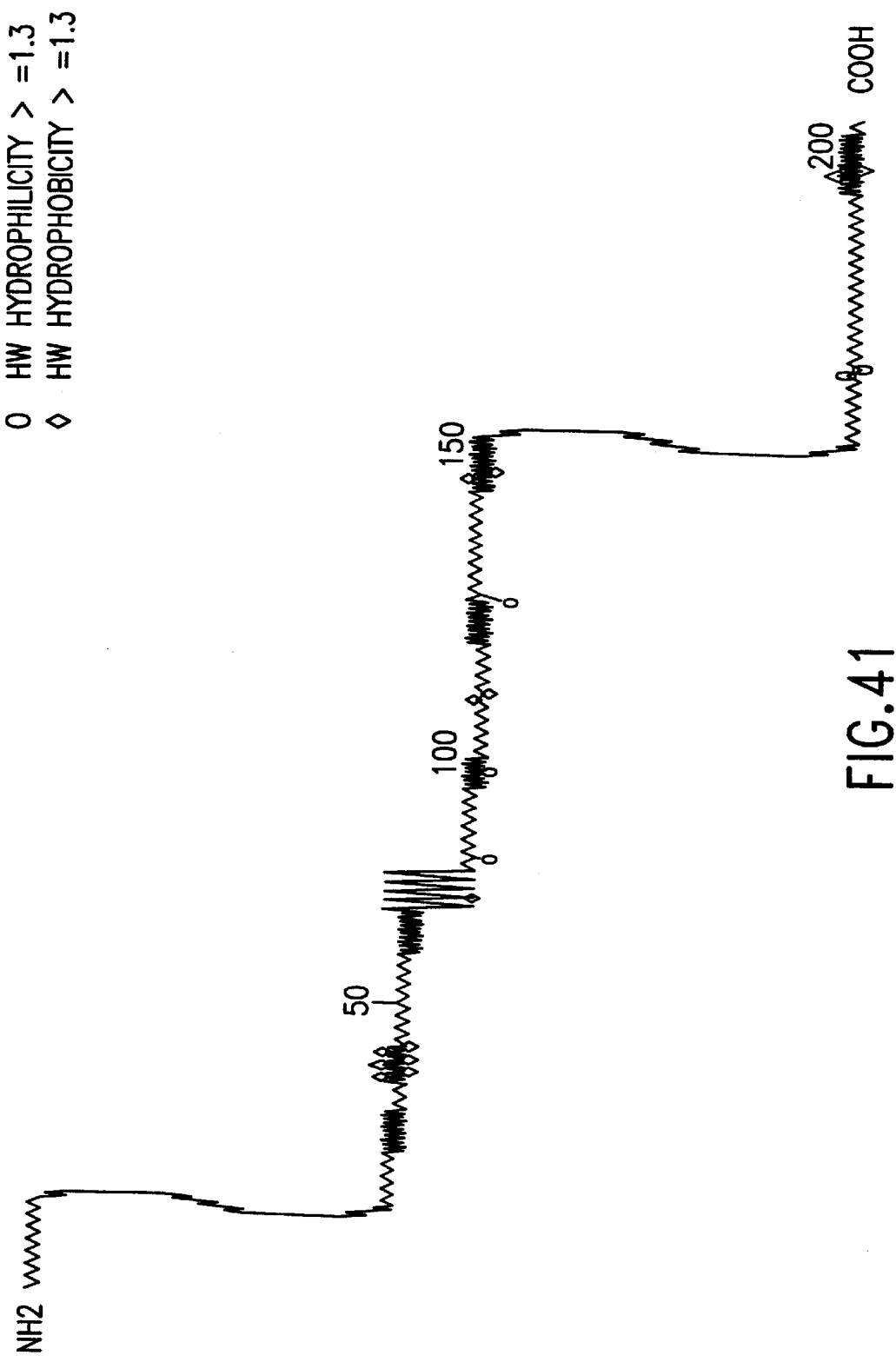
FIG. 41 Structure of mda-7 encoded gene produce as predicted by the Chou-Fosman method.
Figure 42:
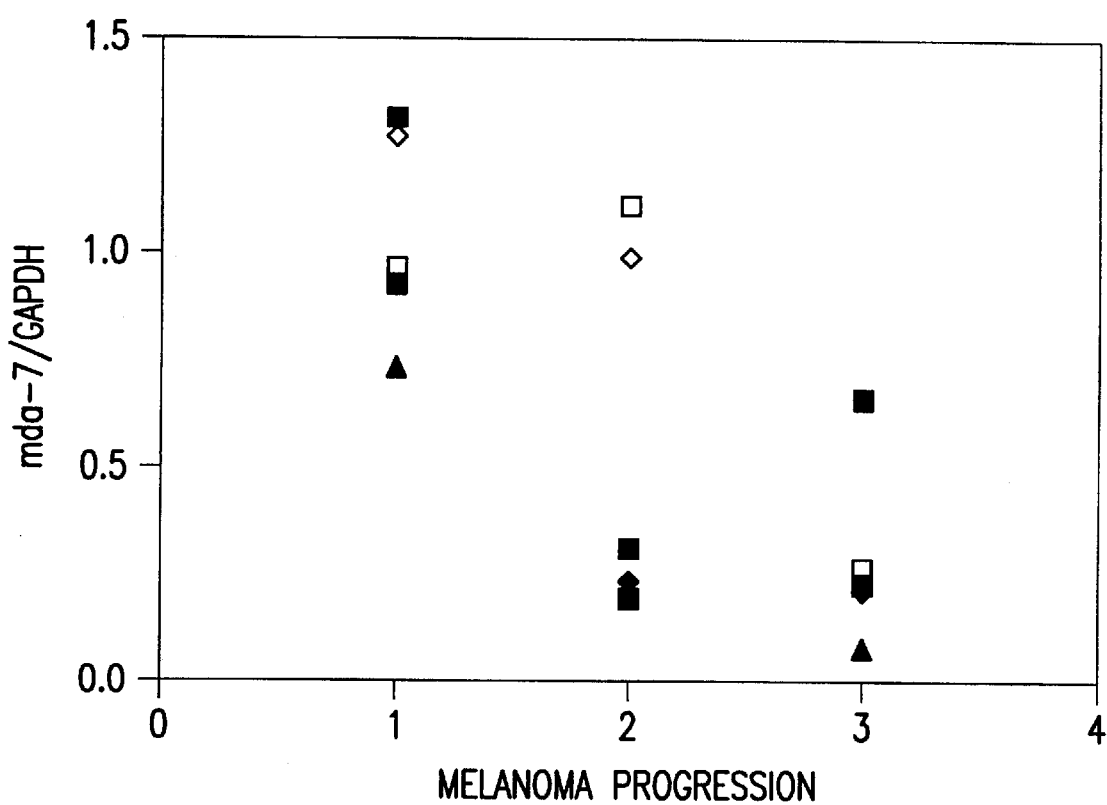
FIG. 42 Relative expression of mda-7 during melanoma progression. The level of mda-7 relative to GAPDH was determined quantitative (comparative) RT-PCR in actively growing cells. The cell lines examined were (1) normal melanocytes; (2) primary melanoma cells, including RGP and VGP cells; and (3) metastatic melanoma cells.
Figure 43:
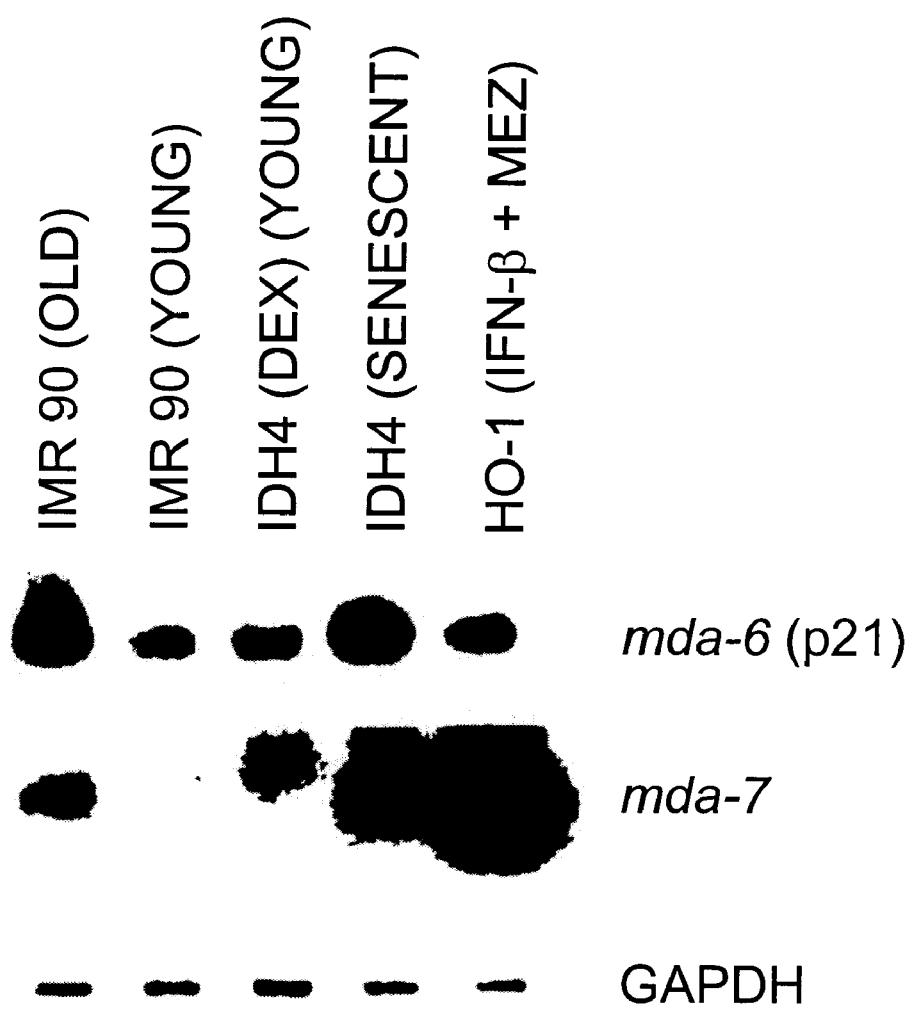
FIG. 43 Expression of mda-6 and mda-7 as a function of aging and senescence in human fibroblast cells. IMR90 cells analyzed at late passage (OLD) versus early passage (YOUNG). IDH4 cells are IMR90 cells immortalized by an SV40 T-antigen (transcriptionally controlled by a dexamethasone (DEX) inducible mouse mammary tumor virus promoter). Growth of IDH4 cells in DEX results in active growth and expression of an immortalized phenotype (a YOUNG IMR90 phenotype). In contrast, removal of DEX results in a shutdown of the T-antigen and loss of proliferative capacity and senescence (SENESCENT). RNA was extracted from the four cell lines and analyzed by reverse transcription-polymerase chain reaction (RT-PCR) using primer sequences specific for mda-6, mda-7 or GAPDH. As a control for expression of these genes, RNA from H0-1 human melanoma cells treated with IFN-β+MEZ (2000 units/ml+10 ng/ml) for 96 hr was used. H0-1 cells under these conditions are irreversibly growth arrested and terminally differentiated.

Insertion of a normal human chromosome 6 into tumorigenic and metastatic C8161 human melanoma cells results in an extinction of the metastatic phenotype with a retention of tumorigenic potential (Table 5) (Welch et al., 1994). These results suggest that chromosome 6 contains a suppressor gene that can revert C8161 cells to a less-progressed stage in melanoma evolution (Welch et al., 1994). If mda-6 expression correlates directly with states of melanoma progression, it would be predicted that actively growing C8161 cells should produce lower levels of mda-6 than actively growing chromosome 6 containing C8161 cells. As anticipated, expression of mda-6 increases in three independently derived chromosome 6 containing C8161 cells (FIG. 37). In addition, treatment of C8161 and neo6/C8161 hybrid clones with IFN-β+MEZ for 96 hr results in growth suppression (Table 5) and increased mda-6 mRNA expression (FIG. 37). These observations indicate a direct relationship between growth suppression and metastatic suppression in human melanoma cells and elevated expression of mda-6 (p21).

TABLE 5

Properties of human melanoma cells containing a microcell-transferred chromosome 6

| Cell Types[1] | Tumorigenicity[2] | Metastasis[3] |
|---|---|---|
| C8161 | + | + |
| C8161/6.1 (neo6/C8161.1) | + | − |
| C8161/6.2 (neo6/C8161.2) | + | − |
| C8161/6.3 (neo6/C8161.3) | + | − |

| Cell Types[1] | nm23[4] | mda-6[5] | % growth inhibition[6] |
|---|---|---|---|
| C8161 | +/− | +/− | 92 |
| C8161/6.1 (neo6/C8161.1) | +++ | +++ | 67 |
| C8161/6.2 (neo6/C8161.2) | + to ++ | +++ | 86 |
| C8161/6.3 (neo6/C8161.3) | ++ | ++ | 89 |

[1]A neomycin-tagged normal human chromosome 6 was transferred into C8161 by microcell-mediated chromosome transfer as previously described (Welch et al., 1994). Retention of chromosome 6 in cell lines and tumor tissue was verified using PCR-RFLP with D6S87 and D6S37.
[2]Tumorigenicity was determined by injection of $1 \times 10^6$ to $1 \times 10^7$ cells subcutaneously or intradermally into the dorsolateral flank of 3-1/2 to 4-week old, female athymic nude mice (Harlan Sprague Dawley). +, palpable tumors form within 2 weeks after injection.
[3]Development of lung metastases following s.c., i.d. ($1 \times 10^6$ cells) or i.v. ($1 \times 10^6$ cells) injection of tumor cells. Spontaneous metastases were evaluated in the same mice in which tumorigenicity was assessed. At necropsy all organs were examined for grossly visible nodules. Lack of metastases was verified by histologic analysis of randomly submitted samples. Experimental metastases was measured in mice receiving a single cell suspension of viable cells into the lateral tail vein.
[4]Expression of nm23-H1 determined using Northern blot of total RNA (10–20 μg) using the 0.9 kb fragment of nm23-H1 (Welch et al., 1994).
[5]Expression of mda-6/WAF1/CIP1 determined using Northern blot of total RNA (15 μg) using the mda-6 cDNA insert (Jiang & Fisher, 1993).
[6]Cell growth was determined by counting cells following 96 hr continuous treatment with IFN-β (1000 units/ml) + MEZ (10 ng/ml). Results are the average percent growth inhibition verus untreated control cultures for triplicate plates that varied by ≦10% (Jiang et al., 1993).

Experimental Discussion

The specific genomic changes that mediate melanoma development and progression remain to be elucidated (Herlyn, 1990; Kerbel, 1990; Clark, 1991). To directly approach this question and to begin to identify and clone genes involved in growth control and differentiation in human melanoma cells applicants have used subtraction hybridization (Jiang & Fisher, 1993; Jiang et al., 1994a). cDNA libraries were constructed from untreated H0-1 human melanoma cells and these cDNAs were subtracted from cDNA libraries prepared from H0-1 cells treated with the combination of IFN-β plus MEZ that induces an irreversible loss of proliferative ability and terminal differentiation (Fisher et al., 1985; Jiang & Fisher, 1993; Jiang et al., 1993, 1994a). This approach has resulted in the identification of several novel mda cDNA clones that display enhanced expression as a function of growth suppression and induction of terminal differentiation in human melanoma cells (Jiang & Fisher, 1993; Jiang et al., 1994a). In the present study applicants have analyzed mda-6 (Jiang & Fisher, 1993; Jiang et al., 1994a), whose open reading frame sequence (FIG. 30) is identical to the genes WAF1, CIP1 and SDI1 (El-Deiry et al., 1993; Harper et al., 1993; Noda et al., 1994). WAF1 was cloned using a strategy designed to identify inducible down-stream genes that are directly controlled by and might mediate the growth suppressing activity of the tumor suppressor gene p53 (El-Deiry et al., 1993). Introduction of WAF1 cDNA into human brain, lung and colon tumor cell cultures results in growth suppression (El-Deiry et al., 1993). In addition, WAF1 is induced by DNA damage in wild-type p53-containing cells and during the process of p53-associated $G_1$ arrest or apoptosis (El-Deiry et al., 1994). CIP1 was identified using an improved two-hybrid system and encodes a 21-kDa product that is a potent inhibitor of cyclin-dependent kinases (Harper et al., 1993). CIP1 induces growth suppression in normal diploid fibroblasts but only marginally inhibits growth in SV40-transformed diploid fibroblasts (Harper et al., 1993). SDI1 was identified and cloned from senescent human fibroblasts using an expression screening strategy designed to detect cDNAs that could prevent young fibroblasts from initiating DNA synthesis (Noda et al., 1994). The current studies indicate that mda-6 (WAF1/CIP1/SDI1) expression is also related to growth regulation in human melanoma cells and its reduced expression may contribute to the progressive changes observed in the evolution of melanocytes into metastatic melanomas.

Cancer is a progressive disease often affected by the altered expression of oncogenes that promote the cancer phenotype and tumor suppressor genes that inhibit the cancer phenotype (for review see: Fisher, 1984; Bishop, 1991; Vogelstein & Kinzler, 1992; Lane, 1992). Recent evidence indicates that the tumor suppressor gene p53 is a major component in the carcinogenic process (for review see: Vogelstein & Kinzler, 1992; Lane, 1992; Greenblatt et al., 1994). Inactivation of wild type p53 or expression of a mutant p53 phenotype has been found in a large number of human cancer subtypes (for review see: Vogelstein & Kinzler, 1992; Lane, 1992; Greenblatt et al., 1994). Intensive effort has been directed toward elucidating the mechanism by which wild type p53 regulates cell growth and prevents expression of the tumorigenic phenotype and the process by which p53 inactivation or mutagenic changes promote these processes. In this context, the identification of genes positively controlled by wild type p53, such as WAF1/CIP1, may prove important in defining the mechanism of action of this critical tumor suppressor gene and provide information about the process of tumor progression.

Metastatic human melanomas appear to be unique among human cancers in their low frequency of p53 mutations and the prevalence of wild-type p53 protein in advanced cancers (Volkenandt et al., 1991; Castresana et al., 1993; Greenblatt et al., 1994; Montano et al., 1994; Lu & Kerbel, 1994). Studies by Loganzo et al. (1994) show that metastatic melanoma cells contain two- to 20-fold more p53 protein, in the majority of samples representing wild-type p53, than do melanocytes. Similarly, a large proportion of the human melanoma cell lines presently analyzed also contain wild-type p53 protein. In normal melanocytes, the level of mda-6 (p21) is higher than in metastatic melanomas, even though metastatic melanoma may contain more p53 (FIG. 35) (Loganzo et al., 1994). The increased level of p53 protein in melanoma cells appears to be a consequence of stabilization of the protein, i.e., the half-life is two- to five-fold greater than in melanocytes, irrespective of whether they contain wild-type or mutant-p53 (Loganzo et al., 1994). The stabilization of wt p53 protein in human melanoma cells does not result from the binding of this protein to either MDM2 or heat shock protein (Loganzo et al., 1994). The mechanism underlying this stabilization of wild-type p53 in metastatic melanomas is not presently known, but it might reflect a defective regulation of p53 that could allow these tumor cells to escape cell cycle arrest even in the presence of elevated p53. In fact, disturbances in p53 expression are a common occurrence in human melanomas and these abnormalities increase with progression (for review see: Lu & Kerbel, 1994). These findings suggest that melanoma may represent a novel malignancy, in that it can coexist and evolve to more aggressive stages even in the presence of elevated levels of nuclear localized wt p53 protein. However, it is also possible that the wild-type p53 protein in metastatic human melanoma cells is functionally inactive (perhaps by interacting with other melanoma proteins) or the wild-type p53 protein is normal, i.e., can both bind and transcriptionally activate target genes, but the downstream genes normally responsive to wild-type p53 are defective in metastatic human melanoma. The inability of wild-type p53 to elevate mda-6 levels in metastatic melanoma, and consequently to induce proliferative control, could directly contribute to the increased instability of the evolving and progressing melanoma (Livingstone et al., 1992; Yin et al., 1992; Lu & Kerbel, 1994).

In human melanoma, mda-6 is induced rapidly (within 15 min) and remains elevated following serum starvation as well as remaining elevated during terminal differentiation (FIGS. 31A–E). In contrast, glioblastoma multiforme cells blocked in $G_0$ by serum starvation or blocked in $G_1$ by mimosine treatment do not display increased levels of wild-type p53 or WAF1/CIP1 (El-Deiry et al., 1994). Induction of apoptosis after IL3 withdrawal, which also does not increase wild-type p53 levels, and DNA damage of cells containing a mutant p53 does not result in elevated levels of WAF1/CIP1 (El-Deiry et al., 1994). Recent studies suggest that wild-type p53 may not be obligatory for induction of WAF1/CIP1 (p21). Michieli et al. (1994) document a transient induction of WAF1/CIP1 following stimulation of growth arrested cells either containing or lacking wild-type p53 (fibroblasts from p53 knock out mice lacking p53 protein) with various growth factors. Jiang et al. (1994b) demonstrate that treatment of human promyelocytic leukemia HL-60 cells, which do not express p53, with agents inducing either granulocytic or macrophage/monocyte differentiation results in the rapid activation and persistent expression of mda-6 (p21). Steinman et al. (1994) also provide evidence that p21 is upregulated during induction of differentiation in a number of cell types, including hematopoietic and hepatoma cells, in a p53-independent pathway. All three of these studies also provide evidence that p21 is an immediate early response gene that is induced in the absence of protein synthesis.

The present study provides additional evidence indicating that induction of p21 expression is independent of wild-type p53 expression in human melanoma cells. An interesting, yet somewhat paradoxical observation, is the temporal decrease in wild-type p53 protein with a corresponding increase in p21 protein during the process of growth arrest and induction of terminal differentiation in H0-1 melanoma cells (FIG. 34). In a number of cell culture model systems, p53 mRNA decreases as a function of growth suppression and the induction of differentiation (Shen et al., 1983; Mercer et al., 1984; Dony et al., 1985; Shobat et al., 1987; Khochbin et al., 1988; Richon et al., 1989; Hayes et al., 1991). Wild type p53 displays sequence-specific DNA-binding activity, sequence-specific transcriptional activation and induces growth suppression in a number of cell types, whereas all of these properties are lost in various mutant forms of the p53 protein (Ron, 1994; Pietenpol et al., 1994). The reduced levels of mda-6 (p21) in actively growing melanoma, even in the presence of high levels of wild type p53, and the elevations in p21 levels following wild type p53 suppression suggest that high levels of p21 expression may not be compatible with high levels of wild type p53 in human melanoma. This may occur because wild type p53 is inducing a downstream gene that may directly or indirectly modify p21 expression. The induction of growth arrest and terminal differentiation program by IFN-β+MEZ in H0-1 cells may result in genotypic changes that mediate an inhibition of wild type p53 expression and consequently the absence of the downstream inhibitor of p21 expression. Alternatively, the wild type p53 protein that is present in metastatic melanoma may be functionally inactive or a downstream pathway modified by wild type p53 may be aberrant in progressing melanoma cells. In this context, the inverse relationship observed between wild type p53 and p21 protein levels may be associated with but not functionally relevant to growth arrest and terminal differentiation induced by MEZ and IFN-β+MEZ.

In the present study applicants have not directly assayed for the effect of mda-6 on progression in human melanoma. However, experiments utilizing chromosome 6 containing C8161 cells provide indirect evidence that mda-6 (WAF1/CIP1/SDI1), which is located on chromosome 6p21.2 (El-Deiry et al., 1993), can directly modulate in vivo tumor growth and metastatic progression in human melanoma cells. Transfer of a normal chromosome 6 into the human melanoma cell lines UACC-903 and UACC-091 results in a suppression of tumorigenicity (Trent et al., 1990; Milikin et al., 1991), whereas microcell transfer of a normal chromosome 6 into the tumorigenic and metastatic human melanoma cell line C8161 results in a suppression of metastasis but a retention of tumorigenic potential (Welch et al., 1994). C8161 microcell hybrids (neo6/C8161) also display a small but significant increase in tumor latency time and have slower tumor growth rates in vivo than parental C8161 cells (Welch et al., 1994). However, even 30 additional weeks in animals does not result in metastatic lesions in mice injected with any of the three independent neo6/C8161 hybrids (Welch et al., 1994). In the present study, applicants demonstrate that C8161 cells contain lower levels of mda-6 than three neo6/C8161 hybrids. Treatment with the combination of IFN-β+MEZ results in enhanced expression of mda-6 and growth suppression in parental C8161 and all three neo6/C8161 hybrid clones. These results strongly implicate mda-6 as a potential mediator of growth control and metastatic progression in human melanoma cells. mda-6 has now been cloned into the pMAMneo vector, that allows inducible expression of the inserted gene by dexamethasone (DEX) and which also contains a neomycin resistance gene permitting clonal isolation in G418 in the absence of mda-6 expression (Jiang et al., in preparation). Electroporation of this gene into C8161 cells has resulted in the isolation of G418-resistant cultures containing the pMAMneo-mda-6 construct. When grown in the presence of DEX, mda-6 expression is induced and growth is inhibited, whereas no growth suppression or mda-6 expression occurs in the absence of DEX (Jiang et al., in preparation). These genetically modified C8161 cells, and melanoma cells containing an inducible antisense mda-6 gene, will prove useful in directly determining the effect of mda-6 expression on melanoma growth, differentiation and tumor progression.

Recent studies indicate that p21, the protein encoded by mda-6 (WAF1/CIP1/SDI1), is a major contributor to many important cellular processes, including cell cycle regulation, cell growth, DNA repair and DNA replication (Xiong et al., 1992, 1993a, 1993b; Gu et al., 1993; Harper et al., 1993; El-Deiry et al., 1993, 1994; Waga et al., 1994; Li et al., 1994). p21 is a ubiquitous inhibitor of all cyclin-dependent kinases (Xiong et al., 1993b). The levels of p21 vary depending on the specific stage of the cell cycle and the interaction between p21 and specific cyclin-CDK enzymes appears to occur when these enzymes function in cell cycle control (Li et al., 1994). In the present study applicants demonstrate that mda-6 (WAF1/CIP1/SDI1) expression inversely correlates with growth, differentiation and progression in human melanoma cells. These observations suggest that p21, that is encoded by mda-6, can affect cellular differentiation and neoplastic progression in human melanoma cells. The relative levels of mda-6 are higher in growing human melanocyte and nevus cell lines than in RGP, VGP and metastatic melanomas, suggesting the possibility that expression of this suppressor protein may negatively regulate tumor progression. This possibility is supported by the observation that mda-6 expression decreases in Matrigel-progressed early VGP melanomas and mda-6 expression increases in chromosome 6 metastasis-suppressed C8161 melanoma cells. A direct relationship between mda-6 expression and melanoma growth and differentiation is indicated by the ability of IFN-β+MEZ to induce growth suppression and with continuous exposure terminal differentiation in human melanoma cells. Apparently, increased levels of mda-6 can be tolerated by human melanoma cells resulting in or correlating with growth arrest. However, the persistence of elevated levels of p21 in terminally differentiated human melanoma cells may be necessary to prevent cells from reentering the cell cycle, a mandatory requirement for terminal cell differentiation. In this context, identification of agent(s) that can increase mda-6 (WAF1/CIP1/SDI1) expression in metastatic human melanoma cells may prove beneficial in the therapy of this malignancy by directly inducing an irreversible loss of proliferative capacity and terminal cell differentiation.

Materials and Methods

Cell Lines and Culture Conditions

H0-1 melanoma cells were established from a melanotic melanoma obtained from a 49-year-old female and were used between passage 125 and 160 (Fisher et al., 1985, 1986; Giovanella et al., 1976). FM516-SV is a normal human melanocyte culture immortalized by the SV40 T-antigen gene (Melber et al., 1989). Normal human melanocytes, FM713, FM723, FM741, FM841 and FM793, and a dysplastic nevus, N3153, were established from patients as described previously (Mancianti et al., 1988). WM35 was derived from an RGP primary human melanoma and WM278, WM1341B, WM793 and WM902B were derived from early VGP primary human melanomas (Herlyn, 1990; Herlyn et al., 1989). WM Matrigel progressed WM35, WM1341B and WM793 cells, referred to as P1-N1 and P2-N1 that indicates first and second passage through nude mice injected with the appropriate cell type plus Matrigel, were developed as described (MacDougall et al., 1993; Kobayashi et al., 1994). C8161 is a highly metastatic amelanotic human melanoma cell line derived from an abdominal wall metastasis (Welch et al., 1991). C8161 clones containing a normal human chromosome 6, designated C8161/6.1 (neo6/C8161.1), C8161/6.2 (neo6/

C8161.2) and C8161/6.3 (neo6/C8161.3), were established as described (Welch et al., 1994). Additional human melanoma cell lines isolated from patients with metastatic melanomas included F0-1, L0-1, SH-1, WM239 and WM239A (Giovanella et al., 1976; Fisher et al., 1985; Herlyn et al., 1989; Herlyn, 1990). Media and culture conditions used to grow the various cell types are described in the indicated references.

Cell Growth and Terminal Cell Differentiation Assays

Cell growth and terminal differentiation assays were performed as described previously (Fisher et al., 1985, 1986; Jiang et al., 1993). Induction of terminal cell differentiation following 96 h growth in IFN-β+MEZ was monitored by an irreversible loss of proliferative potential without a loss of cell viability (Fisher et al., 1985, 1986; Jiang et al., 1993). Briefly, cells were grown for 96 h in the presence of the various inducing agents, the inducers were removed and cultures were washed 3× in medium without serum followed by the addition of inducer-free medium. Cultures were incubated for an additional 3, 6 and 10 d with a medium change without inducers every 3 d. Cell numbers were determined at d 4, 7, 10 and 14 after the beginning of the assay. Terminal differentiation was indicated by the absence of cell number increases and the retention of cell viability over the 7 to 14 d incubation in the absence of inducers.

Subtraction Hybridization, RACE and Sequence Analysis

Identification and cloning of mda-6 by subtraction hybridization was achieved as described (Jiang & Fisher, 1993). A full-length mda-6 cDNA was isolated by screening a differentiation inducer-treated H0-1 cDNA library (Jiang & Fisher, 1993) and using the procedure of rapid amplification of cDNA ends (RACE) as described (Frohman et al., 1988; Loh et al., 1989; Ohara et al., 1989). Sequence analysis was determined as described (Sanger et al., 1977; Su et al., 1993). The complete sequence of mda-6 consists of 2149 nucleotides (U09579 in GenBank) and the longest open reading frame starting with a methionine codon at position 95 in the nucleotide sequence encodes a 164-amino acid polypeptide. Compared with the current protein database releases using the GCG/TFASTA program, the predicted mda-6 amino acid sequence is identical to the sequences of WAF1/CIP1/SDI1 (El-Deiry et al., 1993; Harper et al., 1993; Noda et al., 1994).

RNA Isolation, Northern Blotting and RT-PCR

Total cytoplasmic RNA was isolated and Northern blotting hybridization was performed as described (Reddy et al., 1991; Su et al., 1991; Jiang et al., 1992). Ten μg of RNA was denatured with glyoxal/DMSO, electrophoresed on 1.0% agarose gels, transferred to nylon membranes and hybridized to a $^{32}$p-labeled p53 probe (Baker et al., 1990). The nylon membrane was stripped and hybridized to a $^{32}$p-labeled mda-6 probe (Jiang and Fisher, 1993) and then after a second stripping the membrane was hybridized to a $^{32}$p-labeled rat GAPDH probe (Fort et al., 1985), as described previously (Reddy et al., 1991; Su et al., 1991; Jiang et al., 1992). Following hybridization, the filters were washed and exposed for autoradiography (Reddy et al., 1991; Su et al., 1991; Jiang et al., 1992). mda-6 and GAPDH gene expression were also determined by reverse transcription-polymerase chain reaction (RT-PCR) as described (Adollahi et al., 1991; Lin et al., 1994; Jiang et al., 1994b). Total cytoplasmic RNA was treated with 0.5 units DNase (Boehringer-Mannheim Biochemicals)/μg RNA in 15% glycerol, 10 mM Tris, pH 7.5, 2.5 mM $MgCl_2$, 0.1 mM EDTA, 80 mM KCl, 1 mM $CaCl_2$ and 1 unit/ml RNasin (Promega) at 30° C. for 10 min. RNA was extracted with phenol-chloroform, precipitated with sodium acetate/ethanol and RNA pellets were resuspended in diethylpyrocarbonate-treated $H_2O$. One μg of total RNA was reverse transcribed with 200 units of murine leukemia virus reverse transcriptase (Bethesda Research Laboratories) in 20 μl containing 1 mM deoxyribonucleotide triphosphates, 4 mM MgCl2, 10 mM Tris, pH 8.3, 50 mM KCl, 0.001% gelatin and 0.2 μg oligo-dT primer. Samples were adjusted to 100 μl with buffer containing 0.2 mM deoxyribonucleotide triphosphates, 2 mM MgCl2, 10 mM Tris, pH 8.3, 50 mM KCl and 0.001% gelatin. Fifty pmol of each primer, 1.5 units Taq DNA polymerase (Perkin-Elmer Cetus) were added and samples were covered with mineral oil, heated at 95° C. for 5 min and subjected to 25 cycles of PCR in a Perkin-Elmer Thermal Cycler using 1 mm denaturation at 94° C., 2 min annealing at 55° C. and 3 min polymerization at 72° C. After extraction with chloroform, 20 μl of products were electrophoresed, blotted onto nylon filters and hybridized with an mda-6 or GAPDH specific probe. The mda-6 primers were 5' to 3' CTCCAAGTACACTAAGCACT (SEQ ID. NO:26) and TAGTTCTACCTCAGGCAGCT (SEQ ID NO:27) (corresponding to nt 1527 to 1546) (GenBank accession number U09579); and the GAPDH primers were 5' to 3' TCTTACTCCTTGGAGGCCATG (SEQ ID NO:28) and CGTCTTCACCACCACCATGGAGAA (SEQ ID NO:29) (corresponding to nt 1070 to 1053) (Tokunaga et al., 1987).

Immunoprecipitation Analyses

Immunoprecipitation analyses were performed as described previously (Duigou et al., 1991; Su et al., 1993; Jiang et al., 1994b). Logarithmically growing H0-1 cells were either untreated or treated for 24, 48, 72 or 96 h with IFN-β (2000 units/ml), MEZ (10 ng/ml) or IFN-β+MEZ (2000 units/ml+10 ng/ml) in 10-cm plates. Cultures were starved of methionine for 1 h at 37° C. in methionine-free medium, cells were concentrated by pelleting and labeled for 1 h (p53) or 4 h (p21 and Actin) at 37° in 1 ml of the same medium with 100 μCi of [$^{35}$S] (NEN; Express $^{35}$S). After labeling, the cells were washed twice with ice-cold phosphate-buffered saline and lysed for 1 h on ice by the addition of RIPC (20 mM Tris-base, pH 7.5, 500 mM NaCl, 0.05% Nonidet P-40, 100 μg/ml phenylmethylsulfonyl fluoride and 0.02% sodium azide). The lysate was clarified by centrifugation in an Eppendorf microfuge at 10,000×g for 10 min at 4° C. H0-1 samples containing 4×10$^6$ counts were incubated with 2 μg of p53 monoclonal antibody (Ab1; PAb421) (Oncogene Sciences), WAF1/CIP1 (C-19) (Santa Cruz Biotechnology) (or MDA-6 peptide-derived) rabbit polyclonal IgG or actin monoclonal antibody (Oncogene Sciences) with rocking at 4° C. for 24 h. Labeled cell lysates were also prepared from F0-1, L0-1, SH-1, WM239, FM516-SV, SW480, MeWo, human skin fibroblasts and Saos-2 cells. Samples containing 4×10$^6$ counts were incubated with 2 μg of the p53 monoclonal antibody Ab1 (PAb421) or Ab3 (PAb240) (Oncogene Sciences). The next day, 30 μl (packed volume) of protein G-agarose (Oncogene Sciences) was added to each tube, and incubation with rocking at 4° C. continued for another hour. The protein G pellets were then washed five times with 1 ml of ice-cold RIPC:phosphate-buffered saline (1:1, v/v). Thirty μl of sodium dodecyl sulfate-polyacrylamide gel electrophoresis buffer were added to the pellets, and the sample was heated at 87° C. for 3 min. The samples were loaded onto an 10% polyacrylamide gel and run overnight at 40 V. The gel contained Rainbow protein markers (Amersham) for sizing. Gels were fixed with 10% acetic acid plus 10% methanol for 30 min, incubated in DMSO for 30 min, incubated with 10% 2,5-diphenyloxazole in DMSO for 30 min, washed three times with cold water (10 min each), dried, and exposed to film.

REFERENCES OF THE SEVENTH SERIES OF EXPERIMENTS

Abdollahi, A., Lord, K. A., Hoffman-Liebermann, B. & Liebermann, D. A. (1991). Cell Growth Different., 2, 401–407.

Baker, S. J., Markowitz, S., Fearon, E. R., Willson, J. K. V. & Vogelstein, B. (1990). Science, 249, 912–915.

Bishop, M. J. (1991). Cell, 64, 235–248.

Castresana, J. S., Rubio, M.-P., Vazquez, J., Idoate, M., Sober, A. J., Seizinger, B. R. & Barnhill, R. L. (1993). Int. J. Oncol., 55, 562–565.

Clark, W. (1991). Br. J. Cancer, 64, 631–644.

Dony, C., Kessel, M. & Gruss, P. (1985). Nature, 317, 636–639.

Duigou, G. J., Su, Z.-z., Babiss, L. E., Driscoll, B., Fung, Y.-K. T. & Fisher, P. B. (1991). Oncogene, 6, 1813–1824.

El-Deiry, W. S., Tokino, T., Velculescu, V. E., Levy, D. B., Parsons, R., Trent, J. M., Lin, D., Mercer, W. E., Kinzler, K. W. & Vogelstein, B. (1993). Cell, 75, 817–825.

El-Deiry, W. S., Harper, J. W., O'Connor, P. M., Velculescu, V. E., Canman, C. E., Jackman, J., Pietenpol, J. A., Burrell, M., Hill, D. E., Wang, Y., Wiman, K. G., Mercer, W. E., Kastan, M. B., Kohn, K. W., Elledge, S. J., Kinzler, K. W. & Vogelstein, B. (1994). Cancer Res., 54, 1169–1174.

Fisher, P. B. (1984). Tumor Promotion and Cocarcinogenesis In Vitro, Mechanisms of Tumor Promotion, Vol. III, Slaga, T. J. (ed.), CRC Press Inc.: Florida, pp. 57–123.

Fisher, P. B., Hermo, H., Jr., Weinstein, I. B. & Pestka, S. (1985). Interferon Res., 5, 11–22.

Fisher, P. B., Hermo, H., Jr., Solowey, W. E., Dietrich, M. C., Edwalds, G. M., Weinstein, I. B., Langer, J. A., Pestka, S., Giacomini, P., Kusama, M. & Ferrone, S. (1986). Anticancer Res., 6, 765–774.

Fisher, P. B. & Rowley, P. T. (1991). The Status of Differentiation Therapy of Cancer, Vol. II, Waxman, S., Rossi, G. B. & Takaku, F. (eds.), Raven Press: New York, pp. 201–214.

Fort, P., Marty, L., Piechaczyk, M., Sabrouty, S. E., Dani, C., Jeanteur, P. & Blanchard, J. M. (1985). Nucleic Acids Res., 13, 1431–1442.

Frohman, M. A., Dush, M. K. & Martin, G. R. (1988). Proc. Natl. Acad. Sci. USA, 85, 8998–9002.

Giovanella, B. C., Stehlin, J. S., Santamaria, C., Yim, S. O., Morgan, A. C., Williams, L. J., Leibovitz, A., Fialkow, P. Y. & Mumford, D. M. (1976). J. Natl. Cancer Inst., 56, 1131–1142.

Graham, G. M., Guarini, L., Moulton, T. A., Datta, S., Ferrone, S., Giacomini, P., Kerbel, R. S. & Fisher, P. B. (1991). Cancer Immunol. Immunother., 32, 382–390.

Greenblatt, M. S., Bennett, W. P., Hollstein, M. & Harris C. C. (1994). Cancer Res., 54, 4855–4878.

Guarini, L., Graham, G. M., Jiang, H., Ferrone, S., Zucker, S. & Fisher, P. B. (1992). Pigment Cell Res. Suppl., 2, 123–131.

Guarini, L., Temponi, M., Edwalds, G. M., Vita, J. R., Fisher, P. B. & Ferrone, S. (1989). Cancer Immunol. Immunother., 30, 363–370.

Harper, J. W., Adami, G. R., Wei, N., Keyomarsi, K. & Elledge, S. J. (1993). Cell, 75, 805–816.

Hayes, T. E., Valtz, N. L. M. & McKay, R. D. G. (1991). New Biologist, 3, 259–269.

Herlyn, M. (1990). Cancer Metastasis Rev., 9, 101–112.

Herlyn, M., Kath, R., Williams, N., Valyi-Nagy, I. & Rodeck, U. (1989). Adv. Cancer Res., 54, 213–234.

Jiang, H., Su, Z.-z., Boyd, J. & Fisher, P. B. (1993). Mol. Cell. Different., 1 (1), 41–66.

Jiang, H. & Fisher, P. B. (1993). Mol. Cell. Different., 1 (3), 285–299.

Jiang, H., Lin, J. & Fisher, P. B. (1994a). Mol. Cell. Different., 2 (3), in press.

Jiang, H., Su, Z.-z., Datta, S., Guarini, L., Waxman, S. & Fisher, P. B. (1992). Intl. J. Oncology, 1, 227–239.

Jiang, H., Lin, J., Su, Z.-z., Collart, F. R., Huberman, E. & Fisher, P. B. (1994b). Oncogene, in press.

Jimenez J. J. & Yunis, A. A. (1987). Science, 238, 1278–1280.

Kerbel, R. S. (1990). Adv. Cancer Res., 55, 87–132.

Khochbin, S., Principaud, E., Chabanas, A. & Lawrence, J.-J. (1988). J. Mol. Biol., 200, 55–64.

Kobayashi, H., Man, S., MacDougall, J. R., Graham, C. H., Lu, C. & Kerbel, R. S. (1994). Amer. J. Pathol., 144, 776–786.

Lane, D. P. (1992). Nature, 358, 15–16.

Li, Y., Jenkins, C. W., Nichols, M. A. & Xiong, Y. (1994). Oncogene, 9, 2261–2268.

Livingstone, L. R., White, A., Sprouse, J., Livanos, E., Jacks, T. & Tlsty, T. D. (1992). Cell, 70, 923–935.

Loganzo, F., Jr., Nabeya, Y., Maslak, P. & Albino, A. P. (1994). Mol. Cell. Different., 2 (1), 23–43.

Loh, E. Y., Elliott, J. F., Cwirla, S., Lanier, L. L. & Davis, M. M. (1989). Science, 243, 217–220.

Lotan, R. (1993). Retinoids in Oncology, Hong, W. K. & Lotan, R. (eds.), Marcel Dekker, Inc.: New York, pp. 43–72.

Lu, C. & Kerbel, R. S. (1994). Curr. Opin. Oncology, 6, 212–220.

MacDougall, J. R., Kobayashi, H. & Kerbel, R. S. (1993). Mol. Cell. Different., 1 (1), 21–40.

Mancianti, M. L., Herlyn, M., Weil, D., Jambrosic, J., Rodeck, U., Becker, D., Diamond, L., Clark, W. H. & Koprowski, H. (1988). J. Ivest. Dermatol., 90, 134–141.

Melber, K., Zhu, G. & Diamond, L. (1989). Cancer Res., 49, 3650–3655.

Mercer, W. E., Avignolo C. & Baserga, R. (1984). Mol. Cell. Biol., 4, 276–281.

Michieli, P., Chedid, M., Lin, D., Pierce, J. H., Mercer, W. E. & Givol, D. (1994). Cancer Res., 54, 3391–3395.

Millikin, D., Meese, E., Vogelstein, B., Witkowski, C. & Trent, J. M. (1991). Cancer Res., 51, 5449–5453.

Montano, X., Shamsher, M., Whitehead, P., Dawson, K. & Newton, J. (1994). Oncogene, 9, 1455–1459.

Noda, A., Ning, Y., Venable, S. F., Pereira-Smith, O. M. & Smith, J. R. (1994). Exp. Cell Res., 211, 90–98.

Ohara, O., Dorit, R. L. & Gilbert, W. (1989). Proc. Natl. Acad. Sci. USA, 86, 5673–5677.

Pietenpol, J. A., Tokino, T., Thiagalingam, S., El-Deiry, W. S., Kinzler, K. W. & Vogelstein, B. (1994). Proc. Natl. Acad. Sci. USA, 91, 1998–2002.

Reddy, P. G., Graham, G. M., Datta, S., Guarini, L., Moulton, T. A., Jiang, H., Gottesman, M. M., Ferrone, S. & Fisher, P. B. (1991). J. Natl. Cancer Inst., 83, 1307–1315.

Richon, V. M., Ramsay, R. G., Rifkind, R. A. & Marks, P. A. (1989). Oncogene, 4, 165–173.

Ron, D. (1994). Proc. Natl. Acad. Sci. USA, 91, 1985–1986.

Sachs, L. (1978). Nature, 274, 535–539.

Sanger, F., Nicklen, S. & Coulson, A. R. (1977). Proc. Natl. Acad. Sci. USA, 74, 5463–5467.

Shen, D.-W., Real, F. X., DeLeo, A. B., Old, L. J., Marks, P. A. & Rifkind, R. A. (1983). Proc. Natl. Acad. Sci. USA, 80, 5919–5922.

Shobat, O., Greenberg, M., Reisman, D., Oren, M. & Rotter, V. (1987). Oncogene, 1, 277–283.

Steinman, R. A., Hoffman, B., Iro, A., Guillouf, C., Liebermann, D. A. & El-Houseini, M. E. (1994). Oncogene, in press.

Su, Z.-z., Grunberger, D. & Fisher, P. B. (1991). Mol. Carcinog., 4, 231–242.

Su, Z.-z., Leon, J. A., Jiang, H., Austin, V. N., Zimmer, S. G. & Fisher, P. B. (1993). Cancer Res., 53, 1929–1938.

Tokunaga, K., Nakamura, Y., Sakata, K., Fujimori, K., Ohkubo, M., Sawada, K. & Sakiyama, S. (1987). Cancer Res., 47, 5616–5619.

Trent, J. M., Stanbridge, E. J., McBride, H. L., Meese, E. U., Casey, G., Arajo, D. E., Witkowski, C. M. & Nagle, R. B. (1990). Science, 247, 568–571.

Vogelstein, B. & Kinzler, K. W. (1992). Cell, 70, 523–526.

Volkenandt, M., Schlegel, U., Nanus, D. M. & Albino, A. P. (1991). Pigment Cell Res., 4, 35–40.

Waga, S., Hannon, G. J., Beach, D. & Stillman, B. (1994). Nature, 369, 574–578.

Waxman, S., Rossi, G. B. & Takaku, F. (1988). The Status of Differentiation Therapy of Cancer, vol. I, Raven Press Inc.: New York.

Waxman, S., Rossi, G. B. & Takaku, F. (1991). The Status of Differentiation Therapy of Cancer, vol. II, Raven Press Inc.: New York.

Welch, D. R., Bisi, J. E., Miller, B. E., Conaway, D., Seftor, E. A., Yohem, K. H., Gilmore, L. B., Seftor, R. E. B., Nakajima, M. & Hendrix, M. J. C. (1991). Int. J. Cancer, 47, 227–237.

Welch, D. R., Chen, P., Miele, M. E., McGary, C. T., Bower, J. M., Stanbridge, E. J. & Weissman, B. E. (1994). Oncogene, 9, 255–262.

Xiong, Y., Zhang, H. & Beach, D. (1993a). Genes & Develop., 7, 1572–1583.

Xiong, Y., Hannon, G. J., Zhang, H., Casso, D., Kobayashi, R. & Beach, D. (1993b). Nature, 366, 701–704.

Xiong, Y., Zhang, H. & Beach, D. (1992). Cell, 71, 505–514.

Yin, Y., Tainsky, M. A., Bischoff, F. Z., Strong, L. C. & Wahl, G. M. (1992). Cell, 70, 937–948.

EIGHTH SERIES OF EXPERIMENTS

Properties of mda-7 mda-7 is a novel cDNA (it has no sequence homology with previously reported genes in the various DNA data bases). The full-length cDNA contains 1718 nt, the open reading frame extends from nt 275 to no 895 and encodes a protein of 206 amino acids, containing a membrane domain and three potential glycosylation sites.

Expression in H0-1 Human Melanoma Cells

Increased expression of mda-7 after 24 hr treatment of H0-1 cells with recombinant human fibroblast interferon (IFN-β) (2000 units/ml), MEZ (10 ng/ml) and to the greatest extent with IFN-β+MEZ (2000 units/ml+10 ng/ml).

Increased expression of mda-7 is observed in H0-1 cells treated for 96 hr with IFN-β (2000 units/ml), MEZ (10 ng/ml), MPA (3 μM), IFN-β+IFN-γ (1000 units/ml+1000 units/ml), IFN-β+MEZ (2000 units/ml+10 ng/ml, MPA+MEZ (3 μM+10 ng/ml) and RA+MEZ (2.5 μM+10 ng/ml). Maximum induction is observed with IFN-β+MEZ followed by MPA+MEZ and IFN-β+IFN-γ.

The relative level of mda-7 induction correlates with the degree of growth suppression observed H0-1 cells treated with the various growth and differentiation modulating agents. The greatest increase in expression is observed in cells induced to irreversibly lose proliferative capacity and become terminally differentiated by treatment with IFN-β+MEZ.

Expression in Additional Human Melanoma Cells

Increased expression of mda-7 occurs in H0-1, C8161, C8161/6.3 (a C8161 human melanoma cell clone containing an inserted normal human chromosome 6: These cells are tumorigenic in nude mice, but unlike parental C8161 cells they are non-metastatic), F0-1, L0-1, SH-1, WM278 and WM239 human melanoma cells treated with IFN-β+MEZ for 24 hr. This gene is constitutively expressed in immortalized human melanocytes FM5169 (transformed by SV40). However, no increase in expression is observed in FM5169 following IFN-β+MEZ treatment for 24 hr.

mda-7 is either variably expressed or variably induced in all human melanoma cells treated with IFN-β+MEZ. In contrast, although this gene is expressed in melanocytes, no change in expression is observed following a 24 hr treatment with IFN-β+MEZ.

Expression in Human Neuroblastoma Cells mda-7 is not expressed in LAN human neuroblastoma cells as determined by reverse transcription-polymerase chain reaction (RT-PCR). mda-7 expression is not induced by treatment with RA for 5 days, but it is induced after 5 days growth in the medium containing phenylacetate or the combination of phenylacetate and RA.

mda-7 is induced in human neuroblastoma cells as a function of growth arrest and induction of differentiation. Expression of mda-7 may contribute to growth arrest and terminal differentiation in human neuroblastoma cells.

Expression in Human Promyelocytic Leukemia Cells (HL-60) and Histiocytic Lymphoma (U-937) Cell Lines mda-7 expression is not detected in HL-60 and U-937 cells using RT-PCR. mda-7 expression is induced in HL-60 and U-937 cells following treatment with the growth suppressing and differentiation inducing agent TPA. mda-7 expression persists in terminally differentiated HL-60 cells after treatment with TPA for 2 days and RA for 4 days.

mda-7 is induced during differentiation along both granulocytic and agranulocytic (monocytic/macrophage) lineages in human promyelocytic leukemia and histiocytic lymphoma cells. Expression of mda-7 may contribute to the growth arrest and terminal differentiation in hematopoeitic cells.

Expression in Senescent Human Cells mda-7 expression is not detected using RT-PCR in IMR90 human cells displaying proliferative potential (i.e., non-senescent cells). mda-7 expression is detected in IMR90 cells grown for extended times in culture (OLD) and approaching senescence.

mda-7 gene expression inversely correlates with proliferative potential in human cells. mda-7 expression is activated during cellular senescence. This gene may contribute to proliferative capacity in cells and may function as a genetic marker and/or regulatory switch of cellular senescence.

Expression in Normal Cerebellum, a Central Nervous System Tumor (Glioblastoma Multiforme) (GBM) and Normal Skin Fibroblast Cell Lines mda-7 is not expressed de novo in normal cerebellum, GBM or normal skin fibroblasts. Expression of mda-7 is induced in normal cerebellum, GBM and normal skin fibroblasts following a 24 hr treatment with IFN-β+MEZ.

mda-7 is not expressed de novo, but it is susceptible to induction by IFN-β+MEZ in human cerebellum, GBM and normal human skin fibroblasts.

Expression in Colorectal (SW613), Endometrial Adenocarcinoma (HTB113) and Prostate Carcinoma (LNCaP)

mda-7 is expressed de novo in colorectal carcinoma (SW613), endometrial adenocarcinoma (HTB113) or prostate carcinoma (LNCaP). mda-7 is not induced in colorectal carcinoma (SW613), endometrial adenocarcinoma (HTB113) or prostate carcinoma (LNCaP) cells following a 24 h treatment with IFN-β+MEZ.

This gene is neither expressed de novo nor inducible by IFN-β+MEZ human carcinomas.

Effect of Various Treatment Protocols on Expression in H0-1 Cells

Treatment with IFN-β (2000 units/ml; 24 h), MEZ (10 μg/ml; 24 h), IFN-β+MEZ (2000 units/ml+10 ng/ml; 24 h and 96 h), IFN-α+MEZ (2000 units/ml+10 ng/ml; 24 h), adriamycin (0.1 ng/ml; 24 h), vincristine (0.1 μg/ml; 24 h), and UV (10 joules/mm$^2$ and assayed 24 h later) results in increased mda-7 expression in H0-1 cells. mda-7 is also induced after 96 h treatment with MPA (2 μM), IFN-β+IFN-γ (1000 units/ml+1000 units/ml), MPA+MEZ (3 μM+10 ng/ml) and RA+MEZ (2.5 μM+10 ng/ml). Highest level of expression observed in H0-1 cells treated with IFN-β+MEZ for 24 or 96 h.

No induction in mda-7 expression is observed in H0-1 cells treated with IFN-α (2000 units/ml; 24 h), IFN-γ (2000 units/ml; 96 h), phenyl butyrate (4 mM PB for 24 h, 4 d or 7 d), cis-platinum (0.1 μg/ml; 24 h), gamma irradiation (treated with 3 gray and analyzed after 24 h), actinomycin D (5 μg/ml for 2 h, assayed 24 h later), TNF-α (100 units/ml; 24 h) or VP-16 (5 μg/ml; 24 h).

General Conclusions mda-7 is a growth, differentiation-regulated and senescence-associated novel gene which displays the following properties: 1) it is inducible during terminal differentiation (treatment with IFN-β+MEZ for 96 h) and following treatment for 96 h with many growth modulating and differentiation inducing agents; 2) treatment for 24 h with IFN-β+MEZ results in increased expression in all human melanomas tested, but not in an SV40-immortalized human melanocyte; 3) it is not expressed in growing human neuroblastoma cells but it is inducible following growth suppression and the induction of terminal differentiation 4) it is not expressed in human promyelocytic leukemia (HL-60) and human histiocytic lymphoma (U-937) cells but it is induced following the induction of growth arrest and terminal differentiation; 5) it is not expressed in actively growing human cells but it is induced during cellular senescence; 6) it is not expressed de novo but it is highly inducible by IFN-β+MEZ within 24 h in normal cerebellum, GBM and normal skin fibroblast cells; 7) it is not expressed or inducible in colorectal, endometrial or prostate carcinomas; and 8) increased expression is induced in H0-1 cells treated with adriamycin, vincristine and UV irradiation.

mda-7 is a novel growth, terminal differentiation- and senescence-regulated gene displaying increased expression in all melanomas (but not in melanocytes), and in normal skin fibroblasts and in both normal cerebellum and GBM cells treated with IFN-β+MEZ. mda-7 is not expressed de novo, but it is induced during growth arrest and differentiation in human neuroblastoma, leukemia and histiocytic lymphoma cells. mda-7 is not expressed in growing nonsenescent cells but it is expressed in senescent cells. In contrast, mda-7 is not expressed or induced in a series of carcinomas. mda-7 may be useful; 1) as a marker for specific tissue lineage's (i.e., melanomas from keratinocytes) (diagnostic applications); 2) in distinguishing fibroblasts (inducible with IFN-β+MEZ) from carcinomas (non-inducible with IFN-β+MEZ) (diagnostic applications); 3) in identifying cells that have lost proliferative capacity and become senescent; 4) in monitoring induction of differentiation in cancer cells resulting during the differentiation therapy of cancer; 5) for the identification of agents capable of inducing growth suppression and various components of the differentiation process (including terminal differentiation) in human melanomas, neuroblastomas, leukemias and lymphomas (drug screening programs to identify new differentiation-inducing and chemotherapeutic agents); and 6) distinguishing melanocytes, and perhaps nevi, from early and late stage melanoma cells (diagnostic applications). This gene (used in a sense orientation in an appropriate expression vector) may also prove useful in inhibiting growth and inducing terminal differentiation in human melanomas (therapeutic applications). When used in an antisense orientation and inserted into bone marrow cells this gene might prevent damage resulting from chemotherapy and radiation (therapeutic applications).

What is claimed is:

1. An isolated nucleic acid encoding the amino acid sequence shown in FIGS. 38A–B (SEQ ID NO:7).

2. The nucleic acid of claim 1, wherein the nucleic acid is a cDNA.

3. The nucleic acid of claim 1, further comprising a promoter wherein the promoter controls the expression of the nucleic acid.

4. The nucleic acid of claim 3, wherein the promoter is an inducible promoter.

5. The nucleic acid of claim 3, wherein the promoter is a tissue-specific promoter.

6. The nucleic acid of claim 3, wherein the promoter is a bacteriophage promoter.

7. The nucleic acid of claim 6, wherein the bacteriophage promoter is T3, T7 or SP6.

8. The nucleic acid of claim 3, wherein the promoter is a promoter of RNA transcriptase.

9. A pharmaceutical composition which comprises the nucleic acid of claim 1, 3, 4, 5, 6, 7 or 8.

10. The pharmaceutical composition of claim 9, wherein the nucleic acid is combined with a liposome.

11. A vector comprising the nucleic acid of claim 1.

12. The vector of claim 11, wherein the vector is a plasmid, a bacteriophage, a cosmid or a retroviral vector.

13. The vector of claim 11, wherein the vector is a plasmid vector ATCC Accession No. 75905.

14. The vector of claim 11, wherein the vector is a plasmid vector ATCC Accession No. 75906.

15. A host cell comprising the vector of claim 11.

16. The host cell of claim 15, wherein the host cell is stably transformed.

17. The host cell of claim 15, wherein the host cell is a tumor cell.

18. The host cell of claim 15, wherein the host cell is a neuroblastoma cell, a leukemic cell, a lymphatic cell, a fibroblast, a melanoma cell, a glioblastoma cell, a colorectal carcinoma cell, a breast carcinoma cell, an ovarian carcinoma cell or a prostate carcinoma cell.

* * * * *